US012582104B2

(12) United States Patent
Patel et al.

(10) Patent No.: US 12,582,104 B2
(45) Date of Patent: Mar. 24, 2026

(54) MUTANT MYOCILIN DISEASE MODEL AND USES THEREOF

(71) Applicant: Regeneron Pharmaceuticals, Inc., Tarrytown, NY (US)

(72) Inventors: Gaurang Patel, North Brunswick, NJ (US); Charleen Hunt, Montvale, NJ (US); Yajun Tang, White Plains, NY (US); Qing Fang, Chappaqua, NY (US); Guochun Gong, Pleasantville, NY (US); Ying Hu, Scarsdale, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/717,225

(22) PCT Filed: Dec. 8, 2022

(86) PCT No.: PCT/US2022/081149
§ 371 (c)(1),
(2) Date: Jun. 6, 2024

(87) PCT Pub. No.: WO2023/108047
PCT Pub. Date: Jun. 15, 2023

(65) Prior Publication Data
US 2025/0040522 A1      Feb. 6, 2025

Related U.S. Application Data

(60) Provisional application No. 63/287,281, filed on Dec. 8, 2021.

(51) Int. Cl.
*A01K 67/0275*      (2024.01)
*C07K 14/005*      (2006.01)
*C07K 14/47*      (2006.01)
*C12N 9/22*      (2006.01)
*C12N 15/113*      (2010.01)
*C12N 15/86*      (2006.01)

(52) U.S. Cl.
CPC ........ *A01K 67/0275* (2013.01); *C07K 14/005* (2013.01); *C07K 14/47* (2013.01); *C12N 9/22* (2013.01); *C12N 15/113* (2013.01); *C12N 15/86* (2013.01); *A01K 2207/15* (2013.01); *A01K 2217/072* (2013.01); *A01K 2227/105* (2013.01); *A01K 2267/0306* (2013.01); *C12N 2310/20* (2017.05); *C12N 2740/15043* (2013.01); *C12N 2750/14143* (2013.01); *C12N 2795/18122* (2013.01)

(58) Field of Classification Search
CPC .. A01K 67/0275; C07K 14/005; C07K 14/47; C12N 9/22; C12N 15/113; C12N 15/86
See application file for complete search history.

(56) References Cited

U.S. PATENT DOCUMENTS

| | | | |
|---|---|---|---|
| 5,942,435 A | 8/1999 | Wheeler | |
| 6,248,867 B1 * | 6/2001 | Nguyen ............... | C12Q 1/6883 |
| | | | 435/69.7 |
| 6,586,251 B2 | 7/2003 | Economides et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 10,329,582 B2 | 6/2019 | Lee et al. | |
| 10,385,359 B2 | 8/2019 | Lee et al. | |
| 10,550,372 B2 | 2/2020 | Konermann et al. | |
| 10,577,630 B2 | 3/2020 | Zhang et al. | |
| 10,760,064 B2 | 9/2020 | Joung et al. | |
| 10,941,404 B2 | 3/2021 | Gottesman et al. | |
| 11,001,829 B2 | 5/2021 | Zhang et al. | |
| 11,519,004 B2 | 12/2022 | Hunt et al. | |
| 11,591,581 B2 | 2/2023 | Zhang et al. | |
| 11,597,919 B2 | 3/2023 | Konermann et al. | |
| 2008/0078000 A1 | 3/2008 | Poueymirou et al. | |
| 2014/0178879 A1 | 6/2014 | Economides et al. | |
| 2014/0235933 A1 | 8/2014 | Lee et al. | |
| 2014/0310828 A1 | 10/2014 | Lee et al. | |

(Continued)

FOREIGN PATENT DOCUMENTS

| | | | |
|---|---|---|---|
| CA | 2324480 A1 | 10/1999 | |
| EP | 3064585 A1 | 9/2016 | |

(Continued)

OTHER PUBLICATIONS

Zhou et al., Investigative Ophthalmology and Visual Science (2008) 49(5): 1932 (Year: 2008).*
Zhu, et al., Nature Communications (2019) 10: 1845 (Year: 2019).*
Acosta, et al., Genesis (2018) 56(5): e23212 (Year: 2018).*
Addgene Product Catalogue, plasmid #61425, pp. 10-13, retrieved at www.addgene.org/61425/ on Apr. 26, 2022, (2022).
Baeumler, et al., "Engineering Synthetic Signaling Pathways with Programmable dCas9-Based Chimeric Receptors," Cell Rep., 20(11):2639-2653, (2017).

(Continued)

*Primary Examiner* — Evelyn Y Pyla
*Assistant Examiner* — Katherine R Small
(74) *Attorney, Agent, or Firm* — Alston & Bird LLP

(57)                    ABSTRACT

Non-human animal genomes, non-human animal cells, and non-human animals comprising a humanized MYOC locus and methods of making and using such non-human animal genomes, non-human animal cells, and non-human animals are provided. Non-human animal cells or non-human animals comprising a humanized MYOC locus express a human myocilin protein or a chimeric myocilin protein, fragments of which are from human myocilin. Methods are provided for using such non-human animals comprising a humanized MYOC locus to assess in vivo efficacy of human-myocilin-targeting reagents and reagents for treating glaucoma.

27 Claims, 35 Drawing Sheets

Specification includes a Sequence Listing.

(56) References Cited

U.S. PATENT DOCUMENTS

| | | | |
|---|---|---|---|
| 2015/0071899 A1 | 3/2015 | Liu et al. |
| 2015/0376628 A1 | 12/2015 | Schoenherr et al. |
| 2015/0376651 A1 | 12/2015 | Frendewey et al. |
| 2016/0058889 A1 | 3/2016 | Olson et al. |
| 2016/0145646 A1 | 5/2016 | Frendewey et al. |
| 2016/0151491 A1 | 6/2016 | Rabinovich et al. |
| 2016/0208288 A1 | 7/2016 | Liu et al. |
| 2016/0222416 A1 | 8/2016 | Church et al. |
| 2016/0237456 A1 | 8/2016 | Church et al. |
| 2016/0243260 A1 | 8/2016 | Blits |
| 2016/0257974 A1 | 9/2016 | Bradley et al. |
| 2016/0281072 A1 | 9/2016 | Zhang |
| 2016/0326548 A1 | 11/2016 | Cost |
| 2016/0355797 A1 | 12/2016 | Konermann et al. |
| 2017/0107536 A1 | 4/2017 | Zhang et al. |
| 2017/0204407 A1 | 7/2017 | Gilbert et al. |
| 2017/0239370 A1 | 8/2017 | Zhu et al. |
| 2018/0057810 A1 | 3/2018 | Zhang et al. |
| 2018/0110877 A1 | 4/2018 | Wilson et al. |
| 2018/0119122 A1 | 5/2018 | Zhang et al. |
| 2018/0179553 A1 | 6/2018 | Watson et al. |
| 2018/0185516 A1 | 7/2018 | Ansell et al. |
| 2019/0002869 A1 | 1/2019 | Yin et al. |
| 2019/0032053 A1 | 1/2019 | Ji et al. |
| 2019/0038780 A1 | 2/2019 | Largaespada et al. |
| 2019/0106693 A1 | 4/2019 | Rinn et al. |
| 2019/0233814 A1 | 8/2019 | Zhang et al. |
| 2019/0284572 A1 | 9/2019 | Hunt et al. |
| 2019/0365924 A1 | 12/2019 | Conway et al. |
| 2019/0376060 A1 | 12/2019 | Vora et al. |
| 2019/0376090 A1 | 12/2019 | Joung et al. |
| 2019/0390195 A1 | 12/2019 | Tondera et al. |
| 2020/0115687 A1 | 4/2020 | Konermann et al. |
| 2020/0248168 A1 | 8/2020 | Lundberg et al. |
| 2020/0392541 A1 | 12/2020 | Zhang et al. |
| 2021/0079394 A1 | 3/2021 | Hunt et al. |
| 2021/0102206 A1 | 4/2021 | Liao et al. |
| 2021/0269831 A1 | 9/2021 | Zhang et al. |
| 2023/0040053 A1 | 2/2023 | Piao et al. |
| 2023/0123296 A1 | 4/2023 | Hunt et al. |

FOREIGN PATENT DOCUMENTS

| | | | | |
|---|---|---|---|---|
| EP | 2877571 B1 | 5/2018 |
| EP | 3392337 A1 | 10/2018 |
| EP | 3003392 B1 | 10/2019 |
| EP | 3045537 A1 | 2/2020 |
| EP | 3080271 B1 | 2/2020 |
| EP | 3620524 A1 | 3/2020 |
| KR | 10-2017-0054493 A | 5/2017 |
| WO | WO 2013/071440 A1 | 5/2013 |
| WO | WO 2014/093622 A2 | 6/2014 |
| WO | WO 2014/093701 A1 | 6/2014 |
| WO | WO 2014/130706 A1 | 8/2014 |
| WO | WO 2014/172489 A2 | 10/2014 |
| WO | WO 2014/197568 A2 | 12/2014 |
| WO | WO 2015/006294 A2 | 1/2015 |
| WO | WO 2015/035139 A2 | 3/2015 |
| WO | WO 2015/040075 A1 | 3/2015 |
| WO | WO 2015/042557 A1 | 3/2015 |
| WO | WO 2015/088643 A1 | 6/2015 |
| WO | WO 2015/089486 A2 | 6/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/049258 A2 | 3/2016 |
| WO | WO 2016/081923 A2 | 5/2016 |
| WO | WO 2016/094872 A1 | 6/2016 |
| WO | WO 2016/094874 A1 | 6/2016 |
| WO | WO 2016/137949 A1 | 9/2016 |
| WO | WO 2016/149484 A2 | 9/2016 |
| WO | WO 2016/176191 A1 | 11/2016 |
| WO | WO 2017/011721 A1 | 1/2017 |
| WO | WO 2017/087780 A1 | 5/2017 |
| WO | WO 2017/106657 A1 | 6/2017 |
| WO | WO 2017/173054 A1 | 10/2017 |
| WO | WO 2017/180915 A2 | 10/2017 |
| WO | WO 2018/007871 A1 | 1/2018 |
| WO | WO 2018/009869 A1 | 1/2018 |
| WO | WO 2018/085644 A1 | 5/2018 |
| WO | WO 2018/096343 A1 | 5/2018 |
| WO | WO 2018/107026 A1 | 6/2018 |
| WO | WO 2018/107028 A1 | 6/2018 |
| WO | WO 2018/119354 A1 | 6/2018 |
| WO | WO 2018/154380 A1 | 8/2018 |
| WO | WO 2019/027728 A1 | 2/2019 |
| WO | WO-2019183123 A1 * | 9/2019 | ......... A01K 67/0275 |
| WO | WO 2019/236081 A1 | 12/2019 |
| WO | WO 2019/237069 A1 | 12/2019 |
| WO | WO 2019/246203 A1 | 12/2019 |
| WO | WO 2020/142714 A1 | 7/2020 |
| WO | WO 2021/108363 A1 | 6/2021 |
| WO | WO 2023/278406 A1 | 1/2023 |
| WO | WO 2023/108047 A1 | 6/2023 |

OTHER PUBLICATIONS

Barthold, "Genetically altered mice: phenotypes, no phenotypes, and Faux phenotypes," Genetica, 122(1):75-88, (2004).

Birling, et al., "Modeling human disease in rodents by CRISPR/Cas9 genome editing," Mamm. Genome, 28(7-8):291-301, (2017).

Brevini, et al., "No shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Burova, et al., "Characterization of the Anti-PD-1 Antibody REGN2810 and Its Antitumor Activity in Human PD-1 Knock-In Mice," Mol. Cancer Ther., 16(5):861-870, (2017).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Cas9 SAM, "Cas9-Activators with SAM" [Retrieved from the Internet Oct. 19, 2017 <http://sam.genone-engineering.org/>].

Chavez, et al., "Comparison of Cas9 activators in multiple species," Nat. Methods, 13(7):563-567, (2016).

Chow et al., "AAV-mediated direct in vivo CRISPR screen identifies functional suppressors in glioblastoma," Nat. Neurosci. 20(10):1329-1341 plus supplementary materials, (Aug. 14, 2017).

Clark, et al., "A future for transgenic livestock," Nat. Rev. Genet., 4(10):825-833, (2003).

Comes et al., "Evidence for a role of angiopoietin-like 7 (ANGPTL7) in extracellular matrix formation of the human trabecular meshwork: implications for glaucoma," Genes Cells, 16(2):243-259, (2011).

Dahlman, et al., "Orthogonal gene knockout and activation with a catalytically active Cas9 nuclease," Nat. Biotechnol., 33(11):1159-1161, (2015).

Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.

Dennis, "Welfare Issues of Genetically Modified Animals," ILAR J., 43(2):100-109, (2002).

Devoy et al.,. "Genomically humanized mice: technologies and promises," Nat. Rev. Genet., 13(1):14-20, (2011).

Dominguez, et al., "Beyond editing: repurposing CRISPR-Cas9 for precision genome regulation and interrogation," Nat. Rev. Mol. Cell. Biol., 17(1):5-15, (2016).

Evers, et al., "CRISPR knockout screening outperforms shRNA and CRISPRi in identifying essential genes," Nature Biotechnology, 34(6):631-633 plus Online Methods, (Jun. 2016).

Fernandes et al., "Using genetic mouse models to gain insight into glaucoma: Past results and future possibilities," Exp. Eye Res., 141: 42-56. (Dec. 2015).

Finn, et al., "A Single Administration of CRISPR/Cas9 Lipid Nanoparticles Achieves Robust and Persistent In Vivo Genome Editing," Cell Reports, 22:1-9, (Feb. 27, 2018).

Frendewey, et al., "The Loss-of-Allele Assay for ES Cell Screening and Mouse Genotyping," Methods Enzymol., 476:295-307, (2010).

(56) References Cited

OTHER PUBLICATIONS

Friedrich, et al., "Promoter traps in embryonic stem cells: a genetic screen to identify and mutate developmental genes in mice," Genes Dev., 5(9):1513-1523, (1991).

Genoway, "Humanized Mouse Model," retrieved from https://www.genoway.com/services/customized-mouse/knockin-models/humanisation.htm on May 12, 2018.

Gertz, et al., "Diagnosis, Prognosis, and Therapy of Transthyretin Amyloidosis," J. Am. Coll. Cardiol., 66(21):2451-2466, (2015).

Gomez, et al., "Derivation of cat embryonic stem-like cells from in vitro-produced blastocysts on homologous and heterologous feeder cells," Theriogenology, 74(4): 498-515, (2010).

Graham, et al., "Resources for the design of CRISPR gene editing experiments," Genome Biol., 16:260, (2015).

Haapaniemi et al., "CRISPR-Cas9 genome editing induces a p53-mediated DNA damage response," Nat. Med. doi: 10.1038/s41591-018-0049-z, (Jun. 11, 2018, epub ahead of print).

Harari, et al., "Bridging the Species Divide: Transgenic Mice Humanized for Type-I Interferon Response," PLoS One, 9(1): e84259, (2014).

Herndler-Brandstetter, et al., "Humanized mouse model supports development, function, and tissue residency of human natural killer cells," Proc. Natl. Acad. Sci. U.S.A., 114(45):E9626-E9634, (2017).

Hopkins, et al., "Characterization of Autosomal Dominant Hypercholesterolemia Caused by PCSK9 Gain of Function Mutations and its Specific Treatment With Alirocumab, a PCSK9 Monoclonal Antibody," Circ. Cardiovasc. Genet., 8(6):823-831, (2015).

Houdebine, "Methods to Generate Transgenic Animals," pp. 31-48 in "Genetic Engineering in Livestock: New Applications and Interdisciplinary Perspectives," Ed. Engelhard et al., (2009).

Hunt et al., "Tissue-specific activation of gene expression by the Synergistic Activation Mediator (SAM) CRISPRa system in mice," Nat. Commun., 12(1):2770, (May 13, 2021).

Ihry et al., "p53 inhibits CRISPR-Cas9 engineering in human pluripotent stem cells," Nat. Med. doi: 10.1038/s41591-018-0050-6 (Jun. 11, 2018, epub ahead of print).

Jain et al., "CRISPR-Cas9-based treatment of myocilin-associated glaucoma," Proc. Natl. Acad. Sci. U.S.A., 114(42):11199-11204, (2017).

Jean, et al., "Pluripotent genes in avian stem cells," Dev. Growth Differ., 55(1): 41-51, (2013).

Jensen, "Design principles for nuclease-deficient CRISPR-based transcriptional regulators," FEMS Yeast Res., 18(4), doi: 10.1093/femsyr/foy039, (2018).

Jia, et al., "Next-generation CRISPR/Cas9 transcriptional activation in Drosophila using flySAM," Pros. Natl. Acad. Sci. U.S.A., 115(18), 4719-4724, (Apr. 16, 2018).

Joung, et al., "Genome-scale CRISPR-Cas9 knockout and transcriptional activation screening," Nature Protocols, 12(4):828-863, (2017).

Kawamata, et al., "Generation of genetically modified rats from embryonic stem cells," Proc. Natl. Acad. Sci. U.S.A., 7(32):14223-14228, (2010).

Kim et al., "Targeted Disruption of the Myocilin Gene (Myoc) Suggests that Human Glaucoma-Causing Mutations are Gain of Function," Mol. Cell. Biol., (21(22):7707-7713, (Nov. 2001).

Konermann, et al., "Genome-scale transcriptional activation by an engineered CRISPR-Cas9 complex," Nature, 517:583-588 plus Extended Data, (Jan. 29, 2017).

Kosicki et al., "Repair of double-strand breaks induced by CRISPR-Cas9 leads to large deletions and complex rearrangements," Nat. Biotechnol., 36(8): 765-771, (Jul. 16, 2018).

Kuchtey et al., "Angiopoietin-like 7 secretion is induced by glaucoma stimuli and its concentration is elevated in glaucomatous aqueous humor," Invest. Ophthalmol. Vis. Sci., 49(8):3438-3448, (Aug. 2008).

Kumar, et al., "Transgenic Mouse Technology: Principles and Methods," Methods Mol. Biol., 590:335-362, (2009).

La Russa, et al., "The New State of the Art: Cas9 for Gene Activation and Repression," Mol. Cell. Biol., 35(22):3800-3809, (2015).

Lau, et al., "Targeted Transgene Activation in the Brain Tissue by Systemic Delivery of Engineered AAV1 Expressing CRISPRa," Mol. Ther. Nucleic Acids, 16:637-649, (2019).

Lau, et al., "In vivo genome editing in animals using AAV-CRISPR system: applications to translational research of human disease," F1000Res, 6:2153, doi: 10.12688/f1000research.11243.1, (2017).

Liao, et al., "Amyloid Cardiomyopathy, Disease on the Rise," Circ. Res., 120(12):1865-1867, (2017).

Liao, et al., "In Vivo Target Gene Activation via CRISPR/Cas9-Mediated Trans-epigenetic Modulation," Cell, 171(7):1495-1507.e15 (2017).

Liu, et al., "Editing DNA Methylation in the Mammalian Genome,"(2016).

Liu, et al., "Specific Expression of Interferon-gamma Induced by Synergistic Activation Mediator-Derived Systems Activates Innate Immunity and Inhibits Tumorigenesis," J. Microbiol. Biotechnol., 27(10):1855-1866, (2017).

Lundh, et al., "Bidirectional manipulation of gene expression in adipocytes using CRISPRa and siRNA," Mol. Metab., 6(10):1313-1320, (2017).

Lute, et al., "Human CTLA4 knock-in mice unravel the quantitative link between tumor immunity and autoimmunity induced by anti-CTLA-4 antibodies," Blood, 106(9):3127-3133, (2005).

Lynch et al., "Binding of a glaucoma-associated myocilin variant to the αB-crystallin chaperone impedes protein clearance in trabecular meshwork cells," J. Biol. Chem., 293(52), 20137-20156, (2018).

Malina et al., "Repurposing CRISPR/Cas9 for in situ functional assays," Genes Dev., vol. 27(23):2602-2614, (2013).

Matharu, et al., "CRISPR-mediated activation of a promoter or enhancer rescues obesity caused by haploinsufficiency," Science, 363(6424), doi: 10.1126/science.aau0629, (2019).

Morgens, et al., "Systematic comparison of CRISPR/Cas9 and RNAi screens for essential genes," Nature Biotechnology, 34(6):634-636 plus Online Methods, (Jun. 2016).

Mullins, et al., "Transgenesis in the rat and larger mammals," J. Clin. Invest. 97(7):1557-1560, (1996).

Munoz, et al., "Conventional pluripotency markers are unspecific for bovine embryonic-derived cell-lines," Theriogenology, 69(9): 1159-1164, (2008).

Niemann, "Transgenic farm animals get off the ground. Transgenic Animals in Agriculture, Conference Tahoe City, California, USA. Aug. 24-27, 1997." Transgenic Res., 7(1): 73-75, (1998).

Nishimasu, et al., "Crystal Structure of Cas9 in Complex with Guide RNA and Target DNA," Cell, 156:935-949, (Feb. 27, 2014).

Omer, et al., "CRISPR Correction of a Homozygous Low-Density Lipoprotein Receptor Mutation in Familial Hypercholesterolemia Induced Pluripotent Stem Cells," Hepatol. Commun., 1(9):886-898, (Oct. 16, 2017).

Paris, et al., "Equine embryos and embryonic stem cells: defining reliable markers of pluripotency," Theriogenology, 74(4): 516-524, (2010).

Platt, et al., "CRISPR-Cas9 Knockin Mice for Genome Editing and Cancer Modeling," Cell, 159:440-455, (Oct. 9, 2014).

Poueymirou, et al., "F0 generation mice fully derived from gene-targeted embryonic stem cells allowing immediate phenotypic analyses," Nat. Biotechnol., 25(1):91-99, (2007).

Praveen et a., "ANGPTL7, a therapeutic target for increased intraocular pressure and glaucoma," Commun. Biol., 5(1):1051, (Oct. 1-15, 2022).

Praveen et al., "Genetic and Functional Characterization of ANGPTL7 as a Therapeutic Target for Glaucoma," Research Square, DOI: https://doi.gor/10.21203/rs.3.rs-858876/v1, (Sep. 2021).

Ran et al., "In vivo genome editing using Staphylococcus aureus Cas9," Nature, 520(7546):186-191, (2015).

Rezza, et al., "Unexpected genomic rearrangements at targeted loci associated with CRISPR/Cas9-mediated knock-in," Sci. Rep., 9(1):3486, (2019).

Ristevski, "Making better transgenic models: conditional, temporal, and spatial approaches," Mol. Biotechnol., 29(2):153-163, (2005).

Rogers, et al., "Disruption of the CFTR Gene Produces a Model of Cystic Fibrosis in Newborn Pigs," Science, 321(5897):1837-1841, (2008).

(56)                    References Cited

OTHER PUBLICATIONS

Senis, et al., "CRISPR/Cas9-mediated genome engineering: an adeno-associated viral (AAV) vector toolbox," Biotechnol. J., 9(11):1402-1412, (2014).

Shalem, et al., "Genome-Scale CRISPR-Cas9 Knockout Screening in Human Cells," Science, 343:84-87, (Jan. 3, 2014).

Shalem, et al., "High-throughput functional genomics using CRISPR-Cas9," Nature Reviews: Genetics, 16:299-311, (May 2015).

Shapiro, et al., "PCSK9: From Basic Science Discoveries to Clinical Trials," Circ. Res., 122(10):1420-1438, (2018).

Shepard et al., "Glaucoma-causing myocilin mutants require the Peroxisomal targeting signal-1 receptor (PTS1R) to elevate intraocular pressure," Hum. Mol. Genet., 16(6):609-617, (2007).

Sigmund, "Viewpoint: Are Studies in Genetically Altered Mice Out of Control?," Arterioscler. Thromb. Vasc. Biol., 20(6):1425-1429, (2000).

Sun et al., "ANGPTL7 is transcriptionally regulated by SP1 and modulates glucocorticoid-induced cross-linked actin networks in trabecular meshwork cells via the RhoA/Rock pathway," Cell Death Discov., 8(1):50, (Feb. 2022).

Tanigawa et al., "Rare protein-altering variants in ANGPTL7 lower intraocular pressure and protect against glaucoma," PLoS Genet, 16(5):e1008682, (May 2020).

Tham et al., "Global prevalence of glaucoma and projections of glaucoma burden through 2040: a systematic review and meta-analysis," Ophthalmology, 121(11):2081-2090, (Nov. 2014).

Ueda, et al., "Recent advances in transthyretin amyloidosis therapy," Transl. Neurodegener., 3:19, doi: 10.1186/2047-9158-3-19, (2014).

Valenzuela, et al., "High-throughput engineering of the mouse genome coupled with high-resolution expression analysis," Nat. Biotechnol., 21(6):652-659, (2003).

Vora, et al., "Rational design of a compact CRISPR-Cas9 activator for AAV-mediated delivery," bioRxiv, doi: 10.1101/298620, (2018).

Wakchaure, et al., "Transgenic Animals: A Review on its Various Dimensions and Applications in Animal Biotechnology," International Journal of Emerging Technology and Advanced Engineering, 5(11):210-213, (2015).

Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).

Wangensteen, al et., "Combinatorial genetics in liver repopulation and carcinogenesis with a in vivo CRISPR activation platform," Hepatology, 68(2):663-676, (2018).

Xu, et al., "CRISPR-on-Mediated KLF4 overexpression inhibits the proliferation, migration and invasion of urothelial bladder cancer in vitro and in vivo," Oncotarget, 8(60):102078-102087, (2017).

Yin, et al., "Structure-guided chemical modification of guide RNA enables potent non-viral in vivo genome editing," Nat. Biotechnol., 35(12):1179-1187, (Nov. 13, 2017).

Yin, et al., "Delivery technologies for genome editing," Nat. Rev. Drug Discov., 16(6):387-399, (2017).

Zambrowicz, et al., "Disruption of overlapping transcripts in the ROSA beta geo 26 gene trap strain leads to widespread expression of beta-galactosidase in mouse embryos and hematopoietic cells," Proc. Natl. Acad. Sci. U.S.A., 94(8):3789-3794, (1997).

Zhan et al., "CRISPR/Cas9 for cancer research and therapy," Semin. Cancer Biol., 55:106-119, (2019).

Zhang Lab—CRISPR Mouse Activation Pooled Library (SAM v1) [Retrieved from the Internet Oct. 19, 2017 <https://www.addgene.org/pooled-library/zhang-mouse-sam-v1/>].

Zhang, et al., "CRISPR/gRNA-directed synergistic activation mediator (SAM) induces specific, persistent and robust reactivation of the HIV-1 latent reservoirs," Scientific Reports, 5:16277, (Nov. 5, 2015).

Zhao, et al., "Inconsistency between hepatic expression and serum concentration of transthyretin in mice humanized at the transthyretin locus," Genes to Cells, 13:1257-1268, (2008).

Zhou et al., "Transgenic mice expressing the Tyr437His mutant of human myocilin protein develop glaucoma," Invest. Ophthalmol. Vis. Sci., 49(5):1932-1939, (May 2008).

Zhou, et al., "Developing tTA transgenic rats for inducible and reversible gene expression," Int. J. Biol. Sci., 5(2): 171-181, (2009).

Zhou, et al., "In vivo simultaneous transcriptional activation of multiple genes in the brain using CRISPR-dCas9-activator transgenic mice," Nat. Neurosci., 21(3):440-446, (Jan. 15, 2018).

Zhu et al., "Humanising the mouse genome piece by piece," Nat. Commun., 10(1):1845. (Apr. 2019).

Zode et al., "Reduction of ER stress via a chemical chaperone prevents disease phenotypes in a mouse model of primary open angle glaucoma," J. Clin. Invest., 121(9):3542-3553, (Sep. 2011).

WIPO Application No. PCT/US2022/081149, PCT International Preliminary Report on Patentability mailed Jun. 5, 2024.

WIPO Application No. PCT/US2022/081149, PCT International Search Report and Written Opinion of the International Searching Authority mailed Apr. 20, 2023.

* cited by examiner

*Signal peptide*

```
Human MYOC:  MRFFCARCCSFGPEMPAVQLLLACLVWDVGARTAQLRKANDQSGRCQYTFSVASPNESSCPEQSQAMSVIHNLQRDSST
Mouse MYOC:            MPALHLLFLACLVWGMGARTAQFRKANDRSGRCQYTFVASPNESSCPREDQAMSAIQDLQRDSSI Human MYOC:  QRLDLEATKARLSSLESLLHQLTLDQAARPQETQEGLQRELGTLRRERDQLETQTRELETAYSNLLRDKSVLEEKKRLR
Mouse MYOC:  QHADLESTKARVRSLESLLHQMTLGRVTGTQEAQEGLQGQLGALRRERDQLETQTRDLEAAYNNLLRDKSALEEKRQLE
```

*N-terminal fragment | C-terminal fragment*

*CAPN2 cleavage*

```
Human MYOC:  QENENLARRLESSSQEVARLRRGQCPQTRDTARAVPPGSREVSTWNLDTLAFQELKSELTEVPASRILKESPSGYLRSGE
Mouse MYOC:  QENEDLARRLESSSEEVTRLRRGQCPSTQYPSQDMLPGSREVSQWNLDTLAFQELKSELTEVPASQILKENPSGRPRSKE Human MYOC:  GDTGCGELVWVGEPLTLRTAETITGKYGVWMRDPKPTYPYTQETTWRIDTVGTDVRQVFEYDLISQFMQGYPSKVHILPR
Mouse MYOC:  GDKGCGALVWVGEPVTLRTAETIAGKYGVWMRDPKPTHPYTQESTWRIDTVGTEIRQVFEYSQISQFEQGYPSKVHVLPR Human MYOC:  PLESTGAVVYSGSLYFQGAESRTVIRYELNTETVKAEKEIPGAGYHGQFPYSWGGYTDIDLAVDEAGLWVIYSTDEAKGA
Mouse MYOC:  ALESTGAVVYAGSLYFQGAESRTVVRYELDTETVKAEKEIPGAGYHGHFPYAWGGYTDIDLAVDESGLWVIYSTEEAKGA Human MYOC:  IVLSKLNPENLELEQTWETNIRKQSVANAFIICGTLYTVSSYTSADATVNFAYDTGTGISKTLTIPFKNRYKYSSMIDYN
Mouse MYOC:  IVLSKLNPANLELERTWETNIRKQSVANAFVICGIIYTVSSYSSAHATVNFAYDTKTGTSKTLTIPFTNRYKYSSMIDYN
```

*Y437*

```
Human MYOC:  PLEKKLFAWDNLNMVTYDIKLSKM  (SEQ ID NO: 1)
Mouse MYOC:  PLERKLFAWDNFNMVTYDIKLLEM  (SEQ ID NO: 6)
```

*FIG. 3*

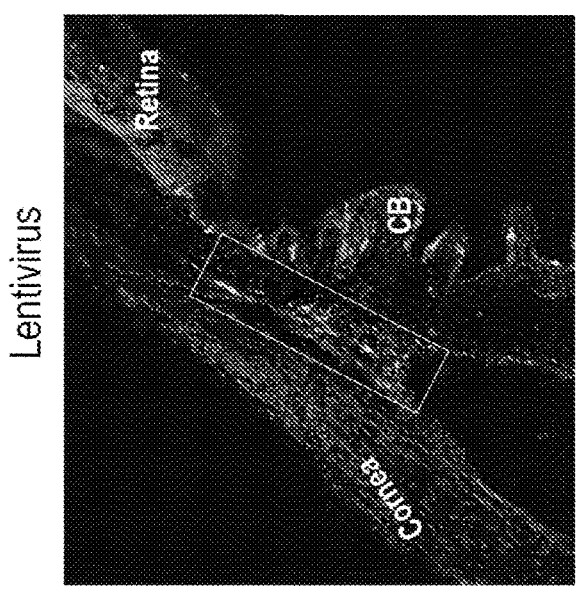
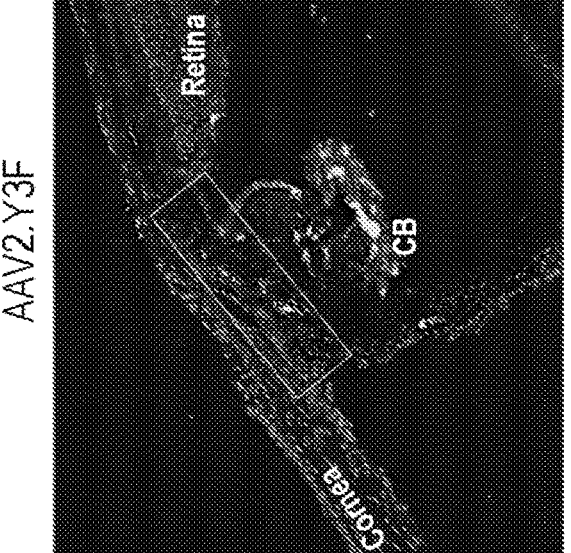
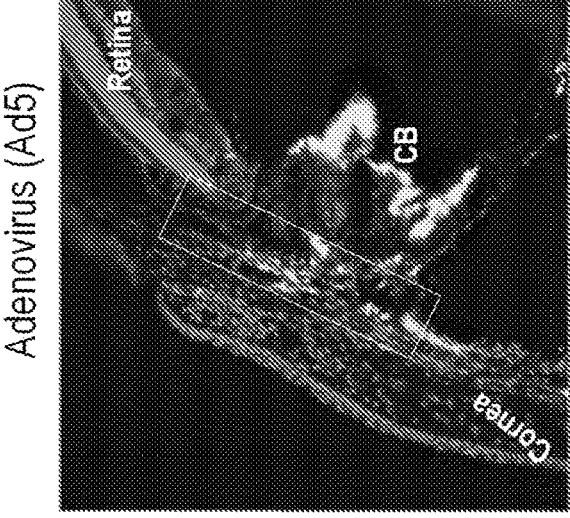
*FIG. 7*

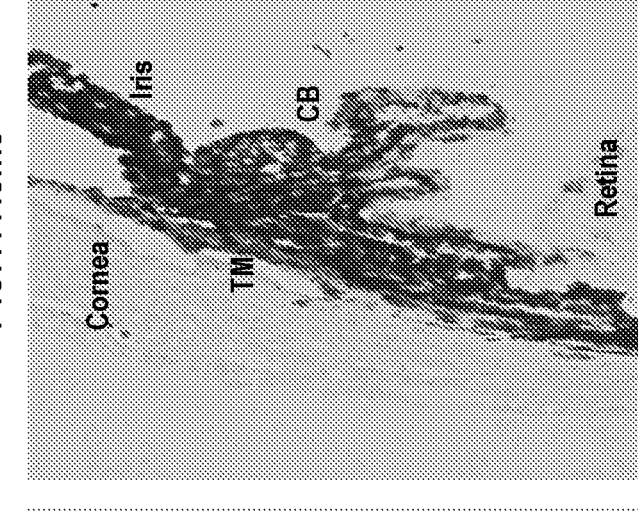
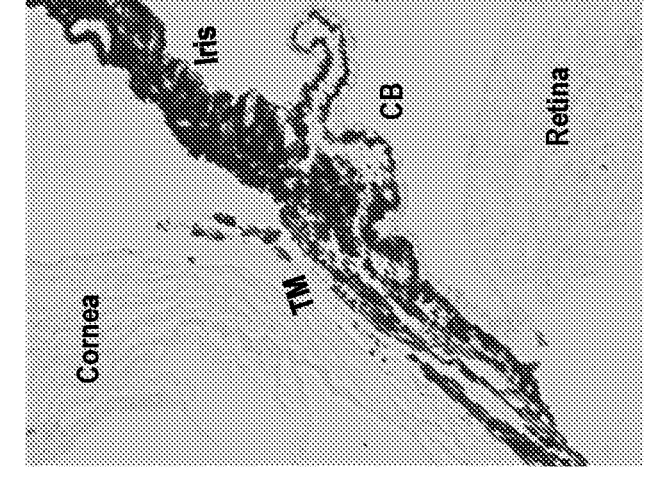
FIG. 14

FIG. 17A

Baseline IOPs
Inject SAM-g4-IC route

Inject siRNA IVT
1ul- 7.5ug dose mRNA KD by
qPCR from
limbal ring
(TM, Iris, CB)

Measure IOP

Measure IOP

Day 0

Week 1-5

Week 6

Weeks 7-11

MUTANT MYOCILIN DISEASE MODEL AND USES THEREOF

CROSS-REFERENCE TO RELATED APPLICATIONS

This application is a 35 U.S.C. § 371 national stage of International Application No. PCT/US2022/081149, filed Dec. 8, 2022, which claims the benefit of U.S. Application 63/287,281, filed Dec. 8, 2021, each of which is herein incorporated by reference in its entirety for all purposes.

REFERENCE TO A SEQUENCE LISTING SUBMITTED AS A TEXT FILE VIA EFS WEB

The Sequence Listing written in file 588714SEQLIST.xml is 302 kilobytes, was created on Dec. 1, 2022, and is hereby incorporated by reference.

BACKGROUND

Mutations in myocilin (MYOC) are responsible for the most common genetic cause of glaucoma, accounting for 8-10% of autosomal dominant familial juvenile open angle glaucoma cases, as well as 2-3% of primary open-angle glaucoma (POAG) cases. MYOC toxic gain-of-function mutant proteins aggregate intracellularly, leading to trabecular meshwork (TM) stress, elevated intraocular pressure (IOP), and glaucoma. Better animal models are needed for replicating glaucoma phenotypes caused by MYOC.

SUMMARY

Non-human animals, non-human animal cells, and non-human animal genomes comprising a humanized MYOC locus are provided, as well as methods of making and using such non-human animals, non-human animal cells, and non-human animal genomes. Also provided are humanized non-human animal MYOC genes, nucleic acids comprising humanized non-human animal MYOC genes, targeting vectors for use in humanizing a non-human animal MYOC gene, and methods of making and using such humanized MYOC genes.

In one aspect, provided are non-human animals, non-human animal cells, and non-human animal genomes comprising in their genome a humanized endogenous MYOC locus in which a region of the endogenous MYOC locus has been deleted and replaced with a corresponding human MYOC sequence. In some such non-human animals, non-human animal cells, and non-human animal genomes, the region of the endogenous MYOC locus comprises both a MYOC exonic sequence and a MYOC intronic sequence and the corresponding human MYOC sequence comprises both a MYOC exonic sequence and a MYOC intronic sequence.

In some such non-human animals, non-human animal cells, and non-human animal genomes, the humanized endogenous MYOC locus comprises a mutation associated with glaucoma. In some such non-human animals, non-human animal cells, and non-human animal genomes, the human MYOC sequence comprises the mutation. In some such non-human animals, non-human animal cells, and non-human animal genomes, the humanized endogenous MYOC locus comprises a Y437H mutation. In some such non-human animals, non-human animal cells, and non-human animal genomes, the human MYOC sequence comprises the Y437H mutation.

In some such non-human animals, non-human animal cells, and non-human animal genomes, the humanized endogenous MYOC locus comprises an endogenous MYOC promoter, wherein the human MYOC sequence is operably linked to the endogenous MYOC promoter. In some such non-human animals, non-human animal cells, and non-human animal genomes, at least one intron and at least one exon of the endogenous MYOC locus have been deleted and replaced with the corresponding human MYOC sequence. In some such non-human animals, non-human animal cells, and non-human animal genomes, the humanized endogenous MYOC locus comprises a human MYOC 3' untranslated region. In some such non-human animals, non-human animal cells, and non-human animal genomes, the endogenous MYOC 5' untranslated region has not been deleted and replaced with the corresponding human MYOC sequence.

In some such non-human animals, non-human animal cells, and non-human animal genomes, the humanized endogenous MYOC locus encodes a human myocilin protein. In some such non-human animals, non-human animal cells, and non-human animal genomes, the human myocilin protein sequence comprises the sequence set forth in SEQ ID NO: 4, and optionally wherein the human myocilin protein sequence is encoded by a coding sequence comprising the sequence set forth in SEQ ID NO: 5.

In some such non-human animals, non-human animal cells, and non-human animal genomes, the entire MYOC coding sequence of the endogenous MYOC locus has been deleted and replaced with the corresponding human MYOC sequence. In some such non-human animals, non-human animal cells, and non-human animal genomes, a region of the endogenous MYOC locus from the MYOC start codon to the MYOC stop codon has been deleted and replaced with the corresponding human MYOC sequence.

In some such non-human animals, non-human animal cells, and non-human animal genomes, a region of the endogenous MYOC locus from the MYOC start codon to the MYOC stop codon has been deleted and replaced with a human MYOC sequence comprising the corresponding human MYOC sequence and a human MYOC 3' untranslated region, the human MYOC sequence comprises a Y437H mutation, the endogenous MYOC 5' untranslated region has not been deleted and replaced with the human MYOC sequence, and the humanized endogenous MYOC locus comprises an endogenous MYOC promoter, wherein the human MYOC sequence is operably linked to the endogenous MYOC promoter.

In some such non-human animals, non-human animal cells, and non-human animal genomes, the human MYOC sequence at the humanized endogenous MYOC locus comprises a sequence at least 90%, at least 95%, at least 96%, at least 97%, at least 98%, at least 99%, or 100% identical to the sequence set forth in SEQ ID NO: 87. In some such non-human animals, non-human animal cells, and non-human animal genomes, the humanized endogenous MYOC locus encodes a myocilin protein comprising a sequence at least 90%, at least 95%, at least 96%, at least 97%, at least 98%, at least 99%, or 100% identical to the sequence set forth in SEQ ID NO: 4. In some such non-human animals, non-human animal cells, and non-human animal genomes, the humanized endogenous MYOC locus comprises a myocilin coding sequence comprising a sequence at least 90%, at least 95%, at least 96%, at least 97%, at least 98%, at least 99%, or 100% identical to the sequence set forth in SEQ ID NO: 5. In some such non-human animals, non-human animal cells, and non-human animal genomes, the humanized endogenous MYOC locus comprises a sequence at least 90%, at least 95%, at least 96%, at least 97%, at least 98%, at least 99%, or 100% identical to the sequence set forth in SEQ ID NO: 88 or 89.

In some such non-human animals, non-human animal cells, and non-human animal genomes, the humanized endogenous MYOC locus does not comprise a selection cassette or a reporter gene. Some such non-human animals, non-human animal cells, and non-human animal genomes are homozygous for the humanized endogenous MYOC locus. Some such non-human animals, non-human animal cells, and non-human animal genomes are heterozygous for the humanized endogenous MYOC locus. In some such non-human animals, non-human animal cells, and non-human animal genomes, the non-human animal comprises the humanized endogenous MYOC locus in its germline.

In some such non-human animals, non-human animal cells, and non-human animal genomes, the non-human animal is a mammal. In some such non-human animals, non-human animal cells, and non-human animal genomes, the non-human animal is a rat or a mouse. In some such non-human animals, non-human animal cells, and non-human animal genomes, the non-human animal is a mouse.

Some such non-human animals, non-human animal cells, and non-human animal genomes further comprise in their genome a genomically integrated expression cassette, wherein the genomically integrated expression cassette comprises: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains. Some such non-human animals, non-human animal cells, and non-human animal genomes further comprise one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus. Optionally, the one or more guide RNAs or one or more expression cassettes that encode the one or more guide RNAs are in the trabecular meshwork.

Some such non-human animals, non-human animal cells, and non-human animal genomes further comprise a second genomically integrated expression cassette that encodes one or more guide RNAs each comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

In some such non-human animals, non-human animal cells, and non-human animal genomes, the first expression cassette is integrated into a Rosa26 locus, the Cas protein is a Cas9 protein comprising mutations corresponding to D10A and N863A when optimally aligned with a *Streptococcus pyogenes* Cas9 protein, the one or more transcriptional activator domains in the chimeric Cas protein comprise VP64, the adaptor protein comprises an MS2 coat protein or a functional fragment or variant thereof, the one or more transcriptional activation domains in the chimeric adaptor protein comprise p65 and HSF1, the non-human animal further comprises one or more guide RNAs or one or more expression cassettes that encode the one or more guide RNAs, the one or more guide RNAs or one or more expression cassettes that encode the one or more guide RNAs are in the trabecular meshwork, each of the one or more guide RNAs comprises two adaptor-binding elements to which the chimeric adaptor protein can specifically bind, the two adaptor-binding elements comprise a first adaptor-binding element within a first loop of each of the one or more guide RNAs and a second adaptor-binding element within a second loop of each of the one or more guide RNAs, and the target sequence is within a region 200 base pairs upstream of the transcription start site and 1 base pair downstream of the transcription start site.

In some such non-human animals, non-human animal cells, and non-human animal genomes, the non-human animal is a mouse, and the one or more guide RNAs target one or more guide RNA target sequences selected from SEQ ID NOS: 90-95. In some such non-human animals, non-human animal cells, and non-human animal genomes, the non-human animal is a mouse, and the one or more guide RNAs target one or more guide RNA target sequences selected from SEQ ID NOS: 93-94. In some such non-human animals, non-human animal cells, and non-human animal genomes, the non-human animal is a mouse, and the one or more guide RNAs target the guide RNA target sequence set forth in SEQ ID NO: 93.

Some such non-human animals or non-human animal cells have at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression relative to a control non-human animal or non-human animal cell that does not comprise the one or more guide RNAs or the one or more expression cassettes that encode the one or more guide RNAs. Some such non-human animals have at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the eye, the limbal ring, the retina, the ciliary body, or the trabecular meshwork relative to a control non-human animal that does not comprise the one or more guide RNAs or the one or more expression cassettes that encode the one or more guide RNAs. Some such non-human animals have at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring or the trabecular meshwork relative to a control non-human animal that does not comprise the one or more guide RNAs or the one or more expression cassettes that encode the one or more guide RNAs. Some such non-human animals have at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring relative to a control non-human animal that does not comprise the one or more guide RNAs or the one or more expression cassettes that encode the one or more guide RNAs. Some such non-human animals have at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the trabecular meshwork relative to a control non-human animal that does not comprise the one or more guide RNAs or the one or more expression cassettes that encode the one or more guide RNAs.

In some such non-human animals, the non-human animal has increased intraocular pressure relative to a wild type non-human animal or a control non-human animal. Optionally, the non-human animal has an intraocular pressure of at least 15, at least 16, at least 17, at least 18, at least 19, at least 20, at least 21, or at least 22 mmHg. Optionally, the non-human animal has an intraocular pressure that is at least 1, at least 2, at least 3, at least 4, at least 5, or at least 6 mmHg higher than the intraocular pressure of the control non-human animal.

In another aspect, provided is a nucleic acid comprising a humanized non-human animal MYOC gene (i.e., a humanized non-human animal MYOC locus as described above) in which a region of the endogenous MYOC gene has been deleted and replaced with a corresponding human MYOC sequence. Optionally, the region of the endogenous MYOC gene comprises both a MYOC exonic sequence and a MYOC intronic sequence and the corresponding human MYOC sequence comprises both a MYOC exonic sequence and a MYOC intronic sequence.

In another aspect, provided is a targeting vector for generating a humanized endogenous MYOC locus (i.e., a humanized endogenous MYOC locus as described above) in which a region of the endogenous MYOC locus has been deleted and replaced with a corresponding human MYOC sequence, wherein the targeting vector comprises an insert nucleic acid comprising the corresponding human MYOC sequence flanked by a 5' homology arm targeting a 5' target sequence at the endogenous MYOC locus and a 3' homology arm targeting a 3' target sequence at the endogenous MYOC locus. Optionally, the region of the endogenous MYOC locus comprises both a MYOC exonic sequence and a MYOC intronic sequence and the corresponding human MYOC sequence comprises both a MYOC exonic sequence and a MYOC intronic sequence.

In another aspect, provided are methods of assessing the activity of a human-MYOC-targeting reagent or a candidate glaucoma therapeutic agent in the non-human animals and non-human animal cells described above. Some such methods comprise: (a) administering the human-MYOC-targeting reagent or the candidate glaucoma therapeutic agent to any of the above non-human animals; and (b) assessing the activity of the human-MYOC-targeting reagent or the candidate glaucoma therapeutic agent in the non-human animal. Some such methods comprise: (a) administering the human-MYOC-targeting reagent or the candidate glaucoma therapeutic agent to any of the above non-human animal cells; and (b) assessing the activity of the human-MYOC-targeting reagent or the candidate glaucoma therapeutic agent in the non-human animal cell.

In some such methods, the non-human animal further comprises in its genome a genomically integrated expression cassette, wherein the genomically integrated expression cassette comprises: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains. Some such methods further comprise administering one or more guide RNAs or one or more expression cassettes that encode the one or more guide RNAs prior to step (a), each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

In some such methods, the non-human animal is a mouse, and the one or more guide RNAs target one or more guide RNA target sequences selected from SEQ ID NOS: 90-95. In some such methods, the non-human animal is a mouse, and the one or more guide RNAs target one or more guide RNA target sequences selected from SEQ ID NOS: 93-94. In some such methods, the non-human animal is a mouse, and the one or more guide RNAs target the guide RNA target sequence set forth in SEQ ID NO: 93.

In some such methods, the guide RNAs or the one or more expression cassettes that encode the one or more guide RNAs are administered via adenovirus-mediated delivery, lentivirus-mediated delivery, or adeno-associated virus (AAV)-mediated delivery. In some such methods, the guide RNAs or the one or more expression cassettes that encode the one or more guide RNAs are administered via recombinant AAV2.Y3F-mediated delivery. In some such methods, the guide RNAs or the one or more expression cassettes that encode the one or more guide RNAs are administered via lentivirus-mediated delivery.

In some such methods, the guide RNAs or the one or more expression cassettes that encode the one or more guide RNAs are administered to the non-human animal via intra-vitreal injection or intracameral injection. In some such methods, the guide RNAs or the one or more expression cassettes that encode the one or more guide RNAs are administered to the non-human animal at least 1 week prior to step (a) or between about 1 week to about 10 weeks prior to step (a).

In some such methods, step (b) comprises assessing the activity of the human-MYOC-targeting reagent or the candidate glaucoma therapeutic agent in the eye of the non-human animal. In some such methods, step (a) comprises administering the human-MYOC-targeting reagent, and wherein step (b) comprises measuring expression of a MYOC messenger RNA encoded by the humanized endogenous MYOC locus. In some such methods, step (a) comprises administering the human-MYOC-targeting reagent, and wherein step (b) comprises measuring expression of a myocilin protein encoded by the humanized endogenous MYOC locus. In some such methods, step (a) comprises administering the human-MYOC-targeting reagent, wherein the human-MYOC-targeting reagent is a genome-editing agent, and wherein step (b) comprises assessing modification of the humanized endogenous MYOC locus. In some such methods, step (b) comprises measuring the frequency of insertions or deletions within the humanized endogenous MYOC locus.

In some such methods, the human-MYOC-targeting reagent comprises a nuclease agent designed to target a region of a human MYOC gene. In some such methods, the nuclease agent comprises a Cas protein and a guide RNA designed to target a guide RNA target sequence in the human MYOC gene. Optionally, the Cas protein is a Cas9 protein.

In some such methods, step (a) comprises administering the human-MYOC-targeting reagent, wherein the human-MYOC-targeting reagent comprises an exogenous donor nucleic acid, wherein the exogenous donor nucleic acid is designed to target the human MYOC gene, and optionally wherein the exogenous donor nucleic acid is delivered via AAV.

In some such methods, the human-MYOC-targeting reagent is an RNAi agent or an antisense oligonucleotide. In some such methods, the human-MYOC-targeting reagent is an antigen-binding protein. In some such methods, the human-MYOC-targeting reagent is small molecule.

In some such methods, assessing the activity of the human-MYOC-targeting reagent or the candidate glaucoma therapeutic agent in the non-human animal comprises assessing intraocular pressure.

In some such methods, the assessing is in comparison to an untreated control non-human animal.

In some such methods, step (a) comprises administering the candidate glaucoma therapeutic agent, and wherein step (b) comprises assessing intraocular pressure. In some such methods, the candidate glaucoma therapeutic agent is a suppressor of aqueous humor formation. In some such methods, the candidate glaucoma therapeutic agent increases outflow of aqueous humor.

In some such methods, the candidate glaucoma therapeutic agent is an ANGPTL7-targeting reagent. In some such methods, the ANGPTL7-targeting reagent is an RNAi agent or an antisense oligonucleotide.

In another aspect, provided are methods of optimizing the activity a human-MYOC-targeting reagent or a candidate glaucoma therapeutic agent. Some such methods comprise: performing any of the above methods of assessing the activity of a human-MYOC-targeting reagent or a candidate glaucoma therapeutic agent in the non-human animals and non-human animal cells a first time in a first non-human animal or a first non-human animal cell; (II) changing a variable and performing the method of step (I) a second time with the changed variable in a second non-human animal or a second non-human animal cell; and (III) comparing the activity of the human-MYOC-targeting reagent or the candidate glaucoma therapeutic agent in step (I) with the activity of the human-MYOC-targeting reagent or the candidate glaucoma therapeutic agent in step (II), and selecting the method resulting in the higher activity.

In another aspect, provided are methods of making any of the above non-human animals comprising a humanized endogenous MYOC locus.

Some such methods comprise: (a) introducing into a non-human animal host embryo a genetically modified non-human animal embryonic stem (ES) cell comprising in its genome a humanized endogenous MYOC locus in which a region of the endogenous MYOC locus has been deleted and replaced with a corresponding human MYOC sequence; and (b) gestating the non-human animal host embryo in a surrogate mother, wherein the surrogate mother produces an F0 progeny genetically modified non-human animal comprising the humanized endogenous MYOC locus. Some such methods further comprise modifying the genome of a non-human animal ES cell to comprise the humanized endogenous MYOC locus prior to step (a).

Some such methods comprise (a) modifying the genome of a non-human animal one-cell stage embryo to comprise in its genome a humanized endogenous MYOC locus in which a region of the endogenous MYOC locus has been deleted and replaced with a corresponding human MYOC sequence, thereby generating a non-human animal genetically modified embryo; and (b) gestating the non-human animal genetically modified embryo in a surrogate mother, wherein the surrogate mother produces an F0 progeny genetically modified non-human animal comprising the humanized endogenous MYOC locus.

Some such methods comprise: crossing the F0 progeny genetically modified non-human animal comprising the humanized endogenous MYOC locus with a non-human animal comprising a genomically integrated expression cassette comprising a nucleic acid encoding a chimeric Clustered Regularly Interspaced Short Palindromic Repeats (CRISPR) associated (Cas) protein comprising a nuclease-inactive Cas protein fused to one or more transcriptional activation domains and further comprising a nucleic acid encoding a chimeric adaptor protein comprising an adaptor protein fused to one or more transcriptional activation domains.

In another aspect, provided are methods of making any of the above non-human animals comprising a humanized endogenous MYOC locus and a genomically integrated expression cassette comprising: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains.

Some such methods comprise: (a) introducing into a non-human animal host embryo a genetically modified non-human animal embryonic stem (ES) cell comprising in its genome: (i) a humanized endogenous MYOC locus in which a region of the endogenous MYOC locus has been deleted and replaced with a corresponding human MYOC sequence; and (ii) a genomically integrated expression cassette comprising a nucleic acid encoding a Cas protein comprising a nuclease-inactive Cas protein fused to one or more transcriptional activation domains and a nucleic acid encoding a chimeric adaptor protein comprising an adaptor protein fused to one or more transcriptional activation domains; and (b) gestating the non-human animal host embryo in a surrogate mother, wherein the surrogate mother produces an F0 progeny genetically modified non-human animal comprising the humanized endogenous MYOC locus and the genomically integrated expression cassette. Some such methods further comprise modifying the genome of a non-human animal ES cell to comprise the humanized endogenous MYOC locus and the genomically integrated expression cassette prior to step (a).

Some such methods comprise: (a) providing a non-human animal one-cell stage embryo comprising in its genome: (i) a humanized endogenous MYOC locus in which a region of the endogenous MYOC locus has been deleted and replaced with a corresponding human MYOC sequence; and (ii) a genomically integrated expression cassette comprising a nucleic acid encoding a Cas protein comprising a nuclease-inactive Cas protein fused to one or more transcriptional activation domains and a nucleic acid encoding a chimeric adaptor protein comprising an adaptor protein fused to one or more transcriptional activation domains; and (b) gestating the non-human animal one-cell stage embryo in a surrogate mother, wherein the surrogate mother produces an F0 progeny genetically modified non-human animal comprising the humanized endogenous MYOC locus and the genomically integrated expression cassette.

In some such methods, the non-human animal is a mouse or a rat. In some such methods, the non-human animal is the mouse.

In another aspect, provided are methods of increasing MYOC expression in a non-human animal. Some such methods comprise administering to any of the above non-human animals (comprising a humanized endogenous MYOC locus and a genomically integrated expression cassette comprising: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains) one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

In some such methods, the non-human animal is a mouse, and the one or more guide RNAs target one or more guide RNA target sequences selected from SEQ ID NOS: 90-95. In some such methods, the non-human animal is a mouse, and the one or more guide RNAs target one or more guide RNA target sequences selected from SEQ ID NOS: 93-94. In some such methods, the non-human animal is a mouse, and the one or more guide RNAs target the guide RNA target sequence set forth in SEQ ID NO: 93.

In some such methods, the guide RNAs or the one or more expression cassettes that encode the one or more guide RNAs are administered via adenovirus-mediated delivery, lentivirus-mediated delivery, or adeno-associated virus (AAV)-mediated delivery. In some such methods, the guide RNAs or the one or more expression cassettes that encode the one or more guide RNAs are administered via recombinant AAV2.Y3F-mediated delivery. In some such methods, the guide RNAs or the one or more expression cassettes that encode the one or more guide RNAs are administered via lentivirus-mediated delivery. In some such methods, the guide RNAs or the one or more expression cassettes that encode the one or more guide RNAs are administered to the non-human animal via intravitreal injection or intracameral injection.

In some such methods, the method results in increased MYOC mRNA or protein expression in the eye, the limbal ring, the retina, the ciliary body, or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the eye, the limbal ring, the retina, the ciliary body, or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring relative to a control non-human animal that does not comprise the one or more guide RNAs or one or more expression cassettes that encode the one or more guide RNAs. In some such methods, the method results in increased MYOC mRNA or protein expression in the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the trabecular meshwork relative to a control non-human animal that does not comprise the one or more guide RNAs or one or more expression cassettes that encode the one or more guide RNAs.

In some such methods, the method results in increased intraocular pressure. Optionally, the method results in the non-human animal having an intraocular pressure that is at least 1, at least 2, at least 3, at least 4, at least 5, or at least 6 mmHg higher than the intraocular pressure of the control non-human animal. Optionally, the method results in an intraocular pressure of at least 15, at least 16, at least 17, at least 18, at least 19, at least 20, at least 21, or at least 22 mmHg.

In another aspect, provided are methods of increasing intraocular pressure in a non-human animal. Some such methods comprise administering to any of the above non-human animals (comprising a humanized endogenous MYOC locus and a genomically integrated expression cassette comprising: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains) one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

In some such methods, the non-human animal is a mouse, and the one or more guide RNAs target one or more guide RNA target sequences selected from SEQ ID NOS: 90-95. In some such methods, the non-human animal is a mouse, and the one or more guide RNAs target one or more guide RNA target sequences selected from SEQ ID NOS: 93-94. In some such methods, the non-human animal is a mouse, and the one or more guide RNAs target the guide RNA target sequence set forth in SEQ ID NO: 93.

In some such methods, the guide RNAs or the one or more expression cassettes that encode the one or more guide RNAs are administered via adenovirus-mediated delivery, lentivirus-mediated delivery, or adeno-associated virus (AAV)-mediated delivery. In some such methods, the guide RNAs or the one or more expression cassettes that encode the one or more guide RNAs are administered via recombinant AAV2.Y3F-mediated delivery. In some such methods, the guide RNAs or the one or more expression cassettes that encode the one or more guide RNAs are administered via lentivirus-mediated delivery. In some such methods, the guide RNAs or the one or more expression cassettes that encode the one or more guide RNAs are administered to the non-human animal via intravitreal injection or intracameral injection.

In some such methods, the method results in increased MYOC mRNA or protein expression in the eye, the limbal ring, the retina, the ciliary body, or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the eye, the limbal ring, the retina, the ciliary body, or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring relative to a control non-human animal that does not comprise the one or more guide RNAs or one or more expression cassettes that encode the one or more guide RNAs. In some such methods, the method results in increased MYOC mRNA or protein expression in the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the trabecular meshwork relative to a control non-human animal that does not comprise the one or more guide RNAs or one or more expression cassettes that encode the one or more guide RNAs.

In some such methods, the method results in increased intraocular pressure. Optionally, the method results in the non-human animal having an intraocular pressure that is at least 1, at least 2, at least 3, at least 4, at least 5, or at least 6 mmHg higher than the intraocular pressure of the control non-human animal. Optionally, the method results in an intraocular pressure of at least 15, at least 16, at least 17, at least 18, at least 19, at least 20, at least 21, or at least 22 mmHg.

In another aspect, provided are methods of increasing modeling glaucoma in a non-human animal. Some such methods comprise administering to any of the above non-human animals (comprising a humanized endogenous MYOC locus and a genomically integrated expression cassette comprising: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains) one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

In some such methods, the non-human animal is a mouse, and the one or more guide RNAs target one or more guide RNA target sequences selected from SEQ ID NOS: 90-95. In some such methods, the non-human animal is a mouse, and the one or more guide RNAs target one or more guide RNA target sequences selected from SEQ ID NOS: 93-94. In some such methods, the non-human animal is a mouse, and the one or more guide RNAs target the guide RNA target sequence set forth in SEQ ID NO: 93.

In some such methods, the guide RNAs or the one or more expression cassettes that encode the one or more guide RNAs are administered via adenovirus-mediated delivery, lentivirus-mediated delivery, or adeno-associated virus (AAV)-mediated delivery. In some such methods, the guide RNAs or the one or more expression cassettes that encode the one or more guide RNAs are administered via recombinant AAV2.Y3F-mediated delivery. In some such methods, the guide RNAs or the one or more expression cassettes that encode the one or more guide RNAs are administered via lentivirus-mediated delivery. In some such methods, the guide RNAs or the one or more expression cassettes that encode the one or more guide RNAs are administered to the non-human animal via intravitreal injection or intracameral injection.

In some such methods, the method results in increased MYOC mRNA or protein expression in the eye, the limbal ring, the retina, the ciliary body, or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the eye, the limbal ring, the retina, the ciliary body, or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring or the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring or the trabecular meshwork relative to a control non-human animal that does not comprise the one or more guide RNAs or one or more expression cassettes that encode the one or more guide RNAs. In some such methods, the method results in increased MYOC mRNA or protein expression in the limbal ring. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the limbal ring relative to a control non-human animal that does not comprise the one or more guide RNAs or one or more expression cassettes that encode the one or more guide RNAs. In some such methods, the method results in increased MYOC mRNA or protein expression in the trabecular meshwork. Optionally, the method results in at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the trabecular meshwork relative to a control non-human animal that does not comprise the one or more guide RNAs or one or more expression cassettes that encode the one or more guide RNAs.

In some such methods, the method results in increased intraocular pressure. Optionally, the method results in the non-human animal having an intraocular pressure that is at least 1, at least 2, at least 3, at least 4, at least 5, or at least 6 mmHg higher than the intraocular pressure of the control non-human animal. Optionally, the method results in an intraocular pressure of at least 15, at least 16, at least 17, at least 18, at least 19, at least 20, at least 21, or at least 22 mmHg.

BRIEF DESCRIPTION OF THE FIGURES

FIG. 3 shows an alignment of the human and mouse myocilin proteins.

FIG. 7 shows Ad5, AAV2.Y3F, and lentivirus expression in the trabecular meshwork (TM), ciliary body (CB), and corneal endothelium (CE). The rectangular boxes show the TM.

FIG. 10A), in the retina (FIG. 10B), and in the cornea (FIG. 10C) following administration of mouse Myoc SAM guide RNAs relative to a control guide RNA.

FIG. 14 shows human MYOC expression as measured by RNASCOPE® following administration of mouse Myoc SAM guide RNAs g4 and g5 or a SAM LacZ control gRNA in SAM mice comprising a humanized MYOC locus comprising a Y437H mutation that are either heterozygous or homozygous for the humanized MYOC locus.

FIG. 17A shows the experimental setup for testing the effect of human MYOC siRNAs #2 and #3 on intraocular pressure (IOP) in SAM mice comprising a humanized MYOC locus comprising a Y437H mutation (SAM-MYOC mice, homozygous for each allele) treated with LV-SAM-g4.

DEFINITIONS

Figure 1:
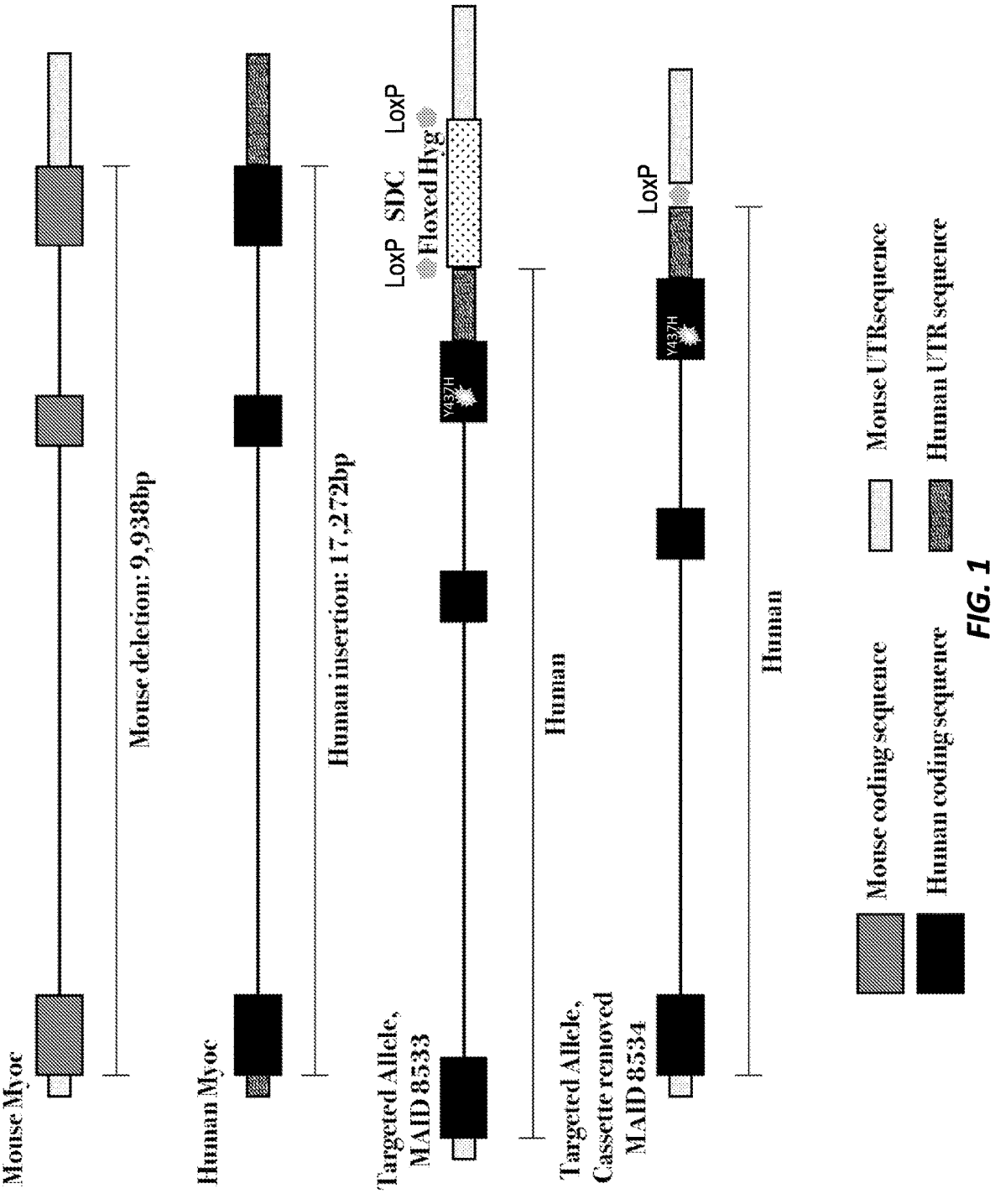
FIG. 1 shows schematics (not drawn to scale) of the wild type mouse Myoc locus, the wild type human MYOC locus, the targeted allele of the humanized mouse MYOC locus comprising a Y437H mutation and with the self-deleting neomycin (SDC-Neo) selection cassette (MAID 8533), and the targeted allele of the humanized mouse MYOC locus comprising a Y437H mutation and with the loxP scar from removal of the SDC-Neo selection cassette (MAID 8534).

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" (amino-terminus) and a "C-terminus" (carboxy-terminus or carboxyl-terminus). The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" or "expression cassette" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues (e.g., liver samples), lipid droplets, proteins, and nucleic acids includes cells, tissues (e.g., liver samples), lipid droplets, proteins, and nucleic acids that are relatively purified with respect to other bacterial, viral, cellular, or other components that may normally be present in situ, up to and including a substantially pure preparation of the cells, tissues (e.g., liver samples), lipid droplets, proteins, and nucleic acids. The term "isolated" also includes cells, tissues (e.g., liver samples), lipid droplets, proteins, and nucleic acids that have no naturally occurring counterpart, have been chemically synthesized and are thus substantially uncontaminated by other cells, tissues (e.g., liver samples), lipid droplets, proteins, and nucleic acids, or has been separated or purified from most other components (e.g., cellular components or organism components) with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a rat cell or rat. For example, an endogenous Myoc sequence of a mouse refers to a native Myoc sequence that naturally occurs at the Myoc locus in the mouse.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a myocilin protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Res.* 28(1):292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "MYOC locus" may refer to the specific location of a MYOC gene, MYOC DNA sequence, myocilin-encoding sequence, or MYOC position on a chromosome of the genome of an organism that has been identified as to where such a sequence resides. A "MYOC locus" may comprise a regulatory element of a MYOC gene, including, for example, an enhancer, a promoter, 5' and/or 3' untranslated region (UTR), or a combination thereof.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

The "coding region" or "coding sequence" of a gene consists of the portion of a gene's DNA or RNA, composed of exons, that codes for a protein. The region begins at the start codon on the 5' end and ends at the stop codon on the 3' end.

A "promoter" is a regulatory region of DNA usually comprising a TATA box capable of directing RNA polymerase II to initiate RNA synthesis at the appropriate transcription initiation site for a particular polynucleotide sequence. In some cases, a promoter may additionally comprise other regions which influence the transcription initiation rate. The promoter sequences disclosed herein modulate transcription of an operably linked polynucleotide. A promoter can be active in one or more of the cell types disclosed herein (e.g., a mouse cell, a rat cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The methods and compositions provided herein employ a variety of different components. Some components throughout the description can have active variants and fragments. The term "functional" refers to the innate ability of a protein or nucleic acid (or a fragment or variant thereof) to exhibit a biological activity or function. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A protein fragment can be, for example, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A nucleic acid fragment can be, for example, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

Amino Acid Categorizations.

| Alanine | Ala | A | Nonpolar | Neutral | 1.8 |
|---|---|---|---|---|---|
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., an organism or body or a cell or tissue within an organism or body) and to processes or reactions that occur within a natural environment. The term "ex vivo" includes cells that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalama1, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Semin. Cell Dev. Biol.* 22(8):886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLoS One* 7:e45768:1-9; and Wang et al. (2013) *Nat. Biotechnol.* 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values 5% of a stated value.

The term "and/or" refers to and encompasses any and all possible combinations of one or more of the associated listed items, as well as the lack of combinations when interpreted in the alternative ("of").

The term "or" refers to any one member of a particular list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Disclosed herein are non-human animal genomes, non-human animal cells, and non-human animals comprising a humanized MYOC locus and methods of making and using such non-human animal cells and non-human animals. In some such non-human animal genomes, non-human animal cells, and non-human animals, the humanized MYOC locus comprises a mutation associated with glaucoma, such as a Y437H mutation. Some such non-human animal genomes, non-human animal cells, and non-human animals further comprise CRISPR/Cas synergistic activation mediator system components. For example, disclosed herein are non-human animal genomes, non-human animal cells, and non-human animals comprising in their genome a Clustered Regularly Interspersed Short Palindromic Repeats (CRISPR)/CRISPR-associated (Cas)-based synergistic activation mediator (SAM) expression cassette and a humanized MYOC locus (e.g., comprising a Y437H mutation) and methods of using such non-human animal cells and non-human animals. AMYOC locus comprising a Y437H mutation refers to a MYOC locus that encodes a myocilin protein comprising a Y437H mutation or comprising a mutation corresponding to the Y437H mutation in human myocilin when the encoded myocilin protein is optimally aligned (greatest number of perfectly matched residues) with human myocilin. The nomenclature of the amino acid position for the Y437H mutation refers to the position of the mutation in the full myocilin protein including the signal peptide. This nomenclature is consistent with nomenclature used in publications describing this mutation.

Also disclosed herein are humanized non-human animal MYOC genes, nucleic acids comprising humanized non-human animal MYOC genes, and targeting vectors for use in humanizing a non-human animal MYOC gene.

Non-human animal cells or non-human animals comprising a humanized MYOC locus express a human myocilin protein or a chimeric myocilin protein comprising one or more fragments of a human myocilin protein. Such non-human animal cells and non-human animals can be used to assess delivery or efficacy of human-myocilin-targeting agents (e.g., CRISPR/Cas9 genome editing agents, RNAi agents, or ASO agents) in vitro or ex vivo or in vivo and can be used in methods of optimizing the delivery of efficacy of such agents in vitro or ex vivo or in vivo. When the SAM expression cassettes are present, they can be used to upregulate transcription of target genes such as the humanized MYOC genes as disclosed herein in vitro, ex vivo or in vivo in order to achieve, for example, higher myocilin expression levels. Such models can be used, for example, to assess delivery or efficacy of candidate therapeutic reagents for glaucoma or to assess delivery or efficacy of candidate glaucoma therapeutic agents or reagents for reducing intraocular pressure (IOP).

In some of the non-human animal cells and non-human animals disclosed herein, some or most or all of the human MYOC genomic DNA is inserted into the corresponding non-human animal MYOC locus. In some of the non-human animal cells and non-human animals disclosed herein, some or most or all of the non-human animal genomic DNA is replaced one-for-one with corresponding human genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. Replacing the non-human animal genomic sequence with the corresponding human genomic sequence is more likely to result in faithful expression of the transgene from the endogenous MYOC locus. Similarly, transgenic non-human animals with transgenic insertion of human-MYOC-coding sequences at a random genomic locus rather than the endogenous non-human-animal MYOC locus will not as accurately reflect the endogenous regulation of MYOC expression. A humanized MYOC allele resulting from replacing most or all of the non-human animal genomic DNA one-for-one with corresponding human genomic DNA or inserting human MYOC genomic sequence in the corresponding non-human MYOC locus will provide the true human target or a close approximation of the true human target of human-MYOC-targeting reagents (e.g., CRISPR/Cas9 reagents, RNAi reagents, or ASO reagents designed to target human MYOC), thereby enabling testing of the efficacy and mode of action of such agents in live animals as well as pharmacokinetic and pharmacodynamics studies in a setting where the humanized protein and humanized gene are the only version of MYOC present.

The methods and compositions disclosed herein can optionally employ non-human animal genomes, non-human animal cells, and non-human animals comprising chimeric Cas protein expression cassettes, chimeric adaptor protein expression cassettes, or synergistic activation mediator (SAM) expression cassettes (e.g., a chimeric Cas protein coding sequence and a chimeric adaptor protein sequence) so that the components can be constitutively available or, for example, available in a tissue-specific or temporal-specific manner. The cassettes can be genomically integrated. Such genomes, non-human animal cells, and non-human animals can also comprise guide RNA expression cassettes (e.g., MYOC guide RNA expression cassettes or MYOC guide RNA array expression cassettes) and/or recombinase expression cassettes as disclosed elsewhere herein. Alternatively, one or more components (e.g., guide RNAs and/or recombinases) can be introduced into the cells and non-human animals by other means to induce transcriptional activation of a target gene (e.g., the humanized MYOC gene).

Non-human animals comprising the SAM expression cassettes simplify the process for upregulating expression of a target gene (e.g., the humanized MYOC gene) in vivo because only the guide RNAs need to be introduced into the non-human animal to activate transcription of a target gene. If the non-human animal also comprises a guide RNA expression cassette, the effects of target gene activation or upregulation can be studied without introducing any further components. In addition, the SAM expression cassettes or guide RNA expression cassettes can optionally be conditional expression cassettes that can be selectively expressed in particular tissues or developmental stages, which can, for example, reduce the risk of Cas-mediated toxicity in vivo. Alternatively, such expression cassettes can be constitutively expressed to enable testing of activity in any and all types of cells, tissues, and organs.

Non-human animal genomes, non-human animal cells, and non-human animals comprising a humanized MYOC locus (e.g., comprising a Y437H mutation as described elsewhere herein) and one or more nucleic acids encoding a chimeric Cas protein, a chimeric adaptor protein, a guide RNA, a recombinase, or any combination thereof (any combination of such SAM system nucleic acids) are provided. The non-human animal genomes, non-human animal cells, or non-human animals can be male or female.

The non-human animal genomes, non-human animal cells, or non-human animals can be heterozygous or homozygous for the humanized MYOC locus (e.g., comprising the Y437H mutation). A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized MYOC locus (e.g., comprising a Y437H mutation described herein) can comprise the humanized MYOC locus in its germline.

The SAM nucleic acids or expression cassettes can be stably integrated into the genome (i.e., into a chromosome) of the non-human animal cell or non-human animal or can be located outside of a chromosome (e.g., extrachromosomally replicating DNA). The SAM nucleic acids or expression cassettes can be randomly integrated into the genome of the non-human animal (i.e., transgenic, or can be integrated into a predetermined region (e.g., a safe harbor locus) of the genome of the non-human animal (i.e., knock in). The target genomic locus at which a SAM nucleic acid or expression cassette is stably integrated can be heterozygous for the nucleic acid or expression cassette or homozygous for the nucleic acid or expression cassette. A non-human animal comprising a stably integrated SAM nucleic acid or expression cassette described herein can comprise the nucleic acid or expression cassette in its germline.

For example, a non-human animal genome, non-human animal cell, or non-human animal can comprise a chimeric Cas protein expression cassette, a chimeric adaptor protein expression cassette, or a synergistic activation mediator (SAM) expression cassette (comprising both a chimeric Cas protein coding sequence and a chimeric adaptor protein sequence) as disclosed herein. In one example, the non-human animal genome, non-human animal cell, or non-human animal comprises a SAM expression cassette comprising both a chimeric Cas protein coding sequence and a chimeric adaptor protein coding sequence. In one example, the SAM expression cassette (or chimeric Cas protein expression cassette or chimeric adaptor protein expression cassette) is stably integrated into the genome. The stably integrated SAM expression cassette (or chimeric Cas protein expression cassette or chimeric adaptor protein expression cassette) can be randomly integrated into the genome of the non-human animal (i.e., transgenic), or it can be integrated into a predetermined region of the genome of the non-human animal (i.e., knock in). In one example, the SAM expression cassette (or chimeric Cas protein expression cassette or chimeric adaptor protein expression cassette) is stably integrated into a predetermined region of the genome, such as a safe harbor locus (e.g., Rosa26). The target genomic locus at which the SAM expression cassette (or chimeric Cas protein expression cassette or chimeric adaptor protein expression cassette) is stably integrated can be heterozygous or homozygous for the SAM expression cassette (or chimeric Cas protein expression cassette or chimeric adaptor protein expression cassette).

Optionally, the non-human animal genome, non-human animal cell, or non-human animal described above can further comprise one or more guide RNA expression cassettes or a guide RNA expression cassette (e.g., guide RNA array expression cassette). The guide RNA expression cassette can be stably integrated into the genome (i.e., into a chromosome) of the non-human animal cell or non-human animal or it can be located outside of a chromosome (e.g., extrachromosomally replicating DNA or introduced into the non-human animal cell or non-human animal via AAV, LNP, or any other means disclosed herein). The guide RNA expression cassette can be randomly integrated into the genome of the non-human animal (i.e., transgenic), or it can be integrated into a predetermined region (e.g., a safe harbor locus) of the genome of the non-human animal (i.e., knock in). The target genomic locus at which the guide RNA expression cassette is stably integrated can be heterozygous or homozygous for the guide RNA expression cassette. In one example, a genome, cell, or non-human animal comprises both a SAM expression cassette (or chimeric Cas protein expression cassette or chimeric adaptor protein expression cassette) and a guide RNA expression cassette. In one example, both cassettes are genomically integrated. The guide RNA expression cassette can be integrated at a different target genomic locus from the SAM expression cassette (or chimeric Cas protein expression cassette or chimeric adaptor protein expression cassette), or it can be genomically integrated at the same target locus (e.g., a Rosa26 locus, such as integrated in the first intron of the Rosa26 locus). For example, the non-human animal genome, non-human animal cell, or non-human animal can be heterozygous for each of a SAM expression cassette (or chimeric Cas protein expression cassette or chimeric adaptor protein expression cassette) and the guide RNA expression cassette, with one allele of the target genomic locus (e.g., Rosa26) comprising the SAM expression cassette (or chimeric Cas protein expression cassette or chimeric adaptor protein expression cassette), and a second allele of the target genomic locus (e.g., Rosa26) comprising the guide RNA expression cassette expression cassette.

Optionally, any of the non-human animal genomes, non-human animal cells, or non-human animals described above can further comprise a recombinase expression cassette. The recombinase expression cassette can be stably integrated into the genome (i.e., into a chromosome) of the non-human animal cell or non-human animal or it can be located outside of a chromosome (e.g., extrachromosomally replicating DNA or introduced into the non-human animal cell or non-human animal via AAV, LNP, HDD, or any other means disclosed herein). The recombinase expression cassette can be randomly integrated into the genome of the non-human animal (i.e., transgenic), or it can be integrated into a predetermined region (e.g., a safe harbor locus) of the genome of the non-human animal (i.e., knock in). The target genomic locus at which the recombinase expression cassette is stably integrated can be heterozygous or homozygous for the recombinase expression cassette. The recombinase expression cassette can be integrated at a different target genomic locus from any of the other expression cassettes disclosed herein, or it can be genomically integrated at the same target locus (e.g., a Rosa26 locus, such as integrated in the first intron of the Rosa26 locus).

Some non-human animals or non-human animal cells described herein (e.g., non-human animals or non-human animal cells comprising a humanized MYOC locus, a SAM expression cassette, and one or more SAM guide RNAs targeting the humanized MYOC locus (or one or more SAM guide RNA expression cassettes) have increased human MYOC mRNA or protein expression relative to a control non-human animal or non-human animal cell (e.g., a non-human animal or non-human animal cell with a humanized MYOC locus as described herein but that has not administered the one or more SAM guide RNAs). In some non-human animals or non-human animal cells, the increased expression is at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, or at least about 15-fold (e.g., at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold). In some non-human animals or non-human animal cells, the increased expression is between at least about 2-fold and at least about 25-fold, between at least about 3-fold and at least about 25-fold, between at least about 4-fold and at least about 25-fold, between at least about 5-fold and at least about 25-fold, between at least about 6-fold and at least about 25-fold, between at least about 7-fold and at least about 25-fold, between at least about 8-fold and at least about 25-fold, between at least about 9-fold and at least about 25-fold, between at least about 10-fold and at least about 25-fold, between at least about 2-fold and at least about 20-fold, between at least about 2-fold and at least about 15-fold, or between at least about 10-fold and at least about 15-fold. The increased human MYOC mRNA or protein expression relative to a control non-human animal can be in the eye, in the limbal ring, in the retina, in the ciliary body, in the trabecular meshwork, or in the cornea. In a specific example, the increased expression is in the limbal ring (trabecular meshwork (TM), iris, and ciliary body (CB)).

Some non-human animals or non-human animal cells described herein (e.g., non-human animals or non-human animal cells comprising a humanized MYOC locus, a SAM expression cassette, and one or more SAM guide RNAs targeting the humanized MYOC locus (or one or more SAM guide RNA expression cassettes) have one or more signs or symptoms of glaucoma. Glaucoma is a chronic optic neuropathy characterized by progressive loss of retinal ganglion cell (RGC) axons, with the resultant irreversible loss of vision. A major risk factor for glaucoma is elevated intraocular pressure (IOP). Elevated IOP is caused by increased resistance to aqueous humor outflow through the structures of trabecular meshwork (TM). Aqueous humor is made by ciliary body, circulates the anterior chamber, and drains through the network of TM. In most glaucoma cases, there is increased resistance to aqueous humor at the TM. Pathogenic MYOC mutant proteins aggregate intracellularly, leading to trabecular meshwork (TM) stress, elevated IOP, and glaucoma. In human glaucomatous TM cells, elevated levels of ER-stress-induced proteins have been detected.

In some non-human animals, the IOP is at least about 15, at least about 16, at least about 17, at least about 18, at least about 19, or at least about 20, at least about 21, or at least about 22 mmHg (e.g., at least 15, at least 16, at least 17, at least 18, at least 19, at least 20, at least 21, or at least 22 mmHg). In one example, the IOP is between about 15 and about 22, between about 16 and about 22, between about 17 and about 22, between about 18 and about 22, between about 19 and about 22, between about 15 and about 21, between about 15 and about 20, or between about 16 and about 21 mmHg (e.g., between 15 and 22, between 16 and 22, between 17 and 22, between 18 and 22, between 19 and 22, between 15 and 21, between 15 and 20, or between 16 and 21 mmHg).

In some non-human animals, the IOP is increased relative to a control non-human animal (e.g., a non-human animal with a humanized MYOC locus as described herein but that has not administered the one or more SAM guide RNAs, or a wild type non-human animal). In one example, the IOP is at least about 1, at least about 2, at least about 3, at least about 4, at least about 5, or at least about 6 mmHg above a control baseline in a control non-human animal (e.g., at least 1, at least 2, at least 3, at least 4, at least 5, or at least 6 mmHg). In one example, the IOP is between about 1 and about 7, between about 2 and about 7, between about 3 and about 7, between about 4 and about 7, between about 5 and about 7, between about 1 and about 6, between about 2 and about 6, between about 3 and about 6, between about 4 and about 6, or between about 5 and about 6 mmHg above a control baseline in a control non-human animal (e.g., between 1 and 6, between 2 and 6, between 3 and 6, between 4 and 6, or between 5 and 6 mmHg). The control baseline can be, for example, the IOP in a non-human animal with a humanized MYOC locus as described herein but that has not administered the one or more SAM guide RNAs, or it can be the IOP in wild type non-human animal, or it can be the IOP in a non-human animal with a humanized MYOC locus as described herein but prior to administration of one or more SAM guide RNAs targeting the humanized MYOC locus.

In some non-human animals, endoplasmic reticulum (ER) stress is increased relative to a control non-human animal (e.g., a non-human animal with a humanized MYOC locus as described herein but that has not administered the one or more SAM guide RNAs, or a wild type non-human animal). Some non-human animals show signs and symptoms of glaucoma as measured by a pattern electroretinogram (PERG). Some non-human animals show retinal ganglion cell (RGC) loss relative to a control non-human animal (e.g., a non-human animal with a humanized MYOC locus as described herein but that has not administered the one or more SAM guide RNAs, or a wild type non-human animal). Some non-human animals show increased outflow resistance of the aqueous humor relative to a control non-human animal (e.g., a non-human animal with a humanized MYOC locus as described herein but that has not administered the one or more SAM guide RNAs, or a wild type non-human animal).

MYOC glaucoma models having transgenic overexpression of human myocilin Y437H show an IOP increase of only about 2-3 mmHg, and the MYOC is expressed everywhere. In addition, the IOP phenotype is lost over breeding. The model described herein has the advantage that the expression is mostly restricted to the target tissue of disease pathology: the trabecular meshwork. In addition, we observe a greater increase in IOP of about 5-6 mmHg.

II. Non-Human Animals Comprising a Humanized MYOC Locus

The nucleic acids, non-human animal genomes, non-human animal cells, and non-human animals disclosed herein comprise a humanized MYOC locus (e.g., comprising a Y437H mutation as described herein). Cells or non-human animals comprising a humanized MYOC locus express a human myocilin protein or a partially humanized, chimeric myocilin protein in which one or more fragments of the native myocilin protein have been replaced with corresponding fragments from human myocilin.

A. Myocilin (MYOC)

The nucleic acids, non-human animal genomes, non-human animal cells, and non-human animals described herein comprise a humanized MYOC locus. Myocilin (also known as trabecular meshwork-induced glucocorticoid response protein or MYOC) is encoded by the MYOC gene (also known as GLC1A or TIGR). Myocilin is a secreted glycoprotein (55-57 kDa). MYOC was first reported as a glucocorticoid-induced gene and protein in cultured human trabecular meshwork (TM) cells. Myocilin mRNA and/or protein are expressed in eye structures including the retina, ciliary body, and trabecular meshwork. It may serve a structural function within the cytoplasm, or it may associate with other molecules within the cell, perhaps as a molecular chaperone. Extracellularly, it may be involved in creating resistance to aqueous outflow by binding to other extracellular molecules or to the cell membrane of TM cells.

Many MYOC mutations cause myocilin to accumulate in the cells of the TM, inducing glaucoma. Mutations in myocilin are the most common genetic cause of primary open angle glaucoma, which is the most common form of glaucoma. However, the mechanisms underlying MYOC-associated glaucoma are not fully understood. A major risk factor for glaucoma is elevated intraocular pressure (IOP) which can be caused by increased resistance to aqueous humor outflow through the structures of the TM. Myocilin is expressed in many ocular tissues that are capable of secreting myocilin into the aqueous humor, including TM cells and the ciliary body. Many different myocilin mutations have been identified. The Y437H mutation is one mutation associated with elevated IOP and development of glaucoma.

Human MYOC maps to 1q24.3 on chromosome 1 (NCBI RefSeq Gene ID 4653; Assembly GRCh38.p13 (GCF_000001405.39); location NC_000001.11 (171635417 . . . 171652688, complement)). The gene has been reported to have 3 exons. The wild type human myocilin protein has been assigned UniProt accession number Q99972. The sequence for the canonical, wild type isoform myocilin (NCBI Accession No. NP_000252.1) is set forth in SEQ ID NO: 1. An mRNA (cDNA) encoding the canonical isoform is assigned NCBI Accession No. NM_000261.2 and is set forth in SEQ ID NO: 2. An exemplary coding sequence (CDS) is set forth in SEQ ID NO: 3 (CCDS ID CCDS1297.1). The full-length human myocilin protein set forth in SEQ ID NO: 1 has 504 amino acids, including a signal peptide (amino acids 1-32) and the mature myocilin (amino acids 33-504), which produces an N-terminal fragment (33-226) and a C-terminal fragment (227-504) following cleavage by CAPN2 following amino acid 226 in the endoplasmic reticulum. Delineations between these domains are as designated in UniProt. Reference to human myocilin includes the canonical (wild type) forms as well as all allelic forms and isoforms. Any other forms of human myocilin have amino acids numbered for maximal alignment with the wild type form, aligned amino acids being designated the same number. An exemplary human myocilin protein comprising a Y437H mutation is set forth in SEQ ID NO: 4. An exemplary coding sequence for a human myocilin protein comprising a Y437H mutation is set forth in SEQ ID NO: 5.

Mouse Myoc maps to 1 H2.1; 1 70.29 cM on chromosome 1 (NCBI RefSeq Gene ID 17926; Assembly GRCm39 (GCF_000001635.27); location NC_000067.7 (162466719 .

.. 162477263)). The gene has been reported to have 3 exons. The wild type mouse myocilin protein has been assigned UniProt accession number 070624. The sequence for the canonical isoform, NCBI Accession No. NP_034995.3, is set forth in SEQ ID NO: 6. An exemplary mRNA (cDNA) isoform encoding the canonical isoform is assigned NCBI Accession No. NM_010865.3 and is set forth in SEQ ID NO: 7. An exemplary coding sequence (CDS) (CCDS ID CCDS15422.1) is set forth in SEQ ID NO: 8. The canonical full-length mouse myocilin protein set forth in SEQ ID NO: 6 has 490 amino acids, including a signal peptide (amino acids 1-18) and the mature myocilin (amino acids 19-490), which produces an N-terminal fragment (19-212) and a C-terminal fragment (213-490) following cleavage by CAPN2 following amino acid 212 in the endoplasmic reticulum. Delineations between these domains are as designated in UniProt. Reference to mouse myocilin includes the canonical (wild type) forms as well as all allelic forms and isoforms. Any other forms of mouse myocilin have amino acids numbered for maximal alignment with the wild type form, aligned amino acids being designated the same number.

Rat Myoc maps to 13q22 on chromosome 13 (NCBI RefSeq Gene ID 81523; Assembly mRatBN7.2 (GCF_015227675.2); location NC_051348.1 (74976730 . . . 74987128)). The gene has been reported to have 3 exons. The wild type rat myocilin protein has been assigned Uni-Prot accession number Q9R1J4. The sequence for the canonical isoform, NCBI Accession No. NP_110492.1, is set forth in SEQ ID NO: 9. An mRNA (cDNA) encoding the canonical isoform is assigned NCBI Accession No. NM_030865.1 and is set forth in SEQ ID NO: 10. An exemplary coding sequence (CDS) encoding the canonical isoform is set forth in SEQ ID NO: 11. The sequence for another isoform, NCBI Accession No. NP_110492.2, is set forth in SEQ ID NO: 12. An mRNA (cDNA) encoding this isoform is assigned NCBI Accession No. NM_030865.2 and is set forth in SEQ ID NO: 13. An exemplary coding sequence (CDS) encoding this isoform is set forth in SEQ ID NO: 14. The canonical full-length rat myocilin protein set forth in SEQ ID NO: 9 has 502 amino acids, including a signal peptide (amino acids 1-31) and the mature myocilin (amino acids 32-502), which produces an N-terminal fragment (32-225) and a C-terminal fragment (226-502) following cleavage by CAPN2 following amino acid 225 in the endoplasmic reticulum. Delineations between these domains are as designated in UniProt. Reference to rat myocilin includes the canonical (wild type) forms as well as all allelic forms and isoforms. Any other forms of rat myocilin have amino acids numbered for maximal alignment with the wild type form, aligned amino acids being designated the same number.

B. Humanized MYOC Loci

Disclosed herein are humanized endogenous MYOC loci in which a segment of an endogenous MYOC locus has been deleted and replaced with a corresponding human MYOC sequence (e.g., a corresponding human MYOC genomic sequence), wherein a humanized myocilin protein is expressed from the humanized endogenous MYOC locus. The corresponding human MYOC sequence can comprise a mutation, such as a mutation associated with glaucoma (e.g., a mutation causing glaucoma). One example of such a mutation is a Y437H mutation. Almost 100 different pathogenic MYOC mutations have been identified, most of which are clustered in exon 3 encoding the olfactomedin domain. Examples of such mutations include Y437H, G364V, and Q368X. See, e.g., Lynch et al. (2018) *J. Biol. Chem.*

293(52):20137-20156 and Jain et al. (2017) *Proc. Natl. Acad. Sci. U.S.A.* 114(42):11199-11204, each of which is herein incorporated by reference in its entirety for all purposes.

A humanized MYOC locus can be a MYOC locus in which the entire MYOC gene is replaced with the corresponding human MYOC sequence (e.g., corresponding orthologous human MYOC sequence) or a codon-optimized version of the corresponding human MYOC sequence, or it can be a MYOC locus in which only a portion of the MYOC gene is replaced with the corresponding human MYOC sequence (i.e., humanized) or a codon-optimized version of the corresponding human MYOC sequence, it can be a MYOC locus in which a portion of a corresponding human MYOC locus or a codon-optimized version of the portion of the corresponding human MYOC locus is inserted, or it can be a MYOC locus in which a portion of the MYOC gene is deleted and a portion of the corresponding human MYOC locus or a codon-optimized version of the portion of the corresponding human MYOC locus is inserted. The portion of the corresponding human MYOC locus that is inserted can, for example, comprise more of the human MYOC locus than is deleted from the endogenous MYOC locus. A human MYOC sequence corresponding to a particular segment of endogenous MYOC sequence refers to the region of human MYOC that aligns with the particular segment of endogenous MYOC sequence when human MYOC and the endogenous MYOC are optimally aligned (greatest number of perfectly matched residues). The corresponding human sequence can comprise, for example, complementary DNA (cDNA) or genomic DNA. Optionally, a codon-optimized version of the corresponding human MYOC sequence can be used and is modified to be codon-optimized based on codon usage in the non-human animal. Replaced or inserted (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, or all 3 exons of the human MYOC gene can be humanized. For example, exons corresponding to exons 1-3 of the human MYOC gene can be humanized. Alternatively, a region of MYOC encoding an epitope recognized by an anti-human-myocilin antigen-binding protein or a region targeted by human-myocilin-targeting reagent (e.g., a small molecule) can be humanized. Likewise, introns corresponding to 1 or all 2 introns of the human MYOC gene can be humanized or can remain endogenous. For example, introns corresponding to the introns between exons 1 and 3 (i.e., introns 1 and 2) of the human MYOC gene can be humanized.

Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. One or both of the human 5' and 3' UTRs can be inserted, and/or one or both of the endogenous 5' and 3' UTRs can be deleted. In a specific example, the human 3' UTR is inserted and the 5' UTR remains endogenous. Depending on the extent of replacement by corresponding human sequences, regulatory sequences, such as a promoter, can be endogenous or supplied by the replacing corresponding human sequence. For example, the humanized MYOC locus can include the endogenous non-human animal MYOC promoter (i.e., the inserted human MYOC sequence of the humanized MYOC coding sequence can be operably linked to the endogenous non-human animal MYOC promoter).

One or more or all of the regions encoding the signal peptide, the mature myocilin, the N-terminal fragment, or the C-terminal fragment can be humanized, or one or more of such regions can remain endogenous. Exemplary coding sequences for a mouse myocilin signal peptide, mature myocilin, N-terminal fragment, and C-terminal fragment are set forth in SEQ ID NOS: 31-34, respectively. Exemplary coding sequences for a rat myocilin signal peptide, mature myocilin, N-terminal fragment, and C-terminal fragment are set forth in SEQ ID NOS: 39-42, respectively. Exemplary coding sequences for a human myocilin signal peptide, mature myocilin, N-terminal fragment, and C-terminal fragment are set forth in SEQ ID NOS: 21-24, respectively. An exemplary coding sequence for a human mature myocilin comprising a Y437H mutation is set forth in SEQ ID NO: 25. An exemplary coding sequence for a human myocilin C-terminal fragment comprising a Y437H mutation is set forth in SEQ ID NO: 26.

For example, all or part of the region of the MYOC locus encoding the signal peptide can be humanized, and/or all or part of the region of the MYOC locus encoding the C-terminal fragment can be humanized, and/or all or part of the region of the MYOC locus encoding the N-terminal fragment domain can be humanized, and/or all or part of the region of the MYOC locus encoding the mature myocilin protein can be humanized. In one example, all of the region of the MYOC locus encoding the myocilin protein (including signal peptide and mature myocilin) is humanized. Optionally, the CDS of the human myocilin protein comprises a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). Optionally, the CDS of the human myocilin protein consists essentially of a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). Optionally, the CDS of the human myocilin protein consists of a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). The myocilin protein is expressed and can retain the activity of the native myocilin and/or human myocilin.

One or more of the regions encoding the signal peptide, the mature myocilin protein, the N-terminal fragment, or the C-terminal fragment can remain endogenous. For example, the region encoding the signal peptide can remain endogenous.

The myocilin protein encoded by the humanized MYOC locus can comprise one or more domains that are from a human myocilin protein and/or one or more domains that are from an endogenous (i.e., native) myocilin protein. Exemplary amino acid sequences for a mouse myocilin signal peptide, mature myocilin protein, N-terminal fragment, and C-terminal fragment are set forth in SEQ ID NOS: 27-30, respectively. Exemplary amino acid sequences for a rat myocilin signal peptide, mature myocilin protein, N-terminal fragment, and C-terminal fragment are set forth in SEQ ID NOS: 35-38, respectively. Exemplary amino acid sequences for a human myocilin signal peptide, mature myocilin protein, N-terminal fragment, and C-terminal fragment are set forth in SEQ ID NOS: 15-18, respectively. An exemplary amino acid sequence for a human mature myocilin protein comprising a Y437H mutation is set forth in SEQ ID NO: 19. An exemplary amino acid sequence for a human myocilin C-terminal fragment comprising a Y437H mutation is set forth in SEQ ID NO: 20.

The myocilin protein can comprise one or more or all of a human myocilin signal peptide, a human myocilin C-terminal fragment, a human myocilin N-terminal fragment, and a human mature myocilin protein. As one example, the myocilin protein encoded by a humanized MYOC locus can be a fully human myocilin protein (i.e., signal peptide and mature myocilin protein).

The myocilin protein encoded by the humanized MYOC locus can also comprise one or more domains that are from the endogenous (i.e., native) non-human animal myocilin protein.

Domains in a chimeric myocilin protein or a fully human myocilin protein that are from a human myocilin protein can be encoded by a fully humanized sequence (i.e., the entire sequence encoding that domain is replaced with the corresponding human MYOC sequence) or can be encoded by a partially humanized sequence (i.e., some of the sequence encoding that domain is replaced with the corresponding human MYOC sequence, and the remaining endogenous (i.e., native) sequence encoding that domain encodes the same amino acids as the corresponding human MYOC sequence such that the encoded domain is identical to that domain in the human myocilin protein). Likewise, domains in a chimeric protein that are from the endogenous myocilin protein cay be encoded by a fully endogenous sequence (i.e., the entire sequence encoding that domain is the endogenous MYOC sequence) or can be encoded by a partially humanized sequence (i.e., some of the sequence encoding that domain is replaced with the corresponding human MYOC sequence, but the corresponding human MYOC sequence encodes the same amino acids as the replaced endogenous MYOC sequence such that the encoded domain is identical to that domain in the endogenous myocilin protein).

As one example, the myocilin protein encoded by the humanized MYOC locus can comprise a fully human myocilin protein (i.e., signal peptide and mature myocilin protein). The myocilin protein is expressed and retains the activity of the native myocilin and/or human myocilin.

For example, the myocilin protein encoded by the humanized MYOC locus can comprise a sequence that is at least about 85%, at least about 90%, at least about 95%, at least about 96%, at least about 97%, at least about 98%, at least about 99%, or about 100% identical to SEQ ID NO: 4 (e.g., at least 85%, at least 90%, at least 95%, at least 96%, at least 97%, at least 98%, at least 99%, or 100% identical to SEQ ID NO: 4). As another example, the myocilin protein encoded by the humanized MYOC locus can consist essentially of a sequence that is at least about 85%, at least about 90%, at least about 95%, at least about 96%, at least about 97%, at least about 98%, at least about 99%, or about 100% identical to SEQ ID NO: 4 (e.g., at least 85%, at least 90%, at least 95%, at least 96%, at least 97%, at least 98%, at least 99%, or 100% identical to SEQ ID NO: 4). As another example, the myocilin protein encoded by the humanized MYOC locus can consist of a sequence that is at least about 85%, at least about 90%, at least about 95%, at least about 96%, at least about 97%, at least about 98%, at least about 99%, or about 100% identical to SEQ ID NO: 4 (e.g., at least 85%, at least 90%, at least 95%, at least 96%, at least 97%, at least 98%, at least 99%, or 100% identical to SEQ ID NO: 4). Optionally, the MYOC coding sequence (CDS) of the humanized MYOC locus can comprise a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). Optionally, the MYOC coding sequence (CDS) of the humanized MYOC locus can consist essentially of a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). Optionally, the MYOC coding sequence (CDS) of the humanized MYOC locus can consist of a sequence that is at least about 85%, at least about 90%, at least about 95%, at least about 96%, at least about 97%, at least about 98%, at least about 99%, or about 100% identical to SEQ ID NO: 5 (or degenerates thereof) (e.g., at least 85%, at least 90%, at least 95%, at least 96%, at least 97%, at least 98%, at least 99%, or 100% identical to SEQ ID NO: 5 (or degenerates thereof)). In each case, the myocilin protein is expressed and can retain the activity of the native myocilin and/or human myocilin.

Optionally, a humanized MYOC locus can comprise other elements. Examples of such elements can include selection cassettes, reporter genes, recombinase recognition sites, or other elements. Alternatively, the humanized MYOC locus can lack other elements (e.g., can lack a selection marker or selection cassette). Examples of suitable reporter genes and reporter proteins are disclosed elsewhere herein. Examples of suitable selection markers include neomycin phosphotransferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized MYOC locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized MYOC locus (e.g., a humanized mouse MYOC locus) is one in which a region from the start codon and stop codon is replaced with the corresponding human sequence from the start codon to the stop codon and including the human MYOC 3' UTR. See FIG. 1 and SEQ ID NOS: 88 and 89. Exemplary sequences for a humanized MYOC locus are set forth in SEQ ID NOS: 88 and 89.

In one specific example, the human MYOC sequence at the humanized endogenous MYOC locus can comprise a sequence at least about 85%, at least about 90%, at least about 95%, at least about 96%, at least about 97%, at least about 98%, at least about 99%, or about 100% identical to the sequence set forth in SEQ ID NO: 87 (e.g., at least 85%, at least 90%, at least 95%, at least 96%, at least 97%, at least 98%, at least 99%, or 100% identical to SEQ ID NO: 87). In another specific example, the humanized MYOC locus can encode a protein comprising a sequence at least about 85%, at least about 90%, at least about 95%, at least about 96%, at least about 97%, at least about 98%, at least about 99%, or about 100% identical to the sequence set forth in SEQ ID NO: 4 (e.g., at least 85%, at least 90%, at least 95%, at least 96%, at least 97%, at least 98%, at least 99%, or 100% identical to SEQ ID NO: 4). In another specific example, the humanized MYOC locus can comprise a coding sequence comprising a sequence at least about 85%, at least about 90%, at least about 95%, at least about 96%, at least about 97%, at least about 98%, at least about 99%, or about 100% identical to the sequence set forth in SEQ ID NO: 5 (e.g., at least 85%, at least 90%, at least 95%, at least 96%, at least 97%, at least 98%, at least 99%, or 100% identical to SEQ ID NO: 5). In another specific example, the humanized MYOC locus can comprise a sequence at least about 85%, at least about 90%, at least about 95%, at least about 96%, at least about 97%, at least about 98%, at least about 99%, or about 100% identical to the sequence set forth in SEQ ID NO: 88 or 89 (e.g., at least 85%, at least 90%, at least 95%, at least 96%, at least 97%, at least 98%, at least 99%, or 100% identical to SEQ ID NO: 88 or 89).

In one specific example, the human MYOC sequence at the humanized endogenous MYOC locus can consist essentially of a sequence at least about 85%, at least about 90%, at least about 95%, at least about 96%, at least about 97%, at least about 98%, at least about 99%, or about 100% identical to the sequence set forth in SEQ ID NO: 87 (e.g., at least 85%, at least 90%, at least 95%, at least 96%, at least 97%, at least 98%, at least 99%, or 100% identical to SEQ ID NO: 87). In another specific example, the humanized MYOC locus can encode a protein consisting essentially of a sequence at least about 85%, at least about 90%, at least about 95%, at least about 96%, at least about 97%, at least about 98%, at least about 99%, or about 100% identical to the sequence set forth in SEQ ID NO: 4 (e.g., at least 85%, at least 90%, at least 95%, at least 96%, at least 97%, at least 98%, at least 99%, or 100% identical to SEQ ID NO: 4). In another specific example, the humanized MYOC locus can comprise a coding sequence consisting essentially of a sequence at least about 85%, at least about 90%, at least about 95%, at least about 96%, at least about 97%, at least about 98%, at least about 99%, or about 100% identical to the sequence set forth in SEQ ID NO: 5 (e.g., at least 85%, at least 90%, at least 95%, at least 96%, at least 97%, at least 98%, at least 99%, or 100% identical to SEQ ID NO: 5). In another specific example, the humanized MYOC locus can consist essentially of a sequence at least about 85%, at least about 90%, at least about 95%, at least about 96%, at least about 97%, at least about 98%, at least about 99%, or about 100% identical to the sequence set forth in SEQ ID NO: 88 or 89 (e.g., at least 85%, at least 90%, at least 95%, at least 96%, at least 97%, at least 98%, at least 99%, or 100% identical to SEQ ID NO: 88 or 89).

In one specific example, the human MYOC sequence at the humanized endogenous MYOC locus can consist of a sequence at least about 85%, at least about 90%, at least about 95%, at least about 96%, at least about 97%, at least about 98%, at least about 99%, or about 100% identical to the sequence set forth in SEQ ID NO: 87 (e.g., at least 85%, at least 90%, at least 95%, at least 96%, at least 97%, at least 98%, at least 99%, or 100% identical to SEQ ID NO: 87). In another specific example, the humanized MYOC locus can encode a protein consisting of a sequence at least about 85%, at least about 90%, at least about 95%, at least about 96%, at least about 97%, at least about 98%, at least about 99%, or about 100% identical to the sequence set forth in SEQ ID NO: 4 (e.g., at least 85%, at least 90%, at least 95%, at least 96%, at least 97%, at least 98%, at least 99%, or 100% identical to SEQ ID NO: 4). In another specific example, the humanized MYOC locus can comprise a coding sequence consisting of a sequence at least about 85%, at least about 90%, at least about 95%, at least about 96%, at least about 97%, at least about 98%, at least about 99%, or about 100% identical to the sequence set forth in SEQ ID NO: 5 (e.g., at least 85%, at least 90%, at least 95%, at least 96%, at least 97%, at least 98%, at least 99%, or 100% identical to SEQ ID NO: 5). In another specific example, the humanized MYOC locus can consist of a sequence at least about 85%, at least about 90%, at least about 95%, at least about 96%, at least about 97%, at least about 98%, at least about 99%, or about 100% identical to the sequence set forth in SEQ ID NO: 88 or 89 (e.g., at least 85%, at least 90%, at least 95%, at least 96%, at least 97%, at least 98%, at least 99%, or 100% identical to SEQ ID NO: 88 or 89).

C. Non-Human Animal Genomes, Non-Human Animal Cells, and Non-Human Animals Comprising a Humanized MYOC Locus Non-human animal genomes, non-human animal cells, and non-human animals comprising a humanized MYOC locus as described elsewhere herein are provided. The genomes, cells, or non-human animals can express a humanized myocilin protein encoded by the humanized MYOC locus. The genomes, cells, or non-human animals can be male or female. The genomes, cells, or non-human animals can be heterozygous or homozygous for the humanized MYOC locus. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized MYOC locus can comprise the humanized MYOC locus in its germline.

The non-human animal genomes or cells provided herein can be, for example, any non-human animal genome or cell comprising a MYOC locus or a genomic locus homologous or orthologous to the human MYOC locus. The genomes can be from or the cells can be eukaryotic cells, which include, for example, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, or a mouse cell. Other non-human mammals include, for example, non-human primates. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell (e.g., a non-ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be eye cells, such as trabecular meshwork cells.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. For example, the primary cells can be eye cells, such as trabecular meshwork cells.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized MYOC locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates and rodents (e.g., mice and rats). The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mamm. Genome* 10(8):836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an RT1$^{av1}$ haplotype. Such strains are available from a variety of sources including Harlan Laboratories. The Dark Agouti (DA) rat strain is characterized as having an agouti coat and an RT1$^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

Some non-human animals or non-human animal cells described herein have one or more signs or symptoms of glaucoma. Glaucoma is a chronic optic neuropathy characterized by progressive loss of retinal ganglion cell (RGC) axons, with the resultant irreversible loss of vision. A major risk factor for glaucoma is elevated intraocular pressure (IOP). Elevated IOP is caused by increased resistance to aqueous humor outflow through the structures of trabecular meshwork (TM). Aqueous humor is made by ciliary body, circulates the anterior chamber, and drains through the network of TM. In most glaucoma cases, there is increased resistance to aqueous humor at the TM. Pathogenic MYOC mutant proteins aggregate intracellularly, leading to trabecular meshwork (TM) stress, elevated IOP, and glaucoma. In human glaucomatous TM cells, elevated levels of ER-stress-induced proteins have been detected.

In some non-human animals, the IOP is at least about 15, at least about 16, at least about 17, at least about 18, at least about 19, at least about 20, at least about 21, or at least about 22 mmHg (e.g., at least 15, at least 16, at least 17, at least 18, at least 19, at least 20, at least 21, or at least 22 mmHg). In one example, the IOP is between about 15 and about 22, between about 16 and about 22, between about 17 and about 22, between about 18 and about 22, between about 19 and about 22, between about 15 and about 21, between about 15 and about 20, or between about 16 and about 21 mmHg (e.g., between 15 and 22, between 16 and 22, between 17 and 22, between 18 and 22, between 19 and 22, between 15 and 21, between 15 and 20, or between 16 and 21 mmHg).

In some non-human animals, the IOP is increased relative to a control non-human animal (e.g., a non-human animal with a humanized MYOC locus as described herein but that has not administered the one or more SAM guide RNAs targeting the humanized MYOC locus, or a wild type non-human animal). In one example, the IOP is at least about 1, at least about 2, at least about 3, at least about 4, at least about 5, or at least about 6 mmHg above a control baseline in a control non-human animal (e.g., at least 1, at least 2, at least 3, at least 4, at least 5, or at least 6 mmHg). In one example, the IOP is between about 1 and about 7, between about 2 and about 7, between about 3 and about 7, between about 4 and about 7, between about 5 and about 7, between about 1 and about 6, between about 2 and about 6, between about 3 and about 6, between about 4 and about 6, or between about 5 and about 6 mmHg above a control baseline in a control non-human animal (e.g., between 1 and 6, between 2 and 6, between 3 and 6, between 4 and 6, or between 5 and 6 mmHg). The control baseline can be, for example, the IOP in a non-human animal with a humanized MYOC locus as described herein but that has not administered the one or more SAM guide RNAs, or it can be the IOP in wild type non-human animal, or it can be the IOP in a non-human animal with a humanized MYOC locus as described herein prior to administration of the one or more SAM guide RNAs.

In some non-human animals, endoplasmic reticulum (ER) stress is increased relative to a control non-human animal (e.g., a non-human animal with a humanized MYOC locus as described herein but that has not administered the one or more SAM guide RNAs, or a wild type non-human animal). Some non-human animals show signs and symptoms of glaucoma as measured by a pattern electroretinogram (PERG). Some non-human animals show retinal ganglion cell (RGC) loss relative to a control non-human animal (e.g., a non-human animal with a humanized MYOC locus as described herein but that has not administered the one or more SAM guide RNAs, or a wild type non-human animal).

Some non-human animals show increased outflow resistance of the aqueous humor relative to a control non-human animal (e.g., a non-human animal with a humanized MYOC locus as described herein but that has not administered the one or more SAM guide RNAs, or a wild type non-human animal).

III. Non-Human Animals Comprising Synergistic Activation Mediator (SAM) Expression Cassettes The non-human animal genomes, non-human animal cells, and non-human animals disclosed herein also comprise Clustered Regularly Interspersed Short Palindromic Repeats (CRISPR)/CRISPR-associated (Cas)-based synergistic activation mediator (SAM) expression cassettes for use in methods of activating transcription of target genes such as the humanized MYOC genes disclosed herein in vitro, ex vivo, or in vivo. The SAM systems described herein comprise chimeric Cas proteins and chimeric adaptor proteins and can be used with guide RNAs as described elsewhere herein to activate transcription of target genes such as the humanized MYOC genes disclosed herein. The guide RNAs can be encoded by genomically integrated expression cassettes, or they can be provided by AAV or any other suitable means. Chimeric Cas proteins (e.g., chimeric Cas proteins, such as chimeric Cas9 proteins, such as a chimeric *Streptococcus pyogenes* Cas9 protein, a chimeric *Campylobacter jejuni* Cas9 protein, or a chimeric *Staphylococcus aureus* Cas9 protein) and chimeric adaptor proteins (e.g., comprising an adaptor protein that specifically binds to an adaptor-binding element within a guide RNA; and one or more heterologous transcriptional activation domains) are described in further detail elsewhere herein.

CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

The methods and compositions disclosed herein employ the CRISPR/Cas systems by using or testing the ability of CRISPR complexes (comprising a guide RNA (gRNA) complexed with a chimeric Cas protein and a chimeric adaptor protein) to induce transcriptional activation of a target genomic locus in vivo.

The non-human animal genomes, non-human animal cells, and non-human animals disclosed herein comprise a chimeric Cas protein expression cassette and/or a chimeric adaptor protein expression cassette. For example, the non-human animal genomes, non-human animal cells, and non-human animals disclosed herein can comprise a synergistic activation mediator (SAM) expression cassette comprising a chimeric Cas protein coding sequence and a chimeric adaptor protein coding sequence.

Such non-human animal genomes, non-human animal cells, or non-human animals comprising a SAM expression cassette have the advantage of needing delivery only of guide RNAs in order to induce transcriptional activation of a target genomic locus. Some such non-human animal genomes, non-human animal cells, or non-human animals also comprise one or more guide RNA expression cassettes or a guide RNA expression cassette so that all components required for transcriptional activation of a target gene are already present. The SAM systems can be used in such cells to provide increased expression of target genes in any desired manner. For example, expression of one or more target genes can be increased in a constitutive manner or in a regulated manner (e.g., inducible, tissue-specific, temporally regulated, and so forth).

A. Chimeric Cas Proteins

Provided are chimeric Cas proteins that can bind to the guide RNAs disclosed elsewhere herein to activate transcription of target genes. Such chimeric Cas proteins can comprise: (a) a DNA-binding domain that is a Clustered Regularly Interspaced Short Palindromic Repeats (CRISPR)-associated (Cas) protein or a functional fragment or variant thereof that is capable of forming a complex with a guide RNA and binding to a target sequence; and (b) one or more transcriptional activation domains or functional fragments or variants thereof. For example, such fusion proteins can comprise 1, 2, 3, 4, 5, or more transcriptional activation domains (e.g., two or more heterologous transcriptional activation domains or three or more heterologous transcriptional activation domains). In one example, the chimeric Cas protein can comprise a catalytically inactive Cas protein (e.g., dCas9) and a VP64 transcriptional activation domain or a functional fragment or variant thereof. For example, such a chimeric Cas protein can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the dCas9-VP64 chimeric Cas protein sequence set forth in SEQ ID NO: 43. However, chimeric Cas proteins in which the transcriptional activation domains comprise other transcriptional activation domains or functional fragments or variants thereof and/or in which the Cas protein comprises other Cas proteins (e.g., catalytically inactive Cas proteins) are also provided. Examples of other suitable transcriptional activation domains are provided elsewhere herein.

The transcriptional activation domain(s) can be located at the N-terminus, the C-terminus, or anywhere within the Cas protein. For example, the transcriptional activation domain(s) can be attached to the Rec domain, the Rec2 domain, the HNH domain, or the PI domain of a *Streptococcus pyogenes* Cas9 protein or any corresponding region of an orthologous Cas9 protein or homologous or orthologous Cas protein when optimally aligned with the *S. pyogenes* Cas9 protein. For example, the transcriptional activation domain can be attached to the Rec domain at position 553, the Rec domain at position 575, the Rec2 domain at any position within positions 175-306 or replacing part of or the entire region within positions 175-306, the HNH domain at any position within positions 715-901 or replacing part of or the entire region within positions 715-901, or the PI domain at position 1153 of the *S. pyogenes* Cas9 protein. See, e.g., WO 2016/049258, herein incorporated by reference in its entirety for all purposes. The transcriptional activation domain may be flanked by one or more linkers on one or both sides as described elsewhere herein.

Chimeric Cas proteins can also be operably linked or fused to additional heterologous polypeptides. The fused or linked heterologous polypeptide can be located at the N-terminus, the C-terminus, or anywhere internally within the chimeric Cas protein. For example, a chimeric Cas protein can further comprise a nuclear localization signal. Examples of suitable nuclear localization signals and other modifications to Cas proteins are described in further detail elsewhere herein.

(1) Cas Proteins

Cas proteins generally comprise at least one RNA recognition or binding domain that can interact with guide RNAs. A functional fragment or functional variant of a Cas protein is one that retains the ability to form a complex with a guide RNA and to bind to a target sequence in a target gene (and, for example, activate transcription of the target gene).

In addition to transcriptional activation domain as described elsewhere herein, Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus. In one example, the Cas protein portions of the chimeric Cas proteins disclosed herein have been modified to have decreased nuclease activity (e.g., nuclease activity is diminished by at least about 70%, at least about 75%, at least about 80%, at least about 85%, at least about 90%, at least about 95%, at least about 96%, at least about 97%, at least about 98%, at least about 99%, or 100% compared to a wild type Cas protein) or to lack substantially all nuclease activity (i.e., nuclease activity is diminished by at least 90%, at least 95%, at least 97%, at least 98%, at least 99%, or 100% compared to a wild type Cas protein, or having no more than about 0%, no more than about 1%, no more than about 2%, no more than about 3%, no more than about 5%, or no more than about 10% of the nuclease activity of a wild type Cas protein). A nuclease-inactive Cas protein is a Cas protein having mutations known to be inactivating mutations in its catalytic (i.e., nuclease) domains (e.g., inactivating mutations in a RuvC-like endonuclease domain in a Cpf1 protein, or inactivating mutations in both an HNH endonuclease domain and a RuvC-like endonuclease domain in Cas9) or a Cas protein having nuclease activity diminished by at least about 97%, least about 98%, least about 99%, or 100% compared to a wild type Cas protein. Examples of different Cas protein mutations to reduce or substantially eliminate nuclease activity are disclosed below.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.* Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas creviorricanis* 3, *Prevotella disiens,* and *Porphyromonas macacae.* Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, at least 85%, at least 90%, at least 91%, at least 92%, at least 93%, at least 94%, at least 95%, at least 96%, at least 97%, at least 98%, at least 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) *Mamm. Genome* 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of or a property of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337(6096): 816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes.* Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus.* See, e.g., Sapranauskas et al. (2011) *Nucleic Acids Res.* 39(21):9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9. One example of a catalytically inactive Cas9 protein (dCas9) comprises, consists essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the dCas9 protein sequence set forth in SEQ ID NO: 44.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, in addition to transcriptional activation domains, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282(8):5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification) or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. In one example, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. For example, the Cas protein can be tethered to the 5' end or the 3' end of the labeled nucleic acid.

(2) Transcriptional Activation Domains

The chimeric Cas proteins disclosed herein can comprise one or more transcriptional activation domains. Transcriptional activation domains include regions of a naturally occurring transcription factor which, in conjunction with a DNA-binding domain (e.g., a catalytically inactive Cas protein complexed with a guide RNA), can activate transcription from a promoter by contacting transcriptional machinery either directly or through other proteins such as coactivators. Transcriptional activation domains also include functional fragments or variants of such regions of a transcription factor and engineered transcriptional activation domains that are derived from a native, naturally occurring transcriptional activation domain or that are artificially created or synthesized to activate transcription of a target gene. A functional fragment is a fragment that is capable of activating transcription of a target gene when operably linked to a suitable DNA-binding domain. A functional variant is a variant that is capable of activating transcription of a target gene when operably linked to a suitable DNA-binding domain.

A specific transcriptional activation domain for use in the chimeric Cas proteins disclosed herein comprises a VP64 transcriptional activation domain or a functional fragment or variant thereof. VP64 is a tetrameric repeat of the minimal activation domain from the herpes simplex VP16 activation domain. For example, the transcriptional activation domain can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the VP64 transcriptional activation domain protein sequence set forth in SEQ ID NO: 45.

Other examples of transcriptional activation domains include herpes simplex virus VP16 transactivation domain, VP64 (quadruple tandem repeat of the herpes simplex virus VP16), a NF-κB p65 (NF-κB trans-activating subunit p65) activation domain, a MyoD1 transactivation domain, an HSF1 transactivation domain (transactivation domain from human heat-shock factor 1), RTA (Epstein Barr virus R transactivator activation domain), a SET7/9 transactivation domain, a p53 activation domain 1, a p53 activation domain 2, a CREB (cAMP response element binding protein) activation domain, an E2A activation domain, an NFAT (nuclear factor of activated T-cells) activation domain, and functional fragments and variants thereof. See, e.g., US 2016/0298125, US 2016/0281072, and WO 2016/049258, each of which is herein incorporated by reference in its entirety for all purposes. Other examples of transcriptional activation domains include Gcn4, MLL, Rtg3, Gln3, Oaf1, Pip2, Pdr1, Pdr3, Pho4, Leu3, and functional fragments and variants thereof. See, e.g., US 2016/0298125, herein incorporated by reference in its entirety for all purposes. Yet other examples of transcriptional activation domains include Spl, Vax, GATA4, and functional fragments and variants thereof. See, e.g., WO 2016/149484, herein incorporated by reference in its entirety for all purposes. Other examples include activation domains from Oct1, Oct-2A, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, and TRAB1PC4, and functional fragments and variants thereof. See, e.g., US 2016/0237456, EP3045537, and WO 2011/146121, each of which is incorporated by reference in its entirety for all purposes. Additional suitable transcriptional activation domains are also known. See, e.g., WO 2011/146121, herein incorporated by reference in its entirety for all purposes.

B. Chimeric Adaptor Proteins

Also provided are chimeric adaptor proteins that can bind to the guide RNAs disclosed elsewhere herein. The chimeric adaptor proteins disclosed herein are useful in dCas-synergistic activation mediator (SAM)-like systems to increase the number and diversity of transcriptional activation domains being directed to a target sequence within a target gene to activate transcription of the target gene. Nucleic acids encoding the chimeric adaptor proteins can be genomically integrated in a cell or non-human animal (e.g., a cell or non-human animal comprising a genomically integrated chimeric Cas protein expression cassette) as disclosed elsewhere herein, or the chimeric adaptor proteins or nucleic acids can be introduced into such cells and non-human animals using methods disclosed elsewhere herein (e.g., LNP-mediated delivery or AAV-mediated delivery).

Such chimeric adaptor proteins comprise: (a) an adaptor (i.e., adaptor domain or adaptor protein) that specifically binds to an adaptor-binding element within a guide RNA; and (b) one or more heterologous transcriptional activation domains. For example, such fusion proteins can comprise 1, 2, 3, 4, 5, or more transcriptional activation domains (e.g., two or more heterologous transcriptional activation domains or three or more heterologous transcriptional activation domains). In one example, such chimeric adaptor proteins can comprise: (a) an adaptor (i.e., an adaptor domain or adaptor protein) that specifically binds to an adaptor-binding element in a guide RNA; and (b) two or more transcriptional activation domains. For example, the chimeric adaptor protein can comprise: (a) an MS2 coat protein adaptor that specifically binds to one or more MS2 aptamers in a guide RNA (e.g., two MS2 aptamers in separate locations in a guide RNA); and (b) one or more (e.g., two or more transcriptional activation domains). For example, the two transcriptional activation domains can be p65 and HSF1 transcriptional activation domains or functional fragments or variants thereof. However, chimeric adaptor proteins in which the transcriptional activation domains comprise other transcriptional activation domains or functional fragments or variants thereof are also provided.

The one or more transcriptional activation domains can be fused directly to the adaptor. Alternatively, the one or more transcriptional activation domains can be linked to the adaptor via a linker or a combination of linkers or via one or more additional domains. Likewise, if two or more transcriptional activation domains are present, they can be fused directly to each other or can be linked to each other via a linker or a combination of linkers or via one or more additional domains. Linkers that can be used in these fusion proteins can include any sequence that does not interfere with the function of the fusion proteins. Exemplary linkers are short (e.g., 2-20 amino acids) and are typically flexible (e.g., comprising amino acids with a high degree of freedom such as glycine, alanine, and serine). Some specific examples of linkers comprise one or more units consisting of GGGS (SEQ ID NO: 46) or GGGGS (SEQ ID NO: 47), such as two, three, four, or more repeats of GGGS (SEQ ID NO: 46) or GGGGS (SEQ ID NO: 47) in any combination. Other linker sequences can also be used.

The one or more transcriptional activation domains and the adaptor can be in any order within the chimeric adaptor protein. As one option, the one or more transcriptional activation domains can be C-terminal to the adaptor and the adaptor can be N-terminal to the one or more transcriptional activation domains. For example, the one or more transcriptional activation domains can be at the C-terminus of the chimeric adaptor protein, and the adaptor can be at the N-terminus of the chimeric adaptor protein. However, the one or more transcriptional activation domains can be C-terminal to the adaptor without being at the C-terminus of the chimeric adaptor protein (e.g., if a nuclear localization signal is at the C-terminus of the chimeric adaptor protein). Likewise, the adaptor can be N-terminal to the one or more transcriptional activation domains without being at the N-terminus of the chimeric adaptor protein (e.g., if a nuclear localization signal is at the N-terminus of the chimeric adaptor protein). As another option, the one or more transcriptional activation domains can be N-terminal to the adaptor and the adaptor can be C-terminal to the one or more transcriptional activation domains. For example, the one or more transcriptional activation domains can be at the N-terminus of the chimeric adaptor protein, and the adaptor can be at the C-terminus of the chimeric adaptor protein. As yet another option, if the chimeric adaptor protein comprises two or more transcriptional activation domains, the two or more transcriptional activation domains can flank the adaptor.

Chimeric adaptor proteins can also be operably linked or fused to additional heterologous polypeptides. The fused or linked heterologous polypeptide can be located at the N-terminus, the C-terminus, or anywhere internally within the chimeric adaptor protein. For example, a chimeric adaptor protein can further comprise a nuclear localization signal. A specific example of such a protein comprises an MS2 coat protein (adaptor) linked (either directly or via an NLS) to a p65 transcriptional activation domain C-terminal to the MS2 coat protein (MCP), and HSF1 transcriptional activation domain C-terminal to the p65 transcriptional activation domain. Such a protein can comprise from N-terminus to C-terminus: an MCP; a nuclear localization signal; a p65 transcriptional activation domain; and an HSF1 transcriptional activation domain. For example, a chimeric adaptor protein can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the MCP-p65-HSF1 chimeric adaptor protein sequence set forth in SEQ ID NO: 48.

Chimeric adaptor proteins can also be fused or linked to one or more heterologous polypeptides that provide for subcellular localization. Such heterologous polypeptides can include, for example, one or more nuclear localization signals (NLS) such as the SV40 NLS and/or an alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. An NLS can comprise, for example, a stretch of basic amino acids, and can be a monopartite sequence or a bipartite sequence. Optionally, the chimeric adaptor protein comprises two or more NLSs, including an NLS (e.g., an alpha-importin NLS) at the N-terminus and/or an NLS (e.g., an SV40 NLS) at the C-terminus.

Chimeric adaptor proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a pol-yarginine peptide sequence. See, e.g., WO 2014/089290 and WO2013/176772, each of which is herein incorporated by reference in its entirety for all purposes. As another example, chimeric adaptor proteins can be fused or linked to a heterologous polypeptide providing increased or decreased stability.

Chimeric adaptor proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Chimeric adaptor proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the chimeric adaptor protein. Likewise, the chimeric adaptor protein can be tethered to the 5' end, the 3' end, or to an internal region within the labeled nucleic acid. That is, the labeled nucleic acid can be tethered in any orientation and polarity.

(1) Adaptor Proteins or Adaptor Domains

Adaptors (i.e., adaptor domains or adaptor proteins) are nucleic-acid-binding domains (e.g., DNA-binding domains and/or RNA-binding domains) that specifically recognize and bind to distinct sequences (e.g., bind to distinct DNA and/or RNA sequences such as aptamers in a sequence-specific manner). Aptamers include nucleic acids that, through their ability to adopt a specific three-dimensional conformation, can bind to a target molecule with high affinity and specificity. Such adaptors can bind, for example, to a specific RNA sequence and secondary structure. These sequences (i.e., adaptor-binding elements) can be engineered into a guide RNA. For example, an MS2 aptamer can be engineered into a guide RNA to specifically bind an MS2 coat protein (MCP). For example, the adaptor can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the MCP sequence set forth in SEQ ID NO: 49.

Some specific examples of adaptors and targets include RNA-binding protein/aptamer combinations that exist within the diversity of bacteriophage coat proteins. For example, the following adaptor proteins or functional fragments or variants thereof can be used: MS2 coat protein (MCP), PP7, Qβ, F2, GA, fr, JP501, M12, R17, BZ13, JP34, JP500, KU1, M11, MX1, TW18, VK, SP, FI, ID2, NL95, TW19, AP205, φCb5, ΦCb8r, ΦCb12r, ΦCb23r, 7s, and PRR1. See, e.g., WO 2016/049258, herein incorporated by reference in its entirety for all purposes. A functional fragment or functional variant of an adaptor protein is one that retains the ability to bind to a specific adaptor-binding element (e.g., ability to bind to a specific adaptor-binding sequence in a sequence-specific manner). For example, a PP7 *Pseudomonas* bacteriophage coat protein variant can be used in which amino acids 68-69 are mutated to SG and amino acids 70-75 are deleted from the wild type protein. See, e.g., Wu et al. (2012) *Biophys. J.* 102(12):2936-2944 and Chao et al. (2007)*Nat. Struct. Mol. Biol.* 15(1):103-105, each of which is herein incorporated by reference in its entirety for all purposes. Likewise, an MCP variant may be used, such as a N55K mutant. See, e.g., Spingola and Peabody (1994) *J Biol. Chem.* 269(12):9006-9010, herein incorporated by reference in its entirety for all purposes.

Other examples of adaptor proteins that can be used include all or part of (e.g., the DNA-binding from) endoribonuclease Csy4 or the lambda N protein. See, e.g., U S 2016/0312198, herein incorporated by reference in its entirety for all purposes.

(2) Transcriptional Activation Domains

The chimeric adaptor proteins disclosed herein comprise one or more transcriptional activation domains. Such transcriptional activation domains can be naturally occurring transcriptional activation domains, can be functional fragments or functional variants of naturally occurring transcriptional activation domains, or can be engineered or synthetic transcriptional activation domains. Transcriptional activation domains that can be used include those described for use in chimeric Cas proteins elsewhere herein.

A specific transcriptional activation domain for use in the chimeric adaptor proteins disclosed herein comprises p65 and/or HSF1 transcriptional activation domains or functional fragments or variants thereof. The HSF1 transcriptional activation domain can be a transcriptional activation domain of human heat shock factor 1 (HSF1). The p65 transcriptional activation domain can be a transcriptional activation domain of transcription factor p65, also known as nuclear factor NF-kappa-B p65 subunit encoded by the RELA gene. As one example, a transcriptional activation domain can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the p65 transcriptional activation domain protein sequence set forth in SEQ ID NO: 50. As another example, a transcriptional activation domain can comprise, consist essentially of, or consist of an amino acid sequence at least 85%, at least 90%, at least 91%, at least 92%, at least 93%, at least 94%, at least 95%, at least 96%, at least 97%, at least 98%, at least 99%, or 100% identical to the HSF1 transcriptional activation domain protein sequence set forth in SEQ ID NO: 51.

C. SAM Guide RNAs and Guide RNA Arrays

Also provided are guide RNAs or guide RNA arrays that can bind to the chimeric Cas proteins and chimeric adaptor proteins disclosed elsewhere herein to activate transcription of target genes. Nucleic acids encoding the guide RNAs can be genomically integrated in a non-human animal cell or non-human animal (e.g., a SAM-ready cell or non-human animal) as disclosed elsewhere herein, or the guide RNAs or nucleic acids can be introduced into such non-human animal cells and non-human animals using methods disclosed elsewhere herein (e.g., LNP-mediated delivery or AAV-mediated delivery). The delivery method can be selected to provide tissue-specific delivery of the recombinase as disclosed elsewhere herein.

A nucleic acid encoding the guide RNAs or guide RNA array can encode one or more guide RNAs (or if guide RNAs are being introduced into the non-human animal cell or non-human animal, one or more guide RNAs can be introduced). For example, 2 or more, 3 or more, 4 or more, or 5 or more guide RNAs can be encoded or introduced. Each guide RNA coding sequence can be operably linked to the same promoter (e.g., a U6 promoter) or a different promoter (e.g., each guide RNA coding sequence is operably linked to its own U6 promoter). Two or more of the guide RNAs can target a different target sequence in a single target gene. For example, 2 or more, 3 or more, 4 or more, or 5 or more guide RNAs can each target a different target sequence in a single target gene. Similarly, the guide RNAs can target multiple target genes (e.g., 2 or more, 3 or more, 4 or more, or 5 or more target genes). Examples of guide RNA target sequences are disclosed elsewhere herein.

(1) Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. A guide RNA can refer to either a CRISPR RNA (crRNA) or the combination of a crRNA and a trans-activating CRISPR RNA (tracrRNA). The crRNA and tracrRNA can be associated as a single RNA molecule (single guide RNA or sgRNA) or in two separate RNA molecules (dual guide RNA or dgRNA). For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs. In some of the methods and compositions disclosed herein, a gRNA is a *S. pyogenes* Cas9 gRNA or an equivalent thereof.

An exemplary two-molecule gRNA comprises a crRNA-like ("CRISPR RNA" or "targeter-RNA" or "crRNA" or "crRNA repeat") molecule and a corresponding tracrRNA-like ("trans-activating CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 73). Any of the DNA-targeting segments disclosed herein can be joined to the 5' end of SEQ ID NO: 73 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. Examples of tracrRNA sequences comprise, consist essentially of, or consist of any one of

```
                                    (SEQ ID NO: 74)
AGCAUAGCAAGUUAAAAUAAGGCUAGUCCGUUAUCAACUUGAAAAAGUG
GCACCGAGUCGGUGCUUU, (SEQ ID NO: 75)
AAACAGCAUAGCAAGUUAAAAUAAGGCUAGUCCGUUAUCAACUUGAAAA
AGUGGCACCGAGUCGGUGCUUUU,
or (SEQ ID NO: 76)
GUUGGAACCAUUCAAAACAGCAUAGCAAGUUAAAAUAAGGCUAGUCCGU
UAUCAACUUGAAAAAGUGGCACCGAGUCGGUGC.
```

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339(6121):823-826; Jinek et al. (2012) *Science* 337(6096): 816-821; Hwang et al. (2013) *Nat. Biotechnol.* 31(3):227-229; Jiang et al. (2013) *Nat. Biotechnol.* 31(3):233-239; and Cong et al. (2013) *Science* 339(6121):819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, at least about 15, at least about 17, at least about 18, at least about 19, at least about 20, at least about 25, at least about 30, at least about 35, or at least about 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, about 18, about 19, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

In one example, the DNA-targeting segment can be about 20 nucleotides in length. However, shorter and longer sequences can also be used for the targeting segment (e.g., 15-25 nucleotides in length, such as 15, 16, 17, 18, 19, 20, 21, 22, 23, 24, or 25 nucleotides in length). The degree of identity between the DNA-targeting segment and the corresponding guide RNA target sequence (or degree of complementarity between the DNA-targeting segment and the other strand of the guide RNA target sequence) can be, for example, about 75%, about 80%, about 85%, about 90%, about 95%, about 96%, about 97%, about 98%, about 99%, or about 100%. The DNA-targeting segment and the corresponding guide RNA target sequence can contain one or more mismatches. For example, the DNA-targeting segment of the guide RNA and the corresponding guide RNA target sequence can contain 1-4, 1-3, 1-2, 1, 2, 3, or 4 mismatches (e.g., where the total length of the guide RNA target sequence is at least 17, at least 18, at least 19, or at least 20 or more nucleotides). For example, the DNA-targeting segment of the guide RNA and the corresponding guide RNA target sequence can contain 1-4, 1-3, 1-2, 1, 2, 3, or 4 mismatches where the total length of the guide RNA target sequence 20 nucleotides.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA)

may comprise, consist essentially of, or consist of all or a portion of a wild type tracrRNA sequence (e.g., about or more than about 20, about or more than about 26, about or more than about 32, about or more than about 45, about or more than about 48, about or more than about 54, about or more than about 63, about or more than about 67, about or more than about 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471(7340):602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of:

```
                                    (version 1; SEQ ID NO: 77)
GUUUUAGAGCUAGAAAUAGCAAGUUAAAAUAAGGCUAGUCCGUUAUCAA
CUUGAAAAAGUGGCACCGAGUCGGUGCU;

(version 2; SEQ ID NO: 78)
GUUGGAACCAUUCAAAACAGCAUAGCAAGUUAAAAUAAGGCUAGUCCGU
UAUCAACUUGAAAAAGUGGCACCGAGUCGGUGC;

(version 3; SEQ ID NO: 79)
GUUUUAGAGCUAGAAAUAGCAAGUUAAAAUAAGGCUAGUCCGUUAUCAA
CUUGAAAAAGUGGCACCGAGUCGGUGC;

(version 4; SEQ ID NO: 80)
GUUUAAGAGCUAUGCUGGAAACAGCAUAGCAAGUUUAAAUAAGGCUAGU
CCGUUAUCAACUUGAAAAAGUGGCACCGAGUCGGUGC;

(version 5; SEQ ID NO: 81)
GUUUUAGAGCUAGAAAUAGCAAGUUAAAAUAAGGCUAGUCCGUUAUCAA
CUUGAAAAAGUGGCACCGAGUCGGUGCUUUUUUU;

(version 6; SEQ ID NO: 82)
GUUUUAGAGCUAGAAAUAGCAAGUUAAAAUAAGGCUAGUCCGUUAUCAA
CUUGAAAAAGUGGCACCGAGUCGGUGCUUUU;
or (version 7; SEQ ID NO: 83)
GUUUAAGAGCUAUGCUGGAAACAGCAUAGCAAGUUUAAAUAAGGCUAGU
CCGUUAUCAACUUGAAAAAGUGGCACCGAGUCGGUGCUUUUUU.
```

Guide RNAs targeting any of the guide RNA target sequences disclosed herein (e.g., any of SEQ ID NOS: 90-95) can include, for example, a DNA-targeting segment (e.g., any of SEQ ID NOS: 96-101) on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA). In a specific example, guide RNAs targeting SEQ ID NO: 93 or 94 can include, for example, a DNA-targeting segment of SEQ ID NO: 99 or 100 on the 5' end of the guide RNA fused to any of the exemplary guide RNA scaffold sequences on the 3' end of the guide RNA. In another specific example, guide RNAs targeting SEQ ID NO: 93 can include, for example, a DNA-targeting segment of SEQ ID NO: 99 on the 5' end of the guide RNA fused to any of the exemplary guide RNA scaffold sequences on the 3' end of the guide RNA.

Guide RNAs can include modifications or sequences that provide for additional desirable features (e.g., modified or regulated stability; subcellular targeting; tracking with a fluorescent label; a binding site for a protein or protein complex; and the like). Guide RNAs can include one or more modified nucleosides or nucleotides, or one or more non-naturally and/or naturally occurring components or configurations that are used instead of or in addition to the canonical A, G, C, and U residues. Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, such as transcriptional activators); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

Chemical modifications such at hose listed above can be combined to provide modified gRNAs and/or mRNAs comprising residues (nucleosides and nucleotides) that can have two, three, four, or more modifications. For example, a modified residue can have a modified sugar and a modified nucleobase. In one example, every base of a gRNA is modified (e.g., all bases have a modified phosphate group, such as a phosphorothioate group). For example, all or substantially all of the phosphate groups of a gRNA can be replaced with phosphorothioate groups. Alternatively or additionally, a modified gRNA can comprise at least one modified residue at or near the 5' end. Alternatively or additionally, a modified gRNA can comprise at least one modified residue at or near the 3' end.

Some gRNAs comprise one, two, three or more modified residues. For example, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the positions in a modified gRNA can be modified nucleosides or nucleotides.

Unmodified nucleic acids can be prone to degradation. Exogenous nucleic acids can also induce an innate immune response. Modifications can help introduce stability and reduce immunogenicity. Some gRNAs described herein can contain one or more modified nucleosides or nucleotides to introduce stability toward intracellular or serum-based nucleases. Some modified gRNAs described herein can exhibit a reduced innate immune response when introduced into a population of cells.

The gRNAs disclosed herein can comprise a backbone modification in which the phosphate group of a modified residue can be modified by replacing one or more of the oxygens with a different substituent. The modification can include the wholesale replacement of an unmodified phosphate moiety with a modified phosphate group as described herein. Backbone modifications of the phosphate backbone can also include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the non-bridging oxygens with one of the above atoms or groups of atoms can render the phosphorous atom chiral. The stereogenic phosphorous atom can possess either the "R" configuration (Rp) or the "S" configuration (Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Scaffolds that can mimic nucleic acids can also be constructed wherein the phosphate linker and ribose sugar are replaced by nuclease resistant nucleoside or nucleotide surrogates. Such modifications may comprise backbone and sugar modifications. In some embodiments, the nucleobases can be tethered by a surrogate backbone. Examples can include, without limitation, the morpholino, cyclobutyl, pyrrolidine and peptide nucleic acid (PNA) nucleoside surrogates.

The modified nucleosides and modified nucleotides can include one or more modifications to the sugar group (a sugar modification). For example, the 2' hydroxyl group (OH) can be modified (e.g., replaced with a number of different oxy or deoxy substituents. Modifications to the 2' hydroxyl group can enhance the stability of the nucleic acid since the hydroxyl can no longer be deprotonated to form a 2'-alkoxide ion.

Examples of 2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). The 2' hydroxyl group modification can be 2'-O-Me. Likewise, the 2' hydroxyl group modification can be a 2'-fluoro modification, which replaces the 2' hydroxyl group with a fluoride. The 2' hydroxyl group modification can include locked nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). The 2' hydroxyl group modification can include unlocked nucleic acids (UNA) in which the ribose ring lacks the C2'-C3' bond. The 2' hydroxyl group modification can include the methoxyethyl group (MOE), $(OCH_2CH_2OCH_3$, e.g., a PEG derivative).

Deoxy 2' modifications can include hydrogen (i.e. deoxyribose sugars, e.g., at the overhang portions of partially dsRNA); halo (e.g., bromo, chloro, fluoro, or iodo); amino (wherein amino can be, e.g., NH2; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar modification can comprise a sugar group which may also contain one or more carbons that possess the opposite stereochemical configuration than that of the corresponding carbon in ribose. Thus, a modified nucleic acid can include nucleotides containing e.g., arabinose, as the sugar. The modified nucleic acids can also include abasic sugars. These abasic sugars can also be further modified at one or more of the constituent sugar atoms. The modified nucleic acids can also include one or more sugars that are in the L form (e.g. L-nucleosides).

The modified nucleosides and modified nucleotides described herein, which can be incorporated into a modified nucleic acid, can include a modified base, also called a nucleobase. Examples of nucleobases include, but are not limited to, adenine (A), guanine (G), cytosine (C), and uracil (U). These nucleobases can be modified or wholly replaced to provide modified residues that can be incorporated into modified nucleic acids. The nucleobase of the nucleotide can be independently selected from a purine, a pyrimidine, a purine analog, or pyrimidine analog. In some embodiments, the nucleobase can include, for example, naturally-occurring and synthetic derivatives of a base.

In a dual guide RNA, each of the crRNA and the tracrRNA can contain modifications. Such modifications may be at one or both ends of the crRNA and/or tracrRNA. In a sgRNA, one or more residues at one or both ends of the sgRNA may be chemically modified, and/or internal nucleosides may be modified, and/or the entire sgRNA may be chemically modified. Some gRNAs comprise a 5' end modification. Some gRNAs comprise a 3' end modification.

The guide RNAs disclosed herein can comprise one of the modification patterns disclosed in WO 2018/107028 A1, herein incorporated by reference in its entirety for all purposes. The guide RNAs disclosed herein can also comprise one of the structures/modification patterns disclosed in US 2017/0114334, herein incorporated by reference in its entirety for all purposes. The guide RNAs disclosed herein can also comprise one of the structures/modification patterns disclosed in WO 2017/136794, WO 2017/004279, US 2018/0187186, or US 2019/0048338, each of which is herein incorporated by reference in its entirety for all purposes.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Rep.* 22(9):2227-2235, each of which is herein incorporated by reference in its entirety for all purposes. Other possible modifications are described in more detail elsewhere herein. In a specific example, a guide RNA includes 2'-O-methyl analogs and 3' phosphorothioate internucleotide linkages at the first three 5' and 3' terminal RNA residues. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

As one example, any of the guide RNAs described herein can comprise at least one modification. In one example, the at least one modification comprises a 2'-O-methyl (2'-O-Me) modified nucleotide, a phosphorothioate (PS) bond between nucleotides, a 2'-fluoro (2'-F) modified nucleotide, or a combination thereof. For example, the at least one modification can comprise a 2'-O-methyl (2'-O-Me) modified nucleotide. Alternatively or additionally, the at least one modification can comprise a phosphorothioate (PS) bond between nucleotides. Alternatively or additionally, the at least one modification can comprise a 2'-fluoro (2'-F) modified nucleotide. In one example, a guide RNA described herein comprises one or more 2'-O-methyl (2'-O-Me) modified nucleotides and one or more phosphorothioate (PS) bonds between nucleotides.

The modifications can occur anywhere in the guide RNA. As one example, the guide RNA comprises a modification at one or more of the first five nucleotides at the 5' end of the guide RNA, the guide RNA comprises a modification at one or more of the last five nucleotides of the 3' end of the guide RNA, or a combination thereof. For example, the guide RNA can comprise phosphorothioate bonds between the first four nucleotides of the guide RNA, phosphorothioate bonds between the last four nucleotides of the guide RNA, or a combination thereof. Alternatively or additionally, the guide RNA can comprise 2'-O-Me modified nucleotides at the first three nucleotides at the 5' end of the guide RNA, can comprise 2'-O-Me modified nucleotides at the last three nucleotides at the 3' end of the guide RNA, or a combination thereof.

Another chemical modification that has been shown to influence nucleotide sugar rings is halogen substitution. For example, 2'-fluoro (2'-F) substitution on nucleotide sugar rings can increase oligonucleotide binding affinity and nuclease stability. Abasic nucleotides refer to those which lack nitrogenous bases. Inverted bases refer to those with linkages that are inverted from the normal 5' to 3' linkage (i.e., either a 5' to 5' linkage or a 3' to 3' linkage).

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap.

In one example, one or more of the first three, four, or five nucleotides at the 5' terminus, and one or more of the last three, four, or five nucleotides at the 3' terminus are modified. The modification can be, for example, a 2'-O-Me, 2'-F, inverted abasic nucleotide, phosphorothioate bond, or other nucleotide modification well known to increase stability and/or performance.

In another example, the first four nucleotides at the 5' terminus, and the last four nucleotides at the 3' terminus can be linked with phosphorothioate bonds.

In another example, the first three nucleotides at the 5' terminus, and the last three nucleotides at the 3' terminus can comprise a 2'-O-methyl (2'-O-Me) modified nucleotide. In another example, the first three nucleotides at the 5' terminus, and the last three nucleotides at the 3' terminus comprise a 2'-fluoro (2'-F) modified nucleotide. In another example, the first three nucleotides at the 5' terminus, and the last three nucleotides at the 3' terminus comprise an inverted abasic nucleotide.

In some guide RNAs (e.g., single guide RNAs), at least one loop (e.g., two loops) of the guide RNA is modified by insertion of a distinct RNA sequence that binds to one or more adaptors (i.e., adaptor proteins or domains). Such adaptor proteins can be used to further recruit one or more heterologous functional domains, such as transcriptional activation domains. Examples of fusion proteins comprising such adaptor proteins (i.e., chimeric adaptor proteins) are disclosed elsewhere herein. For example, an MS2-binding loop ggccAACAUGAGGAUCACCCAUGU-CUGCAGggcc (SEQ ID NO: 52) may replace nucleotides +13 to +16 and nucleotides +53 to +56 of the sgRNA scaffold (backbone) set forth in SEQ ID NO: 77, 79, 81, or 82 or the sgRNA backbone for the *S. pyogenes* CRISPR/Cas9 system described in WO 2016/049258 and Konermann et al. (2015) *Nature* 517(7536):583-588, each of which is herein incorporated by reference in its entirety for all purposes. See, e.g., FIG. 6. The guide RNA numbering used herein refers to the nucleotide numbering in the guide RNA scaffold sequence (i.e., the sequence downstream of the DNA-targeting segment of the guide RNA). For example, the first nucleotide of the guide RNA scaffold is +1, the second nucleotide of the scaffold is +2, and so forth. Residues corresponding with nucleotides +13 to +16 in SEQ ID NO: 77, 79, 81, or 82 are the loop sequence in the region spanning nucleotides +9 to +21 in SEQ ID NO: 77, 79, 81, or 82, a region referred to herein as the tetraloop. Residues corresponding with nucleotides +53 to +56 in SEQ ID NO: 77, 79, 81, or 82 are the loop sequence in the region spanning nucleotides +48 to +61 in SEQ ID NO: 77, 79, 81, or 82, a region referred to herein as the stem loop 2. Other stem loop sequences in SEQ ID NO: 77, 79, 81, or 82 comprise stem loop 1 (nucleotides +33 to +41) and stem loop 3 (nucleotides +63 to +75). The resulting structure is an sgRNA scaffold in which each of the tetraloop and stem loop 2 sequences have been replaced by an MS2 binding loop. The tetraloop and stem loop 2 protrude from the Cas9 protein in such a way that adding an MS2-binding loop should not interfere with any Cas9 residues. Additionally, the proximity of the tetraloop and stem loop 2 sites to the DNA indicates that localization to these locations could result in a high degree of interaction between the DNA and any recruited protein, such as a transcriptional activator. Thus, in some sgRNAs, nucleotides corresponding to +13 to +16 and/or nucleotides corresponding to +53 to +56 of the guide RNA scaffold set forth in SEQ ID NO: 77, 79, 81, or 82 or corresponding residues when optimally aligned with any of these scaffold/backbones are replaced by the distinct RNA sequences capable of binding to one or more adaptor proteins or domains. Alternatively or additionally, adaptor-binding sequences can be added to the 5' end or the 3' end of a guide RNA. An exemplary guide RNA scaffold comprising MS2-binding loops in the tetraloop and stem loop 2 regions can comprise, consist essentially of, or consist of the sequence set forth in SEQ ID NO: 66 or 71. An exemplary generic single guide RNA comprising MS2-binding loops in the tetraloop and stem loop 2 regions can comprise, consist essentially of, or consist of the sequence set forth in SEQ ID NO: 68 or 72.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-cogly-colic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

(2) Guide RNA Target Sequences

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

It can be preferable for the target sequence to be adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site, within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair upstream of the transcription start site, or within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair downstream of the transcription start site. Optionally, the target sequence is within the region 200 base pairs upstream of the transcription start site and 1 base pair downstream of the transcription start site (−200 to +1).

The target sequence can be within any gene desired to be targeted for transcriptional activation. In some cases, a target gene may be one that is a non-expressing gene or a weakly expressing gene (e.g., only minimally expressed above background, such as 1.1-fold, 1.2-fold, 1.3-fold, 1.4-fold, 1.5-fold, 1.6-fold, 1.7-fold, 1.8-fold, 1.9-fold, or 2-fold). The target gene may also be one that is expressed at low levels compared to a control gene. The target gene may also be one that is epigenetically silenced. The term "epigenetically silenced" refers to a gene that is not being transcribed or is being transcribed at a level that is decreased with respect to the level of transcription of the gene in a control sample (e.g., a corresponding control cell, such as a normal cell), due to a mechanism other than a genetic change such as a mutation. Epigenetic mechanisms of gene silencing are well known and include, for example, hypermethylation of CpG dinucleotides in a CpG island of the 5' regulatory region of a gene and structural changes in chromatin due, for example, to histone acetylation, such that gene transcription is reduced or inhibited.

Target genes can include genes expressed in particular organs or tissues. Target genes can include disease-associated genes. A disease-associated gene refers to any gene that yields transcription or translation products at an abnormal level or in an abnormal form in cells derived from a disease-affected tissues compared with tissues or cells of a non-disease control. It may be a gene that becomes expressed at an abnormally high level, where the altered expression correlates with the occurrence and/or progression of the disease. A disease-associated gene also refers to a gene possessing a mutation or genetic variation that is responsible for the etiology of a disease. The transcribed or translated products may be known or unknown, and may be at a normal or abnormal level.

One specific example of such a target gene is the Myoc gene (e.g., the humanized MYOC locus described elsewhere herein). Examples of guide RNA target sequences (not including PAM) in the mouse Myoc gene are set forth in SEQ ID NOS: 90-95. Guide RNA DNA-targeting segments corresponding to the guide RNA target sequences set forth in SEQ ID NOS: 90-95 are set forth in SEQ ID NOS: 96-101, respectively. A specific example of a guide RNA target sequence is SEQ ID NO: 93 or 94 (with corresponding DNA-targeting segments set forth in SEQ ID NO: 99 or 100, respectively). Another specific example of a guide RNA target sequence is SEQ ID NO: 93 (with the corresponding DNA-targeting segment set forth in SEQ ID NO: 99).

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where $N_2$ is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are GN$_{19}$NGG (SEQ ID NO: 84) or N$_{20}$NGG (SEQ ID NO: 85). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., GGN$_{20}$NGG; SEQ ID NO: 86) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 84-86, including the 5' G or GG and the 3' GG or NGG. Yet other guide RNA target sequences plus PAMs can have between 14 and 20 nucleotides in length of SEQ ID NOS: 84-86.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, at least 3, at least 4, at least 5, at least 6, at least 7, at least 8, at least 9, at least 10, at least 15, at least 20, at least 25, at least 30, at least 40, at least 50, at least 75, at least 100, at least 250, at least 500, or at least 1,000 base pairs.

D. Recombinases and Recombinase Deleter Non-Human Animals

Cells or non-human animals comprising a chimeric Cas protein expression cassette, a chimeric adaptor protein expression cassette, a SAM expression cassette, a guide RNA expression cassette (e.g., one or more guide RNA expression cassettes), or a recombinase expression cassette in which the cassette is downstream of a polyadenylation signal or transcription terminator flanked by recombinase recognition sites recognized by a site-specific recombinase as disclosed herein can further comprise a recombinase expression cassette that drives expression of the site-specific recombinase. A nucleic acid encoding the recombinase can be genomically integrated, or the recombinase or nucleic acids can be introduced into such cells and non-human animals using methods disclosed elsewhere herein (e.g., LNP-mediated delivery or AAV-mediated delivery). The delivery method can be selected to provide tissue-specific delivery of the recombinase as disclosed elsewhere herein.

Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The recombinase expression cassette can be integrated at a different target genomic locus from other expression cassettes disclosed herein, or it can be genomically integrated at the same target locus (e.g., a Rosa26 locus, such as integrated in the first intron of the Rosa26 locus). For example, the cell or non-human animal can be heterozygous for each of a SAM expression cassette (or chimeric Cas protein expression cassette or chimeric adaptor protein expression cassette) and the recombinase expression cassette, with one allele of the target genomic locus comprising the SAM expression cassette, and a second allele of the target genomic locus comprising the recombinase expression cassette expression cassette. Likewise, the cell or non-human animal can be heterozygous for each of a guide RNA expression cassette (e.g., guide RNA array expression cassette) and the recombinase expression cassette, with one allele of the target genomic locus comprising the guide RNA expression cassette, and a second allele of the target genomic locus comprising the recombinase expression cassette expression cassette.

The recombinase gene in a recombinase expression cassette can be operably linked to any suitable promoter. Examples of promoters are disclosed elsewhere herein. For example, the promoter can be a tissue-specific promoter or a developmental-stage-specific promoter. Such promoters are advantageous because they can selectively activate transcription of a target gene in a desired tissue or only at a desired developmental stage. For example, in the case of Cas proteins, this can reduce the possibility of Cas-mediated toxicity in vivo. Exemplary promoters for mouse recombinase delete strains are known and are provided, for example, in US 2019/0284572 and WO 2019/183123, each of which is herein incorporated by reference in its entirety for all purposes.

E. Nucleic Acids Encoding Chimeric Cas Protein, Chimeric Adaptor Protein, Guide RNA, Synergistic Activation Mediator, or Recombinase Also provided are nucleic acids encoding a chimeric Cas protein, a chimeric adaptor protein, a guide RNA, a recombinase, or any combination thereof. Chimeric Cas proteins, chimeric adaptor proteins, guide RNAs, and recombinases are described in more detail elsewhere herein. For example, the nucleic acids can be chimeric Cas protein expression cassettes, chimeric adaptor protein expression cassettes, synergistic activation mediator (SAM) expression cassettes comprising nucleic acids encoding both a chimeric Cas protein and a chimeric adaptor protein, guide RNA or guide RNA array expression cassettes, recombinase expression cassettes, or any combination thereof. Such nucleic acids can be RNA (e.g., messenger RNA (mRNA)) or DNA, can be single-stranded or double-stranded, and can be linear or circular. DNA can be part of a vector, such as an expression vector or a targeting vector. The vector can also be a viral vector such as adenoviral, adeno-associated viral, lentiviral, and retroviral vectors. When any of the nucleic acids disclosed herein is introduced into a cell, the encoded chimeric Cas protein, chimeric adaptor protein, or guide RNA can be transiently, conditionally, or constitutively expressed in the cell.

Optionally, the nucleic acids can be codon-optimized for efficient translation into protein in a particular cell or organism. For example, the nucleic acid can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence.

The nucleic acids or expression cassettes can be stably integrated into the genome (i.e., into a chromosome) of the cell or non-human animal or it can be located outside of a chromosome (e.g., extrachromosomally replicating DNA). The stably integrated expression cassettes or nucleic acids can be randomly integrated into the genome of the non-human animal (i.e., transgenic), or they can be integrated into a predetermined region of the genome of the non-human animal (i.e., knock in). In one example, a nucleic acid or expression cassette is stably integrated into a safe harbor locus as described elsewhere herein. The target genomic locus at which a nucleic acid or expression cassette is stably integrated can be heterozygous for the nucleic acid or expression cassette or homozygous for the nucleic acid or expression cassette. For example, a target genomic locus or a non-human animal cell or non-human animal can be heterozygous for a SAM expression cassette and heterozygous for a guide RNA expression cassette, optionally with each being at the same target genomic locus on different alleles.

A nucleic acid or expression cassette described herein can be operably linked to any suitable promoter for expression in vivo within a non-human animal or in vitro or ex vivo within a cell. The non-human animal can be any suitable non-human animal as described elsewhere herein. As one example, a nucleic acid or expression cassette (e.g., a chimeric Cas protein expression cassette, a chimeric adaptor protein expression cassette, or a SAM cassette comprising nucleic acids encoding both a chimeric Cas protein and a chimeric adaptor protein) can be operably linked to an endogenous promoter at a target genomic locus, such as a Rosa26 promoter. Alternatively, cassette nucleic acid or expression cassette can be operably linked to an exogenous promoter, such as a constitutively active promoter (e.g., a CAG promoter or a U6 promoter), a conditional promoter, an inducible promoter, a temporally restricted promoter (e.g., a developmentally regulated promoter), or a spatially restricted promoter (e.g., a cell-specific or tissue-specific promoter). Such promoters are well-known and are discussed elsewhere herein. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters.

For example, a nucleic acid encoding a guide RNA can be operably linked to a U6 promoter, such as a human U6 promoter or a mouse U6 promoter. Specific examples of suitable promoters (e.g., for expressing a guide RNA) include an RNA polymerase III promoter, such as a human U6 promoter, a rat U6 polymerase III promoter, or a mouse U6 polymerase III promoter.

Optionally, the promoter can be a bidirectional promoter driving expression of one gene (e.g., a gene encoding a chimeric Cas protein) and a second gene (e.g., a gene encoding a guide RNA or a chimeric adaptor protein) in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express two genes simultaneously allows for the generation of compact expression cassettes to facilitate delivery.

One or more of the nucleic acids can be together in a multicistronic expression construct. For example, a nucleic acid encoding a chimeric Cas protein and a nucleic acid encoding a chimeric adaptor protein can be together in a bicistronic expression construct. See, e.g., FIGS. 4A and 4B. Multicistronic expression vectors simultaneously express two or more separate proteins from the same mRNA (i.e., a transcript produced from the same promoter). Suitable strategies for multicistronic expression of proteins include, for example, the use of a 2A peptide and the use of an internal ribosome entry site (IRES). For example, such constructs can comprise: (1) nucleic acids encoding one or more chimeric Cas proteins and one or more chimeric adaptor proteins; (2) nucleic acids encoding two or more chimeric adaptor proteins; (3) nucleic acids encoding two or more chimeric Cas proteins; (4) nucleic acids encoding two or more guide RNAs or two or more guide RNA arrays; (5) nucleic acids encoding one or more chimeric Cas proteins and one or more guide RNAs or guide RNA arrays; (6) nucleic acids encoding one or more chimeric adaptor proteins and one or more guide RNAs or guide RNA arrays; or (7) nucleic acids encoding one or more chimeric Cas proteins, one or more chimeric adaptor proteins, and one or more guide RNAs or guide RNA arrays. As one example, such multicistronic vectors can use one or more internal ribosome entry sites (IRES) to allow for initiation of translation from an internal region of an mRNA. As another example, such multicistronic vectors can use one or more 2A peptides. These peptides are small "self-cleaving" peptides, generally having a length of 18-22 amino acids and produce equimolar levels of multiple genes from the same mRNA. Ribosomes skip the synthesis of a glycyl-prolyl peptide bond at the C-terminus of a 2A peptide, leading to the "cleavage" between a 2A peptide and its immediate downstream peptide. See, e.g., Kim et al. (2011) *PLoS One* 6(4):e18556, herein incorporated by reference in its entirety for all purposes. The "cleavage" occurs between the glycine and proline residues found on the C-terminus, meaning the upstream cistron will have a few additional residues added to the end, while the downstream cistron will start with the proline. As a result, the "cleaved-off" downstream peptide has proline at its N-terminus. 2A-mediated cleavage is a universal phenomenon in all eukaryotic cells. 2A peptides have been identified from picornaviruses, insect viruses and type C rotaviruses. See, e.g., Szymczak et al. (2005) *Expert Opin. Biol. Ther.* 5(5):627-638, herein incorporated by reference in its entirety for all purposes. Examples of 2A peptides that can be used include Thoseaasigna virus 2A (T2A); porcine teschovirus-1 2A (P2A); equine rhinitis A virus (ERAV) 2A (E2A); and FMDV 2A (F2A). Exemplary T2A, P2A, E2A, and F2A sequences include the following: T2A (EGRGSLLTCGDVEENPGP; SEQ ID NO: 53); P2A (ATNFSLLKQAGDVEENPGP; SEQ ID NO: 54); E2A (QCTNYALLKLAGDVESNPGP; SEQ ID NO: 55); and F2A (VKQTLNFDLLKLAGDVESNPGP; SEQ ID NO: 56). GSG residues can be added to the 5' end of any of these peptides to improve cleavage efficiency.

Any of the nucleic acids or expression cassettes can also comprise a polyadenylation signal or transcription terminator upstream of a coding sequence. The term polyadenylation signal sequence refers to any sequence that directs termination of transcription and addition of a poly-A tail to the mRNA transcript. In eukaryotes, transcription terminators are recognized by protein factors, and termination is followed by polyadenylation, a process of adding a poly(A) tail to the mRNA transcripts in presence of the poly(A) polymerase. The mammalian poly(A) signal typically consists of a core sequence, about 45 nucleotides long, that may be flanked by diverse auxiliary sequences that serve to enhance cleavage and polyadenylation efficiency. The core sequence consists of a highly conserved upstream element (AATAAA or AAUAAA) in the mRNA, referred to as a poly A recognition motif or poly A recognition sequence), recognized by cleavage and polyadenylation-specificity factor (CPSF), and a poorly defined downstream region (rich in Us or Gs and Us), bound by cleavage stimulation factor (CstF). Examples of transcription terminators that can be used include, for example, the human growth hormone (HGH) polyadenylation signal, the simian virus 40 (SV40) late polyadenylation signal, the rabbit beta-globin polyadenylation signal, the bovine growth hormone (BGH) polyadenylation signal, the phosphoglycerate kinase (PGK) polyadenylation signal, an AOX1 transcription termination sequence, a CYC1 transcription termination sequence, or any transcription termination sequence known to be suitable for regulating gene expression in eukaryotic cells. For example, a chimeric Cas protein expression cassette, a chimeric adaptor protein expression cassette, a SAM expression cassette, a guide RNA expression cassette, or a recombinase expression cassette can comprise a polyadenylation signal or transcription terminator upstream of the coding sequence(s) in the expression cassette. The polyadenylation signal or transcription terminator can be flanked by recombinase recognition sites recognized by a site-specific recombinase. Optionally, the recombinase recognition sites also flank a selection cassette comprising, for example, the coding sequence for a drug resistance protein. Optionally the recombinase recognition sites do not flank a selection cassette. The polyadenylation signal or transcription terminator prevents transcription and expression of the protein or RNA encoded by the coding sequence (e.g., chimeric Cas protein, chimeric adaptor protein, guide RNA, or recombinase). However, upon exposure to the site-specific recombinase, the polyadenylation signal or transcription terminator will be excised, and the protein or RNA can be expressed.

Such a configuration for an expression cassette (e.g., a chimeric Cas protein expression cassette or a SAM expression cassette) can enable tissue-specific expression or developmental-stage-specific expression in non-human animals comprising the expression cassette if the polyadenylation signal or transcription terminator is excised in a tissue-specific or developmental-stage-specific manner. For example, in the case of the chimeric Cas protein, this may reduce toxicity due to prolonged expression of the chimeric Cas protein in a cell or non-human animal or expression of the chimeric Cas protein at undesired developmental stages or in undesired cell or tissue types within a non-human animal. See, e.g., Parikh et al. (2015) *PLoS One* 10(1): e0116484, herein incorporated by reference in its entirety for all purposes. Excision of the polyadenylation signal or transcription terminator in a tissue-specific or developmental-stage-specific manner can be achieved if a non-human animal comprising the expression cassette further comprises a coding sequence for the site-specific recombinase operably linked to a tissue-specific or developmental-stage-specific promoter. The polyadenylation signal or transcription terminator will then be excised only in those tissues or at those developmental stages, enabling tissue-specific expression or developmental-stage-specific expression. In one example, a chimeric Cas protein, a chimeric adaptor protein, a chimeric Cas protein and a chimeric adaptor protein, or a guide RNA can be expressed in a liver-specific manner. Examples of such promoters that have been used to develop such "recombinase deleter" strains of non-human animals are disclosed elsewhere herein.

Any transcription terminator or polyadenylation signal can be used. A "transcription terminator" as used herein refers to a DNA sequence that causes termination of transcription. In eukaryotes, transcription terminators are recognized by protein factors, and termination is followed by polyadenylation, a process of adding a poly(A) tail to the mRNA transcripts in presence of the poly(A) polymerase.

The mammalian poly(A) signal typically consists of a core sequence, about 45 nucleotides long, that may be flanked by diverse auxiliary sequences that serve to enhance cleavage and polyadenylation efficiency. The core sequence consists of a highly conserved upstream element (AATAAA or AAUAAA) in the mRNA, referred to as a poly A recognition motif or poly A recognition sequence), recognized by cleavage and polyadenylation-specificity factor (CPSF), and a poorly defined downstream region (rich in Us or Gs and Us), bound by cleavage stimulation factor (CstF). Examples of transcription terminators that can be used include, for example, the human growth hormone (HGH) polyadenylation signal, the simian virus 40 (SV40) late polyadenylation signal, the rabbit beta-globin polyadenylation signal, the bovine growth hormone (BGH) polyadenylation signal, the phosphoglycerate kinase (PGK) polyadenylation signal, an AOX1 transcription termination sequence, a CYC1 transcription termination sequence, or any transcription termination sequence known to be suitable for regulating gene expression in eukaryotic cells.

Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The expression cassettes disclosed herein can comprise other components as well. Such expression cassettes (e.g., chimeric Cas protein expression cassette, chimeric adaptor protein expression cassette, SAM expression cassette, guide RNA expression cassette, or recombinase expression cassette) can further comprise a 3' splicing sequence at the 5' end of the expression cassette and/or a second polyadenylation signal following the coding sequence (e.g., encoding the chimeric Cas protein, the chimeric adaptor protein, the guide RNA, or the recombinase). The term 3' splicing sequence refers to a nucleic acid sequence at a 3' intron/exon boundary that can be recognized and bound by splicing machinery. An expression cassette can further comprise a selection cassette comprising, for example, the coding sequence for a drug resistance protein. Examples of suitable selection markers include neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k). Optionally, the selection cassette can be flanked by recombinase recognition sites for a site-specific recombinase. If the expression cassette also comprises recombinase recognition sites flanking a polyadenylation signal upstream of the coding sequence as described above, the selection cassette can be flanked by the same recombinase recognition sites or can be flanked by a different set of recombinase recognition sites recognized by a different recombinase.

An expression cassette can also comprise a nucleic acid encoding one or more reporter proteins, such as a fluorescent protein (e.g., a green fluorescent protein). Any suitable reporter protein can be used. For example, a fluorescent reporter protein as defined elsewhere herein can be used, or a non-fluorescent reporter protein can be used. Examples of fluorescent reporter proteins are provided elsewhere herein. Non-fluorescent reporter proteins include, for example, reporter proteins that can be used in histochemical or bioluminescent assays, such as beta-galactosidase, luciferase (e.g., *Renilla* luciferase, firefly luciferase, and NanoLuc luciferase), and beta-glucuronidase. An expression cassette can include a reporter protein that can be detected in a flow cytometry assay (e.g., a fluorescent reporter protein such as a green fluorescent protein) and/or a reporter protein that can be detected in a histochemical assay (e.g., beta-galactosidase protein). One example of such a histochemical assay is visualization of in situ beta-galactosidase expression histochemically through hydrolysis of X-Gal (5-bromo-4-chloro-3-indoyl-b-D-galactopyranoside), which yields a blue precipitate, or using fluorogenic substrates such as beta-methyl umbelliferyl galactoside (MUG) and fluorescein digalactoside (FDG).

The expression cassettes described herein can be in any form. For example, an expression cassette can be in a vector or plasmid, such as a viral vector. The expression cassette can be operably linked to a promoter in an expression construct capable of directing expression of a protein or RNA (e.g., upon removal of an upstream polyadenylation signal). Alternatively, an expression cassette can be in a targeting vector. For example, the targeting vector can comprise homology arms flanking the expression cassette, wherein the homology arms are suitable for directing recombination with a desired target genomic locus to facilitate genomic integration and/or replacement of endogenous sequence.

The expression cassettes described herein can be in vitro, they can be within a cell (e.g., an embryonic stem cell) ex vivo (e.g., genomically integrated or extrachromosomal), or they can be in an organism (e.g., a non-human animal) in vivo (e.g., genomically integrated or extrachromosomal). If ex vivo, the expression cassette(s) can be in any type of cell from any organism, such as a totipotent cell such as an embryonic stem cell (e.g., a mouse or a rat embryonic stem cell) or an induced pluripotent stem cell (e.g., a human induced pluripotent stem cell). If in vivo, the expression cassette(s) can be in any type of organism (e.g., a non-human animal as described further elsewhere herein).

A specific example of a nucleic acid encoding a catalytically inactive Cas protein can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the dCas9 protein sequence set forth in SEQ ID NO: 44. Optionally, the nucleic acid can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the sequence set forth in SEQ ID NO: 57 (optionally wherein the sequence encodes a protein at least 85%, at least 90%, at least 91%, at least 92%, at least 93%, at least 94%, at least 95%, at least 96%, at least 97%, at least 98%, at least 99%, or 100% identical to the dCas9 protein sequence set forth in SEQ ID NO: 44).

A specific example of a nucleic acid encoding a chimeric Cas protein can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the chimeric Cas protein sequence set forth in SEQ ID NO: 43. Optionally, the nucleic acid can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the sequence set forth in SEQ ID NO: 58 (optionally wherein the sequence encodes a protein at least 85%, at least 90%, at least 91%, at least 92%, at least 93%, at least 94%, at least 95%, at least 96%, at least 97%, at least 98%, at least 99%, or 100% identical to the chimeric Cas protein sequence set forth in SEQ ID NO: 43).

A specific example of a nucleic acid encoding an adaptor can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to MCP sequence set forth in SEQ ID NO: 49. Optionally, the nucleic acid can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the sequence set forth in SEQ ID NO: 59 (optionally wherein the sequence encodes a protein at least 85%, at least 90%, at least 91%, at least 92%, at least 93%, at least 94%, at least 95%, at least 96%, at least 97%, at least 98%, at least 99%, or 100% identical to the MCP sequence set forth in SEQ ID NO: 49).

A specific example of a nucleic acid encoding a chimeric adaptor protein can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the chimeric adaptor protein sequence set forth in SEQ ID NO: 48. Optionally, the nucleic acid can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the sequence set forth in SEQ ID NO: 60 (optionally wherein the sequence encodes a protein at least 85%, at least 90%, at least 91%, at least 92%, at least 93%, at least 94%, at least 95%, at least 96%, at least 97%, at least 98%, at least 99%, or 100% identical to the chimeric adaptor protein sequence set forth in SEQ ID NO: 48).

Specific examples of nucleic acids encoding transcriptional activation domains can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the VP64, p65, or HSF1 sequences set forth in SEQ ID NO: 45, 50, or 51, respectively. Optionally, the nucleic acid can comprise, consist essentially of, or consist of a nucleic acid encoding an amino acid sequence at least 85%, at least 90%, at least 91%, at least 92%, at least 93%, at least 94%, at least 95%, at least 96%, at least 97%, at least 98%, at least 99%, or 100% identical to the sequence set forth in SEQ ID NO: 61, 62, or 63, respectively (optionally wherein the sequence encodes a protein at least 85%, at least 90%, at least 91%, at least 92%, at least 93%, at least 94%, at least 95%, at least 96%, at least 97%, at least 98%, at least 99%, or 100% identical to the VP64, p65, or HSF1 sequences set forth in SEQ ID NO: 45, 50, or 51, respectively).

One exemplary synergistic activation mediator (SAM) expression cassette comprises from 5' to 3': (a) a 3' splicing sequence; (b) a first recombinase recognition site (e.g., loxP site); (c) a coding sequence for a drug resistance gene (e.g., neomycin phosphotransferase (neo$^r$) coding sequence); (d) a polyadenylation signal; (e) a second recombinase recognition site (e.g., loxP site); (f) a chimeric Cas protein coding sequence (e.g., dCas9-NLS-VP64 fusion protein or NLS-dCas9-NLS-VP64 fusion protein); (g) a 2A protein coding sequence (e.g., a P2A or T2A coding sequence); and (e) a chimeric adaptor protein coding sequence (e.g., MCP-NLS-p65-HSF1). Another exemplary synergistic activation mediator (SAM) expression cassette comprises from 5' to 3': (a) a 3' splicing sequence; (b) a first recombinase recognition site (e.g., loxP site); (c) a coding sequence for a drug resistance gene (e.g., neomycin phosphotransferase (neo$^r$) coding sequence); (d) a polyadenylation signal (e.g., PGK polyadenylation signal and/or SV40 polyadenylation signal, such as a combination of a PGK polyadenylation signal and 3 SV40 polyadenylation signals); (e) a second recombinase recognition site (e.g., loxP site); (f) a chimeric Cas protein coding sequence (e.g., dCas9-NLS-VP64 fusion protein or NLS-dCas9-NLS-VP64 fusion protein); (g) a 2A protein coding sequence (e.g., a P2A or T2A coding sequence); (e) a chimeric adaptor protein coding sequence (e.g., MCP-NLS-p65-HSF1); (f) a Woodchuck hepatitis virus posttranscriptional regulatory element (WPRE); and (g) another polyadenylation signal (e.g., BGH polyadenylation signal). See, e.g., FIG. 4A and SEQ ID NO: 64 (coding sequence set forth in SEQ ID NO: 69 and encoding protein set forth in SEQ ID NO: 67).

One exemplary generic guide RNA array expression cassette comprises from 5' to 3': (a) a 3' splicing sequence; (b) a first recombinase recognition site (e.g., rox site); (c) a coding sequence for a drug resistance gene (e.g., puromycin-N-acetyltransferase (puro$^r$) coding sequence); (d) a polyadenylation signal (e.g., PGK polyadenylation signal and/or SV40 polyadenylation signal, such as a combination of a PGK polyadenylation signal and 3 SV40 polyadenylation signals); (e) a second recombinase recognition site (e.g., rox site); (f) a guide RNA array comprising one or more guide RNA genes (e.g., a first U6 promoter followed by a first guide RNA coding sequence and a first terminator sequence, a second U6 promoter followed by a second guide RNA coding sequence and a second terminator sequence, and a third U6 promoter followed by a third guide RNA coding sequence and a third terminator sequence). See, e.g., SEQ ID NO: 65. The region of SEQ ID NO: 65 comprising the promoters and guide RNA coding sequences is set forth in SEQ ID NO: 70. The recombinase recognition sites in the guide RNA array expression cassette can be the same or different from the recombinase recognition sites in the SAM expression cassette (e.g., can be recognized by the same recombinase or a different recombinase).

Another exemplary generic guide RNA array expression cassette comprises one or more guide RNA genes (e.g., a first U6 promoter followed by a first guide RNA coding sequence, a second U6 promoter followed by a second guide RNA coding sequence, and a third U6 promoter followed by a third guide RNA coding sequence). Such an exemplary generic guide RNA array expression cassette is set forth in SEQ ID NO: 70.

F. Genomic Loci for Integration

The nucleic acids and expression cassettes described herein can be genomically integrated at a target genomic locus in a non-human animal cell or a non-human animal. Any target genomic locus capable of expressing a gene can be used.

An example of a target genomic locus into which the nucleic acids or cassettes described herein can be stably integrated is a safe harbor locus in the genome of the non-human animal cell or non-human animal. Interactions between integrated exogenous DNA and a host genome can limit the reliability and safety of integration and can lead to overt phenotypic effects that are not due to the targeted genetic modification but are instead due to unintended effects of the integration on surrounding endogenous genes. For example, randomly inserted transgenes can be subject to position effects and silencing, making their expression unreliable and unpredictable. Likewise, integration of exogenous DNA into a chromosomal locus can affect surrounding endogenous genes and chromatin, thereby altering cell behavior and phenotypes. Safe harbor loci include chromosomal loci where transgenes or other exogenous nucleic acid inserts can be stably and reliably expressed in all tissues of interest without overtly altering cell behavior or phenotype (i.e., without any deleterious effects on the host cell). See, e.g., Sadelain et al. (2012) *Nat. Rev. Cancer* 12:51-58, herein incorporated by reference in its entirety for all purposes. For example, the safe harbor locus can be one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

Figure 5:
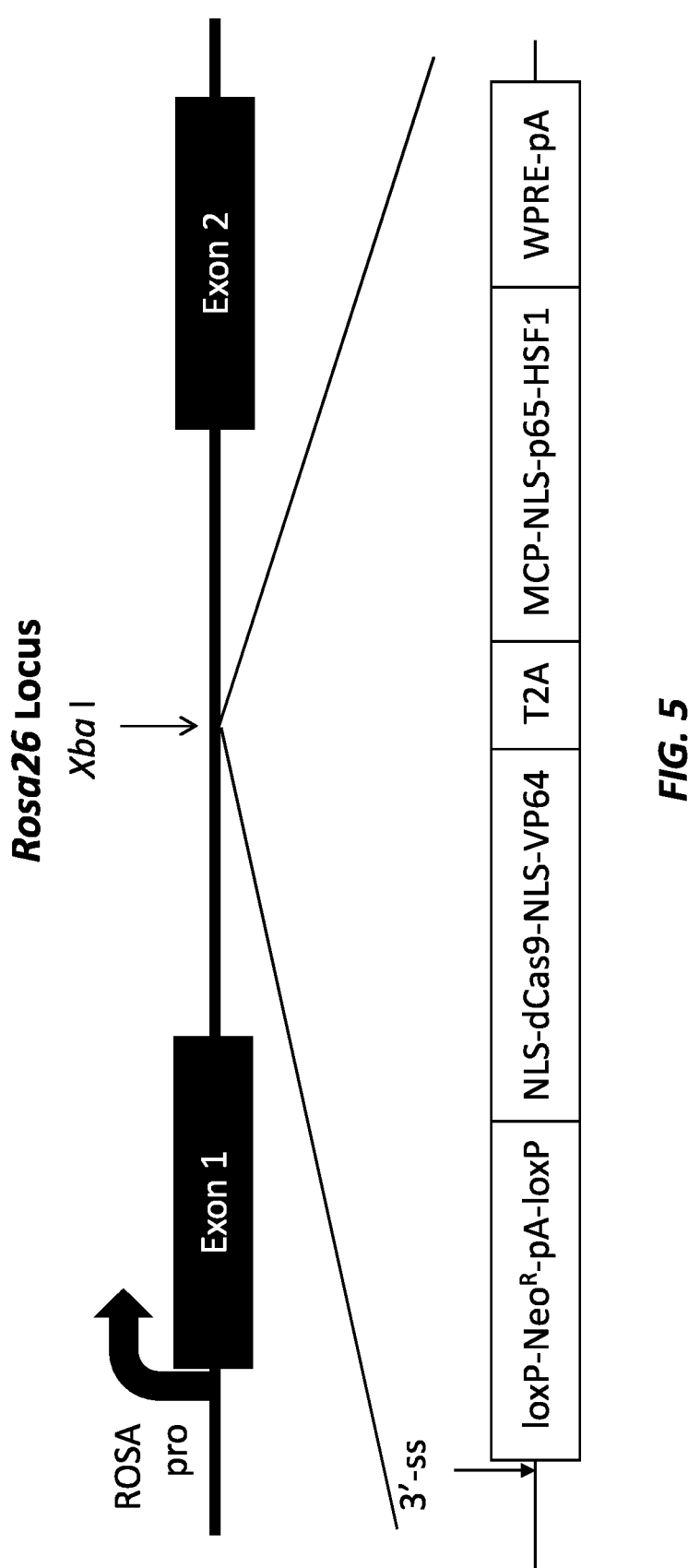
FIG. 5 (not to scale) shows a general schematic for targeting the LSL-SAM allele from FIG. 4A into the first intron of the Rosa26 (R26) locus.

For example, the Rosa26 locus and its equivalent in humans offer an open chromatin configuration in all tissues and is ubiquitously expressed during embryonic development and in adults. See, e.g., Zambrowicz et al. (1997) *Proc. Natl. Acad. Sci. USA* 94:3789-3794, herein incorporated by reference in its entirety for all purposes. In addition, the Rosa26 locus can be targeted with high efficiency, and disruption of the Rosa26 gene produces no overt phenotype. Other examples of safe harbor loci include CCR5, HPRT, AAVS1, and albumin. See, e.g., U.S. Pat. Nos. 7,888,121; 7,972,854; 7,914,796; 7,951,925; 8,110,379; 8,409,861; 8,586,526; and US Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960; and 2013/0122591, each of which is herein incorporated by reference in its entirety for all purposes. Biallelic targeting of safe harbor loci such as the Rosa26 locus has no negative consequences, so different genes or reporters can be targeted to the two Rosa26 alleles. In one example, an expression cassette is integrated into an intron of the Rosa26 locus, such as the first intron of the Rosa26 locus. See, e.g., FIG. 5.

Expression cassettes integrated into a target genomic locus can be operably linked to an endogenous promoter at the target genomic locus or can be operably linked to an exogenous promoter that is heterologous to the target genomic locus. In one example, a chimeric Cas protein expression cassette, chimeric adaptor protein expression cassette, or synergistic activation mediator (SAM) expression cassette is integrated into a target genomic locus (e.g., the Rosa26 locus) and is operably linked to the endogenous promoter at the target genomic locus (e.g., the Rosa26 promoter). In another example, a guide RNA expression cassette is integrated into a target genomic locus (e.g., the Rosa26 locus) and is operably linked to one or more heterologous promoters (e.g., U6 promoter(s), such as a different U6 promoter upstream of each guide RNA coding sequence).

IV. Methods of Using Non-Human Animals Comprising a Humanized MYOC Locus

Various methods are provided for using the non-human animals and non-human animal cells comprising a humanized MYOC locus (e.g., comprising a Y437H mutation) as described elsewhere herein. Such methods can be, for example, for increasing MYOC expression, increasing intraocular pressure, modeling glaucoma, or assessing or optimizing delivery or efficacy of human-MYOC-targeting reagents (e.g., therapeutic molecules or complexes) or candidate glaucoma therapeutic agents in vivo or ex vivo or in vitro. Because the non-human animals and non-human animal cells comprise a humanized MYOC locus, the non-human animals and non-human animal cells will more accurately reflect the efficacy of a human-MYOC-targeting reagent. Such non-human animals and non-human animal cells are particularly useful for testing genome-editing reagents designed to target the human MYOC gene because the non-human animals disclosed herein comprise humanized endogenous MYOC loci rather than transgenic insertions of human MYOC sequence at random genomic loci, and the humanized endogenous MYOC loci comprise corresponding human genomic MYOC sequence from both coding and non-coding regions (e.g., from both exonic and intronic regions) rather than an artificial cDNA sequence. Such non-human animals are also particularly useful for testing candidate glaucoma therapeutic agents because the non-human animals disclosed herein show a phenotype of elevated intraocular pressure that reflects the phenotype observed in glaucoma patients.

A. Methods of Increasing Expression of MYOC, Increasing Intraocular Pressure, or Modeling Glaucoma Various methods are provided for increasing expression of MYOC (e.g., human MYOC), increasing intraocular pressure, or modeling glaucoma in vivo using non-human animals comprising a humanized MYOC locus (e.g., comprising a Y437H mutation) and a SAM expression cassette as described elsewhere herein. Such methods for increasing MYOC expression, increasing intraocular pressure, or modeling glaucoma can comprise administering to the non-human animal one or more guide RNAs or one or more DNAs encoding one or more SAM guide RNAs as described elsewhere herein, thereby increasing expression of MYOC. The methods can increase MYOC mRNA expression and/or protein expression. Such methods for increasing MYOC expression can also be for increasing MYOC expression in a non-human animal cell by administering to the non-human animal cell one or more guide RNAs or one or more DNAs encoding one or more SAM guide RNAs as described elsewhere herein.

Each of the one or more guide RNAs can comprise one or more adaptor-binding elements to which the chimeric adaptor protein can specifically bind, and each of the one or more guide RNAs forms a complex with the chimeric Cas protein and the chimeric adaptor protein and guides them to a target sequence within the humanized MYOC locus, thereby increasing expression of the humanized MYOC locus.

Such methods can further comprise measuring expression of a MYOC messenger RNA encoded by the humanized MYOC locus or measuring expression of a myocilin protein encoded by the humanized MYOC locus after administering the one or more guide RNAs or the one or more DNAs encoding the one or more guide RNAs.

In some methods, the human MYOC mRNA or protein expression is increased at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, or at least about 15-fold (e.g., at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold). In some methods, the human MYOC mRNA or protein expression is increased between at least about 2-fold and at least about 25-fold, between at least about 3-fold and at least about 25-fold, between at least about 4-fold and at least about 25-fold, between at least about 5-fold and at least about 25-fold, between at least about 6-fold and at least about 25-fold, between at least about 7-fold and at least about 25-fold, between at least about 8-fold and at least about 25-fold, between at least about 9-fold and at least about 25-fold, between at least about 10-fold and at least about 25-fold, between at least about 2-fold and at least about 20-fold, between at least about 2-fold and at least about 15-fold, or between at least about 10-fold and at least about 15-fold. The increased human MYOC mRNA or protein expression can be in the eye, in the limbal ring, in the retina, in the ciliary body, in the trabecular meshwork, or in the cornea. In a specific example, the increased expression is in the limbal ring.

In some methods, the non-human animal develops one or more signs or symptoms of glaucoma following adminis-tration of the one or more guide RNAs or the one or more DNAs encoding the one or more guide RNAs. Glaucoma is a chronic optic neuropathy characterized by progressive loss of retinal ganglion cell (RGC) axons, with the resultant irreversible loss of vision. A major risk factor for glaucoma is elevated intraocular pressure (IOP). Elevated IOP is caused by increased resistance to aqueous humor outflow through the structures of trabecular meshwork (TM). Aque-ous humor is made by ciliary body, circulates the anterior chamber, and drains through the network of TM. In most glaucoma cases, there is increased resistance to aqueous humor at the TM. Pathogenic MYOC mutant proteins aggre-gate intracellularly, leading to trabecular meshwork (TM) stress, elevated IOP, and glaucoma.

Such methods can further comprise measuring intraocular pressure (IOP) after administering the one or more guide RNAs or the one or more DNAs encoding the one or more guide RNAs. In one example, the method results in an IOP that is at least about 15, at least about 16, at least about 17, at least about 18, at least about 19, at least about 20, at least about 21, or at least about 22 mmHg (e.g., at least 15, at least 16, at least 17, at least 18, at least 19, at least 20, at least 21, or at least 22 mmHg). In one example, the method results in an IOP between about 15 and about 22, between about 16 and about 22, between about 17 and about 22, between about 18 and about 22, between about 19 and about 22, between about 15 and about 21, between about 15 and about 20, or between about 16 and about 21 mmHg (e.g., between 15 and 22, between 16 and 22, between 17 and 22, between 18 and 22, between 19 and 22, between 15 and 21, between 15 and 20, or between 16 and 21 mmHg).

In some methods, the IOP is increased relative to prior to administration of the one or more guide RNAs or the one or more DNAs encoding the one or more guide RNAs or relative to a control non-human animal (e.g., a non-human animal with a humanized MYOC locus as described herein but that has not administered the one or more guide RNAs, or a wild type non-human animal) by a certain amount. In one example, the IOP is increased by at least about 1, at least about 2, at least about 3, at least about 4, at least about 5, or at least about 6 mmHg (e.g., at least 1, at least 2, at least 3, at least 4, at least 5, or at least 6 mmHg). In one example, the IOP is increased by between about 1 and about 7, between about 2 and about 7, between about 3 and about 7, between about 4 and about 7, between about 5 and about 7, between about 1 and about 6, between about 2 and about 6, between about 3 and about 6, between about 4 and about 6, or between about 5 and about 6 mmHg (e.g., between 1 and 6, between 2 and 6, between 3 and 6, between 4 and 6, or between 5 and 6 mmHg).

The guide RNAs or the DNA encoding the guide RNAs can be administered (introduced into the cell or introduced into the animal such that the guide RNAs or the DNA gain access to the interior of cells in the non-human animal) in any form, in any delivery vehicle, and by any route of administration. For example, the administering of the one or more guide RNAs or the one or more DNAs encoding the one or more guide RNAs can, in some methods, comprise adenovirus-mediated delivery (e.g., recombinant adenovirus type 5 (Ad5)), lentivirus-mediated delivery, adeno-associ-ated virus (AAV)-mediated delivery, or lipid nanoparticle (LNP)-mediated delivery. In one example, the guide RNAs or the DNA encoding the guide RNAs are administered via LNP-mediated delivery (e.g., at a dose between about 0.1 mg/kg to about 2 mg/kg). In another example, the guide RNAs or the DNA encoding the guide RNAs are adminis-tered via AAV-mediated delivery (e.g., using an AAV with a serotype for delivery to the eye, such as recombinant AAV2.Y3F). The guide RNAs can be administered as RNA, or they can be administered as DNA. If administered as DNA, each guide-RNA-encoding sequence can be, in one example, operably linked to a different U6 promoter. The guide RNAs or the DNA encoding the guide RNAs can be administered by any suitable route of administration. In one example, the guide RNAs or the DNA encoding the guide RNAs can be administered via intravitreal injection or intracameral injection.

In some methods, the target sequences for the guide RNAs can comprise a regulatory sequence within the humanized MYOC locus. For example, the regulatory sequence can comprise a promoter or an enhancer. In some methods, the target sequences for the guide RNAs can be within 200 base pairs of the transcription start site of the genetically modified endogenous MYOC locus or can be within a region 200 base pairs upstream of the transcription start site and 1 base pair downstream of the transcription start site.

In some methods, the guide RNAs each comprise two adaptor-binding elements to which the chimeric adaptor protein can specifically bind. For example, a first adaptor-binding element can be within a first loop of each of the one or more guide RNAs, and a second adaptor-binding element can be within a second loop of each of the one or more guide RNAs. In a specific example, each guide RNA can be a single guide RNA comprising a CRISPR RNA (crRNA) portion fused to a transactivating CRISPR RNA (tracrRNA) portion, and the first loop is the tetraloop corresponding to residues 13-16 of SEQ ID NO: 77, 79, 81, or 82, and the second loop is the stem loop 2 corresponding to residues 53-56 of SEQ ID NO: 77, 79, 81, or 82. In another specific example, the adaptor-binding element comprises the sequence set forth in SEQ ID NO: 52. In another specific example, each of the one or more guide RNAs comprises the sequence set forth in SEQ ID NO: 66, 68, 71, or 72.

In one example, the guide RNAs can target a sequence comprising the sequence set forth in any one of SEQ ID NOS: 90-95. Likewise, the guide RNAs can comprise the sequence set forth in any one of SEQ ID NOS: 96-101. In another example, the guide RNAs can target a sequence comprising the sequence set forth in any one of SEQ ID NOS: 93-94. Likewise, the guide RNAs can comprise the sequence set forth in any one of SEQ ID NOS: 99-100. In another example, the guide RNAs can target a sequence comprising the sequence set forth in SEQ ID NO: 93. Likewise, the guide RNA can comprise the sequence set forth in SEQ ID NO: 99.

In some methods, the one or more guide RNAs comprise multiple guide RNAs that target the humanized MYOC locus (e.g., at least two or at least three guide RNAs that target the humanized MYOC locus).

B. Methods of Testing Efficacy of Human-MYOC-Targeting Reagents or Candidate Glaucoma Therapeutic Agents Various methods are provided for assessing delivery or efficacy of human-MYOC-targeting reagents or candidate glaucoma therapeutic agents in vivo or ex vivo or in vitro using non-human animals or non-human animal cells comprising a humanized MYOC locus (e.g., comprising a Y437H mutation) as described elsewhere herein. Such methods can comprise: (a) introducing into the non-human animal a human-MYOC-targeting reagent or a candidate glaucoma therapeutic agent; and (b) assessing the activity of the human-MYOC-targeting reagent or candidate therapeutic agent. Likewise, such methods can comprise: (a) introducing into the non-human animal cell a human-MYOC-targeting reagent or a candidate glaucoma therapeutic agent; and (b) assessing the activity of the human-MYOC-targeting reagent or candidate therapeutic agent. The assessing can be, for example, compared to a control non-human animal or non-human animal cell comprising the humanized MYOC locus that was not administered the human-MYOC-targeting reagent or candidate glaucoma therapeutic agent or compared to the non-human animal or non-human animal cell prior to administration of the human-MYOC-targeting reagent or candidate glaucoma therapeutic agent.

In methods in which the non-human animals or non-human animal cells also comprise CRISPR/Cas synergistic activation mediator system components, such methods can further comprise administering one or more SAM guide RNAs or one or more DNAs encoding one or more SAM guide RNAs as described elsewhere herein to the non-human animal or non-human animal cell prior to step (a), wherein each of the one or more guide RNAs comprises one or more adaptor-binding elements to which the chimeric adaptor protein can specifically bind, and wherein each of the one or more guide RNAs forms a complex with the chimeric Cas protein and the chimeric adaptor protein and guides them to a target sequence within the humanized MYOC locus, thereby increasing expression of the humanized MYOC locus. If the assessing step is performed compared to a control non-human animal or non-human animal cell that was not administered the human-MYOC-targeting reagent or candidate glaucoma therapeutic agent, the methods can further comprise administering the one or more guide RNAs or the one or more DNAs encoding one or more SAM guide RNAs as described elsewhere herein to the control non-human animal or non-human animal cell.

In methods further comprising administering one or more SAM guide RNAs or one or more DNAs encoding one or more SAM guide RNAs as described elsewhere herein to the non-human animal or non-human animal cell prior to step (a), any suitable amount of time can take place between the step of administering one or more SAM guide RNAs or one or more DNAs encoding one or more SAM guide RNAs and the step of administering the human-MYOC-targeting reagent or candidate glaucoma therapeutic agent. In one example, the human-MYOC-targeting reagent or candidate glaucoma therapeutic agent can be administered at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days, at least about 25 days, or at least about 30 days after administering the one or more guide RNAs or the one or more DNAs encoding the one or more guide RNAs. In another example, the human-MYOC-targeting reagent or candidate glaucoma therapeutic agent is administered about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 15 days, about 1 day to about 20 days, about 1 day to about 25 days, or about 1 day to about 30 days after administering the one or more guide RNAs or the one or more DNAs encoding the one or more guide RNAs. In another example, the human-MYOC-targeting reagent or candidate glaucoma therapeutic agent is administered about 1 day to about 30 days, about 2 days to about 30 days, about 3 days to about 30 days, about 4 days to about 30 days, about 5 days to about 30 days, about 6 days to about 30 days, about 7 days to about 30 days, about 8 days to about 30 days, about 9 days to about 30 days, about 10 days to about 30 days, about 15 days to about 30 days, about 20 days to about 30 days, or about 25 days to about 30 days after administering the one or more guide RNAs or the one or more DNAs encoding the one or more guide RNAs. In another example, the human-MYOC-targeting reagent or candidate glaucoma therapeutic agent can be administered at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, or at least about 15 weeks after administering the one or more guide RNAs or the one or more DNAs encoding the one or more guide RNAs. In another example, the human-MYOC-targeting reagent or candidate glaucoma therapeutic agent is administered about 1 week to about 2 weeks, about 1 week to about 3 weeks, about 1 week to about 4 weeks, about 1 week to about 5 weeks, about 1 week to about 6 weeks, about 1 week to about 7 weeks, about 1 week to about 8 weeks, about 1 week to about 9 weeks, about 1 week to about 10 weeks, or about 1 week to about 15 weeks after administering the one or more guide RNAs or the one or more DNAs encoding the one or more guide RNAs. In another example, the human-MYOC-targeting reagent or candidate glaucoma therapeutic agent is administered about 1 week to about 15 weeks, about 2 weeks to about 15 weeks, about 3 weeks to about 15 weeks, about 4 weeks to about 15 weeks, about 5 weeks to about 15 weeks, about 6 weeks to about 15 weeks, about 7 weeks to about 15 weeks, about 8 weeks to about 15 weeks, about 9 weeks to about 15 weeks, or about 10 weeks to about 15 weeks after administering the one or more guide RNAs or the one or more DNAs encoding the one or more guide RNAs.

Such methods can further comprise measuring expression of a MYOC messenger RNA encoded by the humanized MYOC locus or measuring expression of a myocilin protein encoded by the humanized MYOC locus after administering the one or more guide RNAs or the one or more DNAs encoding the one or more guide RNAs and before administering the human-MYOC-targeting reagent or candidate glaucoma therapeutic agent. In one example, the human-MYOC-targeting reagent or candidate glaucoma therapeutic agent is not administered until expression of MYOC mRNA or myocilin protein encoded by the humanized MYOC locus are increased.

In some methods, the human-MYOC-targeting reagent or candidate glaucoma therapeutic agent is not administered until increased human MYOC mRNA or protein expression relative to prior to administration of the one or more guide RNAs or the one or more DNAs encoding the one or more guide RNAs or relative to a control non-human animal or non-human animal cell (e.g., a non-human animal or non-human animal cell with a humanized MYOC locus as described herein but that has not administered the one or more guide RNAs) is observed. In some non-human animals or non-human animal cells, the human-MYOC-targeting reagent or candidate glaucoma therapeutic agent is not administered until human MYOC mRNA or protein expression is increased at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, or at least about 15-fold (e.g., at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold). In some non-human animals or non-human animal cells, the human-MYOC-targeting reagent or candidate glaucoma therapeutic agent is not administered until human MYOC mRNA or protein expression is increased between at least about 2-fold and at least about 25-fold, between at least about 3-fold and at least about 25-fold, between at least about 4-fold and at least about 25-fold, between at least about 5-fold and at least about 25-fold, between at least about 6-fold and at least about 25-fold, between at least about 7-fold and at least about 25-fold, between at least about 8-fold and at least about 25-fold, between at least about 9-fold and at least about 25-fold, between at least about 10-fold and at least about 25-fold, between at least about 2-fold and at least about 20-fold, between at least about 2-fold and at least about 15-fold, or between at least about 10-fold and at least about 15-fold. The increased human MYOC mRNA or protein expression relative to a control non-human animal can be in the eye, in the limbal ring, in the retina, in the ciliary body, in the trabecular meshwork, or in the cornea. In a specific example, the increased expression is in the limbal ring.

In some methods, the human-MYOC-targeting reagent or candidate glaucoma therapeutic agent until one or more signs or symptoms of glaucoma are observed. Glaucoma is a chronic optic neuropathy characterized by progressive loss of retinal ganglion cell (RGC) axons, with the resultant irreversible loss of vision. A major risk factor for glaucoma is elevated intraocular pressure (IOP). Elevated IOP is caused by increased resistance to aqueous humor outflow through the structures of trabecular meshwork (TM). Aqueous humor is made by ciliary body, circulates the anterior chamber, and drains through the network of TM. In most glaucoma cases, there is increased resistance to aqueous humor at the TM. Pathogenic MYOC mutant proteins aggregate intracellularly, leading to trabecular meshwork (TM) stress, elevated IOP, and glaucoma.

Such methods can further comprise measuring intraocular pressure (IOP) after administering the one or more guide RNAs or the one or more DNAs encoding the one or more guide RNAs and before administering the human-MYOC-targeting reagent or candidate glaucoma therapeutic agent. In one example, the human-MYOC-targeting reagent or candidate glaucoma therapeutic agent is not administered until IOP reaches a certain level. In one example, the human-MYOC-targeting reagent or candidate glaucoma therapeutic agent is not administered until IOP is at least about 15, at least about 16, at least about 17, at least about 18, at least about 19, at least about 20, at least about 21, or at least about 22 mmHg (e.g., at least 15, at least 16, at least 17, at least 18, at least 19, at least 20, at least 21, or at least 22 mmHg). In one example, the human-MYOC-targeting reagent or candidate glaucoma therapeutic agent is not administered until IOP is between about 15 and about 22, between about 16 and about 22, between about 17 and about 22, between about 18 and about 22, between about 19 and about 22, between about 15 and about 21, between about 15 and about 20, or between about 16 and about 21 mmHg (e.g., between 15 and 22, between 16 and 22, between 17 and 22, between 18 and 22, between 19 and 22, between 15 and 21, between 15 and 20, or between 16 and 21 mmHg).

Such methods can further comprise measuring intraocular pressure (IOP) after administering the one or more guide RNAs or the one or more DNAs encoding the one or more guide RNAs and before administering the human-MYOC-targeting reagent or candidate glaucoma therapeutic agent. In one example, the human-MYOC-targeting reagent or candidate glaucoma therapeutic agent is not administered until IOP is increased relative to prior to administration of the one or more guide RNAs or the one or more DNAs encoding the one or more guide RNAs or relative to a control non-human animal (e.g., a non-human animal with a humanized MYOC locus as described herein but that has not administered the one or more guide RNAs, or a wild type non-human animal). In one example, the human-MYOC-targeting reagent or candidate glaucoma therapeutic agent is not administered until IOP is at least about 1, at least about 2, at least about 3, at least about 4, at least about 5, or at least about 6 mmHg above a control baseline (e.g., at least 1, at least 2, at least 3, at least 4, at least 5, or at least 6 mmHg). In one example, the human-MYOC-targeting reagent or candidate glaucoma therapeutic agent is not administered until IOP is between about 1 and about 7, between about 2 and about 7, between about 3 and about 7, between about 4 and about 7, between about 5 and about 7, between about 1 and about 6, between about 2 and about 6, between about 3 and about 6, between about 4 and about 6, or between about 5 and about 6 mmHg above a control baseline (e.g., between 1 and 6, between 2 and 6, between 3 and 6, between 4 and 6, or between 5 and 6 mmHg). The control baseline can be, for example, the IOP in a non-human animal with a humanized MYOC locus as described herein but that has not administered the one or more SAM guide RNAs, or it can be the IOP in wild type non-human animal, or it can be the IOP in a non-human animal with a humanized MYOC locus as described herein prior to administration of the one or more SAM guide RNAs.

The guide RNAs or the DNA encoding the guide RNAs can be administered (introduced into the cell or introduced into the animal such that the guide RNAs or the DNA gain access to the interior of cells in the non-human animal) in any form, in any delivery vehicle, and by any route of administration. For example, the administering of the one or more guide RNAs or the one or more DNAs encoding the one or more guide RNAs can, in some methods, comprise adenovirus-mediated delivery (e.g., recombinant adenovirus type 5 (Ad5)), lentivirus-mediated delivery, adeno-associated virus (AAV)-mediated delivery, or lipid nanoparticle (LNP)-mediated delivery. In one example, the guide RNAs or the DNA encoding the guide RNAs are administered via LNP-mediated delivery (e.g., at a dose between about 0.1 mg/kg to about 2 mg/kg). In another example, the guide RNAs or the DNA encoding the guide RNAs are administered via AAV-mediated delivery (e.g., using an AAV with a serotype for delivery to the eye, such as recombinant AAV2.Y3F). The guide RNAs can be administered as RNA, or they can be administered as DNA. If administered as DNA, each guide-RNA-encoding sequence can be, in one example, operably linked to a different U6 promoter. The guide RNAs or the DNA encoding the guide RNAs can be administered by any suitable route of administration. In one example, the guide RNAs or the DNA encoding the guide RNAs can be administered via intravitreal injection or intracameral injection.

In some methods, the target sequences for the guide RNAs can comprise a regulatory sequence within the humanized MYOC locus. For example, the regulatory sequence can comprise a promoter or an enhancer. In some methods, the target sequences for the guide RNAs can be within 200 base pairs of the transcription start site of the genetically modified endogenous MYOC locus or can be within a region 200 base pairs upstream of the transcription start site and 1 base pair downstream of the transcription start site.

In some methods, the guide RNAs each comprise two adaptor-binding elements to which the chimeric adaptor protein can specifically bind. For example, a first adaptor-binding element can be within a first loop of each of the one or more guide RNAs, and a second adaptor-binding element can be within a second loop of each of the one or more guide RNAs. In a specific example, each guide RNA can be a single guide RNA comprising a CRISPR RNA (crRNA) portion fused to a transactivating CRISPR RNA (tracrRNA) portion, and the first loop is the tetraloop corresponding to residues 13-16 of SEQ ID NO: 77, 79, 81, or 82, and the second loop is the stem loop 2 corresponding to residues 53-56 of SEQ ID NO: 77, 79, 81, or 82. In another specific example, the adaptor-binding element comprises the sequence set forth in SEQ ID NO: 52. In another specific example, each of the one or more guide RNAs comprises the sequence set forth in SEQ ID NO: 66, 68, 71, or 72.

In one example, the guide RNAs can target a sequence comprising the sequence set forth in any one of SEQ ID NOS: 90-95. Likewise, the guide RNAs can comprise the sequence set forth in any one of SEQ ID NOS: 96-101. In another example, the guide RNAs can target a sequence comprising the sequence set forth in any one of SEQ ID NOS: 93-94. Likewise, the guide RNAs can comprise the sequence set forth in any one of SEQ ID NOS: 99-100. In another example, the guide RNAs can target a sequence comprising the sequence set forth in SEQ ID NO: 93. Likewise, the guide RNA can comprise the sequence set forth in SEQ ID NO: 99.

In some methods, the one or more guide RNAs comprise multiple guide RNAs that target the humanized MYOC locus (e.g., at least two or at least three guide RNAs that target the humanized MYOC locus).

The human-MYOC-targeting reagent can be a human-MYOC-targeting antibody or antigen-binding protein or any other large molecule or small molecule that targets human myocilin protein. Alternatively, the human-MYOC-targeting reagent can be any biological or chemical agent that targets the human MYOC locus (the human MYOC gene), the human MYOC mRNA, or the human myocilin protein. Likewise, the candidate glaucoma therapeutic agent can be an antibody or antigen-binding protein or any other large molecule or small molecule. Alternatively, the candidate glaucoma therapeutic agent can be any biological or chemical agent. Examples of human-MYOC-targeting reagents or candidate glaucoma therapeutic agents are disclosed elsewhere herein.

A candidate glaucoma therapeutic agent can be a known glaucoma therapeutic agent, a putative glaucoma therapeutic agent, or agent being screened for glaucoma therapeutic activity. In one example, a candidate glaucoma therapeutic agent can be an agent that suppresses aqueous humor formation or increases outflow of aqueous humor. One example is timolol (a beta blocker that suppresses aqueous humor formation). Another example is RHOPRESSA® (a ROCK inhibitor that increases outflow of aqueous humor).

In one example, a candidate glaucoma therapeutic agent can be an ANGPTL7-targeting reagent. The ANGPTL7-targeting reagent can be, for example, a human-ANGPTL7-targeting reagent or a mouse-ANGPTL7-targeting reagent. An ANGPTL7-targeting reagent can be any reagent that targets an ANGPTL7 protein, an ANGPTL7 gene, or an ANGPTL7mRNA. An ANGPTL7-targeting reagent can be, for example, a known ANGPTL7-targeting reagent, can be a putative ANGPTL7-targeting reagent (e.g., candidate reagents designed to target ANGPTL7), or can be a reagent being screened for ANGPTL7-targeting activity.

Angiopoietin-related protein 7 (also known as angiopoietin-like factor, angiopoietin-like protein 7, cornea-derived transcript 6 protein, ANGPTL7, ANGX, and CDT6) is encoded by the ANGPTL7 gene (also known as CDT6). ANGPTL7 is a secreted glycoprotein (49-55 kDa) of the angiopoietin-related family, first discovered in the stromal layer of the cornea, with a role in the formation and organization of the extracellular matrix. ANGPTL7 mRNA and/or protein are abundantly expressed in keratocytes and is involved in maintaining corneal avascularity and transparency as a negative regulator of angiogenesis. ANGPTL7 expression is upregulated by dexamethasone (DEX) in human trabecular meshwork cells TM, the eye tissue associated with regulation of aqueous humor outflow facility. Genome-wide association studies (GWAS) have revealed that certain rare protein-altering variants in ANGPTL7 (including Gln175His and Arg220Cys) have a lower glaucoma risk, suggesting a protective mechanism conferred by lower IOP.

Human ANGPTL7 maps to 1p36.22 on chromosome 1 (NCBI RefSeq Gene ID 10218; Assembly GRCh38.p14 (GCF_000001405.40); location NC_000001.11 (11189355 . . . 11195981)). The wild type human angiopoietin-related protein 7 has been assigned UniProt accession number O43827 and NCBI Accession No. NP_066969.1.

Mouse Angptl7 maps to 4; 4 E2 on chromosome 4 (NCBI RefSeq Gene ID 654812; Assembly GRCm39 (GCF_000001635.27); location NC_000070.7 (148579737 . . . 148584919, complement)). The wild type mouse angiopoietin-related protein 7 has been assigned UniProt accession number Q8R1Q3 and NCBI Accession No. NP_001034643.1.

Rat Angptl7 maps to 5q36 on chromosome 5 (NCBI RefSeq Gene ID 102552055; Assembly mRatBN7.2 (GCF_015227675.2); location NC_051340.1 (158932094 . .

. 158937597, complement)). The wild type rat angiopoietin-related protein 7 protein has been assigned UniProt accession number D3ZDK4 and NCBI Accession No. XP_006239486.1.

For example, an ANGPTL7-targeting reagent can be an antigen-binding protein targeting an epitope of an ANGPTL7 protein (e.g., a human ANGPTL7 protein). Likewise, a candidate glaucoma therapeutic agent can be an antigen-binding protein. The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes). Other human-MYOC-targeting reagents include small molecules targeting a human myocilin protein. Likewise, other candidate glaucoma therapeutic agents include small molecules targeting any suitable target.

Other ANGPTL7-targeting reagents (e.g., human-ANGPTL7-targeting reagents) can include genome editing reagents such as a nuclease agent (e.g., a Clustered Regularly Interspersed Short Palindromic Repeats (CRISPR)/CRISPR-associated (Cas) (CRISPR/Cas) nuclease, a zinc finger nuclease (ZFN), or a Transcription Activator-Like Effector Nuclease (TALEN)) that cleaves a recognition site within the ANGPTL7 gene. Likewise, an ANGPTL7-targeting reagents can be an exogenous donor nucleic acid (e.g., a targeting vector or single-stranded oligodeoxynucleotide (ssODN)) designed to recombine with the ANGPTL7 gene. Likewise, other candidate glaucoma therapeutic agents include genome editing reagents such as nuclease agents or exogenous donor nucleic acids.

Other ANGPTL7-targeting reagents (e.g., human-ANGPTL7-targeting reagents) can include RNAi agents. Likewise, other candidate glaucoma therapeutic agents can include RNAi agents. An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to: short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA. Likewise, other candidate glaucoma therapeutic agents can include RNAi agents.

Other ANGPTL7-targeting reagents (e.g., human-ANGPTL7-targeting reagents) can include antisense oligonucleotides (ASOs). Likewise, other candidate glaucoma therapeutic agents can include ASOs. Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H. Examples of human-MYOC-targeting RNAi agents or antisense oligonucleotides are known. See, e.g., Ackermann et al. (2012) *Amyloid Suppl* 1:43-44 and Coelho et al. (2013) *N. Engl. J. Med.* 369(9): 819-829, each of which is herein incorporated by reference in its entirety for all purposes. Likewise, other candidate glaucoma therapeutic agents can include ASOs.

Other ANGPTL7-targeting reagents (e.g., human-ANGPTL7-targeting reagents) include small-molecule reagents. Likewise, other candidate glaucoma therapeutic agents can include small-molecule reagents.

Such human-MYOC-targeting reagents or candidate glaucoma therapeutic agents can be administered by any delivery method/vehicle (e.g., adenovirus (e.g., recombinant Ad5), lentivirus, AAV, LNP, or injection) and by any route of administration (e.g., intravitreal injection or intracameral injection). Means of delivering complexes and molecules and routes of administration are disclosed in more detail elsewhere herein. In particular methods, the reagents delivered via AAV-mediated delivery. For example, AAV2.Y3F can be used to target the eye. In other particular methods, the reagents are delivered by LNP-mediated delivery. The dose can be any suitable dose.

Methods for assessing activity of the human-MYOC-targeting reagent are well-known and are provided elsewhere herein. Assessment of activity can be in any cell type, any tissue type, or any organ type as disclosed elsewhere herein. In some methods, assessment of activity is in eye cells or in the eye.

If the human-MYOC-targeting reagent is a genome editing reagent (e.g., a nuclease agent), such methods can comprise assessing modification of the humanized MYOC locus. As one example, the assessing can comprise measuring non-homologous end joining (NHEJ) activity at the humanized MYOC locus. This can comprise, for example, measuring the frequency of insertions or deletions within the humanized MYOC locus. For example, the assessing can comprise sequencing the humanized MYOC locus in one or more cells isolated from the non-human animal (e.g., next-generation sequencing). Assessment can comprise isolating a target organ or tissue (e.g., eye) from the non-human animal and assessing modification of humanized MYOC locus in the target organ or tissue. Assessment can also comprise assessing modification of humanized MYOC locus in two or more different cell types within the target organ or tissue. Similarly, assessment can comprise isolating a non-target organ or tissue (e.g., two or more non-target organs or tissues) from the non-human animal and assessing modification of humanized MYOC locus in the non-target organ or tissue. Likewise, if the candidate glaucoma therapeutic agent is a genome editing reagent (e.g., a nuclease agent), such methods can comprise assessing modification of the target locus.

Such methods can also comprise measuring expression levels of the mRNA produced by the humanized MYOC locus, or by measuring expression levels of the protein encoded by the humanized MYOC locus. For example, protein levels can be measured in a particular cell, tissue, or organ type (e.g., eye). Methods for assessing expression of MYOC mRNA or myocilin protein expressed from the humanized MYOC locus are provided elsewhere herein and are well-known.

As one specific example, if the human-MYOC-targeting reagent is a genome editing reagent (e.g., a nuclease agent), percent editing (e.g., total number of insertions or deletions observed over the total number of sequences read in the PCR reaction from a pool of lysed cells) at the humanized MYOC locus can be assessed (e.g., in eye cells). Likewise, if the candidate glaucoma therapeutic agent is a genome editing reagent (e.g., a nuclease agent), percent editing (e.g., total number of insertions or deletions observed over the total number of sequences read in the PCR reaction from a pool of lysed cells) at the target locus can be assessed (e.g., in eye cells).

The various methods provided above for assessing activity in vivo can also be used to assess the activity of human-MYOC-targeting reagents or candidate glaucoma therapeutic agents ex vivo (e.g., in an eye comprising a humanized MYOC locus) or in vitro (e.g., in a cell comprising a humanized MYOC locus) as described elsewhere herein.

In some methods, the human-MYOC-targeting reagent is a nuclease agent, such as a CRISPR/Cas nuclease agent, that targets the human MYOC gene. Such methods can comprise, for example: (a) introducing into the non-human animal a nuclease agent (or a nucleic acid encoding the nuclease agent) designed to cleave the human MYOC gene (e.g., Cas protein such as Cas9 (or a nucleic acid encoding Cas9) and a guide RNA (or a DNA encoding the guide RNA) designed to target a guide RNA target sequence in the human MYOC gene); and (b) assessing modification of the humanized MYOC locus.

In the case of a CRISPR/Cas nuclease, for example, modification of the humanized MYOC locus will be induced when the guide RNA forms a complex with the Cas protein and directs the Cas protein to the humanized MYOC locus, and the Cas/guide RNA complex cleaves the guide RNA target sequence, triggering repair by the cell (e.g., via non-homologous end joining (NHEJ) if no donor sequence is present).

Optionally, two or more guide RNAs (or DNAs encoding the guide RNAs) can be introduced, each designed to target a different guide RNA target sequence within the human MYOC gene. For example, two guide RNAs can be designed to excise a genomic sequence between the two guide RNA target sequences. Modification of the humanized MYOC locus will be induced when the first guide RNA forms a complex with the Cas protein and directs the Cas protein to the humanized MYOC locus, the second guide RNA forms a complex with the Cas protein and directs the Cas protein to the humanized MYOC locus, the first Cas/guide RNA complex cleaves the first guide RNA target sequence, and the second Cas/guide RNA complex cleaves the second guide RNA target sequence, resulting in excision of the intervening sequence.

Optionally, an exogenous donor nucleic acid capable of recombining with and modifying a human MYOC gene is also introduced into the non-human animal. Optionally, the nuclease agent or Cas protein can be tethered to the exogenous donor nucleic acid as described elsewhere herein. Modification of the humanized MYOC locus will be induced, for example, when the guide RNA forms a complex with the Cas protein and directs the Cas protein to the humanized MYOC locus, the Cas/guide RNA complex cleaves the guide RNA target sequence, and the humanized MYOC locus recombines with the exogenous donor nucleic acid to modify the humanized MYOC locus. The humanized MYOC locus can then be repaired with the exogenous donor nucleic acid, for example, via homology-directed repair (HDR) or via NHEJ-mediated insertion. Any type of exogenous donor nucleic acid can be used, examples of which are provided elsewhere herein.

C. Methods of Optimizing Delivery or Efficacy of Human-MYOC-Targeting Reagent or Candidate Glaucoma Therapeutic Agents Various methods are provided for optimizing delivery of human-MYOC-targeting reagents or candidate glaucoma therapeutic agents to a non-human animal cell or non-human animal or optimizing the activity or efficacy of human-MYOC-targeting reagents or candidate glaucoma therapeutic agents in vivo. Such methods can comprise, for example: (a) performing the method of testing the efficacy of a human-MYOC-targeting reagent or candidate glaucoma therapeutic agent as described above a first time in a first non-human animal or first non-human animal cell; (b) changing a variable and performing the method a second time in a second non-human animal (i.e., of the same species) or a second cell with the changed variable; and (c) comparing the activity of the human-MYOC-targeting reagent or candidate glaucoma therapeutic agent in step (a) with the activity of the human-MYOC-targeting reagent or candidate glaucoma therapeutic agent in step (b), and selecting the method resulting in the higher activity.

Methods of measuring delivery, efficacy, or activity of human-MYOC-targeting reagents or candidate glaucoma therapeutic agents are disclosed elsewhere herein. For example, such methods can comprise measuring modification of the humanized MYOC locus. More effective modification of the humanized MYOC locus can mean different things depending on the desired effect within the non-human animal or non-human animal cell. For example, more effective modification of the humanized MYOC locus can mean one or more or all of higher levels of modification, higher precision, higher consistency, or higher specificity. Higher levels of modification (i.e., higher efficacy) of the humanized MYOC locus refers to a higher percentage of cells is targeted within a particular target cell type, within a particular target tissue, or within a particular target organ (e.g., eye). Higher precision refers to more precise modification of the humanized MYOC locus (e.g., a higher percentage of targeted cells having the same modification or having the desired modification without extra unintended insertions and deletions (e.g., NHEJ indels)). Higher consistency refers to more consistent modification of the humanized MYOC locus among different types of targeted cells, tissues, or organs if more than one type of cell, tissue, or organ is being targeted (e.g., modification of a greater number of cell types within the eye). If a particular organ is being targeted, higher consistency can also refer to more consistent modification throughout all locations within the organ (e.g., the eye). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the eye), there is less modification of cells in organs or tissues that are not intended targets).

Alternatively, such methods can comprise measuring expression of MYOC mRNA or myocilin protein. In one example, a more effective human-MYOC-targeting agent or candidate glaucoma therapeutic agent results in a greater decrease in MYOC mRNA or myocilin protein expression. Alternatively, such methods can comprise measuring myocilin activity. In one example, a more effective human-MYOC-targeting agent or candidate glaucoma therapeutic agent results in a greater decrease in myocilin activity.

Alternatively, such methods can comprise measuring one or more signs or symptoms of glaucoma. In one example, a more effective human-MYOC-targeting agent or candidate glaucoma therapeutic agent results in a greater decrease in the one or more signs or symptoms of glaucoma. For example, such methods can comprise measuring intraocular pressure. In one example, a more effective human-MYOC-targeting agent or candidate glaucoma therapeutic agent results in a greater decrease in intraocular pressure.

The variable that is changed can be any parameter. As one example, the changed variable can be the packaging or the delivery method/vehicle by which the human-MYOC-targeting reagent or reagents or candidate glaucoma therapeutic agent or agents are introduced into the cell or non-human animal. Examples of delivery methods/vehicles, such as LNP and AAV, are disclosed elsewhere herein. For example, the changed variable can be the AAV serotype. Alternatively, the changed variable can be the dose of AAV delivered (e.g., about $10^{11}$, about $10^{12}$, about $10^{13}$, or about $10^{14}$ vg/kg of body weight). Similarly, the administering can comprise LNP-mediated delivery, and the changed variable can be the LNP formulation. Alternatively, the administering can comprise LNP-mediated delivery, and the changed variable can be the dose of the LNP delivered (e.g., about 0.01 mg/kg, about 0.03 mg/kg, about 0.1 mg/kg, about 0.3 mg/kg, about 1 mg/kg, about 3 mg/kg, or about 10 mg/kg). As another example, the changed variable can be the route of administration for introduction of the human-MYOC-targeting reagent or reagents or candidate glaucoma therapeutic agent or agents into the cell or non-human animal. Examples of routes of administration, such as intravenous, intravitreal, intraparenchymal, and nasal instillation, are disclosed elsewhere herein.

As another example, the changed variable can be the concentration or amount of the human-MYOC-targeting reagent or reagents or candidate glaucoma therapeutic agent or agents introduced. As another example, the changed variable can be the concentration or the amount of one human-MYOC-targeting reagent or candidate glaucoma therapeutic agent or agents introduced (e.g., guide RNA, Cas protein, exogenous donor nucleic acid, RNAi agent, or ASO) relative to the concentration or the amount of another human-MYOC-targeting reagent or candidate glaucoma therapeutic agent introduced (e.g., guide RNA, Cas protein, exogenous donor nucleic acid, RNAi agent, or ASO).

As another example, the changed variable can be the timing of introducing the human-MYOC-targeting reagent or reagents or candidate glaucoma therapeutic agent or agents relative to the timing of assessing the activity or efficacy of the reagents. As another example, the changed variable can be the number of times or frequency with which the human-MYOC-targeting reagent or reagents or candidate glaucoma therapeutic agent or agents are introduced. As another example, the changed variable can be the timing of introduction of one human-MYOC-targeting reagent or candidate glaucoma therapeutic agent introduced (e.g., guide RNA, Cas protein, exogenous donor nucleic acid, RNAi agent, or ASO) relative to the timing of introduction of another human-MYOC-targeting reagent or candidate glaucoma therapeutic agent introduced (e.g., guide RNA, Cas protein, exogenous donor nucleic acid, RNAi agent, or ASO).

As another example, the changed variable can be the form in which the human-MYOC-targeting reagent or reagents or candidate glaucoma therapeutic agent or agents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. Likewise, RNAi agents and ASOs, for example, can comprise various combinations of modifications for stability, to reduce off-target effects, to facilitate delivery, and so forth.

As another example, the changed variable can be the human-MYOC-targeting reagent or reagents or candidate glaucoma therapeutic agent or agents that are introduced. For example, if the human-MYOC-targeting reagent or candidate glaucoma therapeutic agent comprises a guide RNA, the changed variable can be introducing a different guide RNA with a different sequence (e.g., targeting a different guide RNA target sequence). Similarly, if the human-MYOC-targeting reagent or candidate glaucoma therapeutic agent comprises an RNAi agent or an ASO, the changed variable can be introducing a different RNAi agent or ASO with a different sequence. Likewise, if the human-MYOC-targeting reagent or candidate glaucoma therapeutic agent comprises a Cas protein, the changed variable can be introducing a different Cas protein (e.g., introducing a different Cas protein with a different sequence, or a nucleic acid with a different sequence (e.g., codon-optimized) but encoding the same Cas protein amino acid sequence). Likewise, if the human-MYOC-targeting reagent or candidate glaucoma therapeutic agent comprises an exogenous donor nucleic acid, the changed variable can be introducing a different exogenous donor nucleic acid with a different sequence (e.g., a different insert nucleic acid or different homology arms (e.g., longer or shorter homology arms or homology arms targeting a different region of the human MYOC gene)).

In a specific example, the human-MYOC-targeting reagent or candidate glaucoma therapeutic agent comprises a Cas protein and a guide RNA designed to target a guide RNA target sequence in a human MYOC gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be the guide RNA modification pattern (e.g., a guide RNA with a modification is compared to a guide RNA without the modification).

In another specific example, the human-MYOC-targeting reagent or candidate glaucoma therapeutic agent comprises an RNAi agent or ASO agent targeting human MYOC. In such methods, the changed variable can be the RNAi agent or ASO agent sequence and/or the RNAi agent or ASO agent target sequence. In some such methods, the changed variable can be the RNAi agent or ASO agent modification pattern.

D. Human-MYOC-Targeting Reagents

A human-MYOC-targeting reagent can be any reagent that targets a human myocilin protein, a human MYOC gene, or a human MYOC mRNA. A human-MYOC-targeting reagent can be, for example, a known human-MYOC-targeting reagent, can be a putative human-MYOC-targeting reagent (e.g., candidate reagents designed to target human MYOC), or can be a reagent being screened for human-MYOC-targeting activity. Likewise, a candidate glaucoma therapeutic agent can be a known glaucoma therapeutic agent, a putative glaucoma therapeutic agent, or agent being screened for glaucoma therapeutic activity.

For example, a human-MYOC-targeting reagent can be an antigen-binding protein targeting an epitope of a human myocilin protein. Likewise, a candidate glaucoma therapeutic agent can be an antigen-binding protein. The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes). Other human-MYOC-targeting reagents include small molecules targeting a human myocilin protein. Likewise, other candidate glaucoma therapeutic agents include small molecules targeting any suitable target.

Other human-MYOC-targeting reagents can include genome editing reagents such as a nuclease agent (e.g., a Clustered Regularly Interspersed Short Palindromic Repeats (CRISPR)/CRISPR-associated (Cas) (CRISPR/Cas) nuclease, a zinc finger nuclease (ZFN), or a Transcription Activator-Like Effector Nuclease (TALEN)) that cleaves a recognition site within the human MYOC gene. Likewise, a human-MYOC-targeting reagent can be an exogenous donor nucleic acid (e.g., a targeting vector or single-stranded oligodeoxynucleotide (ssODN)) designed to recombine with the human MYOC gene. Likewise, other candidate glaucoma therapeutic agents include genome editing reagents such as nuclease agents or exogenous donor nucleic acids.

Other human-MYOC-targeting reagents can include RNAi agents. Likewise, other candidate glaucoma therapeutic agents can include RNAi agents. An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to: short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

Other human-MYOC-targeting reagents can include antisense oligonucleotides (ASOs). Likewise, other candidate glaucoma therapeutic agents can include ASOs. Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H. Examples of human-MYOC-targeting RNAi agents or antisense oligonucleotides are known. See, e.g., Ackermann et al. (2012) *Amyloid Suppl* 1:43-44 and Coelho et al. (2013) *N. Engl. J. Med.* 369(9): 819-829, each of which is herein incorporated by reference in its entirety for all purposes.

Other human-MYOC-targeting reagents include small-molecule reagents. Likewise, other candidate glaucoma therapeutic agents can include small-molecule reagents.

In one example, a candidate glaucoma therapeutic agent can be an agent that suppresses aqueous humor formation or increases outflow of aqueous humor. One example is timolol (a beta blocker that suppresses aqueous humor formation). Another example is RHOPRESSA® (a ROCK inhibitor that increases outflow of aqueous humor).

E. Administering Human-MYOC-Targeting Reagents or Candidate Glaucoma Therapeutic Agents and/or SAM Guide RNAs and/or Recombinase Expression Cassettes to Non-Human Animals or Non-Human Animal Cells The methods disclosed herein can comprise introducing into a non-human animal or non-human animal cell various molecules (e.g., human-MYOC-targeting reagents or candidate glaucoma therapeutic agents such as therapeutic molecules or complexes and/or SAM guide RNAs as described herein or DNA encoding SAM guide RNAs and/or recombinases or nucleic acids encoding recombinases), including nucleic acids, proteins, nucleic-acid-protein complexes, protein complexes, or small molecules. "Introducing" includes presenting to the non-human animal cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method/vehicle or different delivery methods/vehicles. Similarly, two or more of the components can be introduced into a non-human animal by the same route of administration or different routes of administration.

In some methods, components of a CRISPR/Cas system are introduced into a non-human animal or non-human animal cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs or RNAi agents or ASOs) introduced into the non-human animal or non-human animal cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of molecule (e.g., a nucleic acid or protein) into a non-human animal cell or non-human animal. Methods for introducing molecules into various cell types are known and include, for example, stable transfection methods, transient transfection methods, and virus-mediated methods.

Transfection protocols as well as protocols for introducing molecules into cells may vary. Non-limiting transfection methods include chemical-based transfection methods using liposomes; nanoparticles; calcium phosphate (Graham et al. (1973) *Virology* 52 (2): 456-67, Bacchetti et al. (1977)*Proc. Natl. Acad. Sci. U.S.A.* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. U.S.A.* 107:15022-15026 and Meyer et al. (2012) *Proc. Natl. Acad. Sci. U.S.A.* 109:9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids can also be accomplished by virus-mediated delivery, such as adenovirus-mediated delivery (e.g., recombinant Ad5), AAV-mediated delivery (e.g., recombinant AAV2.Y3F), or lentivirus-mediated delivery. Other exemplary viruses/viral vectors include retroviruses, vaccinia viruses, poxviruses, and herpes simplex viruses.

The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL. Other exemplary viral titers (e.g., AAV titers) include about $10^{12}$, about $10^{13}$, about $10^{14}$, about $10^{15}$, and about $10^{16}$ vector genomes (vg)/kg of body weight.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8. In a specific example, an AAV2.Y3F serotype is used.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Reports* 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

Exemplary dosing of LNPs includes, for example, about 0.1, about 0.25, about 0.3, about 0.5, about 1, about 2, about 3, about 4, about 5, about 6, about 8, or about 10 mg/kg (mpk) with respect to total RNA (e.g., Cas9 mRNA and gRNA) cargo content. In one example, LNP doses between about 0.01 mg/kg and about 10 mg/kg, between about 0.1 and about 10 mg/kg, or between about 0.01 and about 0.3 mg/kg can be used. For example, LNP doses of about 0.01, about 0.03, about 0.1, about 0.3, about 1, about 3, or about 10 mg/kg can be used.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically. In a specific example, administration in vivo is by intravitreal injection or intracameral injection.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can depend on the half-life of the administered molecules and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

F. Measuring Delivery, Activity, or Efficacy of Human-MYOC-Targeting Reagents or Candidate Glaucoma Therapeutic Agents In Vivo or Ex Vivo The methods disclosed herein can further comprise detecting or measuring activity of human-MYOC-targeting reagents or candidate glaucoma therapeutic agents.

If the human-MYOC-targeting reagent or candidate glaucoma therapeutic agent is a genome editing reagent (e.g., CRISPR/Cas designed to target the human MYOC locus), the measuring can comprise assessing the humanized MYOC locus for modifications. Various methods can be used to identify cells having a targeted genetic modification. The screening can comprise a quantitative assay for assessing modification-of-allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized MYOC locus in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-MYOC-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized MYOC locus comprising, affect expression of the humanized MYOC locus, prevent translation of the humanized MYOC mRNA, or clear the humanized myocilin protein, the measuring can comprise assessing humanized MYOC mRNA or protein expression. This measuring can be, for example, within the eye or particular cell types or regions within the eye.

Production of the humanized myocilin protein can be assessed by any known means. For example, expression can be assessed by measuring levels of the encoded mRNA in the eye of the non-human animal or levels of the encoded protein in the eye of the non-human animal using known assays. For example, the measuring can be to determine if the human-MYOC-targeting reagent or candidate glaucoma therapeutic agent reduces myocilin levels in the non-human animal.

Intraocular pressure can also be assessed by known means, and other phenotypes of glaucoma can be assessed by known means.

The assessing in a non-human animal can be in any cell type from any tissue or organ. For example, the assessment can be in multiple cell types from the same tissue or organ (e.g., eye) or in cells from multiple locations within the tissue or organ. This can provide information about which cell types within a target tissue or organ are being targeted or which sections of a tissue or organ are being reached by the human-MYOC-targeting reagent or candidate glaucoma therapeutic agent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

One example of an assay that can be used are the RNASCOPE™ and BASESCOPE™ RNA in situ hybridization (ISH) assays, which are methods that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe, and it can differentially detect single nucleotide edits and mutations in intact fixed tissue.

The assessment of any of these phenotypes can be at any age of non-human animal, such as at least about 1, at least about 2, at least about 3, at least about 4, at least about 5, at least about 6, at least about 7, at least about 8, at least about 9, at least about 10, at least about 11, or at least about 12 months of age.

The assessment of any of these phenotypes can be done in comparison to a control non-human animal. The control non-human animals can be, for example, the same age as the test non-human animal and/or the same sex as the test non-human animal. The assessment of any of these phenotypes can also be done in comparison to a control non-human animal that is identical to the test non-human animal except not treated with the human-MYOC-targeting reagent or candidate glaucoma therapeutic agent.

The assessment of any of these phenotypes can be in a single non-human animal and assessing changes in that non-human animal. Alternatively, the assessment can be in a population of non-human animals and comparing, for example, the percentage of non-human animals having a particular phenotype.

G. Measuring CRISPR/Cas-Induced Upregulation of Expression of Humanized MYOC Locus In Vivo The methods disclosed herein can further comprise assessing expression of the humanized MYOC locus or upregulation of the humanized MYOC locus by the synergistic activation mediator (SAM) systems disclosed herein.

For example, the method of assessing expression can comprise measuring expression or activity of the encoded MYOC mRNA and/or myocilin protein. For example, levels of the encoded MYOC mRNA or myocilin protein can be measured in the eye. Assays for measuring levels and activity of RNA and proteins are well known.

Assessing expression of the humanized MYOC locus in a non-human animal can be in any cell type from any tissue or organ. For example, expression of the humanized MYOC locus can be assessed in multiple cell types from the same tissue or organ or in cells from multiple locations within the tissue or organ. This can provide information about which cell types within a target tissue or organ are being targeted or which sections of a tissue or organ are being reached by the CRISPR/Cas and modified. As another example, expression of the humanized MYOC locus can be assessed in multiple types of tissue or in multiple organs. In methods in which a particular tissue or organ is being targeted, this can provide information about how effectively that tissue or organ is being targeted and whether there are off-target effects in other tissues or organs.

The assessment can be done in comparison to a control non-human animal. The control non-human animals can be, for example, the same age as the test non-human animal and/or the same sex as the test non-human animal. The control non-human animal can be a wild type animal, a non-human animal with a humanized MYOC locus as described herein but that has not administered the one or more SAM guide RNAs targeting the humanized MYOC locus, or it can be a non-human animal with a humanized MYOC locus as described herein but prior to administration of one or more SAM guide RNAs targeting the humanized MYOC locus.

V. Methods of Making Non-Human Animals Comprising a Humanized MYOC Locus and/or a Synergistic Activation Mediator (SAM) Expression Cassette Various methods are provided for making a non-human animal genome, non-human animal cell, or non-human animal comprising a humanized MYOC locus (e.g., comprising a Y437H mutation as disclosed elsewhere herein). Likewise, various methods are provided for making a humanized MYOC gene or locus (e.g., comprising the Y437H mutation) or for making a non-human animal genome or non-human animal cell comprising a humanized MYOC locus (e.g., comprising the Y437H mutation as disclosed elsewhere herein). Likewise, various methods are provided for making a non-human animal comprising a synergistic activation mediator (SAM) expression cassette (comprising a chimeric Cas protein coding sequence and a chimeric adaptor protein expression coding sequence) and a humanized MYOC locus (e.g., comprising a Y437H mutation as disclosed elsewhere herein). Any convenient method or protocol for producing a genetically modified organism is suitable for producing such a genetically modified non-human animal. See, e.g., Poueymirou et al. (2007) *Nat.*

*Biotechnol.* 25(1):91-99; U.S. Pat. Nos. 7,294,754; 7,576,259; 7,659,442; 8,816,150; 9,414,575; 9,730,434; and 10,039,269, each of which is herein incorporated by reference in its entirety for all purposes (describing mouse ES cells and the VELOCIMOUSE® method for making a genetically modified mouse). See also US 2014/0235933 A1, US 2014/0310828 A1, each of which is herein incorporated by reference in its entirety for all purposes (describing rat ES cells and methods for making a genetically modified rat). See also Cho et al. (2009) *Curr. Protoc. Cell. Biol.* 42:19.11.1-19.11.22 (doi: 10.1002/0471143030.cb1911s42) and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted MYOC locus.

For example, the method of producing a non-human animal comprising a humanized MYOC locus (e.g., comprising a Y437H mutation) can comprise: (1) providing a pluripotent cell (e.g., an embryonic stem (ES) cell such as a mouse ES cell or a rat ES cell) comprising the humanized MYOC locus (e.g., comprising a Y437H mutation); (2) introducing the genetically modified pluripotent cell into a non-human animal host embryo; and (3) gestating the host embryo in a surrogate mother.

As another example, the method of producing a non-human animal comprising a humanized MYOC locus (e.g., comprising a Y437H mutation) can comprise: (1) modifying the genome of a pluripotent cell (e.g., an embryonic stem (ES) cell such as a mouse ES cell or a rat ES cell) to comprise the humanized MYOC locus (e.g., comprising a Y437H mutation); (2) identifying or selecting the genetically modified pluripotent cell comprising the humanized MYOC locus (e.g., comprising a Y437H mutation); (3) introducing the genetically modified pluripotent cell into a non-human animal host embryo; and (4) gestating the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized MYOC locus (e.g., comprising a Y437H mutation) (and capable of transmitting the genetic modification through the germline).

Alternatively, the method of producing the non-human animals described elsewhere herein can comprise: (1) modifying the genome of a one-cell stage embryo to comprise the humanized MYOC locus (e.g., comprising a Y437H mutation) using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucle- ation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by appli- cation of a DC electrical pulse across the contact/fusion plane (electrofusion), by exposure of the cells to fusion- promoting chemicals, such as polyethylene glycol, or by way of an inactivated virus, such as the Sendai virus. A reconstituted cell can be activated by electrical and/or non- electrical means before, during, and/or after fusion of the nuclear donor and recipient oocyte. Activation methods include electric pulses, chemically induced shock, penetra- tion by sperm, increasing levels of divalent cations in the oocyte, and reducing phosphorylation of cellular proteins (as by way of kinase inhibitors) in the oocyte. The activated reconstituted cells, or embryos, can be cultured in well- known media and then transferred to the womb of an animal. See, e.g., US 2008/0092249, WO 1999/005266, US 2004/ 0177390, WO 2008/017234, and U.S. Pat. No. 7,612,250, each of which is herein incorporated by reference in its entirety for all purposes.

The modified cell or one-cell stage embryo can be gen- erated, for example, through recombination by (a) introduc- ing into the cell one or more exogenous donor nucleic acids (e.g., targeting vectors) comprising an insert nucleic acid flanked, for example, by 5' and 3' homology arms corre- sponding to 5' and 3' target sites (e.g., target sites flanking the endogenous sequences intended for deletion and replace- ment with the insert nucleic acid), wherein the insert nucleic acid comprises a human MYOC locus (e.g., comprising a Y437H mutation) to generate a humanized MYOC locus (e.g., comprising a Y437H mutation); and (b) identifying at least one cell comprising in its genome the insert nucleic acid integrated at the endogenous Myoc locus (i.e., identi- fying at least one cell comprising the humanized MYOC locus (e.g., comprising a Y437H mutation)). Likewise, a modified non-human animal genome or humanized non- human animal MYOC locus (e.g., comprising a Y437H mutation) can be generated, for example, through recombi- nation by (a) contacting the genome or gene with one or more exogenous donor nucleic acids (e.g., targeting vectors) comprising 5' and 3' homology arms corresponding to 5' and 3' target sites (e.g., target sites flanking the endogenous sequences intended for deletion and replacement with an insert nucleic acid (e.g., comprising a human MYOC locus (e.g., comprising a Y437H mutation) to generate a human- ized MYOC locus (e.g., comprising a Y437H mutation)) flanked by the 5' and 3' homology arms), wherein the exogenous donor nucleic acids are designed for humaniza- tion of the endogenous non-human animal Myoc locus.

Alternatively, the modified pluripotent cell or one-cell stage embryo can be generated by (a) introducing into the cell: (i) a nuclease agent, wherein the nuclease agent induces a nick or double-strand break at a target site within the endogenous Myoc locus; and (ii) one or more exogenous donor nucleic acids (e.g., targeting vectors) comprising an insert nucleic acid flanked by, for example, 5' and 3' homol- ogy arms corresponding to 5' and 3' target sites (e.g., target sites flanking the endogenous sequences intended for dele- tion and replacement with the insert nucleic acid), wherein the insert nucleic acid comprises a human MYOC locus (e.g., comprising a Y437H mutation) to generate a human- ized MYOC locus (e.g., comprising a Y437H mutation); and (c) identifying at least one cell comprising in its genome the insert nucleic acid integrated at the endogenous Myoc locus (i.e., identifying at least one cell comprising the humanized MYOC locus (e.g., comprising a Y437H mutation)). Like- wise, a humanized non-human animal genome or humanized non-human animal MYOC gene (e.g., comprising a Y437H mutation) can be generated by contacting the genome or gene with: (i) a nuclease agent, wherein the nuclease agent induces a nick or double-strand break at a target site within the endogenous Myoc locus or gene; and (ii) one or more exogenous donor nucleic acids (e.g., targeting vectors) com- prising an insert nucleic acid (e.g., comprising a human MYOC sequence (e.g., comprising a Y437H mutation) to generate a humanized MYOC locus (e.g., comprising a Y437H mutation)) flanked by, for example, 5' and 3' homol- ogy arms corresponding to 5' and 3' target sites (e.g., target sites flanking the endogenous sequences intended for dele- tion and replacement with the insert nucleic acid), wherein the exogenous donor nucleic acids are designed for human- ization of the endogenous Myoc locus (e.g., and introduction of the Y437H mutation). Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes. In one example, the nuclease comprises a Cas9 protein and a guide RNA. In another example, the nuclease comprises a Cas9 protein and two or more, three or more, or four or more guide RNAs.

The step of modifying the genome can, for example, utilize exogenous donor nucleic acids (e.g., targeting vec- tors) to modify a Myoc locus to comprise a humanized MYOC locus (e.g., comprising a Y437H mutation) disclosed herein. As one example, the targeting vector can be for generating a humanized MYOC gene (e.g., comprising a Y437H mutation) at an endogenous Myoc locus (e.g., endogenous non-human animal Myoc locus), wherein the targeting vector comprises a nucleic acid insert comprising human MYOC sequence (e.g., comprising a Y437H muta- tion) to be integrated in the Myoc locus flanked by a 5' homology arm targeting a 5' target sequence at the endog- enous Myoc locus and a 3' homology arm targeting a 3' target sequence at the endogenous Myoc locus. Integration of a nucleic acid insert in the Myoc locus can result in addition of a nucleic acid sequence of interest in the Myoc locus, deletion of a nucleic acid sequence of interest in the Myoc locus, or replacement of a nucleic acid sequence of interest in the Myoc locus (i.e., deleting a segment of the endogenous Myoc locus and replacing with a corresponding human MYOC sequence).

The exogenous donor nucleic acids can be for non- homologous-end-joining-mediated insertion or homologous recombination. Exogenous donor nucleic acids can comprise deoxyribonucleic acid (DNA) or ribonucleic acid (RNA), they can be single-stranded or double-stranded, and they can be in linear or circular form. For example, a donor nucleic acid can be a single-stranded oligodeoxynucleotide (ssODN). Exogenous donor nucleic acids can also comprise a heterologous sequence that is not present at an untargeted endogenous Myoc locus. For example, an exogenous donor nucleic acid can comprise a selection cassette, such as a selection cassette flanked by recombinase recognition sites.

In cells other than one-cell stage embryos, the exogenous donor nucleic acid can be a "large targeting vector" or "LTVEC," which includes targeting vectors that comprise homology arms that correspond to and are derived from nucleic acid sequences larger than those typically used by other approaches intended to perform homologous recombination in cells. See, e.g., US 2004/0018626; WO 2013/163394; U.S. Pat. Nos. 9,834,786; 10,301,646; WO 2015/088643; U.S. Pat. Nos. 9,228,208; 9,546,384; 10,208,317; and US 2019-0112619, each of which is herein incorporated by reference in its entirety for all purposes. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) Nat. Biotechnol. 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

The methods can further comprise identifying a cell or animal having a modified target genomic locus. Various methods can be used to identify cells and animals having a targeted genetic modification. The screening step can comprise, for example, a quantitative assay for assessing modification-of-allele (MOA) of a parental chromosome. See, e.g., US 2004/0018626; US 2014/0178879; US 2016/0145646; WO 2016/081923; and Frendewey et al. (2010) Methods Enzymol. 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

The various methods provided herein allow for the generation of a genetically modified non-human F0 animal wherein the cells of the genetically modified F0 animal comprise the humanized MYOC locus (e.g., comprising a Y437H mutation). It is recognized that depending on the method used to generate the F0 animal, the number of cells within the F0 animal that have the humanized MYOC locus (e.g., comprising a Y437H mutation) will vary. With mice, for example, the introduction of the donor ES cells into a pre-morula stage embryo from the mouse (e.g., an 8-cell stage mouse embryo) via, for example, the VELOCI-MOUSE® method allows for a greater percentage of the cell population of the F0 mouse to comprise cells having the targeted genetic modification. For example, at least 50%, at least 60%, at least 65%, at least 70%, at least 75%, at least 85%, at least 86%, at least 87%, at least 87%, at least 88%, at least 89%, at least 90%, at least 91%, at least 92%, at least 93%, at least 94%, at least 95%, at least 96%, at least 97%, at least 98%, at least 99% or 100% of the cellular contribution of the non-human F0 animal can comprise a cell population having the targeted modification. The cells of the genetically modified F0 animal can be heterozygous for the humanized MYOC locus (e.g., comprising a Y437H mutation) or can be homozygous for the humanized MYOC locus (e.g., comprising a Y437H mutation).

Likewise, various methods are provided for making a non-human animal comprising a synergistic activation mediator (SAM) expression cassette (comprising a chimeric Cas protein coding sequence and a chimeric adaptor protein expression coding sequence) and a humanized MYOC locus (e.g., comprising a Y437H mutation) as disclosed elsewhere herein. Any convenient method or protocol for producing a genetically modified organism is suitable for producing such a genetically modified non-human animal. See, e.g., Poueymirou et al. (2007) Nat. Biotechnol. 25(1):91-99; U.S. Pat. Nos. 7,294,754; 7,576,259; 7,659,442; 8,816,150; 9,414,575; 9,730,434; and 10,039,269, each of which is herein incorporated by reference in its entirety for all purposes (describing mouse ES cells and the VELOCIMOUSE® method for making a genetically modified mouse). See also US 2014/0235933 A1, US 2014/0310828 A1, each of which is herein incorporated by reference in its entirety for all purposes (describing rat ES cells and methods for making a genetically modified rat). See also Cho et al. (2009) Curr. Protoc. Cell. Biol. 42:19.11.1-19.11.22 (doi: 10.1002/0471143030.cb1911s42) and Gama Sosa et al. (2010) Brain Struct. Funct. 214(2-3):91-109, each of which is herein incorporated by reference in its entirety for all purposes. Such genetically modified non-human animals can be generated, for example, by creating a first non-human animal comprising a humanized MYOC locus (e.g., comprising a Y437H mutation), creating a second non-human animal comprising a SAM expression cassette (e.g., genomically integrated SAM expression cassette), and then crossing the first and second non-human animals. Alternatively, such genetically modified non-human animals can be generated by making a genetically modified pluripotent cell comprising the humanized MYOC locus (e.g., comprising a Y437H mutation), further modifying the pluripotent cell to comprise a SAM expression cassette (e.g., genomically integrated SAM expression cassette), and then generating a genetically modified non-human animal from the pluripotent cell. Likewise, such genetically modified non-human animals can be generated by making a genetically modified pluripotent cell comprising a SAM expression cassette (e.g., genomically integrated expression cassette), further modifying the pluripotent cell to comprise the humanized MYOC locus (e.g., comprising a Y437H mutation), and then generating a genetically modified non-human animal from the pluripotent cell. Optionally, the cells are non-human animals can be further modified to comprise a guide RNA expression cassette and/or a recombinase expression cassette as described elsewhere herein.

For example, the method of producing a non-human animal comprising a humanized MYOC locus (e.g., comprising a Y437H mutation) and a SAM expression cassette (and optionally a guide RNA array expression cassette) can comprise: (1) providing a pluripotent cell (e.g., an embryonic stem (ES) cell such as a mouse ES cell or a rat ES cell) comprising in its genome the humanized MYOC locus (e.g., comprising a Y437H mutation) and the SAM expression cassette (and optionally the guide RNA array expression cassette); (2) introducing the genetically modified pluripotent cell into a non-human animal host embryo; and (3) gestating (e.g., implanting and gestating) the host embryo in a surrogate mother.

For example, the method of producing a non-human animal comprising a humanized MYOC locus (e.g., comprising a Y437H mutation) can comprise: (1) modifying the genome of a pluripotent cell (e.g., an embryonic stem (ES) cell such as a mouse ES cell or a rat ES cell) to comprise the humanized MYOC locus (e.g., comprising a Y437H mutation); (2) identifying or selecting the genetically modified pluripotent cell comprising the humanized MYOC locus (e.g., comprising a Y437H mutation); (3) introducing the genetically modified pluripotent cell into a non-human animal host embryo; and (4) gestating (e.g., implanting and gestating) the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized MYOC locus (e.g., comprising a Y437H mutation).

Likewise, the method of producing a non-human animal comprising a SAM expression cassette and/or a guide RNA array expression cassette can comprise: (1) modifying the genome of a pluripotent cell to comprise one or more or all of the expression cassettes; (2) identifying or selecting the genetically modified pluripotent cell comprising the one or more or all of the expression cassettes; (3) introducing the genetically modified pluripotent cell into a non-human animal host embryo; and (4) gestating (e.g., implanting or gestating) the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising one or more or all of the expression cassettes. The non-human animal comprising the humanized MYOC locus (e.g., comprising a Y437H mutation) can then be crossed to the non-human animal comprising the SAM expression cassette and/or the guide RNA array expression cassette.

As another example, the method of producing a non-human animal comprising a humanized MYOC locus (e.g., comprising a Y437H mutation) and a SAM expression cassette (and optionally a guide RNA array expression cassette) can comprise: (1) modifying the genome of a pluripotent cell (e.g., an embryonic stem (ES) cell such as a mouse ES cell or a rat ES cell) to comprise the humanized MYOC locus (e.g., comprising a Y437H mutation) and the SAM expression cassette (and optionally the guide RNA array expression cassette); (2) identifying or selecting the genetically modified pluripotent cell comprising the humanized MYOC locus (e.g., comprising a Y437H mutation) and the SAM expression cassette (and optionally the guide RNA array expression cassette); (3) introducing the genetically modified pluripotent cell into a non-human animal host embryo; and (4) gestating (e.g., implanting and gestating) the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized MYOC locus (e.g., comprising a Y437H mutation).

As another example, the method of producing a non-human animal comprising a humanized MYOC locus (e.g., comprising a Y437H mutation) and a SAM expression cassette can comprise: (1) modifying the genome of a pluripotent cell (e.g., an embryonic stem (ES) cell such as a mouse ES cell or a rat ES cell) to comprise the humanized MYOC locus (e.g., comprising a Y437H mutation); (2) identifying or selecting the genetically modified pluripotent cell comprising the humanized MYOC locus (e.g., comprising a Y437H mutation); (3) modifying the genome of the genetically modified pluripotent cell comprising the humanized MYOC locus (e.g., comprising a Y437H mutation) to comprise the SAM expression cassette; (4) identifying or selecting the genetically modified pluripotent cell comprising SAM expression cassette and the humanized MYOC locus (e.g., comprising a Y437H mutation); (5) introducing the genetically modified pluripotent cell into a non-human animal host embryo; and (6) gestating (e.g., implanting and gestating) the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized MYOC locus (e.g., comprising a Y437H mutation) and the SAM expression cassette.

As another example, the method of producing a non-human animal comprising a humanized MYOC locus (e.g., comprising a Y437H mutation) and a SAM expression cassette can comprise: (1) modifying the genome of a pluripotent cell to comprise the SAM expression cassette; (2) identifying or selecting the genetically modified pluripotent cell comprising the SAM expression cassette; (3) modifying the genome of the genetically modified pluripotent cell comprising the SAM expression cassette to further comprise the humanized MYOC locus (e.g., comprising a Y437H mutation); (4) identifying or selecting the genetically modified pluripotent cell comprising the humanized MYOC locus (e.g., comprising a Y437H mutation) and the SAM expression cassette; (5) introducing the genetically modified pluripotent cell into a non-human animal host embryo; and (6) gestating (e.g., implanting and gestating) the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized MYOC locus (e.g., comprising a Y437H mutation) and the SAM expression cassette.

The methods can further comprise identifying a cell or animal having a modified target genomic locus (i.e., a humanized MYOC locus (e.g., comprising a Y437H mutation) and/or a target genomic locus comprising the SAM expression cassette or the guide RNA expression cassette). Various methods can be used to identify cells and animals having a targeted genetic modification.

The screening step can comprise, for example, a quantitative assay for assessing modification of allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). A modified pluripotent cell comprising a humanized MYOC locus (e.g., comprising a Y437H mutation) can be generated, for example, through recombination by (a) introducing into the cell one or more targeting vectors or exogenous donor nucleic acids comprising an insert nucleic acid flanked by 5' and 3' homology arms corresponding to 5' and 3' target sites, wherein the insert nucleic acid comprises a human MYOC sequence (e.g., comprising a Y437H mutation); and (b) identifying at least one cell comprising in its genome the insert nucleic acid integrated at the endogenous Myoc locus. Alternatively, the modified pluripotent cell can be generated by (a) introducing into the cell: (i) a nuclease agent, wherein the nuclease agent induces a nick or double-strand break at a target sequence within the endogenous Myoc locus; and (ii) one or more targeting vectors comprising an insert nucleic acid flanked by 5' and 3' homology arms corresponding to 5' and 3' target sites located in sufficient proximity to the target sequence, wherein the insert nucleic acid comprises a human MYOC sequence (e.g., comprising a Y437H mutation); and (c) identifying at least one cell comprising a modification (e.g., integration of the insert nucleic acid) at the endogenous Myoc locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

Likewise, a modified pluripotent cell comprising a SAM expression cassette and/or a guide RNA expression cassette can be generated, for example, through recombination by (a) introducing into the cell one or more targeting vectors or exogenous donor nucleic acids comprising an insert nucleic acid flanked by 5' and 3' homology arms corresponding to 5' and 3' target sites, wherein the insert nucleic acid comprises the expression cassette; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a target sequence within the target genomic locus; and (ii) one or more targeting vectors comprising an insert nucleic acid flanked by 5' and 3' homology arms corresponding to 5' and 3' target sites located in sufficient proximity to the target sequence, wherein the insert nucleic acid comprises the expression cassette; and (c) identifying at least one cell comprising a modification (e.g., integration of the insert nucleic acid) at the target genomic locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

In some such methods using cells other than one-cell stage embryos, the targeting vector is a large targeting vector at least 10 kb in length or in which the sum total of the 5' and 3' homology arms is at least 10 kb in length, but other types of exogenous donor nucleic acids can also be used and are well-known. See, e.g., US 2004/0018626; WO 2013/163394; U.S. Pat. Nos. 9,834,786; 10,301,646; WO 2015/088643; U.S. Pat. Nos. 9,228,208; 9,546,384; 10,208,317; and US 2019-0112619, each of which is herein incorporated by reference in its entirety for all purposes. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes. The 5' and 3' homology arms can correspond with 5' and 3' target sequences, respectively, that flank the region being replaced by the insert nucleic acid or that flank the region into which the insert nucleic acid is to be inserted. The exogenous donor nucleic acid or targeting vector can recombine with the target locus via homology directed repair or can be inserted via NHEJ-mediated insertion to generate the modified genomic locus.

The donor cell can be introduced into a host embryo at any stage, such as the blastocyst stage or the pre-morula stage (i.e., the 4-cell stage or the 8-cell stage). Progeny that are capable of transmitting the genetic modification though the germline are generated. See, e.g., U.S. Pat. No. 7,294, 754, herein incorporated by reference in its entirety for all purposes.

Alternatively, the method of producing the non-human animals described elsewhere herein can comprise: (1) modifying the genome of a one-cell stage embryo (e.g., that already comprises a SAM expression cassette) to comprise the humanized MYOC locus (e.g., comprising a Y437H mutation) using the methods described above for modifying pluripotent cells; (2) selecting the genetically modified embryo; and (3) gestating (e.g., implanting and gestating) the genetically modified embryo into a surrogate mother. Progeny that are capable of transmitting the genetic modification though the germline are generated.

Alternatively, the method of producing the non-human animals described elsewhere herein can comprise: (1) modifying the genome of a one-cell stage embryo (e.g., that already comprises a humanized MYOC locus (e.g., comprising a Y437H mutation)) to comprise a SAM expression cassette (and optionally a guide RNA expression cassette) using the methods described above for modifying pluripotent cells; (2) selecting the genetically modified embryo; and (3) gestating (e.g., implanting and gestating) the genetically modified embryo into a surrogate mother. Progeny that are capable of transmitting the genetic modification though the germline are generated.

Alternatively, the method of producing the non-human animals described elsewhere herein can comprise: (1) modifying the genome of a one-cell stage embryo (e.g., that already comprises a SAM expression cassette (and optionally a guide RNA expression cassette)) to comprise a humanized MYOC locus (e.g., comprising a Y437H mutation) using the methods described above for modifying pluripotent cells; (2) selecting the genetically modified embryo; and (3) gestating (e.g., implanting and gestating) the genetically modified embryo into a surrogate mother. Progeny that are capable of transmitting the genetic modification though the germline are generated.

Alternatively, the method of producing the non-human animals described elsewhere herein can comprise: (1) providing a non-human animal one-cell stage embryo comprising in its genome: (i) a humanized MYOC locus; and (ii) a SAM expression cassette; and (2) gestating the non-human animal one-cell stage embryo in a surrogate mother.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized MYOC locus (e.g., comprising a Y437H mutation) and/or the SAM expression cassette. Depending on the method used to generate the F0 animal, the number of cells within the F0 animal that have the humanized MYOC locus (e.g., comprising a Y437H mutation) and/or the SAM expression cassette will vary. With mice, for example, the introduction of the donor ES cells into a pre-morula stage embryo from the mouse (e.g., an 8-cell stage mouse embryo) via, for example, the VELOCI-MOUSE® method allows for a greater percentage of the cell population of the F0 mouse to comprise cells having the targeted genetic modification. For example, at least 50%, at least 60%, at least 65%, at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% of the cellular contribution of the non-human F0 animal can comprise a cell population having the targeted modification.

The cells of the genetically modified F0 animal can be heterozygous for the humanized MYOC locus (e.g., comprising a Y437H mutation) and/or the SAM expression cassette or the guide RNA expression cassette or can be homozygous for the humanized MYOC locus (e.g., comprising a Y437H mutation) and/or the SAM expression cassette or the guide RNA expression cassette.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Human MYOC Protein (NCBI Accession No. NP_000252.1) |
| 2 | DNA | Human MYOC mRNA/cDNA (NCBI Accession No. NM_000261.2) |
| 3 | DNA | Human MYOC CDS (CCDS ID CCDS1297.1) |
| 4 | Protein | Human MYOC Protein Y437H |
| 5 | DNA | Human MYOC CDS Y437H |
| 6 | Protein | Mouse MYOC Protein (NCBI Accession No. NP_034995.3) |
| 7 | DNA | Mouse MYOC mRNA/cDNA (NCBI Accession No. NM_010865.3) |
| 8 | DNA | Mouse MYOC CDS (CCDS ID CCDS15422.1) |
| 9 | Protein | Rat MYOC Protein v1 (NCBI Accession No. NP_110492.1) |
| 10 | DNA | Rat MYOC mRNA/cDNA v1 (NCBI Accession No. NM_030865.1) |
| 11 | DNA | Rat MYOC CDS v1 |
| 12 | Protein | Rat MYOC Protein v2 (NCBI Accession No. NP_110492.2) |
| 13 | DNA | Rat MYOC mRNA/cDNA v2 (NCBI Accession No. NM_030865.2) |
| 14 | DNA | Rat MYOC CDS v2 |
| 15 | Protein | Human MYOC Signal Peptide |
| 16 | Protein | Human MYOC Mature Myocilin |
| 17 | Protein | Human MYOC N-Terminal Fragment |
| 18 | Protein | Human MYOC C-Terminal Fragment |
| 19 | Protein | Human MYOC Mature Myocilin with Y437H Mutation |
| 20 | Protein | Human MYOC C-Terminal Fragment with Y437H Mutation |
| 21 | DNA | Human MYOC Signal Peptide CDS |
| 22 | DNA | Human MYOC Mature Myocilin CDS |
| 23 | DNA | Human MYOC N-Terminal Fragment CDS |
| 24 | DNA | Human MYOC C-Terminal Fragment CDS |
| 25 | DNA | Human MYOC Mature Myocilin with Y437H Mutation CDS |
| 26 | DNA | Human MYOC C-Terminal Fragment with Y437H Mutation CDS |
| 27 | Protein | Mouse MYOC Signal Peptide |
| 28 | Protein | Mouse MYOC Mature Myocilin |
| 29 | Protein | Mouse MYOC N-Terminal Fragment |
| 30 | Protein | Mouse MYOC C-Terminal Fragment |
| 31 | DNA | Mouse MYOC Signal Peptide CDS |
| 32 | DNA | Mouse MYOC Mature Myocilin CDS |
| 33 | DNA | Mouse MYOC N-Terminal Fragment CDS |
| 34 | DNA | Mouse MYOC C-Terminal Fragment CDS |
| 35 | Protein | Rat MYOC Signal Peptide |
| 36 | Protein | Rat MYOC Mature Myocilin |
| 37 | Protein | Rat MYOC N-Terminal Fragment |
| 38 | Protein | Rat MYOC C-Terminal Fragment |
| 39 | DNA | Rat MYOC Signal Peptide CDS |
| 40 | DNA | Rat MYOC Mature Myocilin CDS |
| 41 | DNA | Rat MYOC N-Terminal Fragment CDS |
| 42 | DNA | Rat MYOC C-Terminal Fragment CDS |
| 43 | Protein | dCas9-VP64 chimeric Cas protein |
| 44 | Protein | dCas9 protein |
| 45 | Protein | VP64 transcriptional activation domain |
| 46 | Protein | Linker v1 |
| 47 | Protein | Linker v2 |
| 48 | Protein | MCP-p65-HSF1 chimeric adaptor protein |
| 49 | Protein | MS2 coat protein (MCP) |
| 50 | Protein | p65 transcriptional activation domain |
| 51 | Protein | HSF1 transcriptional activation domain |
| 52 | RNA | MS2-binding loop |
| 53 | Protein | T2A |
| 54 | Protein | P2A |
| 55 | Protein | E2A |
| 56 | Protein | F2A |
| 57 | DNA | Nucleic acid encoding dCas9 protein |
| 58 | DNA | Nucleic acid encoding dCas9-VP64 chimeric Cas protein |
| 59 | DNA | Nucleic acid encoding MCP |
| 60 | DNA | Nucleic acid encoding MCP-p65-HSF1 chimeric adaptor protein |
| 61 | DNA | Nucleic acid encoding VP64 transcriptional activation domain |
| 62 | DNA | Nucleic acid encoding p65 transcriptional activation domain |

TABLE 2-continued

Description of Sequences.

| SEQ ID NO | Type | Description |
|---|---|---|
| 63 | DNA | Nucleic acid encoding HSF1 transcriptional activation domain |
| 64 | DNA | Synergistic activation mediator (SAM) bicistronic expression cassette (dCas9-VP64-T2A-MCP-p65-HSF1) |
| 65 | DNA | Generic guide RNA array expression cassette |
| 66 | RNA | gRNA scaffold with MS2 binding loops |
| 67 | Protein | Synergistic activation mediator (SAM) (dCas9-VP64-T2A-MCP-p65-HSF1) |
| 68 | RNA | Generic single gRNA with MS2 binding loops |
| 69 | DNA | Synergistic activation mediator (SAM) coding sequence (dCas9-VP64-T2A-MCP-p65-HSF1) |
| 70 | DNA | Generic guide RNA array promoters and guide RNA coding sequences |
| 71 | RNA | gRNA scaffold with MS2 binding loops v2 |
| 72 | RNA | Generic single gRNA with MS2 binding loops v2 |
| 73 | RNA | crRNA Tail |
| 74 | RNA | TracrRNA v1 |
| 75 | RNA | TracrRNA v2 |
| 76 | RNA | TracrRNA v3 |
| 77 | RNA | Guide RNA Scaffold v1 |
| 78 | RNA | Guide RNA Scaffold v2 |
| 79 | RNA | Guide RNA Scaffold v3 |
| 80 | RNA | Guide RNA Scaffold v4 |
| 81 | RNA | Guide RNA Scaffold v5 |
| 82 | RNA | Guide RNA Scaffold v6 |
| 83 | RNA | Guide RNA Scaffold v7 |
| 84 | DNA | Guide RNA Target Sequence Plus PAM v1 |
| 85 | DNA | Guide RNA Target Sequence Plus PAM v2 |
| 86 | DNA | Guide RNA Target Sequence Plus PAM v3 |
| 87 | DNA | Human MYOC Sequence at Humanized MYOC Locus |
| 88 | DNA | MAID 8533 |
| 89 | DNA | MAID 8534 |
| 90 | DNA | mGU Target Sequence |
| 91 | DNA | mGU2 Target Sequence |
| 92 | DNA | mGU3 Target Sequence |
| 93 | DNA | mGU4 Target Sequence |
| 94 | DNA | mGU5 Target Sequence |
| 95 | DNA | mGU6 Target Sequence |
| 96 | RNA | mGU DNA-Targeting Segment |
| 97 | RNA | mGU2 DNA-Targeting Segment |
| 98 | RNA | mGU3 DNA-Targeting Segment |
| 99 | RNA | mGU4 DNA-Targeting Segment |
| 100 | RNA | mGU5 DNA-Targeting Segment |
| 101 | RNA | mGU6 DNA-Targeting Segment |
| 102-125 | DNA | Primers and Probes |

EXAMPLES

Example 1. Generation of Mice Comprising a Humanized Myocilin (MYOC) Locus Comprising a Y437H Mutation Glaucoma is the leading cause of irreversible vision loss worldwide. Elevated intraocular pressure (IOP) leads to progressive optic nerve damage. IOP-lowering drugs used to treat glaucoma patients work by two mechanisms: (1) decreasing production of aqueous humor; and (2) increasing aqueous humor outflow. Myocilin (MYOC) was the first gene shown to be associated with autosomal dominant familiar juvenile open angle glaucoma and primary open angle glaucoma. Y437H is a MYOC mutation associated with early-onset glaucoma. Although the normal function of MYOC in the cell is unknown, wild type myocilin protein is secreted, whereas mutant myocilin proteins are retained in the endoplasmic reticulum (ER), leading to ER stress in the trabecular meshwork.

To generate a mouse comprising a humanized myocilin (MYOC) locus comprising a Y437H mutation to model glaucoma, a large targeting vector (LTVEC) comprising a 5' homology arm comprising 134 kb of the mouse Myoc locus and 3' homology arm comprising 86 kb of the mouse Myoc locus was generated to replace a region of 9.9 kb from the mouse Myoc gene with 17.2 kb of the corresponding sequence of the human MYOC gene. Information on mouse Myoc and human MYOC genes is provided in Table 3. A description of the generation of the large targeting vector is provided in Table 4. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

TABLE 3

Mouse Myoc and Human MYOC.

| | Gene Symbol | NCBI Gene ID | RefSeq mRNA ID | UniProt ID | Genomic Assembly | Chromosomal Location |
|---|---|---|---|---|---|---|
| Mouse | Myoc | 17926 | NM_010865.3 | O70624 | GRCm38/mm10 | chr1: 162,639,155-162,649,693(+) |
| Human | MYOC | 4653 | NM_000261.2 | Q99972 | GRCh38/hg38 | chr1: 171,635,417-171,652,688(−) |

TABLE 4

Mouse Myoc Large Targeting Vector.

| | Genome Build | Start | End | Length (bp) |
|---|---|---|---|---|
| 5' Mouse Arm | GRCm38/mm10 | Chr1: 162,505,280 | Chr1: 162,639,263 | 133,986 |
| Human Insert | GRCh38/hg38 | chr1: 171,652,412 | Chr1: 171,652,611 | 74,409 |
| 3' Mouse Arm | GRCm38/mm10 | Chr1: 162,649,202 | Chr1: 162,734,809 | 85,608 |

Specifically, murine Myoc was replaced with human MYOC (mouse chr1:162,639,064-162,649,202 replaced by human chr1:171,652,412-171,652,611). The deleted mouse sequence is the region from the start codon to the stop codon, leaving the endogenous 5' and 3' UTRs. The inserted human sequence begins at the start codon (ATG) and continues through the stop codon and 3' UTR, inclusive of all exons and introns. The human MYOC sequence encodes a Y437H mutant myocilin protein. A self-deleting selection cassette was inserted downstream of the human 3' UTR. This is the MAID 8533 allele (SEQ ID NO: 88). See FIG. 1. After cassette deletion, a loxP site remained downstream of the human 3' UTR. This is the MAID 8534 allele (SEQ ID NO: 89). See FIG. 1.

A sequence for the mouse MYOC signal peptide is set forth in SEQ ID NO: 27, with the corresponding coding sequence set forth in SEQ ID NO: 31. A sequence for the human MYOC signal peptide is set forth in SEQ ID NO: 15, with the corresponding coding sequence set forth in SEQ ID NO: 21. The expected encoded MYOC protein is fully human and comprises a Y437H mutation. See FIG. 1. An alignment of the mouse and human MYOC proteins is shown in FIG. 3. The mouse Myoc (wild type) and human MYOC (Y437H) coding sequences are set forth in SEQ ID NOS: 8 and 5, respectively. The mouse MYOC (wild type)

and human MYOC (Y437H) protein sequences are set forth in SEQ ID NOS: 6 and 4, respectively. The sequences for the expected humanized MYOC coding sequence and the expected humanized MYOC protein are set forth in SEQ ID NOS: 5 and 4, respectively.

Figure 2:
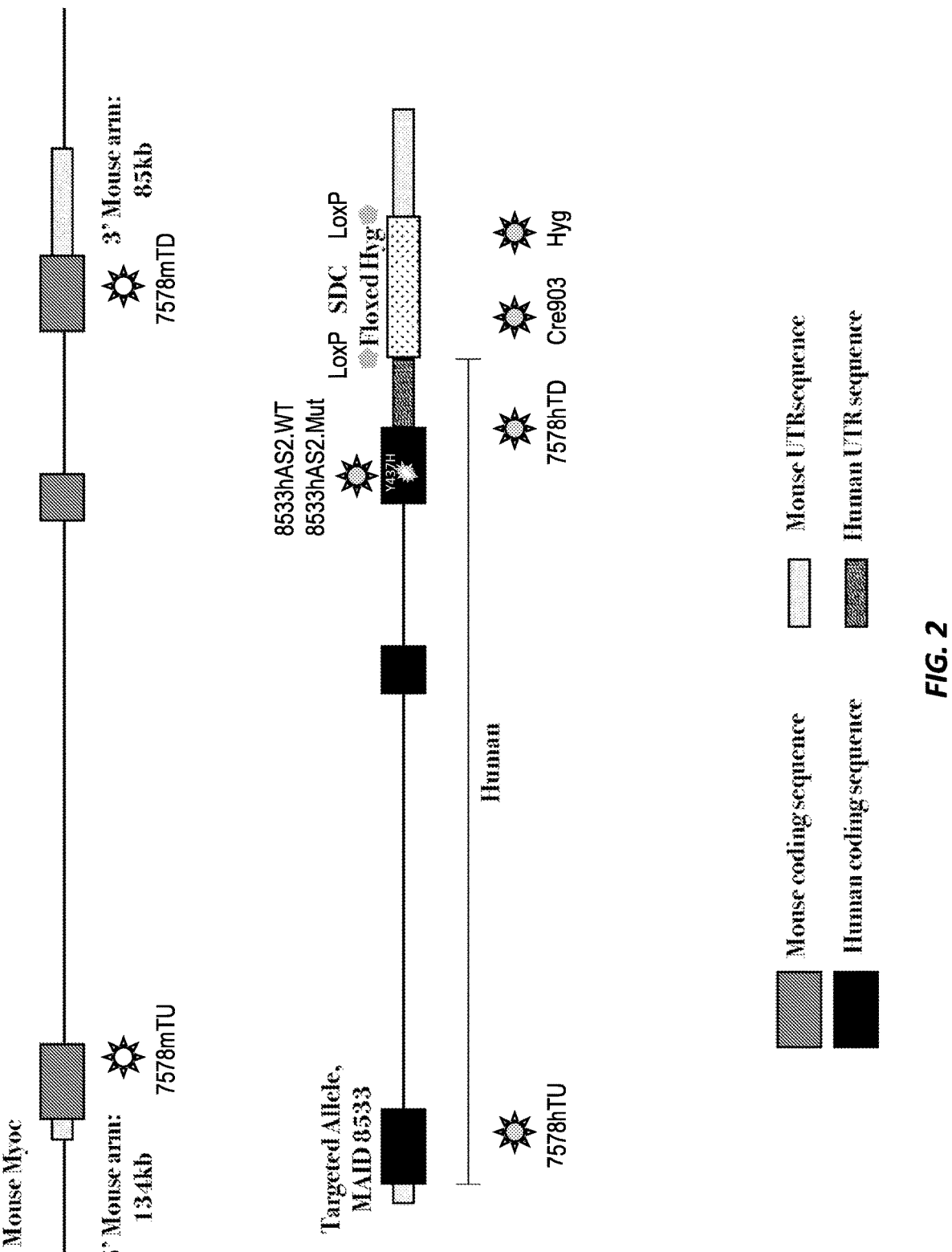
FIG. 2 shows a schematic (not drawn to scale) of the strategy for screening of the humanized mouse MYOC locus, including loss-of-allele assays (7578mTU and 7578mTD), gain-of-allele assays (7578hTU, 7578hTD, Cre903, and Hyg), and allele discrimination assays (8533hAS2.WT and 8533hAS2.Mut).

To generate the mutant allele, the large targeting vector described above was introduced into F1H4 mouse embryonic stem (ES) cells. F1H4 mouse ES cells were derived from hybrid embryos produced by crossing a female C57BL/6NTac mouse to a male 129S6/SvEvTac mouse. See, e.g., US 2015-0376651 and WO 2015/200805, each of which is herein incorporated by reference in its entirety for all purposes. Specifically, $2 \times 10^6$ mouse ES cells (line 8037B-F7) were electroporated with the large targeting vector. Antibiotic selection was performed using hygromycin at a concentration of 75 µg/mL. Following antibiotic selection, colonies were picked, expanded, and screened by TAQMAN®. See FIG. 2. Loss-of-allele assays were performed to detect loss of the endogenous mouse allele, gain-of-allele assays were performed to detect gain of the humanized allele, and allele discrimination assays were performed to detect the Y437H mutation using the primers and probes set forth in Table 5. After TAQMAN® confirmation, the mutation was reconfirmed by sanger sequencing.

TABLE 5

Screening Assays.

| Assay | Primer/Probe | | Sequence | SEQ ID NO |
|---|---|---|---|---|
| 8533hAS2.WT | Fwd | | GCCAATGCCTTCATCATCTGT | 102 |
| | Probe | (FAM) | CCTTGTACACCGTC | 103 |
| | Rev | | GGTAGCATCTGCTGAGGTGTAGCT | 104 |
| 8533hAS2.Mut | Fwd | | GCCAATGCCTTCATCATCTGT | 105 |
| | Probe | (Vic) | CACCTTGCACACCGTC | 106 |
| | Rev | | GGTAGCATCTGCTGAGGTGTAGCT | 107 |
| 7578hTD | Fwd | | CATGGTTACCACAAGCCACAATA | 108 |
| | Probe | (Cal-Orange) | TAAAGGAAGCAGAATAGCTCCTCTGGC | 109 |
| | Rev | | AGAAGCCAACTGTAGTAAATGCA | 110 |
| 7578hTU | Fwd | | GCCTGCCCTTTCTCCTAGAG | 111 |
| | Probe | (FAM) | TGCACAGCTAGCACAAGACAGATGA | 112 |
| | Rev | | GGTGATCGCTGTGCTTTCCTT | 113 |

TABLE 5-continued

Screening Assays.

| Assay | Primer/Probe | Sequence | SEQ ID NO |
|-------|-------------|----------|-----------|
| 7578mTD | Fwd | GGGAGAAGGAAGCTGAAACC | 114 |
| | Probe (Cal-Orange) | TGCTGCCTTTTCTAGACATATGTACTGGA | 115 |
| | Rev | ACCTAGCCCTCCAAGGTTG | 116 |
| | | | |
| 7578mTU | Fwd | GGGCCAGGACAGCACAGTT | 117 |
| | Probe (FAM) | CCGAAAGGCCAATGATCGGAGTG | 118 |
| | Rev | TGGCCACAGTGAAGGTGTA | 119 |
| | | | |
| Cre903 | Fwd | GCACAGCACTGTAAAGGCA | 120 |
| | Probe | ACGGAACTCGAAGGAATTGGTATTGTTGT | 121 |
| | Rev | ACACAGCTATGGGAGAAAGACTG | 122 |
| | | | |
| Hyg | Fwd | TGCGGCCGATCTTAGCC | 123 |
| | Probe | ACGAGCGGGTTCGGCCCATTC | 124 |
| | Rev | TTGACCGATTCCTTGCGG | 125 |

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

F0 mice were generated from the modified ES cells using the VELOCIMOUSE® method. Specifically, mouse ES cell clones comprising the humanized MYOC locus described above that were selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse ES cells are injected through laser-assisted injection into pre-morula stage embryos, e.g., eight-cell-stage embryos, which efficiently yields F0 generation mice that are fully ES-cell-derived. In the VELOCIMOUSE® method, the injected pre-morula stage embryos are cultured to the blastocyst stage, and the blastocyst-stage embryos are introduced into and gestated in surrogate mothers to produce the F0 generation mice. When starting with mouse ES cell clones homozygous for the targeted modification, F0 mice homozygous for the targeted modification are produced. When starting with mouse ES cell clones heterozygous for the targeted modification, subsequent breeding can be performed to produce mice homozygous for the targeted modification.

Example 2. Generation and Validation of SAM Mice

Mice comprising genomically integrated dCas9 synergistic activation mediator (SAM) system components (dCas9-

VP64 and MCP-p65-HSF1) as one transcript driven by the endogenous Rosa26 promoter were generated as described in US 2019/0284572 and WO 2019/183123, each of which is herein incorporated by reference in its entirety for all purposes. Initially, expression of the dCas9 SAM system is blocked by the presence of a floxed neomycin stop cassette. Upon introduction of Cre recombinase, the stop cassette is deleted and dCas9 SAM expression is turned on. We can then introduce guide RNAs or guide RNA arrays (e.g., expressed from a U6 promoter) by integrating them into the other Rosa26 allele for constitutive activation or LNP/AAV introduction for more transient activations. By pairing the dCas9 SAM allele with various Cre delivery methods, we can control the timing and tissue specificity of gene modulation.

Figures 4A, 4B:
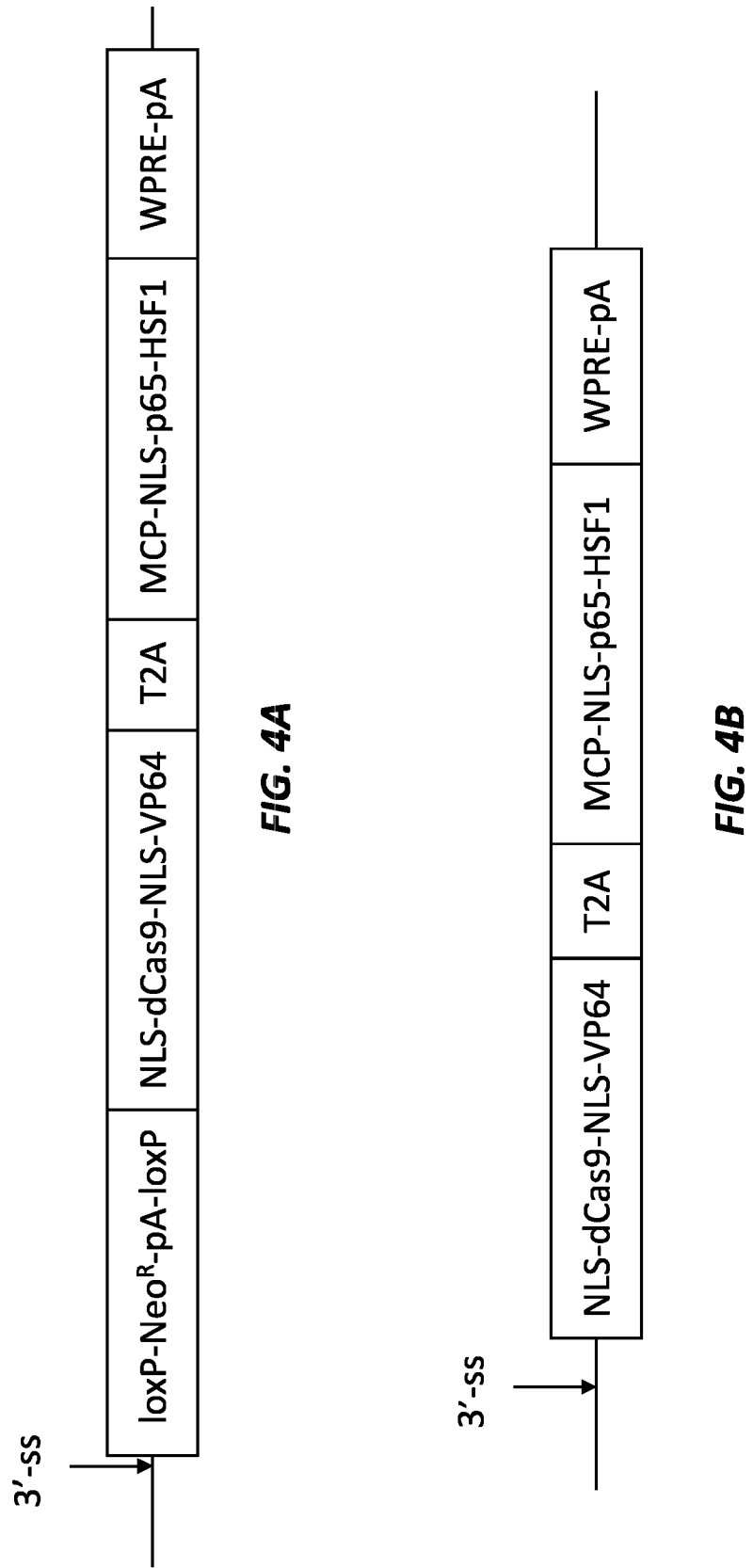
FIG. 4A (not to scale) shows a lox-stop-lox (LSL) dCas9 synergistic activation mediator (SAM) allele (LSL-SAM allele), comprising from 5' to 3': a 3' splicing sequence; a first loxP site; a neomycin resistance gene; a polyadenylation signal; a second loxP site; a dCas9-NLS-VP64 coding sequence (NLS-dCas9-NLS-VP64); a T2A peptide coding sequence; an MCP-NLS-p65-HSF1 coding sequence; and a Woodchuck hepatitis virus posttranscriptional regulatory element (WPRE).
FIG. 4B (not to scale) shows the allele from FIG. 4A with the floxed neomycin resistance gene and polyadenylation signal removed (SAM allele).

The *S. pyogenes* dCas9 coding sequence (CDS) in the expression cassette was codon-optimized for expression in mice. The encoded dCas9 includes the following mutations to render the Cas9 nuclease-inactive: D10A and N863A. The NLS-dCas9-NLS-VP64-T2A-MCP-NLS-p65-HSF1 expression cassette is depicted in FIG. 4A and SEQ ID NO: 64. The synergistic activation mediator (SAM) coding sequence (dCas9-VP64-T2A-MCP-p65-HSF1 or more specifically NLS-dCas9-NLS-VP64-T2A-MCP-NLS-p65-HSF1) is set forth in SEQ ID NO: 69 and encodes the protein set forth in SEQ ID NO: 67. The expression cassette was targeted to the first intron of the Rosa26 locus (see FIG. 5) to take advantage of the strong universal expression of the Rosa26 locus and the ease of targeting the Rosa26 locus. The expression cassette was preceded by a floxed neomycin resistance cassette (neo cassette) with appropriate splicing signals and a strong polyadenylation (polyA) signal. The components of the dCas9 SAM expression cassette from 5' to 3' are shown in Table 6 below.

TABLE 6 dCas9 SAM Expression Cassette Components.

| Component | Nucleotide Region Within SEQ ID NO: 64 |
|-----------|----------------------------------------|
| First loxP site | 1-34 |
| Sequence encoding neomycin phosphotransferase for resistance to neomycin family antibiotics (e.g. G418) | 125-928 |

TABLE 6-continued dCas9 SAM Expression Cassette Components.

| Component | Nucleotide Region Within SEQ ID NO: 64 |
|---|---|
| Polyadenylation signal | 937-2190 |
| Second loxP site | 2218-2251 |
| Codon-optimized dCas9 coding sequence | 2306-6457 |
| NLS | 2309-2356 |
| NLS | 6512-6532 |
| VP64 | 6533-6719 |
| T2A with 5' GSG | 6719-6781 |
| MCP | 6782-7171 |
| NLS | 7226-7246 |
| p65 | 7262-7804 |
| HSF1 | 7829-8200 |
| Woodchuck hepatitis virus posttranscriptional regulatory element (WPRE) | 8224-8820 |

Figure 6:
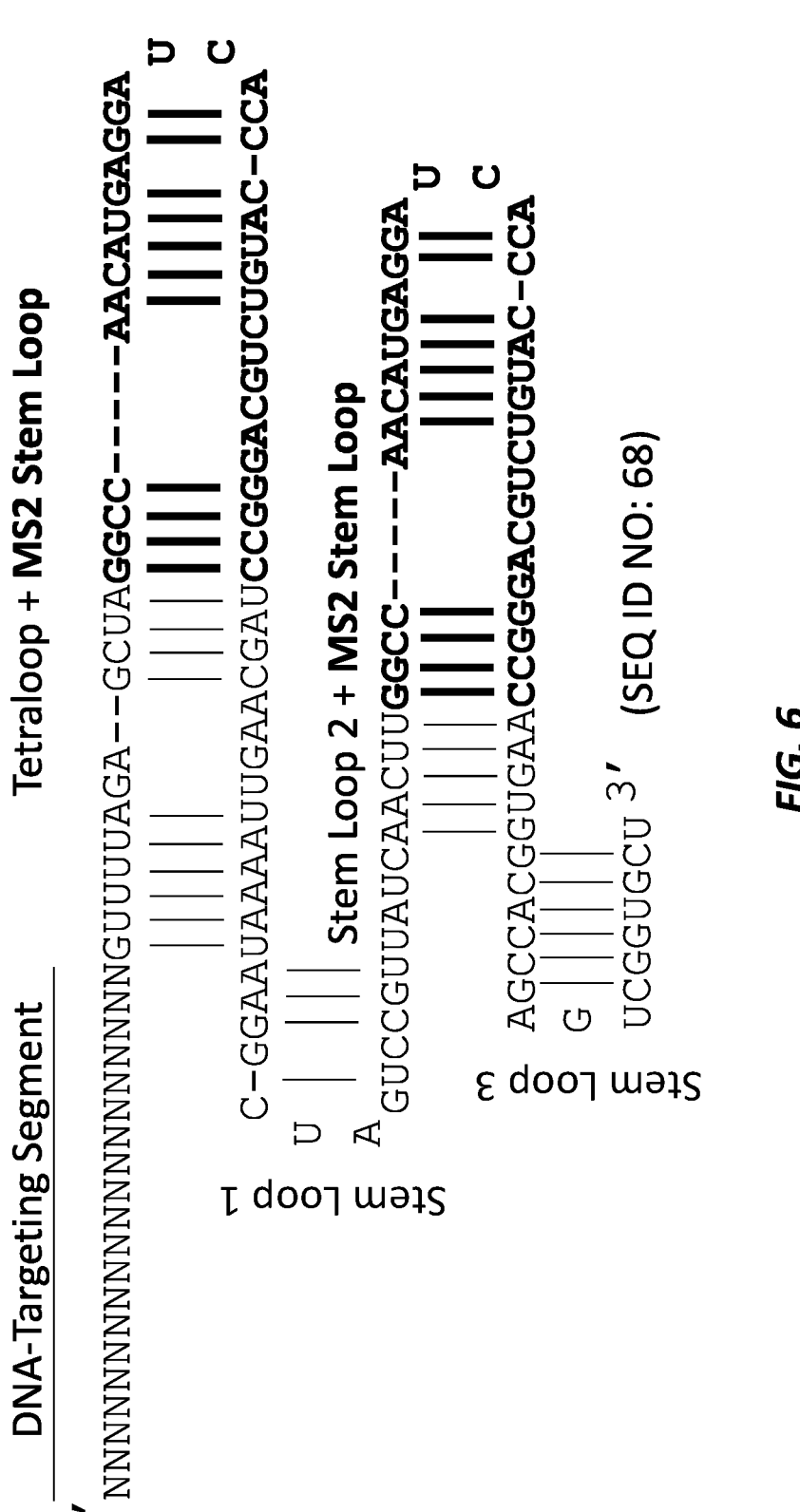
FIG. 6 shows a schematic of a generic single guide RNA (SEQ ID NO: 68) in which the tetraloop and stem loop 2 have been replaced with MS2-binding aptamers to facilitate recruitment of chimeric MS2 coat protein (MCP) fused to transcriptional activation domains.

Prior to removal of the floxed neomycin resistance cassette (neo cassette) by the action of Cre recombinase, the neomycin resistance gene is transcribed and translated; however, the dCas9-NLS-VP64 CDS and MCP-NLS-p65-HSF1 CDS are not expressed due to the presence of the strong poly(A) region, which effectively blocks run-through transcription. See FIG. 4A. Upon removal of the neo cassette by the action of Cre recombinase, however, the hybrid mRNA for the dCas9 and MCP fusion proteins is constitutively expressed by the Rosa26 promoter. See FIG. 4B. dCas9 and MCP expression were validated as described in US 2019/0284572 and WO 2019/183123, each of which is herein incorporated by reference in its entirety for all purposes. The system was validated in vivo using a Ttr guide RNA array as described in US 2019/0284572 and WO 2019/183123, each of which is herein incorporated by reference in its entirety for all purposes. A general schematic of the structure of a SAM guide RNA, including the MS2 stem loops, is shown in FIG. 6.

To validate the SAM mice as a tool to increase expression of the Myoc gene, different viral vectors were first tested for expression in the trabecular meshwork (TM), ciliary body (CB), and corneal endothelium (CE). FIG. 7 shows expression from Ad5, AAV2.Y3F, and lentivirus. Each virus expresses GFP (shown in green), and the blue is DAPI staining showing the cells. Of all vectors tested, Ad5 had the highest transduction efficiency for TM after intravitreal (IVT) injection but caused inflammation, and transgene expression was transient. AAV2.Y3F transduced TM and CB following intracameral (IC) injection. Lentiviruses transduced both TM and CE. Subsequent studies showed that lentivirus is more specific for the TM compared to AAV2.Y3F.

Figures 8, 9:
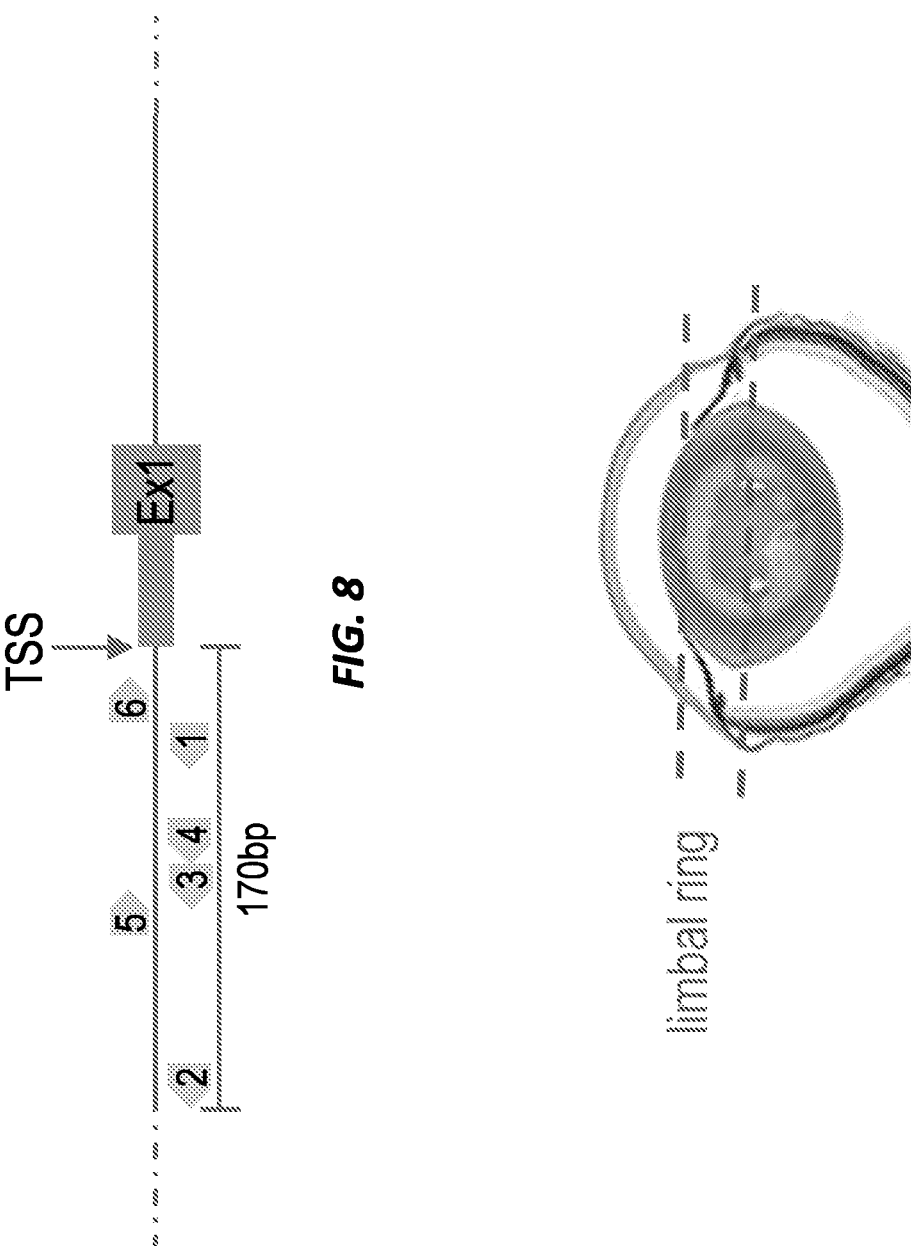
FIG. 8 shows the positions of mouse Myoc SAM guide RNA target sequences.
FIG. 9 shows an eye dissection schematic.

We next validated the SAM mice using guide RNAs targeting the mouse Myoc sequence upstream of the start codon. The regions targeted by the six guide RNAs are shown in FIG. 8. The target sequences for the six guide RNAs are shown in Table 7.

TABLE 7

Mouse Myoc SAM Guide RNA Target Sequences.

| Guide | Target Sequence | SEQ ID NO | PAM |
|---|---|---|---|
| mGU | AAAGACATTTATATATCCTG | 90 | GGG |
| mGU2 | CTTTAAAAACAAAGTGCCGG | 91 | AGG |

TABLE 7-continued

Mouse Myoc SAM Guide RNA Target Sequences.

| Guide | Target Sequence | SEQ ID NO | PAM |
|---|---|---|---|
| mGU3 | CTGGGTTGGACCAGCCATGG | 92 | GGG |
| mGU4 | AGAGGTGATCACATGAAGCT | 93 | GGG |
| mGU5 | GTAATCCTCCTATCCCCCCA | 94 | TGG |
| mGU6 | ACTTCAGGCTTGAGCCAGCA | 95 | GGG |

Figure 10A:
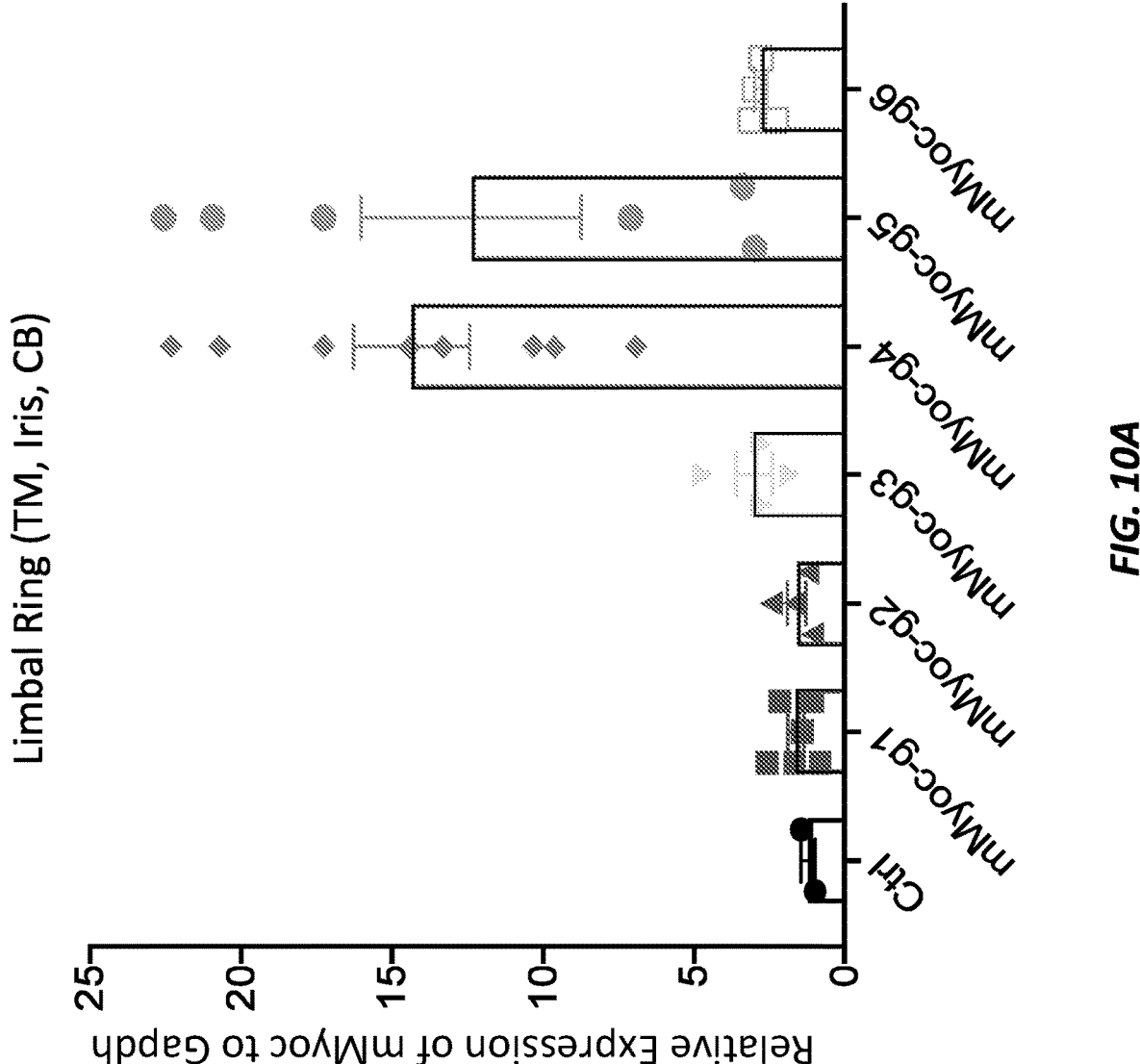
FIGS. 10A-10C show mouse Myoc expression relative to Gapdh expression as measured by qPCR in the limbal ring (trabecular meshwork (TM), iris, and ciliary body (CB)
Figure 10B:
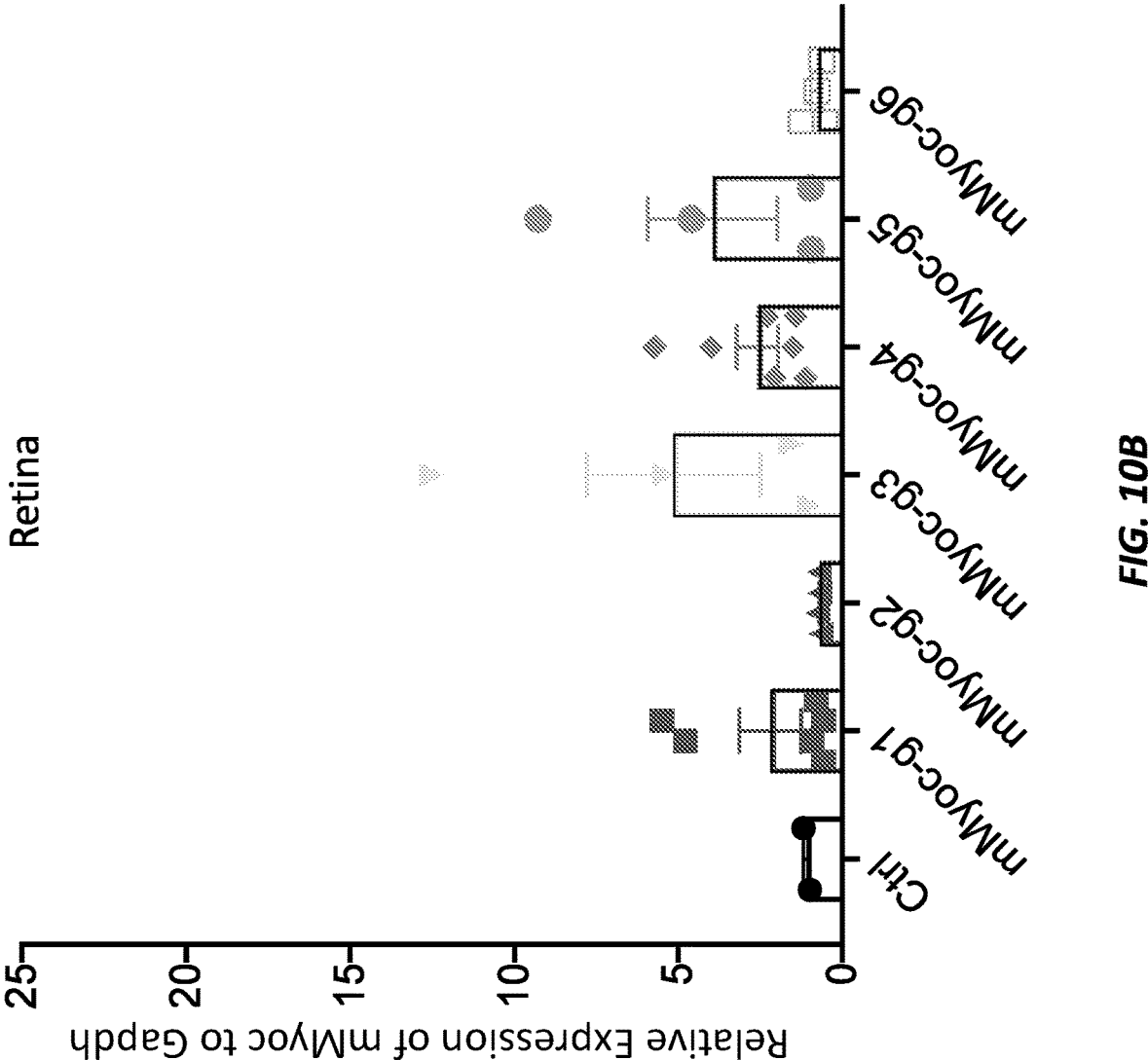
Figure 10C:
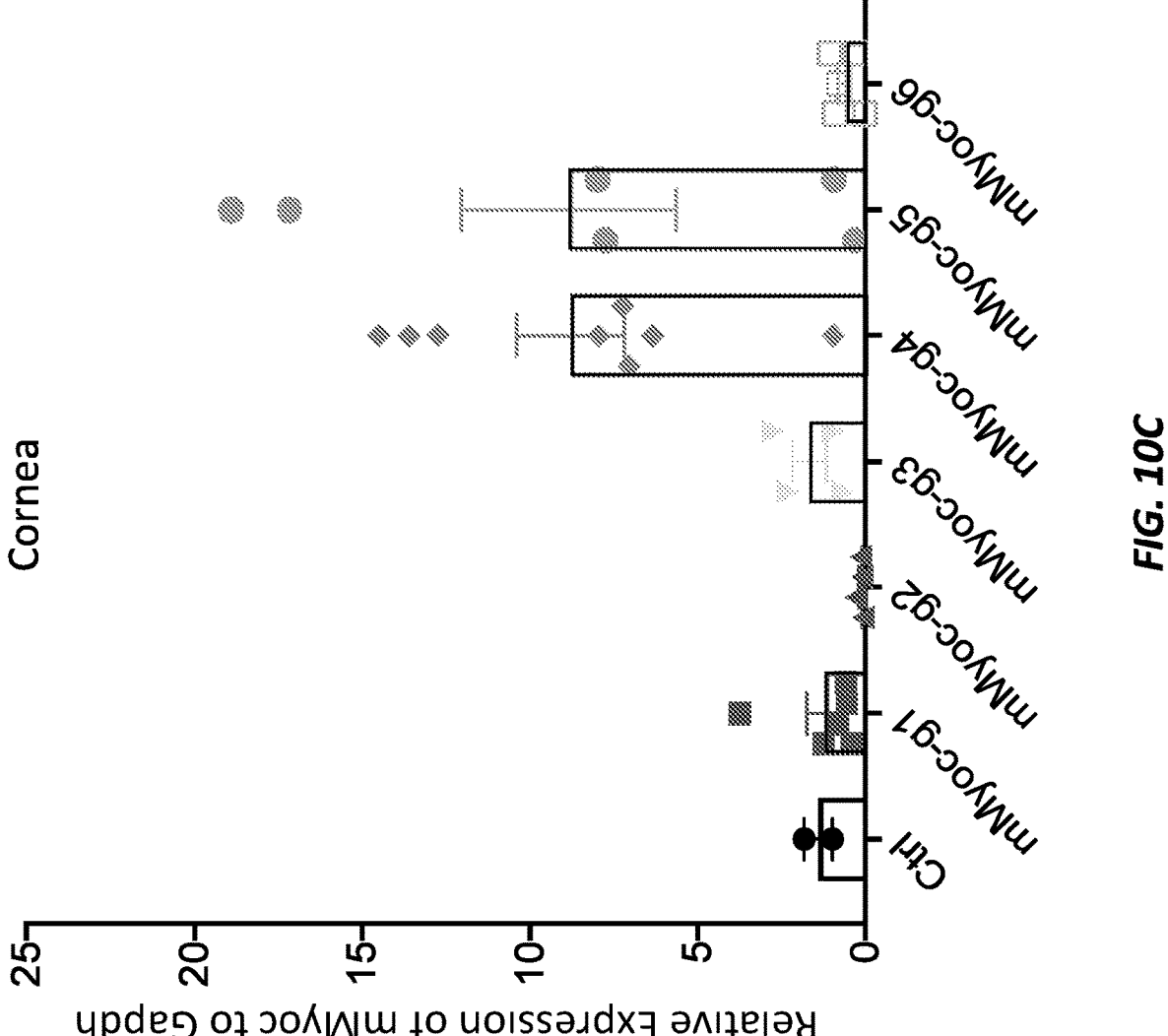

For an initial proof-of-concept, the SAM mice were bilaterally injected with 1 μL (1E+10 vg injected) of the six guide RNAs in AAV.Y3F via the intracameral route at a titer of 1E+13 vg/mL). Four weeks later, the anterior segment was dissected as shown in FIG. 9, and RNA was extracted for qRT-PCR. The results show that mouse Myoc expression was increased in the SAM mice in the limbal ring (trabecular meshwork (TM), iris, and ciliary body (CB); FIG. 10A), in the retina (FIG. 10B), and in the cornea (FIG. 10C) following administration of the mouse Myoc SAM guide RNAs relative to a control guide RNA.

Example 3. Generation of SAM Mice Comprising a Humanized Myocilin (MYOC) Locus Comprising a Y437H Mutation As shown in Example 1, we have generated mice comprising a humanized myocilin (MYOC) locus comprising a Y437H mutation. As shown in Example 2, we have generated and validated mice comprising genomically integrated dCas9 synergistic activation mediator (SAM) system components (dCas9-VP64 and MCP-p65-HSF1) as one transcript driven by the endogenous Rosa26 promoter.

Next, we sought to use the SAM mice to increase expression of the humanized MYOC locus. SAM mice comprising a humanized MYOC locus comprising a Y437H mutation were generated through breeding the mice described in Example 1 to the mice described in Example 2.

Figure 11:
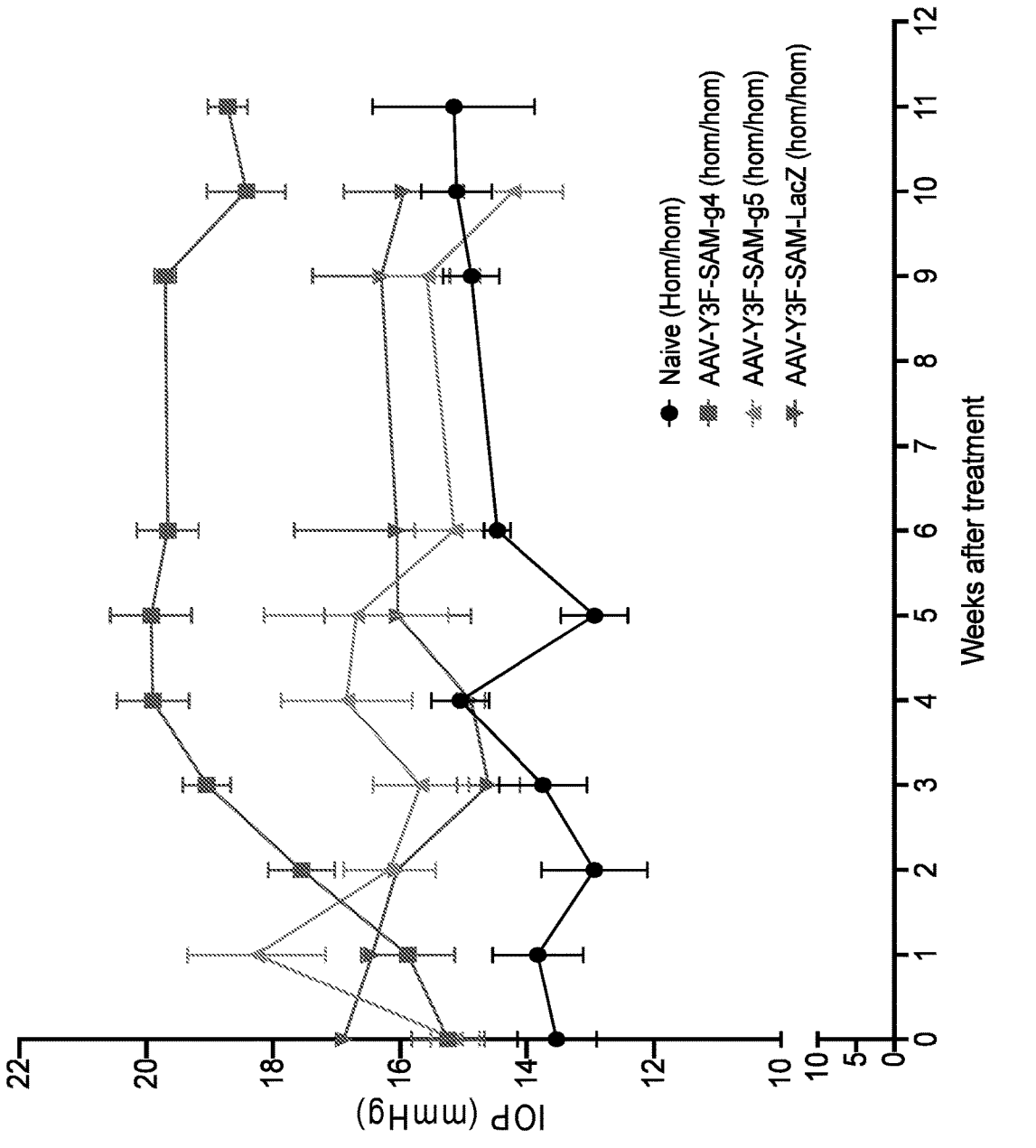
FIG. 11 shows intraocular pressure (IOP) in SAM mice comprising a humanized MYOC locus comprising a Y437H mutation (SAM-MYOC mice, homozygous for each allele) treated with AAV2.Y3F-SAM-g4, AAV2.Y3F-SAM-g5, an AAV2.Y3F-SAM-LacZ control, or nothing (naïve).
Figure 13:
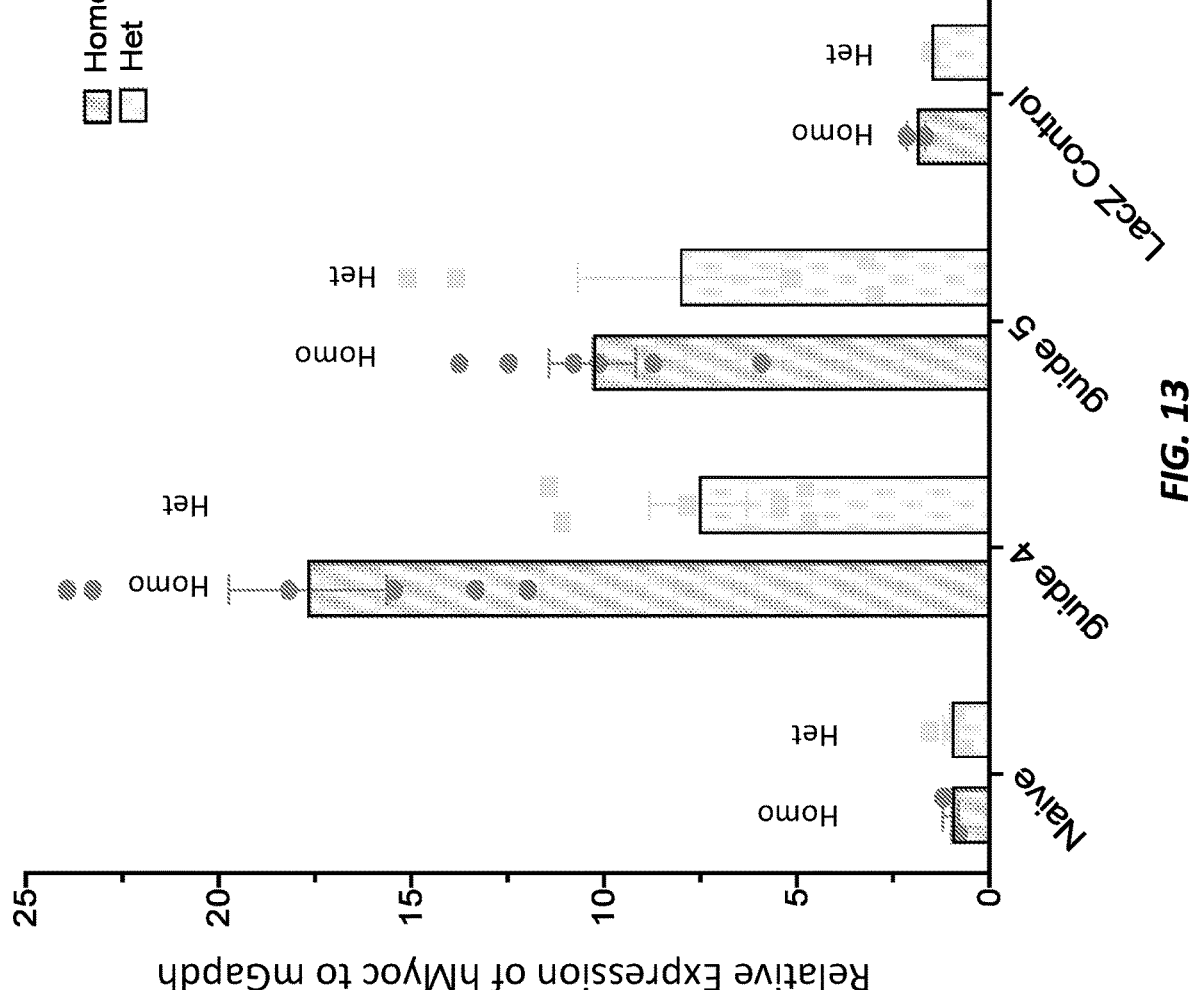
FIG. 13 shows human MYOC expression relative to Gapdh expression as measured by qPCR following administration of mouse Myoc SAM guide RNAs g4 and g5 or a SAM LacZ control gRNA in SAM mice comprising a humanized MYOC locus comprising a Y437H mutation that are either heterozygous or homozygous for the humanized MYOC locus.

Example 4. Validation of SAM Mice Comprising a Humanized Myocilin (MYOC) Locus Comprising a Y437H Mutation as a Glaucoma Model To validate the SAM mice comprising a humanized MYOC locus comprising a Y437H mutation (SAM-MYOC mice), SAM-MYOC mice homozygous or heterozygous for the humanized MYOC locus were treated with AAV2.Y3F-SAM-g4, AAV2.Y3F-SAM-g5, an AAV2.Y3F-SAM-LacZ control, or nothing (naïve). As shown in FIG. 13 (qPCR) and FIG. 14 (RNASCOPE®), a genotype-dependent increase in humanized MYOC Y437H expression was observed at 12 weeks after injection in the limbal ring (trabecular meshwork (TM), iris, and ciliary body (CB)), and this also correlated with increased intraocular pressure as shown in FIG. 11. This validated the SAM-MYOC mice as a suitable MYOC disease model with increased IOP.

Figure 12:
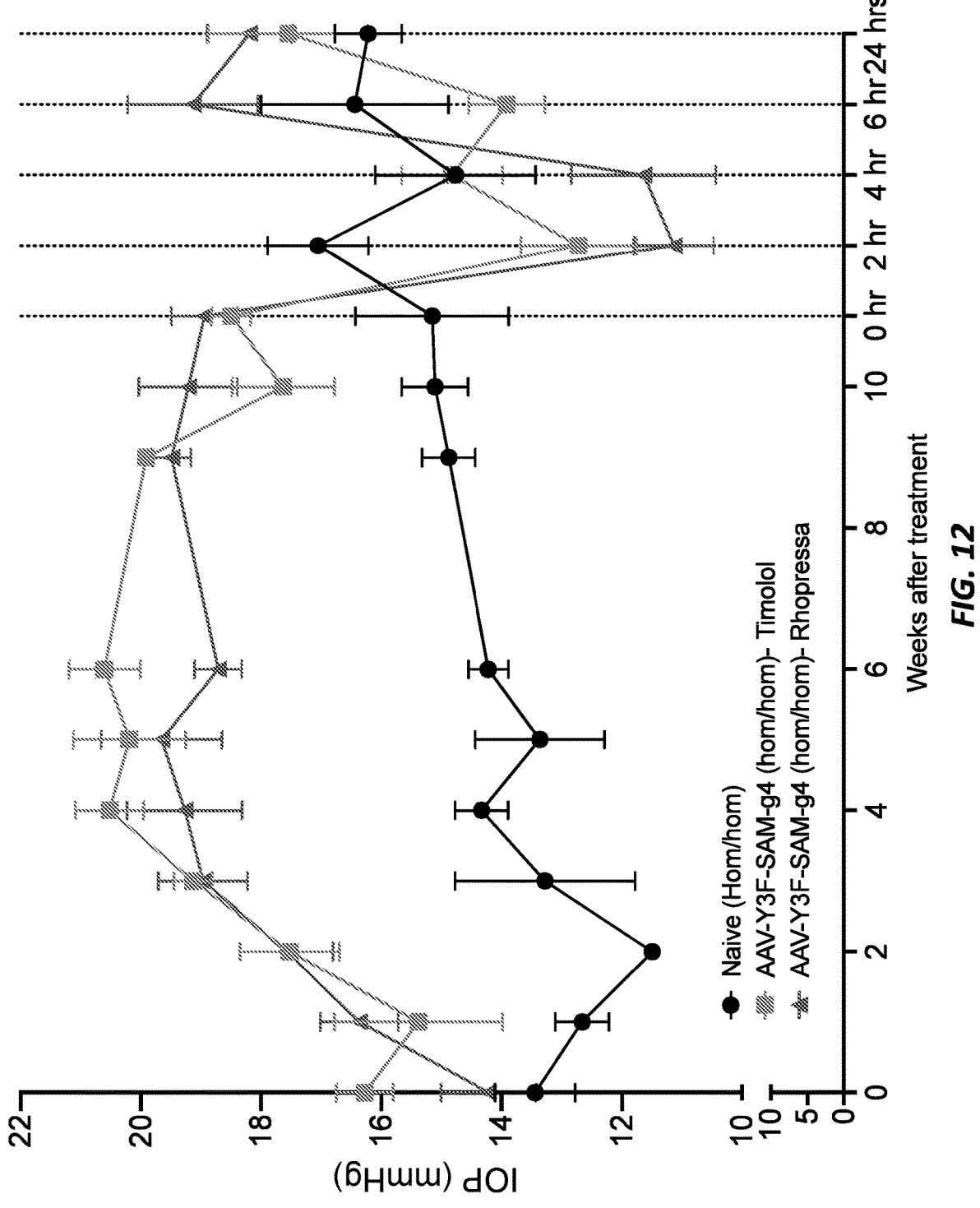
FIG. 12 shows intraocular pressure (IOP) in SAM mice comprising a humanized MYOC locus comprising a Y437H mutation (SAM-MYOC mice, homozygous for each allele) treated with AAV2.Y3F-SAM-g4 or nothing (naïve), and in which the AAV2.Y3F-SAM-g4-treated mice were subsequently treated with either timolol or RHOPRESSA®.

IOP-lowering drugs used to treat glaucoma patients were then tested as a proof-of-concept to determine if they could lower the IOP observed in the SAM-MYOC mice following treatment with SAM-g4. We tested two IOP-lowering drugs: (1) timolol (a beta blocker that suppresses aqueous humor formation); and (2) RHOPRESSA® (a ROCK inhibitor that increases outflow of aqueous humor). At day 0, AAV2.Y3F-SAM-g4 was administered. Approximately 10 weeks later, timolol or RHOPRESSA® was administered. At 0 hours, the IOP was measured, and each eye received one drop of either timolol or RHOPRESSA®, and IOP was measured at 2, 4, 6, and 24 hours after treatment. As shown in FIG. 12, each drug was effective at lowering IOP in the SAM-MYOC mice treated with SAM-g4.

Figure 15A:
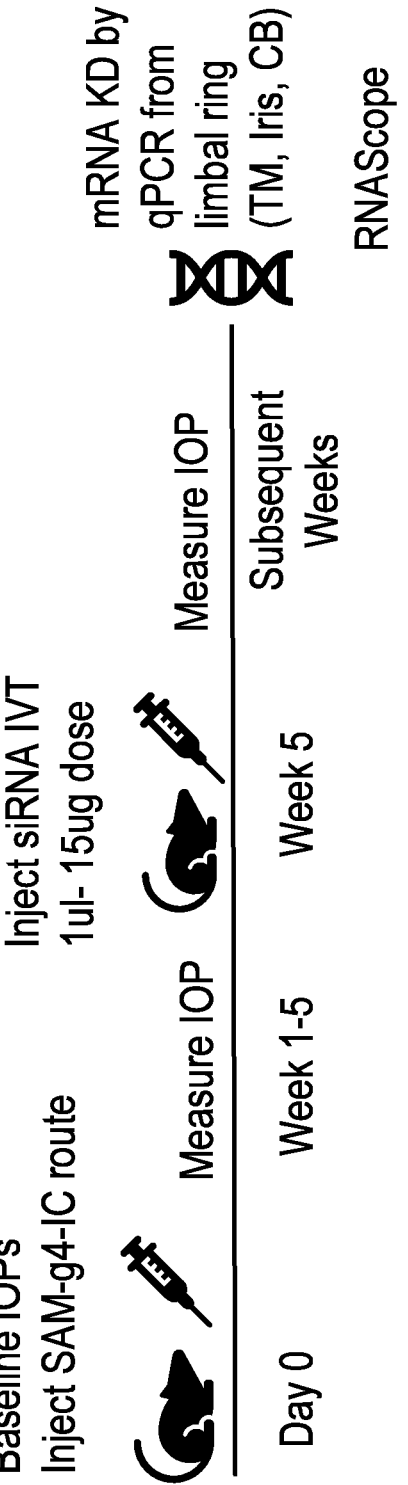
FIG. 15A shows the experimental setup for testing the effect of human MYOC siRNA #1 on intraocular pressure (IOP) in SAM mice comprising a humanized MYOC locus comprising a Y437H mutation (SAM-MYOC mice, homozygous for each allele) treated with a mix of AAV2.Y3F-SAM-g4 and LV-SAM-g4.
Figure 15B:
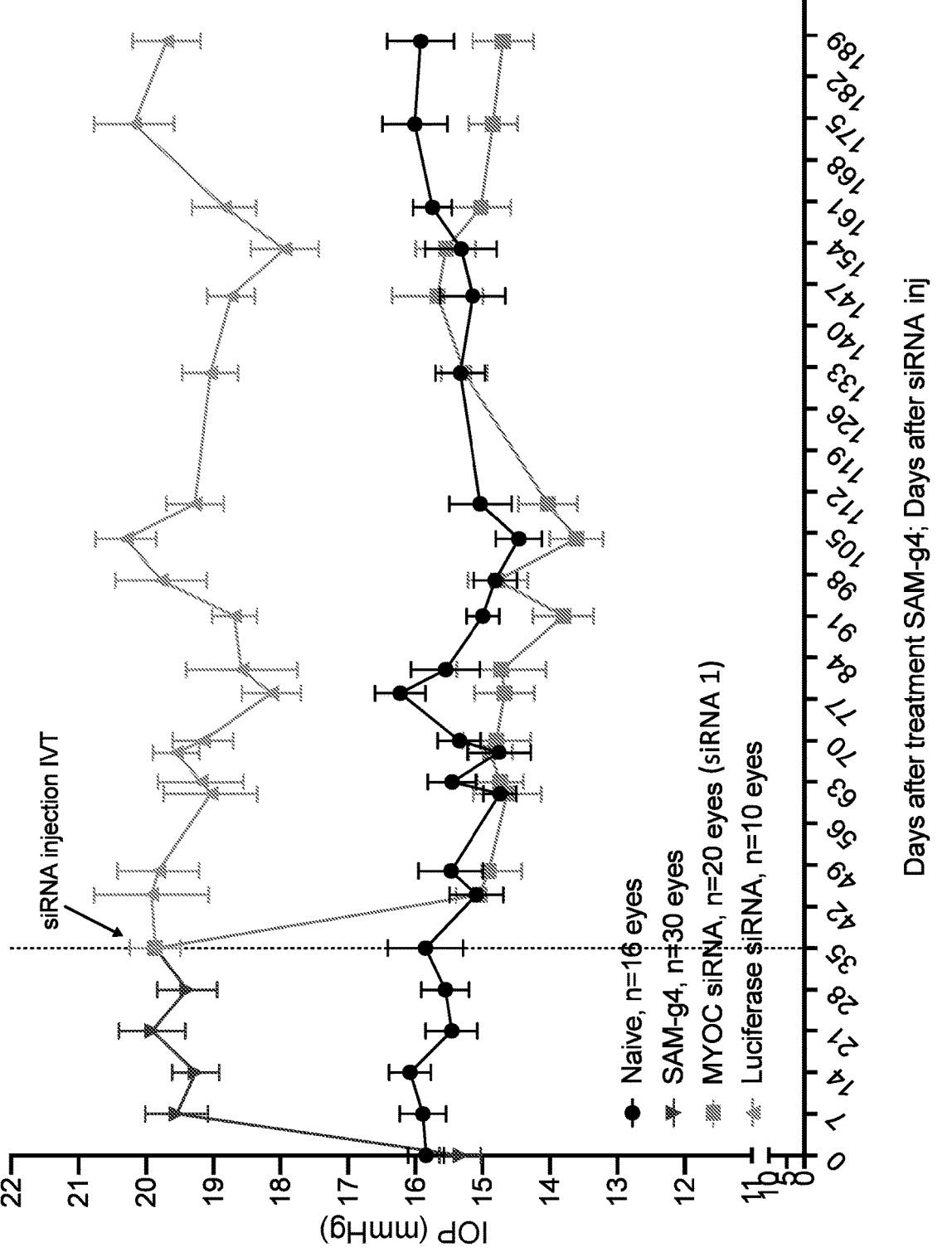
FIG. 15B shows intraocular pressure (IOP) in SAM mice comprising a humanized MYOC locus comprising a Y437H mutation (SAM-MYOC mice, homozygous for each allele) treated with AAV2.Y3F-SAM-g4 or nothing (naïve), and in which the AAV2.Y3F-SAM-g4-treated mice were subsequently treated with either human MYOC siRNA or a control luciferase siRNA.

An siRNA targeting human MYOC was then tested to determine if it could lower the high IOP observed in the SAM-MYOC mice following treatment with SAM-g4. The experimental setup is shown in FIG. 15A. SAM-g4 was administered via intracameral (IC) injection at day 0, and baseline IOP was measured. IOP was then measured over the following five weeks. At week five, MYOC siRNA #1 (1 μL, 15 μg dose) was administered via intravitreal (IVT) injection, and IOP was measured at various timepoints over the subsequent weeks. There were three treatment groups: (1) naïve control mice; (2) SAM-g4-treated mice treated with human MYOC siRNA; and (3) SAM-g4-treated mice treated with luciferase siRNA. As shown in FIG. 15B, the human MYOC siRNA lowered IOP in the SAM-MYOC mice treated with SAM-g4, reversing and returning the IOP to baseline levels starting at D7 after siRNA injection, whereas the luciferase siRNA had no effect on IOP.

Figure 16A:
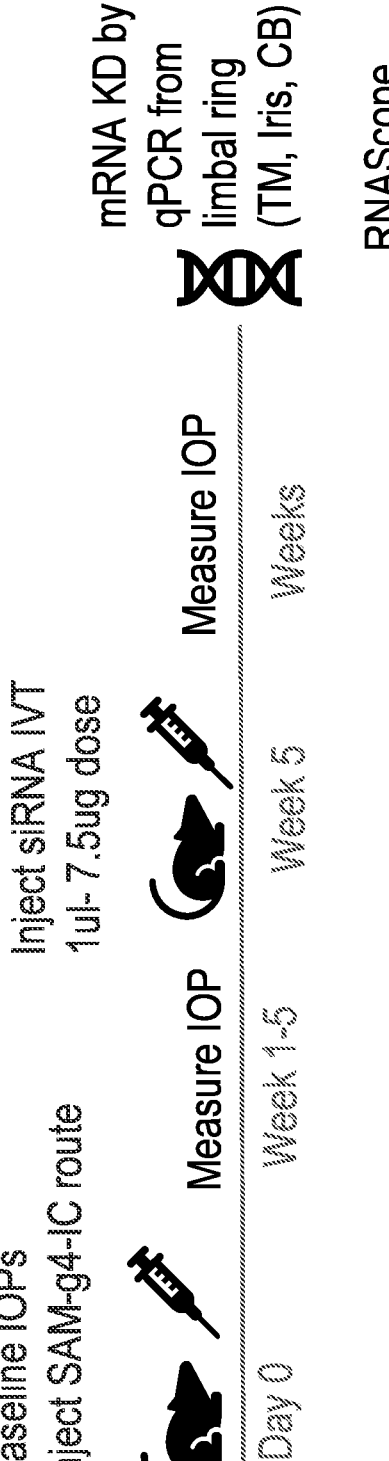
FIG. 16A shows the experimental setup for testing the effect of human MYOC siRNAs #1, #2, #3, #4, and #5 on intraocular pressure (IOP) in SAM mice comprising a humanized MYOC locus comprising a Y437H mutation (SAM-MYOC mice, homozygous for each allele) treated with LV-SAM-g4.
Figure 16B:
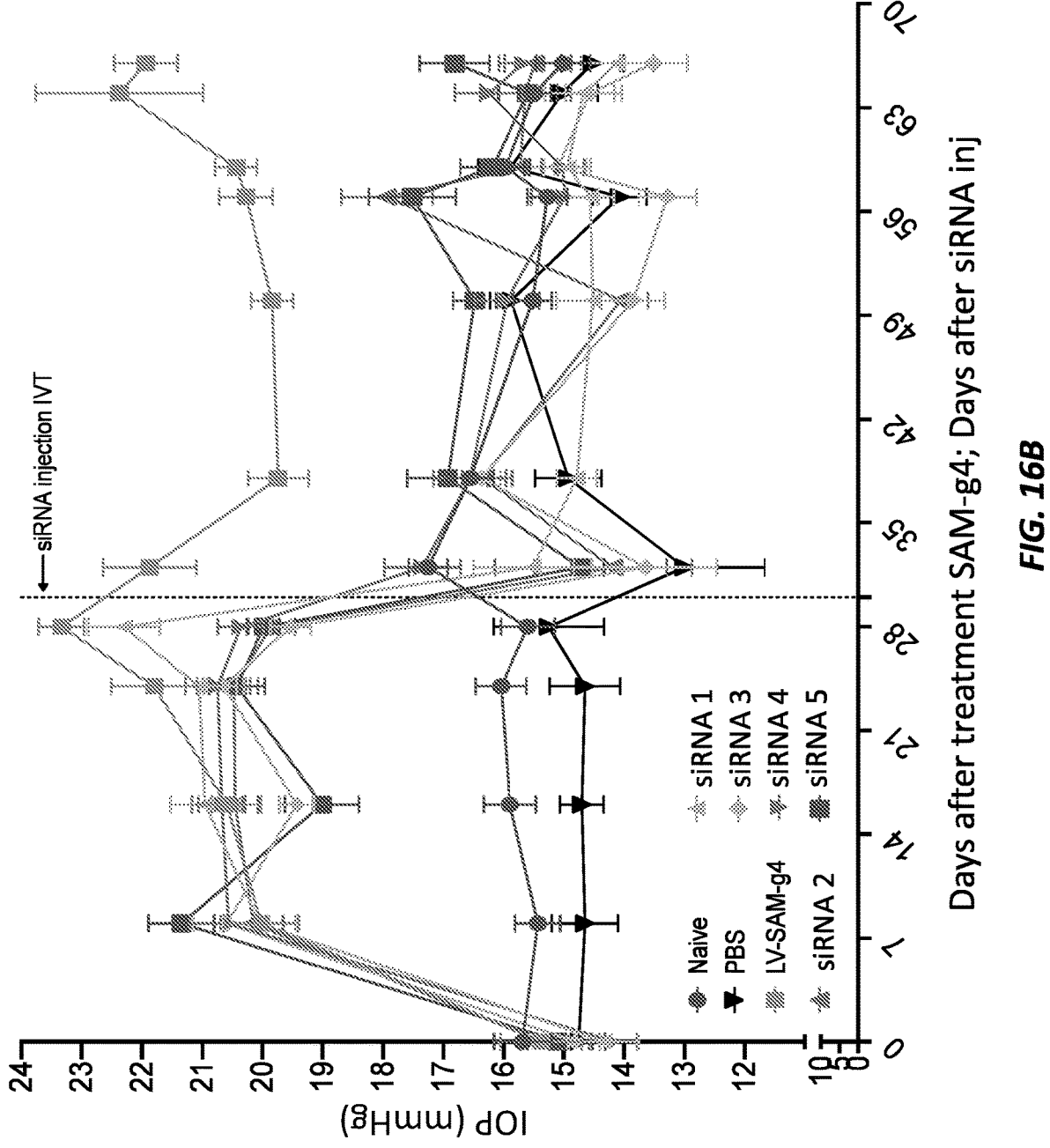
FIG. 16B shows intraocular pressure (IOP) in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with human MYOC siRNA #1, #2, #3, #4, or #5.
Figure 16C:
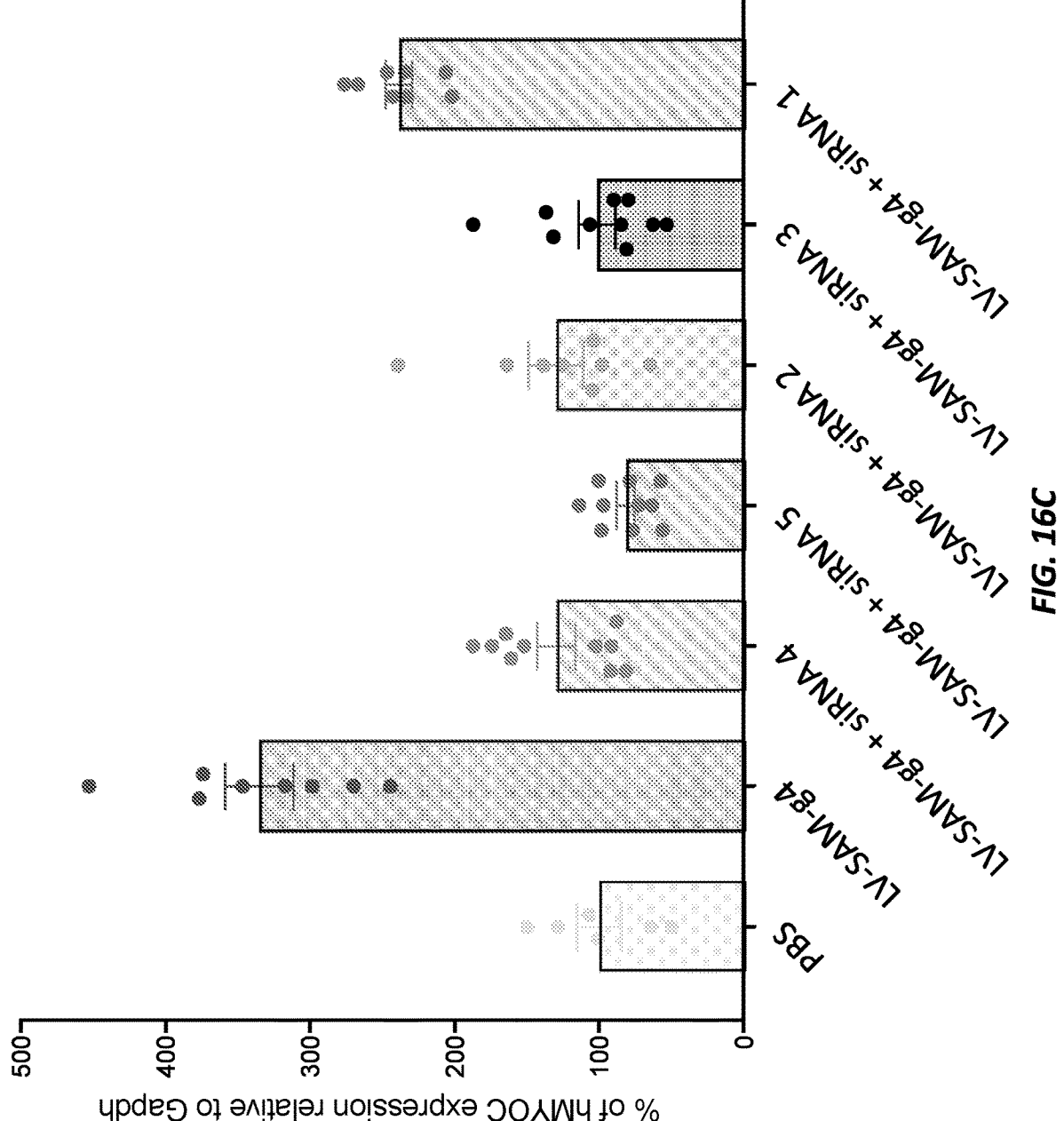
FIG. 16C shows qPCR results showing the percentage of human MYOC mRNA expression relative to Gapdh in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with human MYOC siRNA #1, #2, #3, #4, or #5.
Figure 16D:
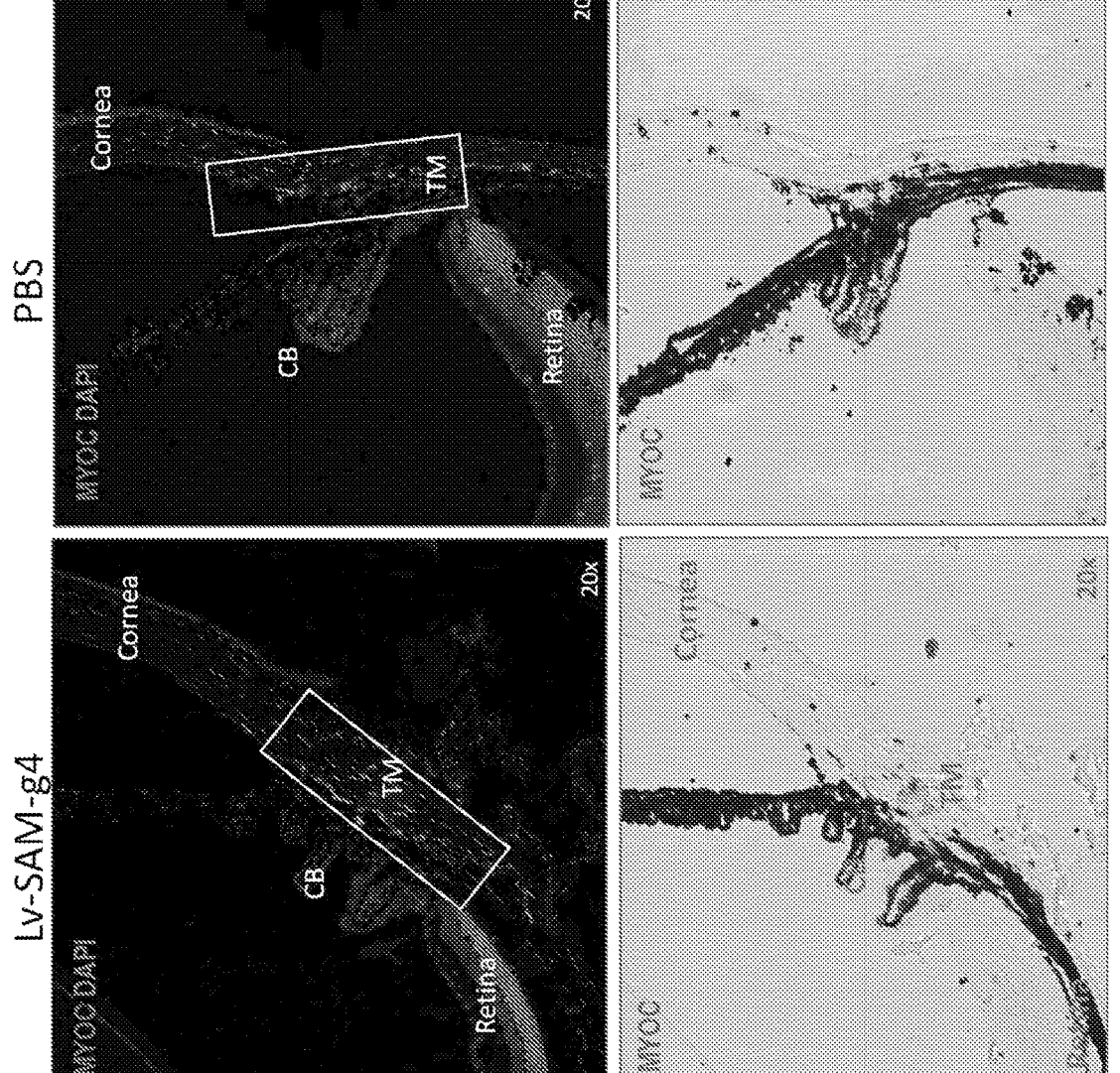
FIG. 16D shows RNASCOPE® analysis of human MYOC mRNA expression in eyes from SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with human MYOC siRNA #2 or #3.
Figure 16D:
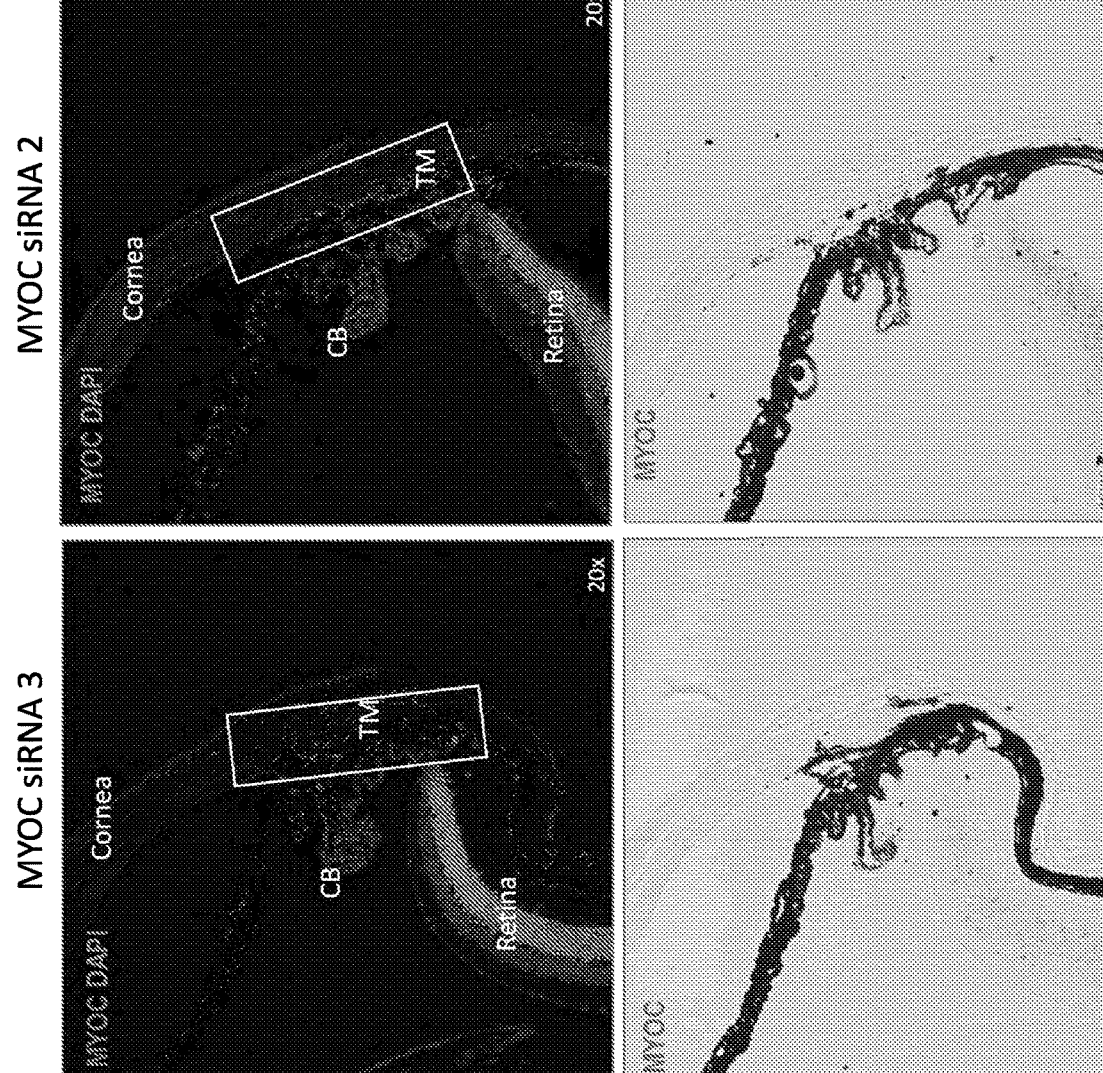

Several additional siRNAs targeting human MYOC were then tested at a lower dose to determine if they could lower the IOP observed in the SAM-MYOC mice following treatment with lentiviral SAM-g4. Mice were bilaterally injected with SAM-g4 and siRNAs. The experimental setup is shown in FIG. 16A. SAM-g4 was administered via intracameral (IC) injection at day 0, and baseline IOP was measured. IOP was then measured over the following five weeks. At week five, MYOC siRNAs #1, #2, #3, #4, and #5 (1 μL, 7.5 μg dose) were administered via intravitreal (IVT) injection, and IOP was measured at various timepoints over the subsequent weeks. mRNA knockdown in the limbal ring was tested by qPCR, and RNASCOPE® analysis was done. The control groups included naïve control mice, PBS-treated mice, and LV-SAM-g4-treated mice. As shown in FIG. 16B, each human MYOC siRNA lowered IOP in the SAM-MYOC mice treated with SAM-g4, reversing and returning the IOP to baseline levels soon after siRNA injection. As shown in FIG. 16C, each human MYOC siRNA decreased human MYOC mRNA expression relative to the LV-SAM-g4 group as measured by qPCR in a sample from the limbal ring. RNASCOPE® analysis confirmed that the siRNAs mediated knockdown of human MYOC mRNA in the SAM-MYOC mice (FIG. 16D).

Figure 17A:
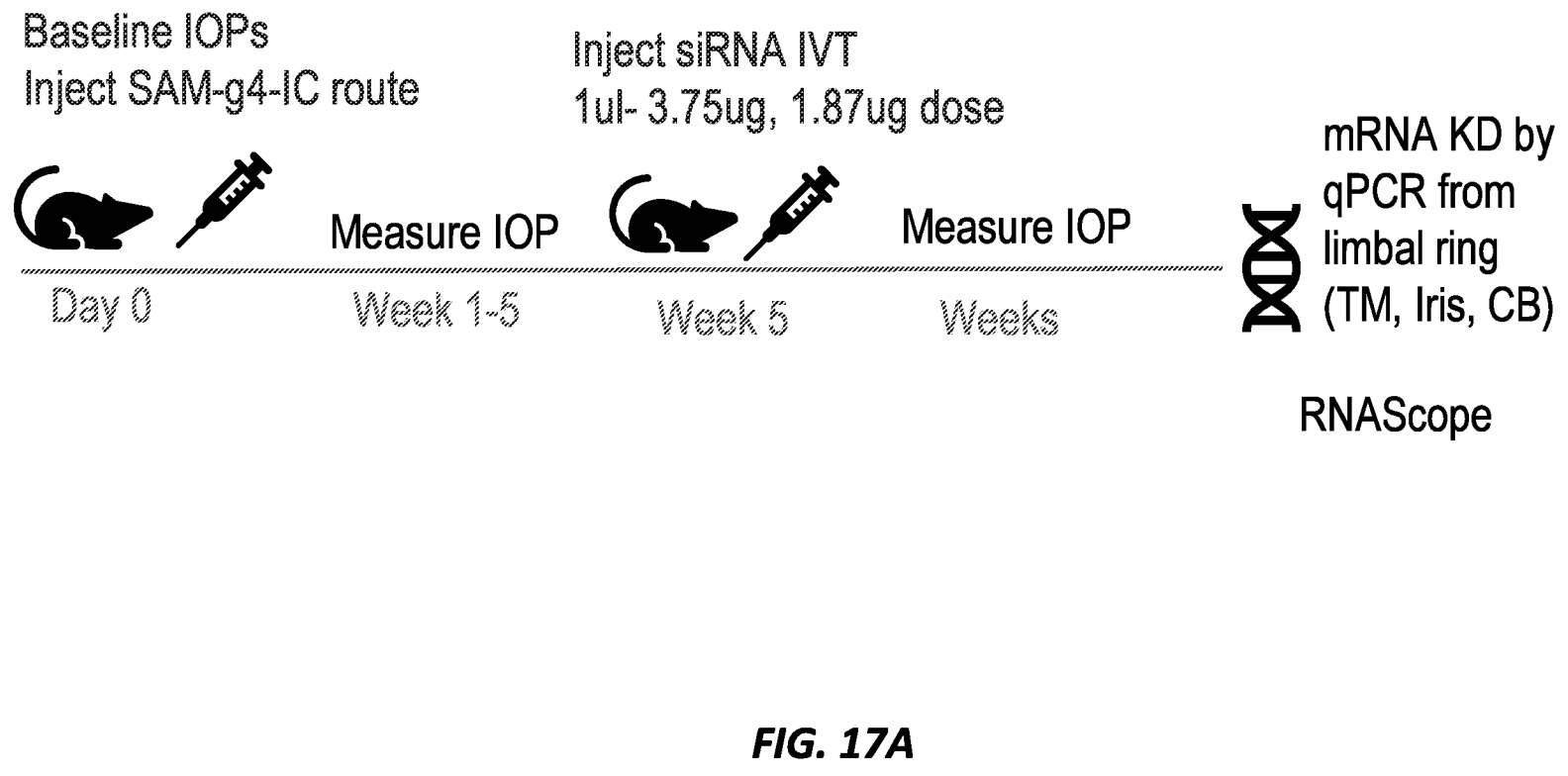
Figure 17B:
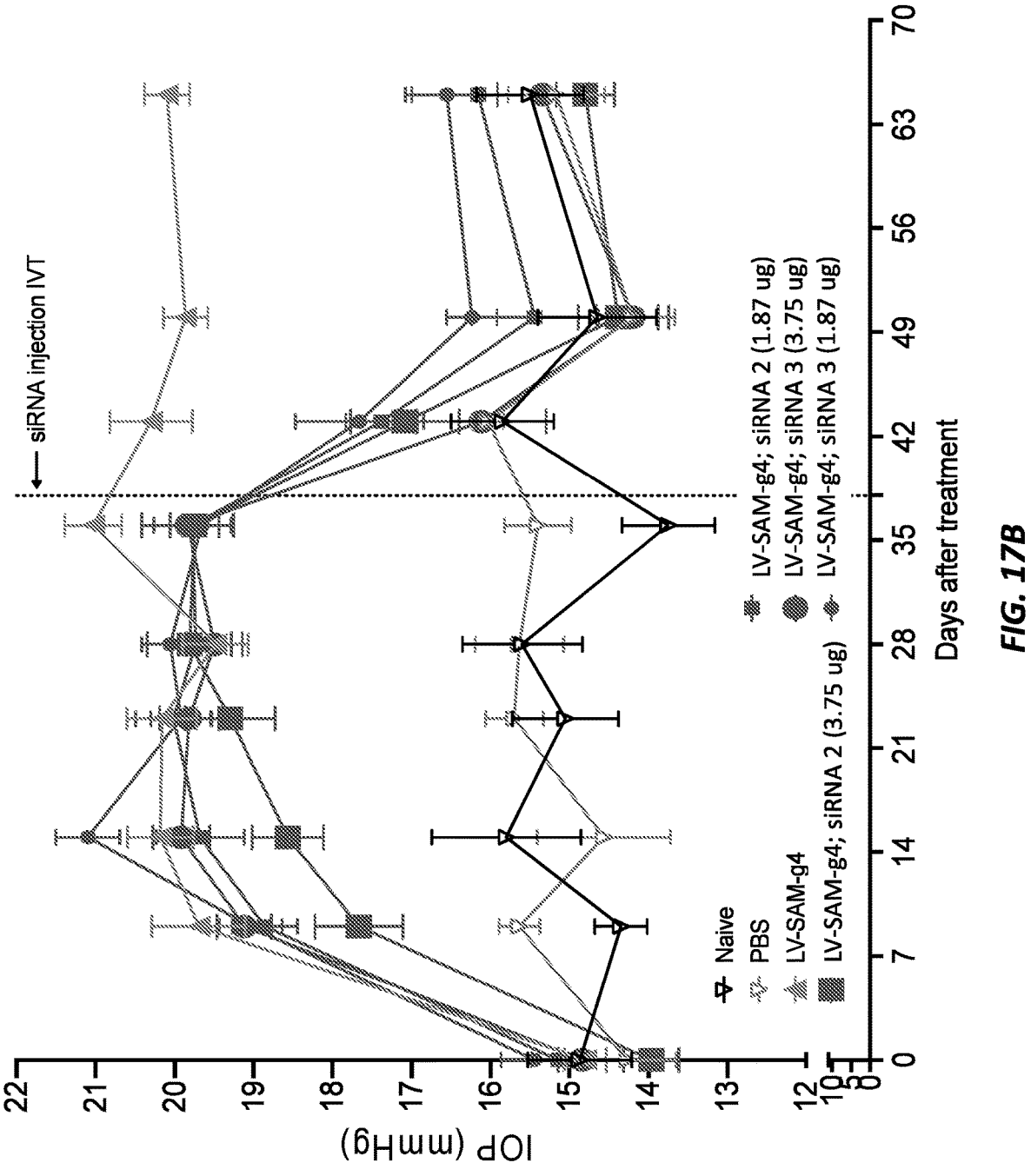
FIG. 17B shows intraocular pressure (IOP) in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with human MYOC siRNA #2 or #3.
Figure 17C:
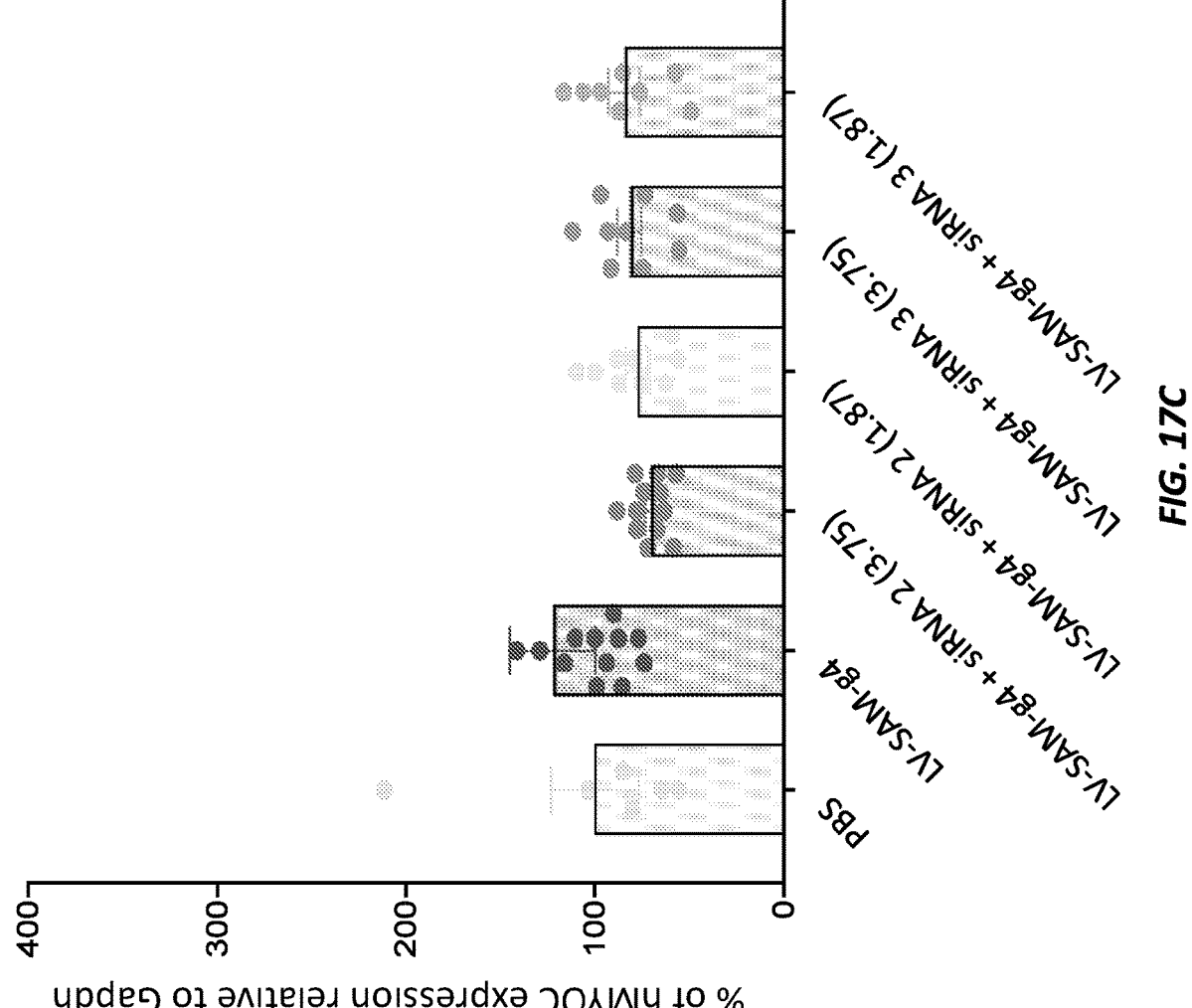
FIG. 17C shows qPCR results showing the percentage of human MYOC mRNA expression relative to Gapdh in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with human MYOC siRNA #2 or #3.

Human MYOC siRNAs #2 and #3 were then tested at even lower doses to determine if they could lower the IOP observed in the SAM-MYOC mice following treatment with lentiviral SAM-g4. Mice were bilaterally injected with SAM-g4 and siRNA. The experimental setup is shown in FIG. 17A. SAM-g4 was administered via intracameral (IC) injection at day 0, and baseline IOP was measured. IOP was then measured over the following five weeks. At week five, MYOC siRNAs #2 and #3 (1 μL, 3.75 μg dose or 1.87 μg dose) were administered via intravitreal (IVT) injection, and IOP was measured at various timepoints over the subsequent weeks. mRNA knockdown in the limbal ring was tested by qPCR, and RNASCOPE® analysis was done. The control groups included naïve control mice, PBS-treated mice, and LV-SAM-g4-treated mice. As shown in FIG. 17B, each human MYOC siRNA lowered IOP in the SAM-MYOC mice treated with SAM-g4 at each dose tested, reversing and returning the IOP to baseline levels soon after siRNA injection. As shown in FIG. 17C, each human MYOC siRNA decreased human MYOC mRNA expression relative to the LV-SAM-g4 group as measured by qPCR in a sample from the limbal ring at each dose tested.

Other MYOC glaucoma models having transgenic overexpression of human myocilin Y437H show an IOP increase of only about 2-3 mmHg, and the MYOC is expressed everywhere. In addition, the IOP phenotype is lost over breeding. The model described herein has the advantage that the expression is mostly restricted to the target tissue of disease pathology: the trabecular meshwork. In addition, we observe a greater increase in IOP of about 5-6 mmHg.

Example 5. Testing Putative Therapeutics with SAM Mice Comprising a Humanized Myocilin (MYOC) Locus Comprising a Y437H Mutation Upon validation of SAM-MYOC mice as a glaucoma model, experiments were performed to validate SAM-MYOC mice as a glaucoma model for testing additional glaucoma targets. The trabecular meshwork (TM) is a tissue located in the anterior chamber angle of the eye which is resistant to the evacuation of aqueous humor and is critical for intraocular pressure (IOP). The secreted glycoprotein angiopoietin-like 7 (ANGPTL7) is a central player in TM pathology and IOP homeostasis. Various pathways implicated in glaucoma, including steroid exposure, and upregulated MYOC and TGF-B2 expression, can lead to increased ANGPTL7 expression, which is associated with TM dysfunction and elevated IOP. Therefore, we designed experiments to test the targeting of ANGPTL7 in SAM-MYOC mice.

Figure 18A:
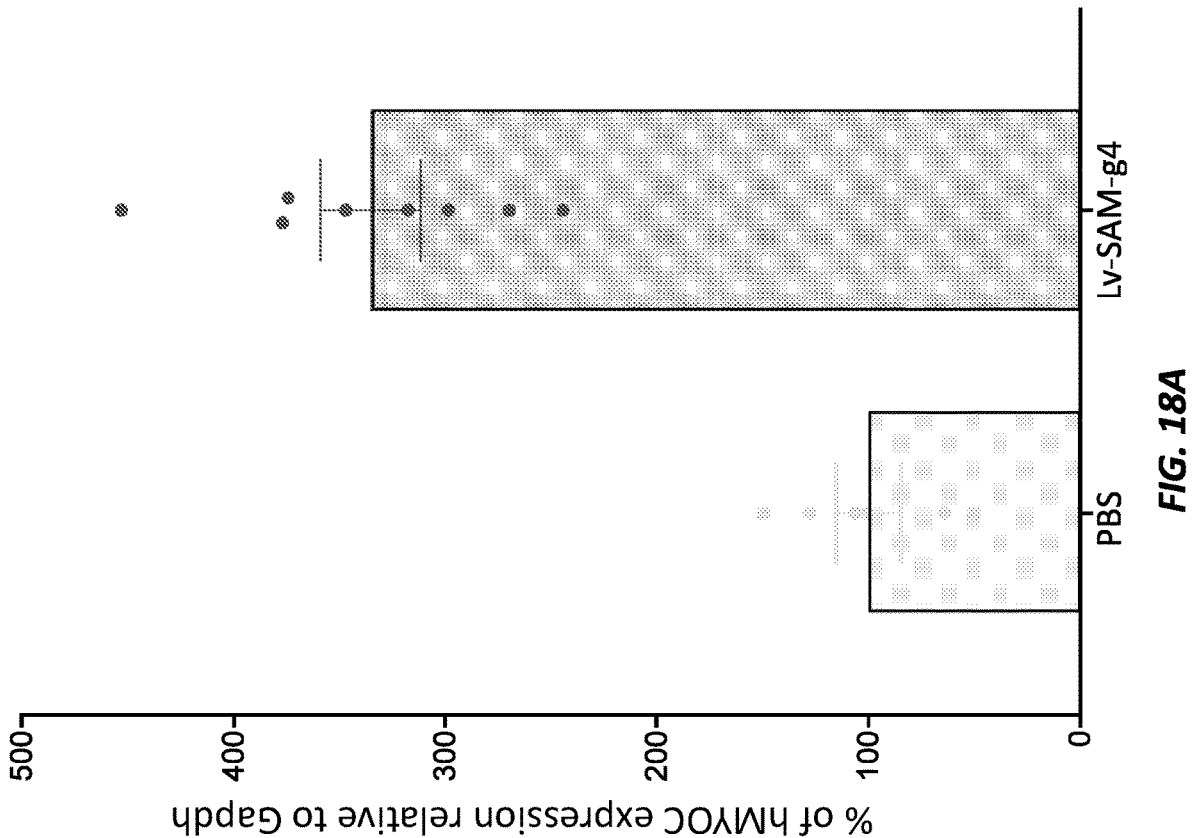
FIG. 18A shows qPCR results showing the percentage of human MYOC mRNA expression relative to Gapdh in SAM mice comprising a humanized MYOC locus comprising a Y437H mutation (SAM-MYOC mice, homozygous for each allele) treated with LV-SAM-g4 or PBS.
Figure 18B:
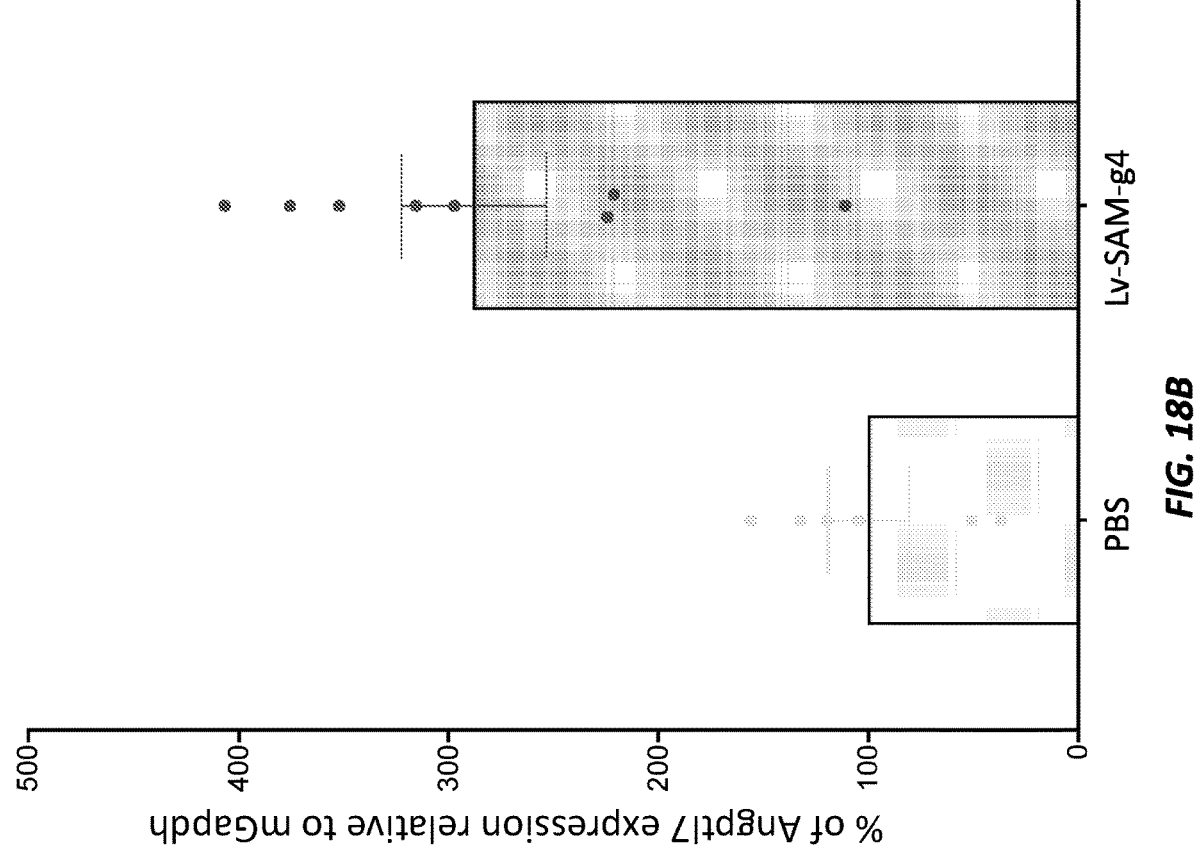
FIG. 18B shows qPCR results showing the percentage of Angptl7 mRNA expression relative to Gapdh in SAM mice comprising a humanized MYOC locus comprising a Y437H mutation (SAM-MYOC mice, homozygous for each allele) treated with LV-SAM-g4 or PBS.
Figure 18C:
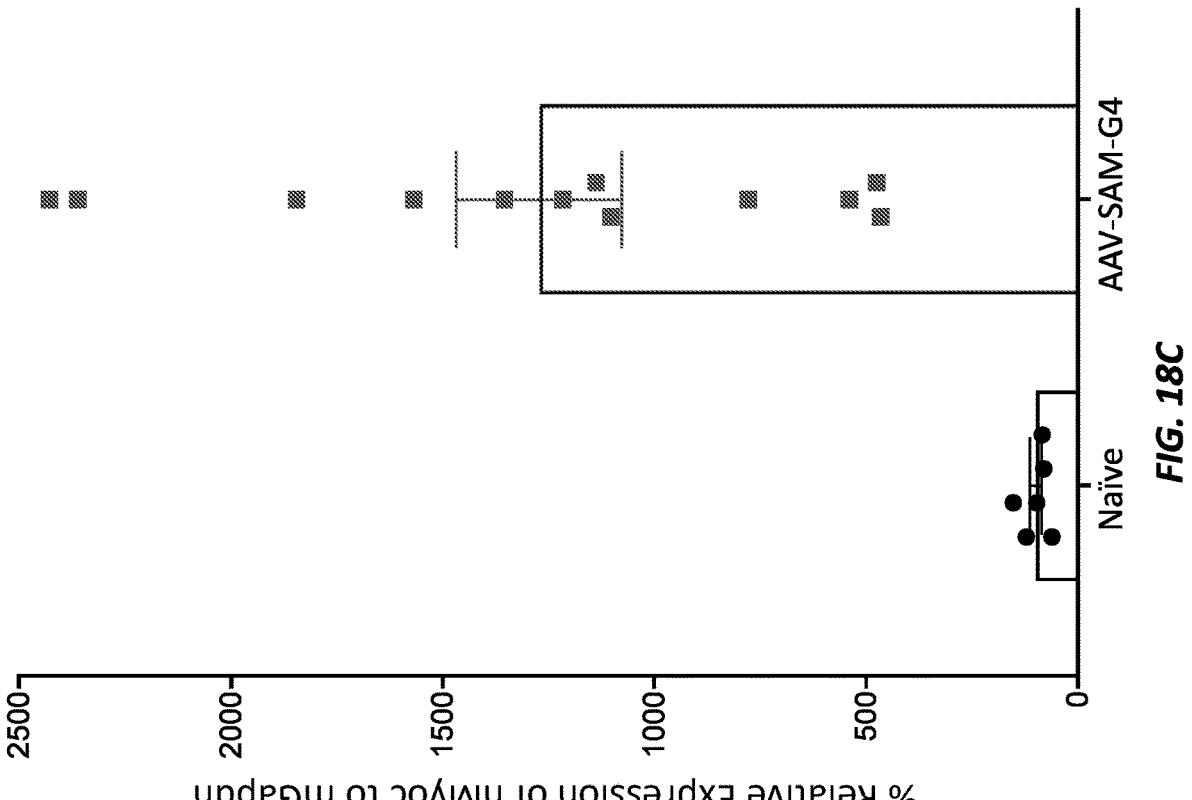
FIG. 18C shows qPCR results showing the percentage of human MYOC mRNA expression relative to Gapdh in SAM mice comprising a humanized MYOC locus comprising a Y437H mutation (SAM-MYOC mice, homozygous for each allele) treated with AAV-SAM-g4 or nothing (naïve).
Figure 18D:
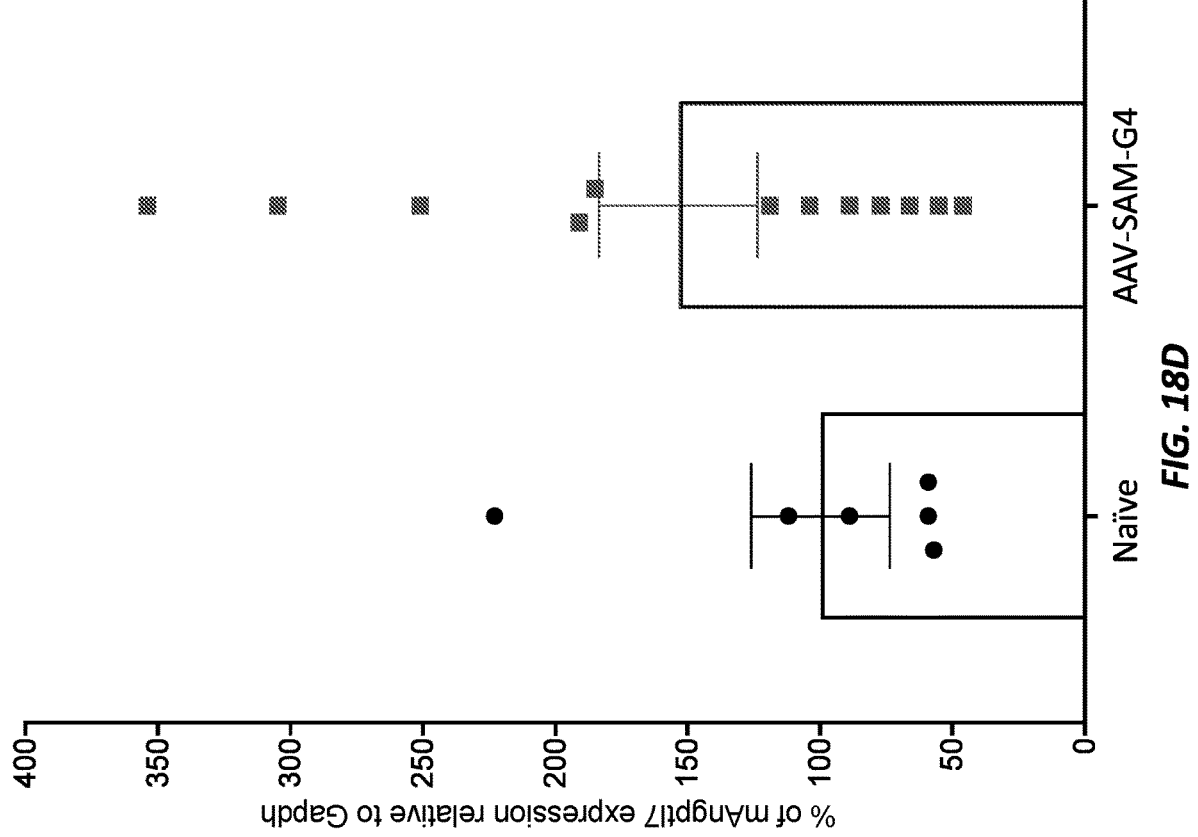
FIG. 18D shows qPCR results showing the percentage of Angptl7 mRNA expression relative to Gapdh in SAM mice comprising a humanized MYOC locus comprising a Y437H mutation (SAM-MYOC mice, homozygous for each allele) treated with AAV-SAM-g4 or nothing (naïve).

Using the SAM-MYOC mouse model described herein, expression of Angptl7 was observed to increase in SAM mice in correlation to MYOC overexpression. As shown by qPCR in FIG. 18A, human MYOC expression increased over 3-fold in mice treated by intracameral (IC) injection with Lv-SAM-g4 compared to the PBS control. Expression of Angptl7 underwent a corresponding increase relative to Gapdh as shown by qPCR in FIG. 18B. Similarly, mice treated with AAV-SAM-g4 showed a significant increase in human MYOC expression relative to Gapdh compared to untreated naïve mice, as shown by qPCR in FIG. 18C. Expression of Angptl7 also increased in mice treated with AAV-SAM-g4 compared to untreated naïve mice as shown by qPCR in FIG. 18D.

Figure 19A:
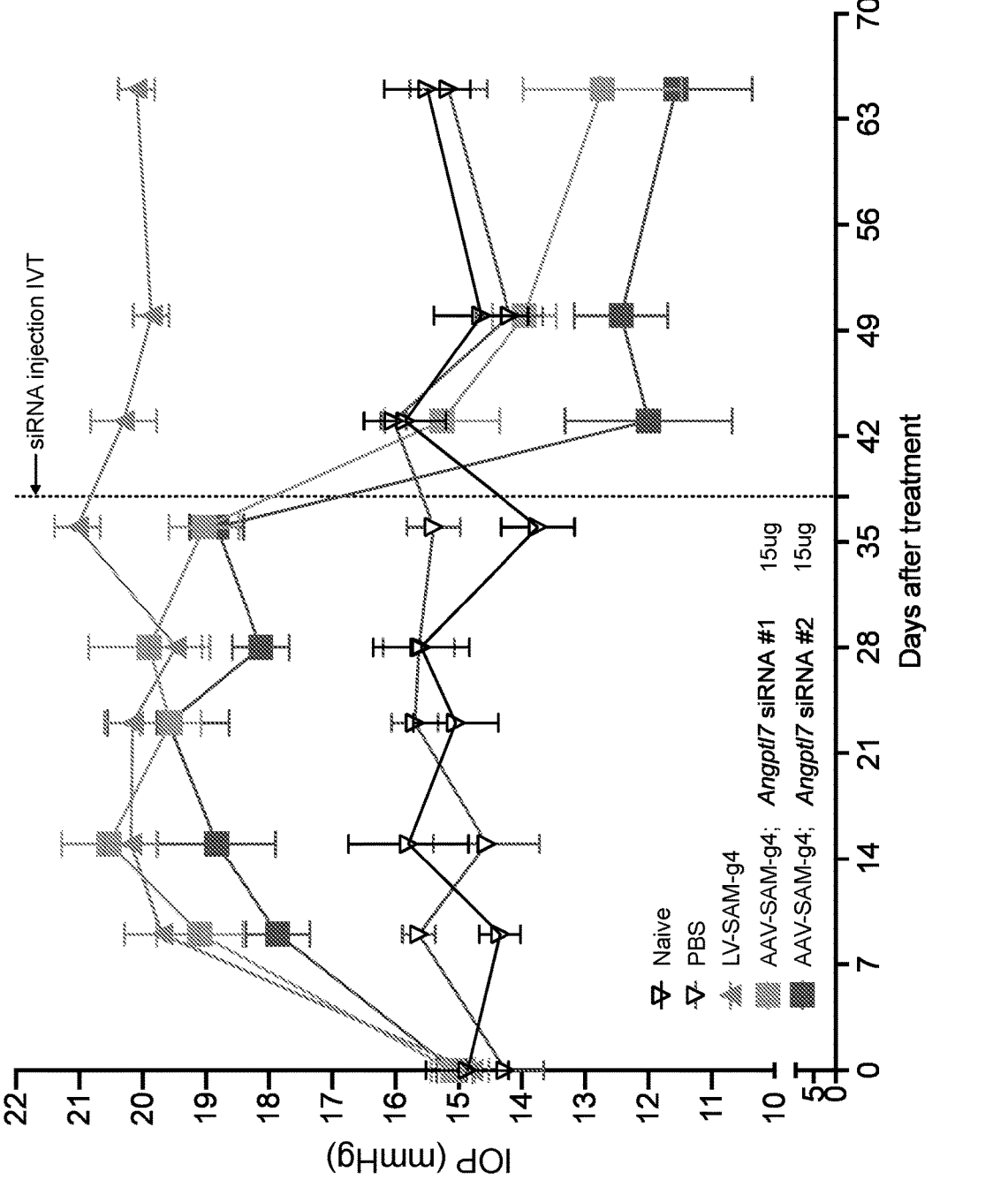
FIG. 19A shows intraocular pressure (IOP) in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with 15 μg of Angptl7 siRNA #1 or #2.
Figure 19B:
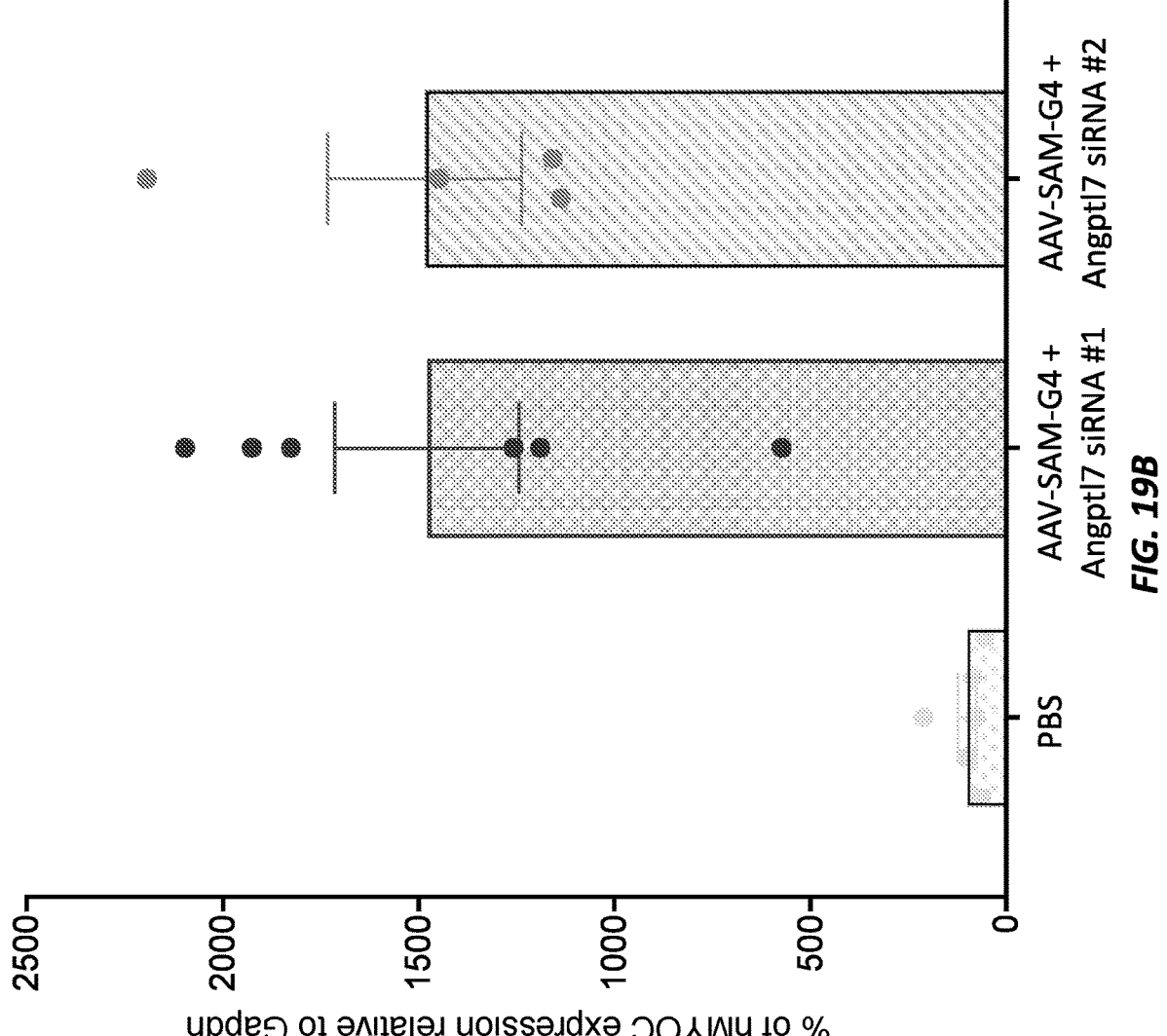
FIG. 19B shows qPCR results showing the percentage of human MYOC mRNA expression relative to Gapdh in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with 15 μg of Angptl7 siRNA #1 or #2.
Figure 19C:
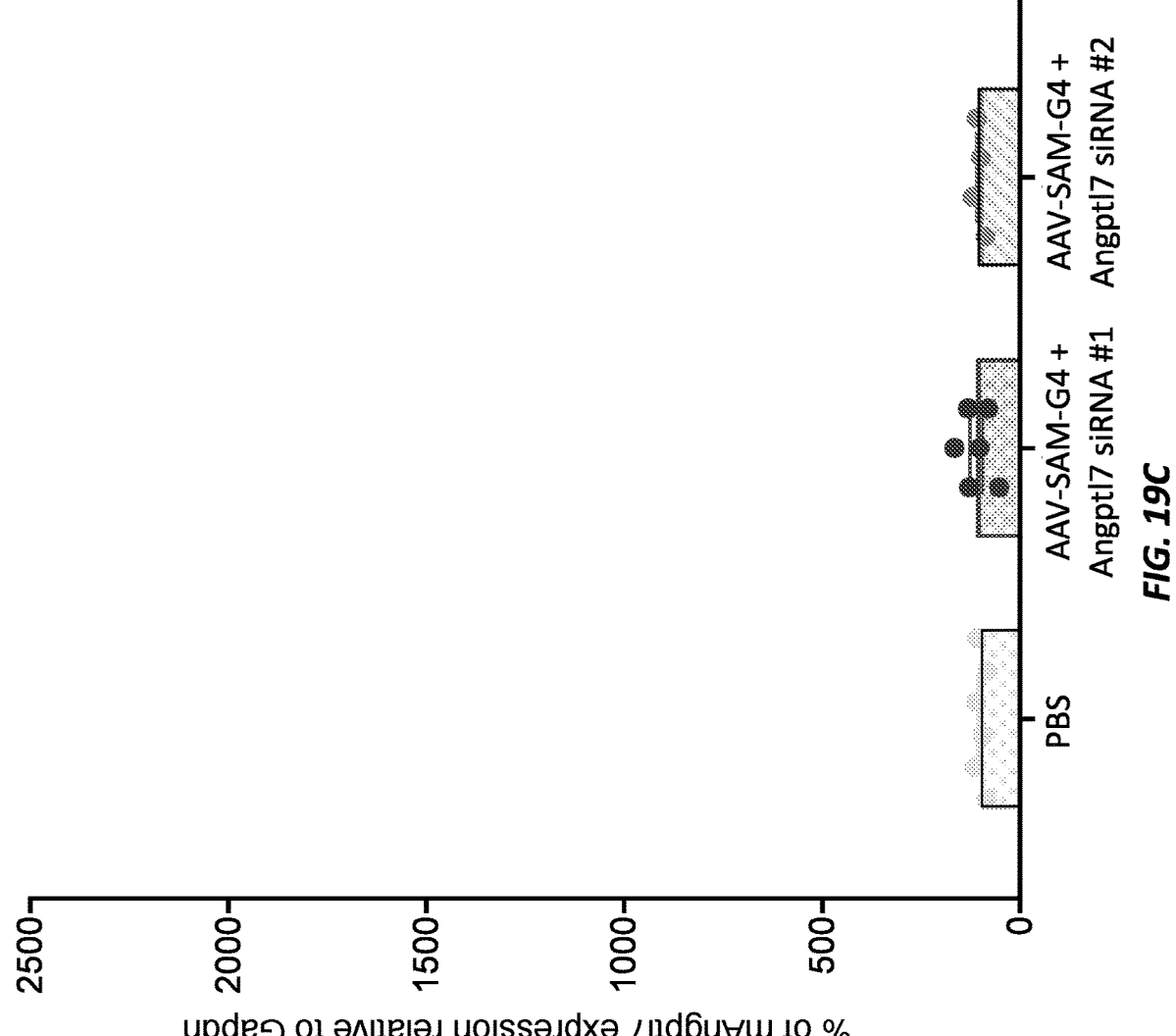
FIG. 19C shows qPCR results showing the percentage of Angptl7 mRNA expression relative to Gapdh in SAM mice comprising a humanized MYOC locus comprising a Y437H mutation (SAM-MYOC mice, homozygous for each allele) treated with LV-SAM-g4 or PBS, and in which the LV-SAM-g4-treated mice were subsequently treated with 15 μg of Angptl7 siRNA #1 or #2.

Following a complimentary approach to the targeting of MYOC, Angptl7 siRNAs #1 and #2 were tested on SAM-MYOC mice treated with LV-SAM-g4 to determine if targeting Angptl7 would also decrease IOP. As shown in FIG. 19A, SAM-g4 was administered via IC injection at day 0, and baseline IOP was measured. IOP was then measured over the following five weeks. At week five, Angptl7 siRNAs #1 and #2 (15 μg dose) were administered via intravitreal (IVT) injection, and IOP was measured at various timepoints over the subsequent weeks. mRNA knockdown in the limbal ring was tested by qPCR. As shown in FIG. 19B, the SAM-MYOC mice treated with AAV-SAM-g4 and either Angptl7 siRNAs #1 or #2 showed substantially increased expression of human MYOC relative to Gapdh compared to control mice treated with PBS. However, these mice treated with AAV-SAM-g4 and either Angptl7 siRNAs #1 or #2 did not show any significantly increased expression of Angptl7 relative to Gapdh compared to control mice treated with PBS, as shown in FIG. 19C.

Figure 20A:
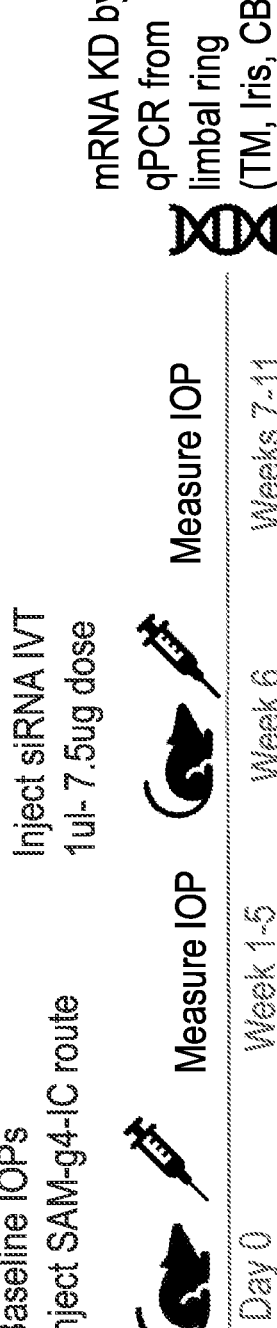
FIG. 20A shows the experimental setup for testing the effect of Angptl7 siRNAs #1 and #2 on intraocular pressure (IOP) in SAM mice comprising a humanized MYOC locus comprising a Y437H mutation (SAM-MYOC mice, homozygous for each allele) treated with LV-SAM-g4.
Figure 20B:
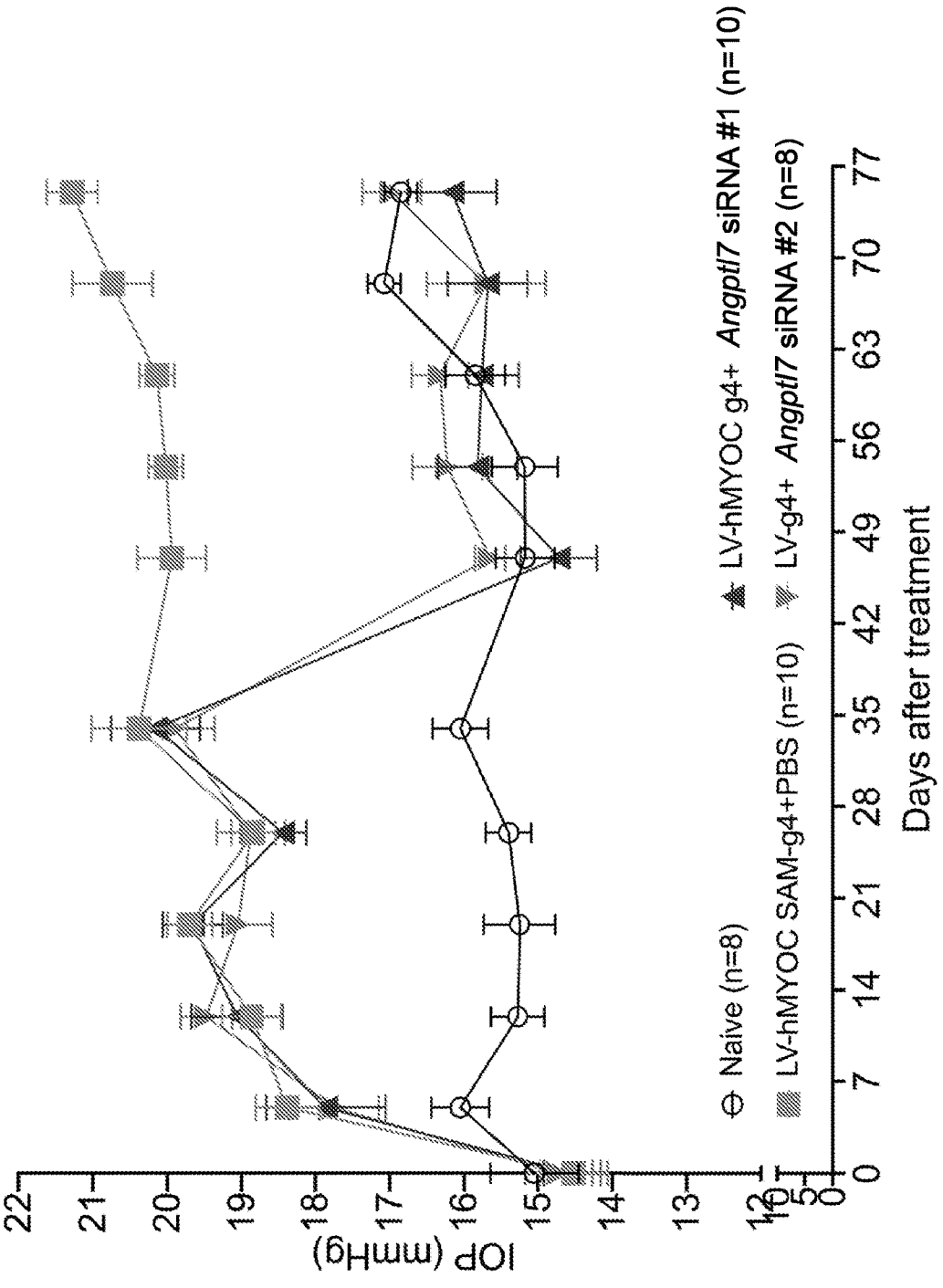
FIG. 20B shows intraocular pressure (IOP) in SAM mice comprising a humanized MYOC locus comprising a Y437H mutation (SAM-MYOC mice, homozygous for each allele) treated with LV-SAM-g4, and in which the LV-SAM-g4-treated mice were subsequently treated with 7.5 μg of Angptl7 siRNA #1 or #2 or PBS.
Figure 20C:
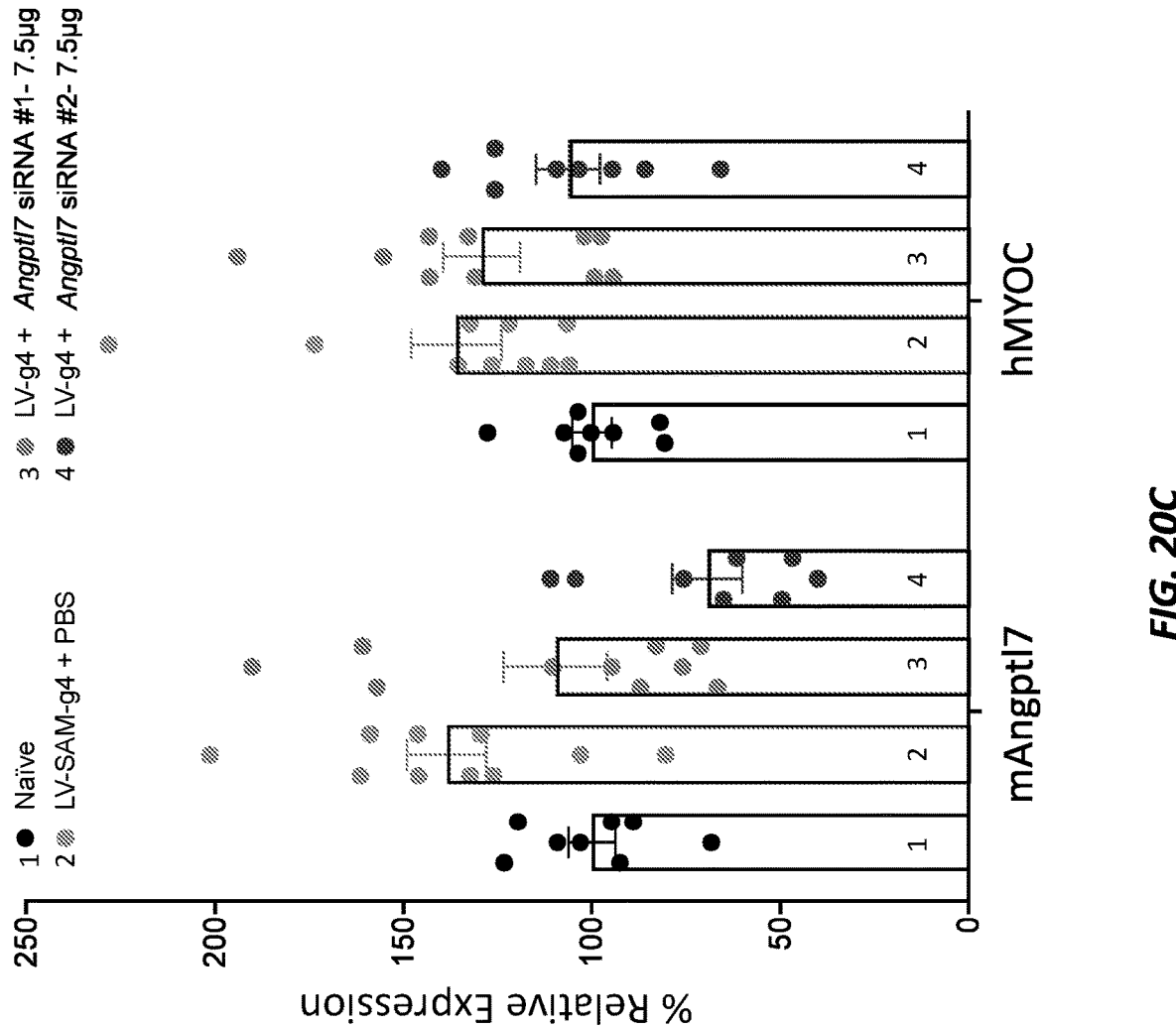
FIG. 20C shows qPCR results showing the percentage of Angptl7 and human MYOC mRNA expression relative to Gapdh in SAM mice comprising a humanized MYOC locus comprising a Y437H mutation (SAM-MYOC mice, homozygous for each allele) treated with LV-SAM-g4 and in which the LV-SAM-g4-treated mice were subsequently treated with 7.5 μg of Angptl7 siRNA #1 or #2 or PBS.

A reduced dose of Angptl7 siRNAs #1 and #2 (7.5 μg dose) was then tested to determine if the lower dose could lower the IOP observed in the SAM-MYOC mice following treatment with lentiviral SAM-g4. The experimental setup is shown in FIG. 20A, wherein mice were bilaterally injected with Lv-SAM-g4 and siRNA. As shown in FIG. 20B, mice injected with Angptl7 siRNAs #1 and #2 (7.5 µg dose) showed a substantial decrease in IOP compared to mice treated with PBS, with a return of IOP similar to untreated naïve mice. The expression of human MYOC and Angptl7 was determined by qPCR for untreated naïve mice and mice treated with LV-SAM-g4 and PBS or Angptl7 siRNAs #1 or #2 (7.5 µg dose), as shown in FIG. 20C. These experiments further show that SAM-MYOC mice can be successfully utilized as a model to assess therapeutic targets for the treatment of glaucoma.

We claim:

1. A non-human animal comprising in its genome a humanized endogenous MYOC locus in which a region of the endogenous MYOC locus has been deleted and replaced with a corresponding human MYOC sequence, wherein the region of the endogenous MYOC locus comprises both a MYOC exonic sequence and a MYOC intronic sequence and the corresponding human MYOC sequence comprises both a MYOC exonic sequence and a MYOC intronic sequence, wherein the non-human animal further comprises in its genome a genomically integrated expression cassette, wherein the genomically integrated expression cassette comprises:

(a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains, wherein the non-human animal further comprises one or more guide RNAs that were administered or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

2. The non-human animal of claim 1, wherein the humanized endogenous MYOC locus comprises a mutation associated with glaucoma, and wherein the human MYOC sequence comprises the mutation.

3. The non-human animal of claim 1, wherein the humanized endogenous MYOC locus comprises a Y437H mutation, and wherein the human MYOC sequence comprises the Y437H mutation.

4. The non-human animal of claim 1, wherein the humanized endogenous MYOC locus comprises an endogenous MYOC promoter, wherein the human MYOC sequence is operably linked to the endogenous MYOC promoter, and/or wherein at least one intron and at least one exon of the endogenous MYOC locus have been deleted and replaced with the corresponding human MYOC sequence, and/or wherein the humanized endogenous MYOC locus comprises a human MYOC 3' untranslated region, and/or wherein the endogenous MYOC 5' untranslated region has not been deleted and replaced with the corresponding human MYOC sequence.

5. The non-human animal of claim 1, wherein the humanized endogenous MYOC locus encodes a human myocilin protein.

6. The non-human animal of claim 5, wherein the human myocilin protein sequence comprises the sequence set forth in SEQ ID NO: 4, or wherein the human myocilin protein sequence is encoded by a coding sequence comprising the sequence set forth in SEQ ID NO: 5.

7. The non-human animal of claim 1, wherein a region of the endogenous MYOC locus from the endogenous MYOC start codon to the endogenous MYOC stop codon has been deleted and replaced with the corresponding human MYOC sequence from the human MYOC start codon to the human MYOC stop codon.

8. The non-human animal of claim 1, wherein a region of the endogenous MYOC locus from the endogenous MYOC start codon to the endogenous MYOC stop codon has been deleted and replaced with a human MYOC sequence comprising the corresponding human MYOC sequence from the human MYOC start codon to the human MYOC stop codon and a human MYOC 3' untranslated region, wherein the human MYOC sequence comprises a Y437H mutation, wherein the endogenous MYOC 5' untranslated region has not been deleted and replaced with the human MYOC sequence, and wherein the humanized endogenous MYOC locus comprises an endogenous MYOC promoter, wherein the human MYOC sequence is operably linked to the endogenous MYOC promoter.

9. The non-human animal of claim 1, wherein:

(i) the human MYOC sequence at the humanized endogenous MYOC locus comprises a sequence at least 90%, at least 95%, at least 96%, at least 97%, at least 98%, at least 99%, or 100% identical to the sequence set forth in SEQ ID NO: 87; and/or (ii) the humanized endogenous MYOC locus encodes a myocilin protein comprising a sequence at least 90%, at least 95%, at least 96%, at least 97%, at least 98%, at least 99%, or 100% identical to the sequence set forth in SEQ ID NO: 4; and/or (iii) the humanized endogenous MYOC locus comprises a myocilin coding sequence comprising a sequence at least 90%, at least 95%, at least 96%, at least 97%, at least 98%, at least 99%, or 100% identical to the sequence set forth in SEQ ID NO: 5; and/or (iv) the humanized endogenous MYOC locus comprises a sequence at least 90%, at least 95%, at least 96%, at least 97%, at least 98%, at least 99%, or 100% identical to the sequence set forth in SEQ ID NO: 88 or 89.

10. The non-human animal of claim 1, wherein the humanized endogenous MYOC locus does not comprise a selection cassette or a reporter gene.

11. The non-human animal of claim 1, wherein the non-human animal is homozygous for the humanized endogenous MYOC locus.

12. The non-human animal of claim 1, wherein the non-human animal comprises the humanized endogenous MYOC locus in its germline.

13. The non-human animal of claim 1, wherein the non-human animal is a mammal.

14. The non-human animal of claim 13, wherein the non-human animal is a rat or a mouse.

15. The non-human animal of claim 14, wherein the non-human animal is the mouse.

16. The non-human animal of claim 1, wherein the one or more guide RNAs or one or more expression cassettes that encode the one or more guide RNAs are in the trabecular meshwork.

17. The non-human animal of claim 1, further comprising a second genomically integrated expression cassette that encodes one or more guide RNAs each comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

18. The non-human animal of claim 1, wherein the genomically integrated expression cassette is integrated into a Rosa26 locus, the Cas protein is a Cas9 protein comprising mutations corresponding to D10A and N863A when optimally aligned with a *Streptococcus pyogenes* Cas9 protein, the one or more transcriptional activation domains in the chimeric Cas protein comprise VP64, the adaptor protein comprises an MS2 coat protein or a functional fragment or variant thereof, the one or more transcriptional activation domains in the chimeric adaptor protein comprise p65 and HSF1, the non-human animal further comprises one or more guide RNAs that were administered or one or more expression cassettes that encode the one or more guide RNAs, the one or more guide RNAs or one or more expression cassettes that encode the one or more guide RNAs are in the trabecular meshwork, each of the one or more guide RNAs comprises two adaptor-binding elements to which the chimeric adaptor protein can specifically bind, the two adaptor-binding elements comprise a first adaptor-binding element within a first loop of each of the one or more guide RNAs and a second adaptor-binding element within a second loop of each of the one or more guide RNAs, and the target sequence is within a region 200 base pairs upstream of a transcription start site of the target gene and 1 base pair downstream of the transcription start site.

19. The non-human animal of claim 1, wherein the non-human animal is a mouse, and wherein the one or more guide RNAs target one or more guide RNA target sequences selected from SEQ ID NOS: 90-95.

20. The non-human animal of claim 1, wherein the non-human animal is a mouse, and wherein the one or more guide RNAs target the guide RNA target sequence set forth in SEQ ID NO: 93.

21. The non-human animal of claim 1, wherein the non-human animal has at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, or at least 15-fold increased MYOC mRNA or protein expression in the eye, the limbal ring, the retina, the ciliary body, or the trabecular meshwork relative to a control non-human animal that does not comprise the one or more guide RNAs or the one or more expression cassettes that encode the one or more guide RNAs.

22. The non-human animal of claim 1, wherein the non-human animal has increased intraocular pressure relative to a wild type non-human animal or a control non-human animal, wherein:

(I) the non-human animal has an intraocular pressure of at least 15, at least 16, at least 17, at least 18, at least 19, at least 20, at least 21, or at least 22 mmHg, and/or (II) the non-human animal has an intraocular pressure that is at least 1, at least 2, at least 3, at least 4, at least 5, or at least 6 mmHg higher than the intraocular pressure of the control non-human animal.

23. A non-human animal cell comprising in its genome a humanized endogenous MYOC locus in which a region of the endogenous MYOC locus has been deleted and replaced with a corresponding human MYOC sequence, wherein the region of the endogenous MYOC locus comprises both a MYOC exonic sequence and a MYOC intronic sequence and the corresponding human MYOC sequence comprises both a MYOC exonic sequence and a MYOC intronic sequence, and wherein the non-human animal cell further comprises in its genome a genomically integrated expression cassette, wherein the genomically integrated expression cassette comprises:

(a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains, and wherein the non-human animal cell further comprises one or more guide RNAs that were administered or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

24. A method of measuring the effect of a human-MYOC-targeting reagent or a candidate glaucoma therapeutic agent on intraocular pressure, comprising:

(a) administering the human-MYOC-targeting reagent or the candidate glaucoma therapeutic agent to the non-human animal of claim 1; and (b) measuring intraocular pressure in the non-human animal in comparison to an untreated control non-human animal.

25. A method of increasing MYOC expression in a non-human animal, wherein the non-human animal comprises in its genome a humanized endogenous MYOC locus in which a region of the endogenous MYOC locus has been deleted and replaced with a corresponding human MYOC sequence, wherein the region of the endogenous MYOC locus comprises both a MYOC exonic sequence and a MYOC intronic sequence and the corresponding human MYOC sequence comprises both a MYOC exonic sequence and a MYOC intronic sequence, wherein the non-human animal further comprises in its genome a genomically integrated expression cassette, wherein the genomically integrated expression cassette comprises:

(a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains, wherein the method comprises administering to the non-human animal one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

26. A method of increasing intraocular pressure in a non-human animal, wherein the non-human animal comprises in its genome a humanized endogenous MYOC locus in which a region of the endogenous MYOC locus has been deleted and replaced with a corresponding human MYOC sequence, wherein the region of the endogenous MYOC locus comprises both a MYOC exonic sequence and a MYOC intronic sequence and the corresponding human MYOC sequence comprises both a MYOC exonic sequence and a MYOC intronic sequence, wherein the non-human animal further comprises in its genome a genomically integrated expression cassette, wherein the genomically integrated expression cassette comprises:

(a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains, wherein the method comprises administering to the non-human animal one or more guide RNAs or one or more expression cassettes that encode the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene, and wherein at least one of the one or more guide RNAs targets the humanized endogenous MYOC locus.

27. A method of modeling glaucoma in a non-human animal, wherein the non-human animal comprises in its genome a humanized endogenous MYOC locus in which a region of the endogenous MYOC locus has been deleted and replaced with a corresponding human MYOC sequence, wherein the region of the endogenous MYOC locus comprises both a MYOC exonic sequence and a MYOC intronic sequence and the corresponding human MYOC sequence comprises both a MYOC exonic sequence and a MYOC intronic sequence, wherein the non-human animal further comprises in its genome a genomically integrated expression cassette, wherein the genomically integrated expression cassette comprises:

(a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor protein fused to one or more transcriptional activation domains,

wherein the method comprises administering to the non-human animal one or more guide RNAs or one or more expression cassettes that encode the one or more guide RNAs, each guide RNA comprising one or more adaptor-binding 5 elements to which the chimeric adaptor protein can specifically bind, wherein each of the one or more guide RNAs is capable of forming a complex with the Cas protein and guiding it to a target sequence within a target gene, and 10 wherein at least one of the one or more guide RNAs targets the humanized endogenous MYOC locus.

\* \* \* \* \*

```
                          SEQUENCE LISTING

Sequence total quantity: 125
SEQ ID NO: 1               moltype = AA  length = 504
FEATURE                    Location/Qualifiers
REGION                     1..32
                           note = MISC_FEATURE - Signal Peptide
REGION                     33..504
                           note = MISC_FEATURE - Mature Myocilin
REGION                     33..226
                           note = MISC_FEATURE - N-Terminal Fragment
REGION                     227..504
                           note = MISC_FEATURE - C-Terminal Fragment
source                     1..504
                           mol_type = protein
                           organism = Homo sapiens
SEQUENCE: 1
MRFFCARCCS FGPEMPAVQL LLLACLVWDV GARTAQLRKA NDQSGRCQYT FSVASPNESS   60
CPEQSQAMSV IHNLQRDSST QRLDLEATKA RLSSLESLLH QLTLDQAARP QETQEGLQRE  120
LGTLRRERDQ LETQTRELET AYSNLLRDKS VLEEEKKRLR QENENLARRL ESSSQEVARL  180
RRGQCPQTRD TARAVPPGSR EVSTWNLDTL AFQELKSELT EVPASRILKE SPSGYLRSGE  240
GDTGCGELVW VGEPLTLRTA ETITGKYGVW MRDPKPTYPY TQETTWRIDT VGTDVRQVFE  300
YDLISQFMQG YPSKVHILPR PLESTGAVVY SGSLYFQGAE SRTVIRYELN TETVKAEKEI  360
PGAGYHGQFP YSWGGYTDID LAVDEAGLWV IYSTDEAKGA IVLSKLNPEN LELEQTWETN  420
IRKQSVANAF IICGTLYTVS SYTSADATVN FAYDTGTGIS KTLTIPFKNR YKYSSMIDYN  480
PLEKKLFAWD NLNMVTYDIK LSKM                                         504

SEQ ID NO: 2               moltype = DNA  length = 2100
FEATURE                    Location/Qualifiers
source                     1..2100
                           mol_type = other DNA
                           organism = Homo sapiens
SEQUENCE: 2
gagccagcaa ggccacccat ccaggcacct ctcagcacag cagagctttc cagaggaagc   60
ctcaccaagc ctctgcaatg aggttcttct gtgcacgttg ctgcagcttt gggcctgaga  120
tgccagctgt ccagctgctg cttctggcct gcctggtgtg ggatgtgggg gccaggacag  180
ctcagctcag gaaggccaat gaccagagtg gccgatgcca gtataccttc agtgtggcca  240
gtcccaatga atccagctgc ccagagcaga gccaggccat gtcagtcatc cataacttac  300
agagagacag cagcacccaa cgcttagacc tggaggccac caaagctcga ctcagctccc  360
tggagagcct cctccaccaa ttgaccttgg accaggctgc caggccccag gagacccagg  420
aggggctgca gagggagctg ggcaccctga ggcgggagcg ggaccagctg gaaacccaaa  480
ccagagagtt ggagactgcc tacagcaacc tcctccgaga caagtcagtt ctggaggaag  540
agaagaagcg actaaggcaa gaaaatgaaa atctggccag gaggttggaa agcagcagcc  600
aggaggtagc aaggctgaga aggggccagt gtccccagac ccgagacact gctcgggctg  660
tgccaccagg ctccagagaa gtttctacgt ggaatttgga cactttggcc ttccaggaac  720
tgaagtccga gctaactgaa gttcctgctt cccgaatttt gaaggagagc ccatctggct  780
atctcaggag tggagaggga gacaccggat gtggagaact agtttgggta ggagagcctc  840
tcacgctgag aacagcagaa acaattactg gcaagtatgg tgtgtggatg cgagacccca  900
agcccaccta ccctacacc caggagacca cgtggagaat cgacacagtt ggcacggatg  960
tccgccaggt ttttgagtat gacctcatca gccagtttat gcagggctac ccttctaagg 1020
ttcacatact gcctaggcca ctggaaagca cgggtgctgt ggtgtactcg gggagcctct 1080
atttccaggg cgctgagtcc agaactgtca taagatatga gctgaatacc gagacagtga 1140
aggctgagaa ggaaatccct ggagctggct accacggaca gttcccgtat tcttggggtg 1200
gctacacgga cattgacttg gctgtggatg aagcaggcct ctgggtcatt tacagcaccg 1260
atgaggccaa aggtgccatt gtcctctcca aactgaaccc agagaatctg gaactcgaac 1320
aaacctggga gacaaacatc cgtaagcagt cagtcgccaa tgccttcatc atctgtggca 1380
ccttgtacac cgtcagcagc tacacctcag cagatgctac cgtcaacttt gcttatgaca 1440
caggcacagg tatcagcaag accctgacca tcccattcaa gaaccgctat aagtacagca 1500
gcatgattga ctacaacccc ctggagaaga gctcttttgc ctgggacaac ttgaacatgg 1560
tcacttatga catcaagctc tccaagatgt gaaaagcctc caagctgtac aggcaatggc 1620
agaaggagat gctcagggct cctgggggga gcaggctgaa gggagagcca gccagccagg 1680
gcccaggcag ctttgactgc tttccaagtt ttcattaatc cagaaggatg aacatggtca 1740
ccatctaact attcaggaat tgtagtctga gggcgtagac aatttcatat aataaaatatc 1800
ctttatcttc tgtcagcatt tatgggatgt ttaatgacat agttcaagtt ttcttgtgat 1860
ttggggcaaa agctgtaagg cataatagtt tcttcctgaa aaccattgct cttgcatgtt 1920
acatggttac cacaagccac aataaaaagc ataacttcta aaggaagcag aatagctcct 1980
ctggccagca tcgaatataa gtaagatgca tttactacag ttggcttcta atgcttcaga 2040
tagaatacag ttgggtctca cataacccct tacattgtga aataaaattt tcttacccaa 2100

SEQ ID NO: 3               moltype = DNA  length = 1515
FEATURE                    Location/Qualifiers
misc_feature              1..96
```

-continued

```
                         note = Signal Peptide
misc_feature            97..1512
                         note = Mature Myocilin
misc_feature            97..678
                         note = N-Terminal Fragment
misc_feature            679..1512
                         note = C-Terminal Fragment
source                  1..1515
                         mol_type = other DNA
                         organism = Homo sapiens
SEQUENCE: 3
atgaggttct tctgtgcacg ttgctgcagc tttgggcctg agatgccagc tgtccagctg    60
ctgcttctgg cctgcctggt gtgggatgtg ggggccagga cagctcagct caggaaggcc   120
aatgaccaga gtggccgatg ccagtatacc ttcagtgtgg ccagtcccaa tgaatccagc   180
tgcccagagc agagccaggc catgtcagtc atccataact tacagagaga cagcagcacc   240
caacgcttag acctggaggc caccaaagct cgactcagct ccctggagag cctcctccac   300
caattgacct tggaccaggc tgccaggccc caggagaccc aggaggggct gcagagggag   360
ctgggcaccc tgaggcggga gcgggaccag ctggaaacc aaaccagaga gttggagact   420
gcctacagca acctcctccg agacaagtca gttctggagg aagagaagaa gcgactaagg   480
caagaaaatg agaatctggc caggaggttg gaaagcagca gccaggaggt agcaaggctg   540
agaaggggc agtgtcccca gacccgagac actgctcggg ctgtgccacc aggctccaga   600
gaagtttcta cgtggaattt ggacactttg gccttccaga aactgaagtc cgagctaact   660
gaagttcctg cttcccgaat tttgaaggag agcccatctg gctatctcag gagtggagag   720
ggagacaccg gatgtggaga actagtttgg gtaggagagc ctctcacgct gagaacagca   780
gaaacaatta ctggcaagta tggtgtgtgg atgcgagacc ccaagcccac ctacccctac   840
acccaggaga ccacgtggag aatcgacaca gttggccagg atgtccgcca ggttttttga   900
tatgacctca tcagccagtt tatgcagggc taccttcta aggttcacat actgcctagg   960
ccactggaaa gcacgggtgc tgtggtgtac tcggggagcc tctatttcca gggcgctgag  1020
tccagaactg tcataagata tgagctgaat accgagacag tgaaggctga gaaggaaatc  1080
cctggagctg gctaccacgg acagttcccg tattcttggg gtggctacac ggacattgac  1140
ttggctgtgg atgaagcagg cctctgggtc atttacagca ccgatgaggc caaaggtgcc  1200
attgtcctct ccaaactgaa cccagagaat ctggaactcg aacaaacctg ggagacaaac  1260
atccgtaagc agtcagtcgc caatgccttc atcatctgtg gcaccttgta caccgtcagc  1320
agctacacct cagcagatgc taccgtcaac tttgcttatg acacaggcac aggtatcagc  1380
aagaccctga ccatcccatt caagaaccgc tataagtaca gcagcatgat tgactacaac  1440
cccctggaga agaagctctt tgcctgggac aacttgaaca tggtcactta tgacatcaag  1500
ctctccaaga tgtga                                                   1515

SEQ ID NO: 4                molype = AA  length = 504
FEATURE                     Location/Qualifiers
REGION                      1..32
                            note = MISC_FEATURE - Signal Peptide
REGION                      33..504
                            note = MISC_FEATURE - Mature Myocilin
REGION                      33..226
                            note = MISC_FEATURE - N-Terminal Fragment
REGION                      227..504
                            note = MISC_FEATURE - C-Terminal Fragment
source                      1..504
                            mol_type = protein
                            organism = Homo sapiens
SEQUENCE: 4
MRFFCARCCS FGPEMPAVQL LLLACLVWDV GARTAQLRKA NDQSGRCQYT FSVASPNESS    60
CPEQSQAMSV IHNLQRDSST QRLDLEATKA RLSSLESLLH QLTLDQAARP QETQEGLQRE   120
LGTLRRERDQ LETQTRELET AYSNLLRDKS VLEEEKKRLR QENENLARRL ESSSQEVARL   180
RRGQCPQTRD TARAVPPGSR EVSTWNLDTL AFQELKSELT EVPASRILKE SPSGYLRSGE   240
GDTGCGELVW VGEPLTLRTA ETITGKYGVW MRDPKPTYPY TQETTWRIDT VGTDVRQVFE   300
YDLISQFMQG YPSKVHILPR PLESTGAVVY SGSLYFQGAE SRTVIRYELN TETVKAEKEI   360
PGAGYHGQFP YSWGGYTDID LAVDEAGLWV IYSTDEAKGA IVLSKLNPEN LELEQTWETN   420
IRKQSVANAF IICGTLHTVS SYTSADATVN FAYDTGTGIS KTLTIPFKNR YKYSSMIDYN   480
PLEKKLFAWD NLNMVTYDIK LSKM                                          504

SEQ ID NO: 5                molype = DNA  length = 1515
FEATURE                     Location/Qualifiers
misc_feature               1..96
                            note = Signal Peptide
misc_feature               97..1512
                            note = Mature Myocilin
misc_feature               97..678
                            note = N-Terminal Fragment
misc_feature               679..1512
                            note = C-Terminal Fragment
source                      1..1515
                            mol_type = other DNA
                            organism = Homo sapiens
SEQUENCE: 5
atgaggttct tctgtgcacg ttgctgcagc tttgggcctg agatgccagc tgtccagctg    60
ctgcttctgg cctgcctggt gtgggatgtg ggggccagga cagctcagct caggaaggcc   120
aatgaccaga gtggccgatg ccagtatacc ttcagtgtgg ccagtcccaa tgaatccagc   180
```

```
tgcccagagc agagccaggc catgtcagtc atccataact tacagagaga cagcagcacc  240
caacgcttag acctggaggc caccaaagct cgactcagct ccctggagag cctcctccac  300
caattgacct tggaccaggc tgccaggccc caggagaccc aggaggggct gcagagggag  360
ctgggcaccc tgaggcggga gcgggaccag ctggaaaccc aaaccagaga gttggagact  420
gcctacagca acctcctccg agacaagtca gttctggagg agagaagaa gcgactaagg  480
caagaaaatg agaatctggc caggaggttg gaaagcagca gccaggaggt agcaaggctg  540
agaagggcc agtgtcccca gacccgagac actgctcggg ctgtgccacc aggctccaga  600
gaagtttcta cgtggaattt ggacactttg gccttccagg aactgaagtc cgagctaact  660
gaagttcctg cttcccgaat tttgaaggag agcccatctg gctatctcag gagtggagag  720
ggagacaccg gatgtgagga actagtttgg gtaggagagc ctctcacgct gagaacagca  780
gaaacaatta ctggcaagta tggtgtgtgg atgcgagacc ccaagcccac ctaccctac  840
acccaggaga ccacgtggag aatcgacaca gttggcacgg atgtccgcca ggttttgag  900
tatgacctca tcagccagtt tatgcaggc tacccttcta aggttcacat actgcctagg  960
ccactggaaa gcacgggtgc tgtggtgtac tcggggaacc tctatttcca gggcgctgag 1020
tccagaactg tcataagata tgagctgaat accgagacag tgaaggctga gaaggaaatc 1080
cctggagctg ctaccacgg acagttcccg tattcttggg gtggctacac ggacattgac 1140
ttggctgtgg atgaagcagg cctctgggtc atttacagca ccgatgaggc caaaggtgcc 1200
attgtcctct ccaaactgaa cccagagaat ctggaactcg aacaaacctg ggagacaaac 1260
atccgtaagc agtcagtcgc caatgccttc atcatctgtg gcaccttgca caccgtcagc 1320
agctacacct cagcagatgc taccgtcaac tttgcttatg acacaggcac aggtatcagc 1380
aagaccctga ccatcccatt caagaaccgc tataagtaca gcagcatgat tgactacaac 1440
cccctggaga agaagctctt tgcctgggac aacttgaaca tggtcactta tgacatcaag 1500
ctctccaaga tgtga                                                  1515
```

```
SEQ ID NO: 6              moltype = AA  length = 490
FEATURE                   Location/Qualifiers
REGION                    1..18
                          note = MISC_FEATURE - Signal Peptide
REGION                    19..490
                          note = MISC_FEATURE - Mature Myocilin
REGION                    19..212
                          note = MISC_FEATURE - N-Terminal Fragment
REGION                    213..490
                          note = MISC_FEATURE - C-Terminal Fragment
source                    1..490
                          mol_type = protein
                          organism = Mus musculus
SEQUENCE: 6
MPALHLLFLA CLVWGMGART AQFRKANDRS GRCQYTFTVA SPNESSCPRE DQAMSAIQDL  60
QRDSSIQHAD LESTKARVRS LESLLHQMTL GRVTGTQEAQ EGLQGQLGAL RRERDQLETQ 120
TRDLEAAYNN LLRDKSALEE EKRQLEQENE DLARRLESSS EEVTRLRRGQ CPSTQYPSQD 180
MLPGSREVSQ WNLDTLAFQE LKSELTEVPA SQILKENPSG RPRSKEGDKG CGALVWVGEP 240
VTLRTAETIA GKYGVWMRDP KPTHPYTQES TWRIDTVGTE IRQVFEYSQI SQFEQGYPSK 300
VHVLPRALES TGAVVYAGSL YFQGAESRTV VRYELDTETV KAEKEIPGAG YHGHFPYAWG 360
GYTDIDLAVD ESGLWVIYST EEAKGAIVLS KLNPANLELE RTWETNIRKQ SVANAFVICG 420
ILYTVSSYSS AHATVNFAYD TKTGTSKTLT IPFTNRYKYS SMIDYNPLER KLFAWDNFNM 480
VTYDIKLLEM                                                        490
```

```
SEQ ID NO: 7              moltype = DNA  length = 2093
FEATURE                   Location/Qualifiers
source                    1..2093
                          mol_type = other DNA
                          organism = Mus musculus
SEQUENCE: 7
gagccagcag ggccacccat ccagacactt tgcaggagaa ctttccagaa gaaacctcac  60
ccagcctcca cactgctgtc cttctctgca cgctgctgca gctgtggtcc caagatgcca 120
gctctccatc tgctgtttct ggcctgcttg gtgtggggga atggggggccag acagcacag 180
ttccgaaagg ccaatgatcg gagtggccga tgccaataca ccttcactgt ggccagcccc 240
aatgaatcta gctgcccaag ggaggaccag gccatgtcac ccatccaaga ccttcagaga 300
gacagcagca tccagcatgc agacctagag tccaccaag cccgggtcag atccctggag 360
agtctcctcc accagatgac cttgggccga gttactggga cccaggaggc ccaagagggg 420
ctgcagggcc agtggggtgc cctgaggaga gaacgggacc agctggagac ccaaaccagg 480
gatctggagg cagcctataa caatctcctt cgagataagt cggctttaga ggaagagaag 540
aggcagcaag aacaagagaa tgaagatttg gccaggaggc tagaaagcag cagcgaggag 600
gtaacaaggc tgcggagggg ccagtgtcct tccacccagt accctctca ggacatgctg 660
ccaggctcca gggaagtctc tcagtggaat ttggacacgt tggccttcca ggaattgaag 720
tcagagttaa ctgaggttcc tgcttcccaa atcttgaagg aaaatccatc tggccgaccc 780
aggagcaaag aaggagacaa aggatgtgga gcgctagtgt gggtaggaga gccagtcacc 840
ctgaggacag ctgaaacaat cgctggacaag tatggagtgt ggatgagaga ccccaagccc 900
acccacccct acacccagga aagcacatgg aggattgaca cggttggcac agagatccgc 960
caggtgtttg agtacagtca gataagccag ttcgagcagg gctatccttc caaggtccat 1020
gtgctccctc gggcactgga gagcacgggt gctgtggtgt atgcggggag cctctatttc 1080
cagggggctg agtccagaac tgtggtcagg tatgagctag acacggagac cgtgaaggca 1140
gagaaggaaa ttcctggagc tggctaccac ggacacttcc cgtacgcgtg gggtggctac 1200
acagacattg acttagctgt ggatgagagc ggcctctggg tcatctacag cacggaggaa 1260
gccaaggggg ccatagtcct ctccaaattg aacccagcga acctggaact tgagcgtacc 1320
tgggagacta acatccgtaa gcagtctgtg gccaatgcct ttgttatctg tggcatcttg 1380
tacacggtga gcagctactc ttcagcccat gcaaccgtca acttcgccta cgacactaaa 1440
acggggacca gtaagaccct gaccatccca ttcacgaatc gctacaagta cagcagtatg 1500
```

```
attgactaca accccctgga gaggaagctg tttgcctggg acaacttcaa catggtcacc   1560
tatgatatca agctcttgga gatgtgagga gcctctatgc ctaccagcaa aggccagaaa   1620
aggtgaagtt ccgggctccc gggtgaagca gctgtcagca gaggcagcca gatgcatgga   1680
gtttctcctc ctgctaaaga ttttgtttat ccgggtcaat gtacagctag ctcccctctg   1740
actgacacgt cctccaggct tgtatagtcg catagactct gttctcttct gtcagctttc   1800
aaagggctgt tcctctttta aaaatcacat agtgtagcag tccagaggaa aaactagaag   1860
taaggttgtt tcttcatgaa accattgctt ttgcacgcta ttatggttac cataagcttt   1920
gcgaggcagc ggcggttctg cggagcgacc gctcctgtgg ttagaactgc tcctgccgaa   1980
ggtgtattat actccagggg gcttctagtg ctacagatac agcatgtggt tgggtggtac   2040
gtaaaccctt tgccctgtga aataaagtta tcttacatga aaaaaaaaaa aaa           2093
```

```
SEQ ID NO: 8              moltype = DNA   length = 1473
FEATURE                   Location/Qualifiers
misc_feature              1..54
                          note = Signal Peptide
misc_feature              55..1470
                          note = Mature Myocilin
misc_feature              55..636
                          note = N-Terminal Fragment
misc_feature              637..1470
                          note = C-Terminal Fragment
source                    1..1473
                          mol_type = other DNA
                          organism = Mus musculus
SEQUENCE: 8
atgccagctc tccatctgct gtttctggcc tgcttggtgt ggggaatggg ggccaggaca   60
gcacagttcc gaaaggccaa tgatcggagt ggccgatgcc aatacacctt cactgtggcc   120
agccccaatg aatctagctg cccaaggag gaccaggcca tgtcagccat ccaagacctt   180
cagagagaca gcagcatcca gcatgcagac ctagagtcca ccaaggcccg ggtcagatcc   240
ctggagagtc tcctccacca gatgaccttg ggccgagtta ctgggaccca ggaggcccaa   300
gaggggctgc agggccagtt gggtgccctg aggagagaac gggaccagct ggagacccaa   360
accagggatc tggaggcagc ctataacaat ctccttcgag ataagtcggc tttagaggaa   420
gagaagaggc agctggaaca agagaatgaa gatttggcca ggaggctaga aagcagcagc   480
gaggaggtaa caaggctgcg gaggggccag tgtccttcca cccagtaccc ctctcaggac   540
atgctgccag gctccaggga agtctctcag tggaatttgg acacgttggc cttccaggaa   600
ttgaagtcag agttaactga ggttcctgct tcccaaatct tgaaggaaaa tccatctggc   660
cgacccagga gcaaagaagg agacaaagga tgtggagcgc tagtctgggt aggagagcca   720
gtcaccctga ggacagctga acaatcgct ggcaagtatg gagtgtggat gagagacccc   780
aagccaccc accctacac ccaggaaagc acatggagga ttgacacggt tggcacagag   840
atccgccagg tgtttgagta cagtcagata agccagttcg agcagggcta tccttccaag   900
gtccatgtgc tccctcgggc actggagagc acgggtgctg tggtgtatgc ggggagcctc   960
tatttccagg gggctgagtc cagaactgtg gtcaggtatg agctagacac ggagaccgtg   1020
aaggcagaga aggaaattcc tggagctggc taccacggac acttcccgta cgcgtggggt   1080
ggctacacag acattgactt agctgtggat gagagcggcc tctgggtcat ctacagcacg   1140
gaggaagcca aggggccat agtcctctcc aaattgaacc cagcgaacct ggaacttgag   1200
cgtacctggg agactaacat ccgtaagcag tctgtggcca atgcctttgt tatctgtggc   1260
atcttgtaca cggtgagcag ctactcttca gcccatgcaa acttccaatt cgcctacgac   1320
actaaaacgg ggaccagtaa gaccctgacc atcccattca cgaatcgcta caagtacagc   1380
agtatgattg actacaaccc cctggagagg aagctgtttg cctgggacaa cttcaacatg   1440
gtcacctatg atatcaagct cttggagatg tga                                1473
```

```
SEQ ID NO: 9              moltype = AA   length = 502
FEATURE                   Location/Qualifiers
REGION                    1..31
                          note = MISC_FEATURE - Signal Peptide
REGION                    32..502
                          note = MISC_FEATURE - Mature Myocilin
REGION                    32..225
                          note = MISC_FEATURE - N-Terminal Fragment
REGION                    226..502
                          note = MISC_FEATURE - C-Terminal Fragment
source                    1..502
                          mol_type = protein
                          organism = Rattus norvegicus
SEQUENCE: 9
MPSCAYCCSC GPKMPALQLL FLACLVWGMG ARTAQFRKAN DRSGRCQYTF TVASPSESSC   60
PREDQAMSAI QDLQRDSSIQ HADLESTKAR VRSLESLLHQ MTSGGVTGTQ EVQEGLQGQL   120
GALRRERDQL ETQTRDLEVA YNNLLRDKSA LEEEKRQLEQ ENKDLARRLE GSSQEVARLR   180
RGQCPSTHHP SQDMLPGSRE VSQWNLDTLA FQELKSELTE VPASQILKNQ SGHPRSKEGD   240
KGCGVLMWVG EPVTLRTAET ITGKYGVWMR DPKPTHPYTQ ETTWRIDTVG TGIRQVFEYS   300
QISQFEQGYP SKVHVLPQAL ESTGAVVYSG SLYFQGAESR TVLRYELNTE TVKAEKEIPG   360
AGYHGQFPYA WGGYTDIDLA VDESGLWVIY STEETRGAIV LSKLNPENLE LESTWETNIR   420
KQSVANAFVI CGILYTVSSY SSVHATINFA YDTNTGISKT LTIPFKNRYK YSSMVDYNPL   480
ERKLFAWDNF NMVTYDIKLS EM                                            502
```

```
SEQ ID NO: 10             moltype = DNA   length = 2068
FEATURE                   Location/Qualifiers
source                    1..2068
                          mol_type = other DNA
```

```
                          organism = Rattus norvegicus
SEQUENCE: 10
ggagccagca gggccaccca tccagacacc ttgcagcaga gccttctaga agtaagcctc   60
acccagccct cataccgatg ccctcctgtg catactgctg cagctgcggt cccaagatgc  120
cagctctcca gctgctgttt ctggcctgcc tggtgtgggg aatgggggcc aggacagcac  180
agttccgaaa ggccaacgat cggagtggtc gatgccagta caccttcact gtggccagcc  240
ccagtgaatc tagctgccca agggaggacc aggccatgtc agccatccag gaccttcaga  300
gagatagcag catccagcat gcagacctag agtccaccaa ggcccgggtc agatccctgg  360
agagtctcct ccaccagatg acctcaggcg gagttactgg gacccaggag gtccaggagg  420
ggctacaagg ccagctgggt gccctgagga gagagcggga ccagctggag acgcaaacca  480
gggatctgga ggtagcctat aacaatctcc tgagagacaa atcagctttg gaggaagaga  540
agaggcagct ggaacaagag aataaagatt tggccaggag gctagaaggc agcagccagg  600
aggtagcaag gctgaggaga ggccagtgtc cctcaaccca ccacccctct caggacatgt  660
tgccaggctc cagggaagtc tctcagtgga atttggacac gttggctttc caggaactga  720
agtcagaact aacagaggtt cctgcttccc aaatcttgaa gaatcaatct ggtcatccca  780
ggagcaaaga gggagacaaa ggatgtggag tgctaatgtg ggtaggagag ccagtcaccc  840
tgaggacagc tgagacaatc actggaaagt atggagtatg gatgagagac cccaagccca  900
ctcacccta cacccaggag accacttgga ggattgacac ggttggcaca ggcatccgcc  960
aggtgtttga gtacagtcag ataagccagt tcgagcaggg ctatccttca aaggtccatg 1020
tgctccccca ggcactggaa agcacaggtg ctgtggtgta ctcggggagc ctctatttcc 1080
agggtgctga gtccagaact gtgctcaggt atgaactgaa cacagaaaca gtgaaggcag 1140
agaaggaaat tcctggagct ggctaccatg gacagttccc atacgcatgg ggtggctaca 1200
cagacatcga cttagctgtg gatgagagcg gcctctgggt catctatagc acagaggaaa 1260
ccagaggagc catagtcctc tccaaattga acccagagaa cctggaactt gagagtacct 1320
gggagaccaa catccgtaag cagtctgtgg ctaatgcctt tgttatctgt ggcatcttgt 1380
acacggtgag cagctactct tcagtccatg caaccatcaa ctttgcctat gacactaaca 1440
ctgggatcag caagaccctg accatcccat tcaagaatcg ctacaaatac agcagcatgg 1500
tcgactacaa cccctggag aggaaactct ttgcctggga caacttcaac atggtcacct 1560
atgatatcaa gctctcagag atgtgaggag cctctatccc taccagagaa ggcagaaaaa 1620
gggggaagtt ccaggctccc aggtgaagca gctgcaggag gaggcagcca gatgctgggg 1680
gcttctgctt ctcaagattt gtttgtccaa gtcaatacct cggggcttgt acagttgcat 1740
atattctgct ctcttctgtc agctttcaaa aggggtgttc atcttttaaa aatcatatag 1800
tgtacaatcc aagaaaaact agaattgttg tttcctcatg aaacattgct ttttgccaag 1860
ctgtatggtt actaccagac cttgagaggc agcaacagtt ctacccaaga ggagggagat 1920
aacggggagg gggtgaccac cactcctgtg gttagaactg ctcctgcagt atttactcca 1980
gtttctaagg ctacagatat agcatgtaca ttaaaccctt tgccctgtga aataaagtta 2040
tcttacacga cgttaaaaaa aaaaaaaaa                                    2068

SEQ ID NO: 11            moltype = DNA  length = 1509
FEATURE                  Location/Qualifiers
misc_feature            1..93
                        note = Signal Peptide
misc_feature            94..1506
                        note = Mature Myocilin
misc_feature            94..675
                        note = N-Terminal Fragment
misc_feature            676..1506
                        note = C-Terminal Fragment
source                  1..1509
                        mol_type = other DNA
                        organism = Rattus norvegicus
SEQUENCE: 11
atgccctcct gtgcatactg ctgcagctgc ggtcccaaga tgccagctct ccagctgctg   60
tttctggcct gcctggtgtg gggaatgggg gccaggacag cacagttccg aaaggccaac  120
gatcggagtg gtcgatgcca gtacaccttc actgtggcca gccccagtga atctagctcc  180
ccaagggagg accaggccat gtcagccatc caggaccttc agagagatag cagcatccag  240
catgcagacc tagagtccac caaggcccgg gtcagatccc tggagagtct cctccaccag  300
atgacctcag gcggagttac tgggacccag gaggtccagg aggggctaca ggccagctg  360
ggtgccctga ggagagagcg ggaccagctg gagacgcaaa ccagggatct ggaggtagcc  420
tataacaatc tcctgagaga caaatcagct ttggaggaag agaagaggca gctggaacaa  480
gagaataaag atttggccag gaggctagaa ggcagcagcc aggaggtagc aaggctgagg  540
agaggccagt gtccctcaac ccaccacccc tctcaggaca tgttgccagg ctccagggaa  600
gtctctcagt ggaatttgga cacgttggct ttccaggaac tgaagtcaga actaacagag  660
gttcctgctt cccaaatctt gaagaatcaa tctggtcatc caaggagcaa agagggatg   720
aaaggatgtg gagtgctaat gtgggtagga gagccagtca ccctgaggac agctgagaca  780
atcactggaa agtatggagt atggatgaga gaccccaagc ccactcaccc ctacacccag  840
gagaccactt ggaggattga cacggttggc acaggcatcc gccaggtgtt tgagtacagt  900
cagataagcc agttcgagca gggctatcct tcaaaggtcc atgtgctccc ccaggcactg  960
gaaagcacag gtgctgtggt gtactcgggg agcctctatt tccagggtgc tgagtccaga 1020
actgtgctca ggtatgaact gaacacagaa acagtgaagg cagagaagga aattcctgga 1080
gctggctacc atggacagtt cccatacgca tggggtggct acacagacat cgacttagct 1140
gtggatgaga gcggcctctg gtcatctat agcacagagg aaaccagagg agccatagtc 1200
ctctccaaat tgaacccaga gaacctggaa cttgagagta cctgggagac caacatccgt 1260
aagcagtctg tggctaatgc ctttgttatc tgtggcatct tgtacacggt gagcagctac 1320
tcttcagtcc atgcaaccat caactttgcc tatgacacta acactgggat cagcaagacc 1380
ctgaccatcc cattcaagaa tcgctacaaa tacagcagca tggtcgacta caacccctg  1440
gagaggaaac tctttgcctg ggacaacttc aacatggtca cctatgatat caagctctca 1500
gagatgtga                                                         1509
```

-continued

```
SEQ ID NO: 12            moltype = AA   length = 502
FEATURE                  Location/Qualifiers
source                   1..502
                         mol_type = protein
                         organism = Rattus norvegicus
SEQUENCE: 12
MPSCAYCCSC GPKMPALQLL FLACLVWGMG ARTAQFRKAN DRSGRCQYTF TVASPSESSC    60
PREDQAMSAI QDLQRDSSIQ HADLESTKAR VRSLESLLHQ MTSGGVTGTQ EVQEGLQGQL   120
GALRRERDQL ETQTRDLEVA YNNLLRDKSA LEEEKRQLEQ ENKDLARRLE GSSQEVARLR   180
RGQCPSTHHP SQDMLPGSRE VSQWNLDTLA FQELKSELTE VPASQILKNQ SGHPRSKEGD   240
KGCGVLMWVG EPVTLRTAET ITGKYGVWMR DPKPTHPYTQ ETTWRIDTVG TGIRQVFEYS   300
QISQFEQGYP SKVHVLPQAL ESTGAVVYAG SLYFQGAESR TVLRYELNTE TVKAEKEIPG   360
AGYHGQFPYA WGGYTDIDLA VDESGLWVIY STEENRGAIV LSKLNPENLE LESTWETNIR   420
KQSVANAFVI CGILYTVSSY SSVHATINFA YDTNTGISKT LTIPFKNRYK YSSMVDYNPL   480
ERKLFAWDNF NMVTYDIKLS EM                                            502

SEQ ID NO: 13            moltype = DNA   length = 2052
FEATURE                  Location/Qualifiers
source                   1..2052
                         mol_type = other DNA
                         organism = Rattus norvegicus
SEQUENCE: 13
gagccagcag ggccacccat ccagacacct tgcagcagag ccttctagaa gaagcctcac    60
ccagccttca taccgatgcc ctcctgtgca tactgctgca gctgcggtcc caagatgcca   120
gctctccagc tgctgtttct ggcctgcctg gtatggggaa tgggggccag gacagcacag   180
ttccgaaagg ccaacgatcg gagtggtcga tgccagtaca ccttcactgt ggccagcccc   240
agtgaatcta gctgcccaag ggaggaccag gccatgtcag ccatccagga ccttcagaga   300
gatagcagca tccagcatgc agacctagag tccaccaagg cccgggtcag atccctggag   360
agtctcctcc accagatgac ctcaggcgga gttactggga cccaggaggt ccaggagggg   420
ctacaaggcc agctgggtgc cctgaggaga gagcgggacc agctggagac ccaaaccagg   480
gatctggagg tagcctataa caatctcctg agagacaaat cagctttgga ggaagagaag   540
aggcagctgg aacaagagaa taaagatttg gccaggaggc tagaaggcag cagccaggag   600
gtagcaaggc tgaggagagg ccagtgtccc tcaacccacc acccctctca ggacatgttg   660
ccaggctcca gggaagtctc tcagtggaat ttggacacgt tggctttcca ggaactgaag   720
tcagaactaa cagaggttcc tgcttcccaa atcttgaaga atcaatctgg tcatcccagg   780
agcaaagagg gagacaaagg atgtggagtg ctaatgtggg taggagagcc agtcaccctg   840
aggacagctg agacaatcac tggaaagtat ggagtatgga tgagagaccc caagcccact   900
cacccctaca cccaggagac cacttggagg attgacacgt tggcacagg catccgccag   960
gtgtttgagt acagtcagat aagccagttc gagcaggct atccttcaaa ggtccatgtg   1020
ctccccagg cactggaaag cacaggtgct gtggtgtatg cagggagcct gtatttccag   1080
ggtgctgagt ccagaactgt gctcaggtat gaactgaaca cagaaacagt gaaggcagag   1140
aaggaaattc ctggagctgg ctaccatgga cagttcccat acgcatgggg tggctacaca   1200
gacatagact agctgtggga tgagagtggc ctctgggtca tctatagcac agaggaaaac   1260
agaggagcca tagtcctctc caaattgaac ccagagaacc tggaacttga gagtacctgg   1320
gagaccaaca tccgtaagca gtctgtggct aatgcctttg ttatctgtgg catcttgtac   1380
acggtgagca gctactcttc agtccatgca accatcaact ttgcctatga cactaacact   1440
gggatcagca gacccctgac catcccattc aagaatcgat acaaatacag cagcatggtc   1500
gactacaacc ccctggagag gaaactcttt gcctgggaca acttcaacat ggtcacctat   1560
gatatcaagc tctcagagat gtgaggagcc tctatcccta ccagagaagg cagaaaaagg   1620
gggaagttcc aggctcccag gtgaagcagc tgcaagagga ggcagccaga tgctgggggc   1680
ttctgcttct caagattttg tttgtccagg tcaataccct gggcttgta cagttgcata   1740
tattctgctc tcttctgtca gctttccaag gggtgttcat cttttaaaaa tcatatagtg   1800
tagcagtcca gagaaaaact agaagtgttg tttcctcatg aaaccattgc ttttgcaagc   1860
tgtatggtta ctacaaacct tgagaggcag caacagttct accaagagga gggagataac   1920
ggggagggg tgaccaccac tcctgtggtt agaactgctc ctgcagtatt tactccagtt   1980
tctaaggcta cagatatagc atgtacatta aacccttgc cctgtgaaat aaagttatct   2040
tacacgacgt ta                                                      2052

SEQ ID NO: 14            moltype = DNA   length = 1509
FEATURE                  Location/Qualifiers
source                   1..1509
                         mol_type = other DNA
                         organism = Rattus norvegicus
SEQUENCE: 14
atgccctcct gtgcatactg ctgcagctgc ggtcccaaga tgccagctct ccagctgctg    60
tttctggcct gcctggtatg gggaatgggg gccaggacag cacagttccg aaaggccaac   120
gatcggagtg tcgatgcca gtacaccttc actgtggcca gccccagtga atctagctgc   180
ccaagggagg accaggccat gtcagccatc caggaccttc agagagatag cagcatccag   240
catgcagacc tagagtccac caaggcccgg gtcagatcct ggagagtct cctccaccag   300
atgacctcag gcggagttac tgggacccag gaggtccagg aggggctaca aggccagctg   360
ggtgccctga ggagagagcg ggaccagctg gagacccaaa ccaggatct ggaggtagcc   420
tataacaatc tcctgagaga caaatcagct ttggaggaag agaagaggca gctgaacaa   480
gagaataaag atttggccag gaggctagaa ggcagcagcc aggaggtagc aaggctgagg   540
agagccagt gtccctcaac ccaccaccc tctcaggaca tgttgccagg ctccagggag   600
gtctctcagt ggaatttgga cacgttggct ttccaggaac tgaagtcaga actaacagag   660
gttcctgctt cccaaatctt gaagaatcaa tctggtcatc ccaggagcaa agagggagac   720
aaaggatgtg gagtgctaat gtgggtagga gagccagtca ccctgaggac agctgagaca   780
atcactggaa agtatggagt atggatgaga gaccccaagc ccactcaccc ctacacccag   840
gagaccactt ggaggattga cacgttggc acaggcatcc gccaggtgtt tgagtacagt   900
```

```
cagataagcc agttcgagca gggctatcct tcaaaggtcc atgtgctccc ccaggcactg  960
gaaagcacag gtgctgtggt gtatgcaggg agcctgtatt tccagggtgc tgagtccaga  1020
actgtgctca ggtatgaact gaacacagaa acagtgaagg cagagaagga aattcctgga  1080
gctggctacc atggacagtt cccatacgca tggggtggct acacagacat agacttagct  1140
gtggatgaga gtggcctctg ggtcatctat agcacagagg aaaacagagg agccatagtc  1200
ctctccaaat tgaacccaga gaacctggaa cttgagagta cctgggagac caacatccgt  1260
aagcagtctg tggctaatgc ctttgttatc tgtggcatct tgtacacggt gagcagctac  1320
tcttcagtcc atgcaaccat caactttgcc tatgacacta acactgggat cagcaagacc  1380
ctgaccatcc cattcaagaa tcgctacaaa tacagcagca tggtcgacta caacccctg   1440
gagaggaaac tctttgcctg ggacaacttc aacatggtca cctatgatat caagctctca  1500
gagatgtga                                                         1509
```

```
SEQ ID NO: 15          moltype = AA  length = 32
FEATURE                Location/Qualifiers
source                 1..32
                       mol_type = protein
                       organism = Homo sapiens
SEQUENCE: 15
MRFFCARCCS FGPEMPAVQL LLLACLVWDV GA                                32
```

```
SEQ ID NO: 16          moltype = AA  length = 472
FEATURE                Location/Qualifiers
source                 1..472
                       mol_type = protein
                       organism = Homo sapiens
SEQUENCE: 16
RTAQLRKAND QSGRCQYTFS VASPNESSCP EQSQAMSVIH NLQRDSSTQR LDLEATKARL   60
SSLESLLHQL TLDQAARPQE TQEGLQRELG TLRRERDQLE TQTRELETAY SNLLRDKSVL  120
EEEEKKRLRQE NENLARRLES SSQEVARLRR GQCPQTRDTA RAVPPGSREV STWNLDTLAF  180
QELKSELTEV PASRILKESP SGYLRSGEGD TGCGELVWVG EPLTLRTAET ITGKYGVWMR  240
DPKPTYPYTQ ETTWRIDTVG TDVRQVFEYD LISQFMQGYP SKVHILPRPL ESTGAVVYSG  300
SLYFQGAESR TVIRYELNTE TVKAEKEIPG AGYHGQFPYS WGGYTDIDLA VDEAGLWVIY  360
STDEAKGAIV LSKLNPENLE LEQTWETNIR KQSVANAFII CGTLYTVSSY TSADATVNFA  420
YDTGTGISKT LTIPFKNRYK YSSMIDYNPL EKKLFAWDNL NMVTYDIKLS KM          472
```

```
SEQ ID NO: 17          moltype = AA  length = 194
FEATURE                Location/Qualifiers
source                 1..194
                       mol_type = protein
                       organism = Homo sapiens
SEQUENCE: 17
RTAQLRKAND QSGRCQYTFS VASPNESSCP EQSQAMSVIH NLQRDSSTQR LDLEATKARL   60
SSLESLLHQL TLDQAARPQE TQEGLQRELG TLRRERDQLE TQTRELETAY SNLLRDKSVL  120
EEEEKKRLRQE NENLARRLES SSQEVARLRR GQCPQTRDTA RAVPPGSREV STWNLDTLAF  180
QELKSELTEV PASR                                                   194
```

```
SEQ ID NO: 18          moltype = AA  length = 278
FEATURE                Location/Qualifiers
source                 1..278
                       mol_type = protein
                       organism = Homo sapiens
SEQUENCE: 18
ILKESPSGYL RSGEGDTGCG ELVWVGEPLT LRTAETITGK YGVWMRDPKP TYPYTQETTW   60
RIDTVGTDVR QVFEYDLISQ FMQGYPSKVH ILPRPLESTG AVVYSGSLYF QGAESRTVIR  120
YELNTETVKA EKEIPGAGYH GQFPYSWGGY TDIDLAVDEA GLWVIYSTDE AKGAIVLSKL  180
NPENLELEQT WETNIRKQSV ANAFIICGTL YTVSSYTSAD ATVNFAYDTG TGISKTLTIP  240
FKNRYKYSSM IDYNPLEKKL FAWDNLNMVT YDIKLSKM                         278
```

```
SEQ ID NO: 19          moltype = AA  length = 472
FEATURE                Location/Qualifiers
source                 1..472
                       mol_type = protein
                       organism = Homo sapiens
SEQUENCE: 19
RTAQLRKAND QSGRCQYTFS VASPNESSCP EQSQAMSVIH NLQRDSSTQR LDLEATKARL   60
SSLESLLHQL TLDQAARPQE TQEGLQRELG TLRRERDQLE TQTRELETAY SNLLRDKSVL  120
EEEEKKRLRQE NENLARRLES SSQEVARLRR GQCPQTRDTA RAVPPGSREV STWNLDTLAF  180
QELKSELTEV PASRILKESP SGYLRSGEGD TGCGELVWVG EPLTLRTAET ITGKYGVWMR  240
DPKPTYPYTQ ETTWRIDTVG TDVRQVFEYD LISQFMQGYP SKVHILPRPL ESTGAVVYSG  300
SLYFQGAESR TVIRYELNTE TVKAEKEIPG AGYHGQFPYS WGGYTDIDLA VDEAGLWVIY  360
STDEAKGAIV LSKLNPENLE LEQTWETNIR KQSVANAFII CGTLHTVSSY TSADATVNFA  420
YDTGTGISKT LTIPFKNRYK YSSMIDYNPL EKKLFAWDNL NMVTYDIKLS KM          472
```

```
SEQ ID NO: 20          moltype = AA  length = 278
FEATURE                Location/Qualifiers
source                 1..278
                       mol_type = protein
                       organism = Homo sapiens
SEQUENCE: 20
```

```
ILKESPSGYL RSGEGDTGCG ELVWVGEPLT LRTAETITGK YGVWMRDPKP TYPYTQETTW    60
RIDTVGTDVR QVFEYDLISQ FMQGYPSKVH ILPRPLESTG AVVYSGSLYF QGAESRTVIR   120
YELNTETVKA EKEIPGAGYH GQFPYSWGGY TDIDLAVDEA GLWVIYSTDE AKGAIVLSKL   180
NPENLELEQT WETNIRKQSV ANAFIICGTL HTVSSYTSAD ATVNFAYDTG TGISKTLTIP   240
FKNRYKYSSM IDYNPLEKKL FAWDNLNMVT YDIKLSKM                          278
```

```
SEQ ID NO: 21           moltype = DNA   length = 96
FEATURE                 Location/Qualifiers
source                  1..96
                        mol_type = other DNA
                        organism = Homo sapiens
SEQUENCE: 21
atgaggttct tctgtgcacg ttgctgcagc tttgggcctg agatgccagc tgtccagctg    60
ctgcttctgg cctgcctggt gtgggatgtg ggggcc                              96
```

```
SEQ ID NO: 22           moltype = DNA   length = 1416
FEATURE                 Location/Qualifiers
source                  1..1416
                        mol_type = other DNA
                        organism = Homo sapiens
SEQUENCE: 22
aggacagctc agctcaggaa ggccaatgac cagagtggcc gatgccagta taccttcagt    60
gtggccagtc ccaatgaatc cagctgccca gagcagagcc aggccatgtc agtcatccat   120
aacttacaga gagacagcag cacccaacgc ttagacctgg aggccaccaa agctcgactc   180
agctccctgg agagcctcct ccaccaattg accttggacc aggctgccag gccccaggag   240
acccaggagg ggctgcagag ggagctgggc accctgaggc gggagcggga ccagctggaa   300
acccaaacca gagagttgga gactgcctac agcaacctcc tccgagacaa gtcagttctg   360
gaggaagaga agaagcgact aaggcaagaa aatgagaatc tggccaggag gttggaaagc   420
agcagccagg aggtagcaag gctgagaagg ggccagtgtc cccagacccg agacactgct   480
cgggctgtgc caccaggctc cagagaagtt tctacgtgga atttggacac tttggccttc   540
caggaactga agtccgagct aactgaagtt cctgcttccc gaattttgaa ggagagccca   600
tctggctatc tcaggagtgg agagggagac accggatgtg gagaactagt tttgggtagga   660
gagcctctca cgctgagaac agcagaaaca attactggca agtatggtgt gtggatgcga   720
gaccccaagc ccacctaccc ctacacccag gagaccacgt ggagaatcga cacagttggc   780
acggatgtcc gccaggtttt tgagtatgac ctcatcagcc agtttatgca gggctaccct   840
tctaaggttc acatactgcc taggccactg gaaagcacgg gtgctgtggt gtactcgggg   900
agcctctatt tccagggcgc tgagtccaga actgtcataa gatatgagct gaataccgag   960
acagtgaagg ctgagaagga aatccctgga gctggctacc acggacagtt cccgtattct  1020
tggggtggct acacggacat tgacttggct gtggatgaag caggcctctg ggtcatttac  1080
agcaccgatg aggccaaagg tgccattgtc ctctccaaac tgaacccaga gaatctggaa  1140
ctcgaacaaa cctgggagac aaacatccgt aagcagtcag tcgccaatgc cttcatcatc  1200
tgtggcacct tgtacaccgt cagcagctac acctcagcag atgctaccgt caactttgct  1260
tatgacacag gcacaggtat cagcaagacc ctgaccatcc cattcaagaa ccgctataag  1320
tacagcagca tgattgacta caaccccctg gagaagaagc tctttgcctg ggacaacttg  1380
aacatggtca cttatgacat caagctctcc aagatg                            1416
```

```
SEQ ID NO: 23           moltype = DNA   length = 582
FEATURE                 Location/Qualifiers
source                  1..582
                        mol_type = other DNA
                        organism = Homo sapiens
SEQUENCE: 23
aggacagctc agctcaggaa ggccaatgac cagagtggcc gatgccagta taccttcagt    60
gtggccagtc ccaatgaatc cagctgccca gagcagagcc aggccatgtc agtcatccat   120
aacttacaga gagacagcag cacccaacgc ttagacctgg aggccaccaa agctcgactc   180
agctccctgg agagcctcct ccaccaattg accttggacc aggctgccag gccccaggag   240
acccaggagg ggctgcagag ggagctgggc accctgaggc gggagcggga ccagctggaa   300
acccaaacca gagagttgga gactgcctac agcaacctcc tccgagacaa gtcagttctg   360
gaggaagaga agaagcgact aaggcaagaa aatgagaatc tggccaggag gttggaaagc   420
agcagccagg aggtagcaag gctgagaagg ggccagtgtc cccagacccg agacactgct   480
cgggctgtgc caccaggctc cagagaagtt tctacgtgga atttggacac tttggccttc   540
caggaactga agtccgagct aactgaagtt cctgcttccc ga                      582
```

```
SEQ ID NO: 24           moltype = DNA   length = 834
FEATURE                 Location/Qualifiers
source                  1..834
                        mol_type = other DNA
                        organism = Homo sapiens
SEQUENCE: 24
attttgaagg agagcccatc tggctatctc aggagtggag agggagacac cggatgtgga    60
gaactagttt gggtaggaga gcctctcacg ctgagaacag cagaaacaat tactggcaag   120
tatggtgtgt ggatgcgaga ccccaagccc acctacccct acacccagga gaccacgtgg   180
agaatcgaca cagttggcac ggatgtccgc caggtttttg agtatgacct catcagccag   240
tttatgcagg gctacccttc taaggttcac atactgccta ggccactgga aagcacgggt   300
gctgtggtgt actcggggag cctctatttc cagggcgctg agtccagaac tgtcataaga   360
tatgagctga ataccgagac agtgaaggct gagaaggaaa tccctggagc tggctaccac   420
ggacagttcc cgtattcttg gggtggctac acggacattg acttggctgt ggatgaagca   480
ggcctctggg tcatttacag caccgatgag gccaaaggtg ccattgtcct ctccaaactg   540
aacccagaga atctggaact cgaacaaacc tgggagacaa acatccgtaa gcagtcagtc   600
```

```
gccaatgcct tcatcatctg tggcaccttg tacaccgtca gcagctacac ctcagcagat    660
gctaccgtca actttgctta tgacacaggc acaggtatca gcaagaccct gaccatccca    720
ttcaagaacc gctataagta cagcagcatg attgactaca acccctgga gaagaagctc     780
tttgcctggg acaacttgaa catggtcact tatgacatca agctctccaa gatg          834

SEQ ID NO: 25              moltype = DNA  length = 1416
FEATURE                   Location/Qualifiers
source                    1..1416
                          mol_type = other DNA
                          organism = Homo sapiens
SEQUENCE: 25
aggacagctc agctcaggaa ggccaatgac cagagtggcc gatgccagta taccttcagt     60
gtggccagtc ccaatgaatc cagctgccca gagcagagcc aggccatgtc agtcatccat    120
aacttacaga gagacagcag cacccaacgc ttagacctgg aggccaccaa agctcgactc    180
agctccctgg agagcctcct ccaccaattg accttggacc aggctgccag gccccaggag    240
acccaggagg ggctgcagag ggagctgggc accctgaggc gggagcggga ccagctggaa    300
acccaaacca gagagttgga gactgcctac agcaacctcc tccgagacaa gtcagttctg    360
gaggaagaga agaagcgact aaggcaagaa aatgagaatc tggccaggag gttggaaagc    420
agcagccagg aggtagcaag gctgagaagg ggccagtgtc cccagacccg agacactgct    480
cgggctgtgc caccaggctc cagagaagtt tctacgtgga atttggacac tttggccttc    540
caggaactga agtccgagct aactgaagtt cctgcttccc gaattttgaa ggagagccca    600
tctggctatc tcaggagtgg agaggggagac accggatgtg gagaactagt ttgggtagga    660
gagcctctca cgctgagaac agcagaaaca attactggca agtatggtgt gtggatgcga    720
gaccccaagc ccacctaccc ctacacccag gagaccacgt ggagaatcga cacagttggc    780
acggatgtcc gccaggtttt tgagtatgac ctcatcagcc agtttatgca gggctaccct    840
tctaaggttc acatactgcc taggccactg gaaagcacgg gtgctgtggt gtactcgggg    900
agcctctatt tccagggcgc tgagtccaga actgtcataa gatatgagct gaataccgag    960
acagtgaagg ctgagaagga aatccctgga gctggctacc acggacagtt cccgtattct   1020
tggggtggct acacggacat tgacttggct gtggatgaag caggcctctg ggtcatttac   1080
agcaccgatg aggccaaagg tgccattgtc ctctccaaac tgaacccaga gaatctggaa   1140
ctcgaacaaa cctgggagac aaacatccgt aagcagtcag tcgccaatgc cttcatcatc   1200
tgtggcacct tgcacaccgt cagcagctac acctcagcag atgctaccgt caactttgct   1260
tatgacacag gcacaggtat cagcaagacc ctgaccatcc cattcaagaa ccgctataag   1320
tacagcagca tgattgacta caacccctg gagaagaagc tctttgcctg ggacaacttg   1380
aacatggtca cttatgacat caagctctcc aagatg                            1416

SEQ ID NO: 26              moltype = DNA  length = 834
FEATURE                   Location/Qualifiers
source                    1..834
                          mol_type = other DNA
                          organism = Homo sapiens
SEQUENCE: 26
attttgaagg agagcccatc tggctatctc aggagtggag aggggagacac cggatgtgga     60
gaactagttt gggtaggaga gcctctcacg ctgagaacag cagaaacaat tactggcaag    120
tatggtgtgt ggatgcgaga ccccaagccc acctaccct acacccagga gaccacgtgg     180
agaatcgaca cagttggcac ggatgtccgc caggtttttg agtatgacct catcagccag    240
tttatgcag gctacccttc taaggttcac atactgccta ggccactgg aaagcacggg      300
gctgtggtgt actcggggag cctctatttc cagggcgctg agtccagaac tgtcataaga    360
tatgagctga ataccgagac agtgaaggct gagaaggaaa tccctggagc tggctaccac    420
ggacagttcc cgtattcttg gggtggctac acggacattg acttggctgt ggatgaagca    480
ggcctctgg tcatttacag caccgatgag gccaaaggt ccattgtcct ctccaaactg     540
aacccagaga atctggaact cgaacaaacc tgggagacaa acatccgtaa gcagtcagtc    600
gccaatgcct tcatcatctg tggcaccttg cacaccgtca gcagctacac ctcagcagat    660
gctaccgtca actttgctta tgacacaggc acaggtatca gcaagaccct gaccatccca    720
ttcaagaacc gctataagta cagcagcatg attgactaca acccctgga gaagaagctc     780
tttgcctggg acaacttgaa catggtcact tatgacatca agctctccaa gatg          834

SEQ ID NO: 27              moltype = AA  length = 18
FEATURE                   Location/Qualifiers
source                    1..18
                          mol_type = protein
                          organism = Mus musculus
SEQUENCE: 27
MPALHLLFLA CLVWGMGA                                                     18

SEQ ID NO: 28              moltype = AA  length = 472
FEATURE                   Location/Qualifiers
source                    1..472
                          mol_type = protein
                          organism = Mus musculus
SEQUENCE: 28
RTAQFRKAND RSGRCQYTFT VASPNESSCP REDQAMSAIQ DLQRDSSIQH ADLESTKARV     60
RSLESLLHQM TLGRVTGTQE AQEGLQGQLG ALRRERDQLE TQTRDLEAAY NNLLRDKSAL    120
EEEKRQLEQE NEDLARRLES SSEEVTRLRR GQCPSTQYPS QDMLPGSREV SQWNLDTLAF    180
QELKSELTEV PASQILKENP SGRPRSKEGD KGCGALVWVG EPVTLRTAET IAGKYGVWMR    240
DPKPTHPYTQ ESTWRIDTVG TEIRQVFEYS QISQFEQGYP SKVHVLPRAL ESTGAVVYAG    300
SLYFQGAESR TVVRYELDTE TVKAEKEIPG AGYHGHFPYA WGGYTDIDLA VDESGLWVIY    360
STEEAKGAIV LSKLNPANLE LERTWETNIR KQSVANAFVI CGILYTVSSY SSAHATVNFA    420
YDTKTGTSKT LTIPFTNRYK YSSMIDYNPL ERKLFAWDNF NMVTYDIKLL EM            472
```

```
SEQ ID NO: 29              moltype = AA   length = 194
FEATURE                    Location/Qualifiers
source                     1..194
                           mol_type = protein
                           organism = Mus musculus
SEQUENCE: 29
RTAQFRKAND RSGRCQYTFT VASPNESSCP REDQAMSAIQ DLQRDSSIQH ADLESTKARV  60
RSLESLLHQM TLGRVTGTQE AQEGLQGQLG ALRRERDQLE TQTRDLEAAY NNLLRDKSAL  120
EEEKRQLEQE NEDLARRLES SSEEVTRLRR GQCPSTQYPS QDMLPGSREV SQWNLDTLAF  180
QELKSELTEV PASQ                                                    194

SEQ ID NO: 30              moltype = AA   length = 278
FEATURE                    Location/Qualifiers
source                     1..278
                           mol_type = protein
                           organism = Mus musculus
SEQUENCE: 30
ILKENPSGRP RSKEGDKGCG ALVWVGEPVT LRTAETIAGK YGVWMRDPKP THPYTQESTW  60
RIDTVGTEIR QVFEYSQISQ FEQGYPSKVH VLPRALESTG AVVYAGSLYF QGAESRTVVR  120
YELDTETVKA EKEIPGAGYH GHFPYAWGGY TDIDLAVDES GLWVIYSTEE AKGAIVLSKL  180
NPANLELERT WETNIRKQSV ANAFVICGIL YTVSSYSSAH ATVNFAYDTK TGTSKTLTIP  240
FTNRYKYSSM IDYNPLERKL FAWDNFNMVT YDIKLLEM                          278

SEQ ID NO: 31              moltype = DNA   length = 54
FEATURE                    Location/Qualifiers
source                     1..54
                           mol_type = other DNA
                           organism = Mus musculus
SEQUENCE: 31
atgccagctc tccatctgct gtttctggcc tgcttggtgt ggggaatggg ggcc          54

SEQ ID NO: 32              moltype = DNA   length = 1416
FEATURE                    Location/Qualifiers
source                     1..1416
                           mol_type = other DNA
                           organism = Mus musculus
SEQUENCE: 32
aggacagcac agttccgaaa ggccaatgat cggagtggcc gatgccaata caccttcact  60
gtggccagcc ccaatgaatc tagctgccca agggaggacc aggccatgtc agccatccaa  120
gaccttcaga gagacagcag catccagcat gcagacctag agtccaccaa ggcccgggtc  180
agatccctgg agagtctcct ccaccagatg accttgggcc gagttactgg gacccaggag  240
gcccaagagg ggctgcaggg ccagttgggt gccctgagga gaaacggga ccagctggag  300
acccaaacca gggatctgga ggcagcctat aacaatctcc ttcgagataa gtcggcttta  360
gaggaagaga gaggcagct ggaacaagag aatgaagatt tggccaggag gctagaaagc  420
agcagcgagg aggtaacaag gctgcggagg ggccagtgtc cttccaccca gtaccctct  480
caggacatgc tgccaggctc cagggaagtc tctcagtgga atttggacac gttggcttc  540
caggaattga agtcagagtt aactgaggtt cctgcttccc aaatcttgaa ggaaaatcca  600
tctggccgac ccaggagcaa agaaggagac aaaggatgtg gagcgctagt ctgggtagga  660
gagccagtca ccctgaggac agctgaaaca atcgctggca agtatggagt gtggatgaga  720
gacccaagc ccacccaccc ctacacccag gaaagcacat ggaggattga cacggttggc  780
acagagatcc gccaggtgtt tgagtacagt cagataagcc agttcgagca gggctatcct  840
tccaaggtcc atgtgctccc tcgggcactg gagagcacgg gtgctgtggt gtatgcgggg  900
agcctctatt tccagggggc tgagtccaga actgtggtca ggtatgagct agacacggag  960
accgtgaagg cagagaagga aattcctgga gctggctacc acggacactt cccgtacgcg  1020
tggggtggct acacagacat tgacttagtc gtggatgaga gcggcctctg ggtcatctac  1080
agcacggagg aagccaaggg ggccatagtc ctctccaaat tgaacccagc gaacctggaa  1140
cttgagcgta cctgggagac taacatccgt aagcagtctg tggccaatgc ctttgttatc  1200
tgtggcatct tgtatacggt gagcagctac tcttcagccc atgcaaccgt caacttcgcc  1260
tacgacacta aaacggggac cagtaagacc ctgaccatcc cattcacgaa tcgctacaag  1320
tacagcagta tgattgacta caaccccctg gagaggaagc tgtttgcctg ggacaacttc  1380
aacatggtca cctatgatat caagctcttg gagatg                            1416

SEQ ID NO: 33              moltype = DNA   length = 582
FEATURE                    Location/Qualifiers
source                     1..582
                           mol_type = other DNA
                           organism = Mus musculus
SEQUENCE: 33
aggacagcac agttccgaaa ggccaatgat cggagtggcc gatgccaata caccttcact  60
gtggccagcc ccaatgaatc tagctgccca agggaggacc aggccatgtc agccatccaa  120
gaccttcaga gagacagcag catccagcat gcagacctag agtccaccaa ggcccgggtc  180
agatccctgg agagtctcct ccaccagatg accttgggcc gagttactgg gacccaggag  240
gcccaagagg ggctgcaggg ccagttgggt gccctgagga gaaacggga ccagctggag  300
acccaaacca gggatctgga ggcagcctat aacaatctcc ttcgagataa gtcggcttta  360
gaggaagaga gaggcagct ggaacaagag aatgaagatt tggccaggag gctagaaagc  420
agcagcgagg aggtaacaag gctgcggagg ggccagtgtc cttccaccca gtaccctct  480
caggacatgc tgccaggctc cagggaagtc tctcagtgga atttggacac gttggcttc  540
caggaattga agtcagagtt aactgaggtt cctgcttccc aa                      582
```

```
SEQ ID NO: 34              moltype = DNA   length = 834
FEATURE                    Location/Qualifiers
source                     1..834
                           mol_type = other DNA
                           organism = Mus musculus
SEQUENCE: 34
atcttgaagg aaaatccatc tggccgaccc aggagcaaag aaggagacaa aggatgtgga   60
gcgctagtct gggtaggaga gccagtcacc ctgaggacag ctgaaacaat cgctggcaag  120
tatggagtgt ggatgagaga ccccaagccc acccacccct acacccagga aagcacatgg  180
aggattgaca cggttggcac agagatccgc caggtgtttg agtacagtca gataagccag  240
ttcgagcagg gctatccttc caaggtccat gtgctcctc gggcactgga gagcacgggt  300
gctgtggtgt atgcggggag cctctatttc cagggggctg agtccagaac tgtggtcagg  360
tatgagctag acacggaaac cgtgaaggca gagaaggaaa ttcctggagc tggctaccac  420
ggacacttcc cgtacgcgtg gggtggctac acagacattg acttagctgt ggatgagagc  480
ggcctctggg tcatctacag cacggaggaa gccaagggg ccatagtcct ctccaaattg  540
aacccagcga acctggaact tgagcgtacc tgggagacta acatccgtaa gcagtctgtg  600
gccaatgcct ttgttatctg tggcatcttg tacacggtga gcagctactc ttcagcccat  660
gcaaccgtca acttcgccta cgacactaaa acgggaccca gtaagaccct gaccatccca  720
ttcacgaatc gctacaagta cagcagtatg attgactaca accccctgga gaggaagctg  780
tttgcctggg acaacttcaa catggtcacc tatgatatca agctcttgga gatg         834

SEQ ID NO: 35              moltype = AA   length = 31
FEATURE                    Location/Qualifiers
source                     1..31
                           mol_type = protein
                           organism = Rattus norvegicus
SEQUENCE: 35
MPSCAYCCSC GPKMPALQLL FLACLVWGMG A                                    31

SEQ ID NO: 36              moltype = AA   length = 471
FEATURE                    Location/Qualifiers
source                     1..471
                           mol_type = protein
                           organism = Rattus norvegicus
SEQUENCE: 36
RTAQFRKAND RSGRCQYTFT VASPSESSCP REDQAMSAIQ DLQRDSSIQH ADLESTKARV    60
RSLESLLHQM TSGGVTGTQE VQEGLQGQLG ALRRERDQLE TQTRDLEVAY NNLLRDKSAL   120
EEEKRQLEQE NKDLARRLEG SSQEVARLRR GQCPSTHHPS QDMLPGSREV SQWNLDTLAF   180
QELKSELTEV PASQILKNQS GHPRSKEGDK GCGVLMWVGE PVTLRTAETI TGKYGVWMRD   240
PKPTHPYTQE TTWRIDTVGT GIRQVFEYSQ ISQFEQGYPS KVHVLPQALE STGAVVYSGS   300
LYFQGAESRT VLRYELNTET VKAEKEIPGA GYHGQFPYAW GGYTDIDLAV DESGLWVIYS   360
TEETRGAIVL SKLNPENLEL ESTWETNIRK QSVANAFVIC GILYTVSSYS SVHATINFAY   420
DTNTGISKTL TIPFKNRYKY SSMVDYNPLE RKLFAWDNFN MVTYDIKLSE M             471

SEQ ID NO: 37              moltype = AA   length = 194
FEATURE                    Location/Qualifiers
source                     1..194
                           mol_type = protein
                           organism = Rattus norvegicus
SEQUENCE: 37
RTAQFRKAND RSGRCQYTFT VASPSESSCP REDQAMSAIQ DLQRDSSIQH ADLESTKARV    60
RSLESLLHQM TSGGVTGTQE VQEGLQGQLG ALRRERDQLE TQTRDLEVAY NNLLRDKSAL   120
EEEKRQLEQE NKDLARRLEG SSQEVARLRR GQCPSTHHPS QDMLPGSREV SQWNLDTLAF   180
QELKSELTEV PASQ                                                     194

SEQ ID NO: 38              moltype = AA   length = 277
FEATURE                    Location/Qualifiers
source                     1..277
                           mol_type = protein
                           organism = Rattus norvegicus
SEQUENCE: 38
ILKNQSGHPR SKEGDKGCGV LMWVGEPVTL RTAETITGKY GVWMRDPKPT HPYTQETTWR    60
IDTVGTGIRQ VFEYSQISQF EQGYPSKVHV LPQALESTGA VVYSGSLYFQ GAESRTVLRY   120
ELNTETVKAE KEIPGAGYHG QFPYAWGGYT DIDLAVDESG LWVIYSTEET RGAIVLSKLN   180
PENLELESTW ETNIRKQSVA NAFVICGILY TVSSYSSVHA TINFAYDTNT GISKTLTIPF   240
KNRYKYSSMV DYNPLERKLF AWDNFNMVTY DIKLSEM                            277

SEQ ID NO: 39              moltype = DNA   length = 93
FEATURE                    Location/Qualifiers
source                     1..93
                           mol_type = other DNA
                           organism = Rattus norvegicus
SEQUENCE: 39
atgccctcct gtgcatactg ctgcagctgc ggtcccaaga tgccagctct ccagctgctg    60
tttctggcct gcctggtgtg gggaatgggg gcc                                  93

SEQ ID NO: 40              moltype = DNA   length = 1413
FEATURE                    Location/Qualifiers
```

```
source                  1..1413
                        mol_type = other DNA
                        organism = Rattus norvegicus
SEQUENCE: 40
aggacagcac agttccgaaa ggccaacgat cggagtggtc gatgccagta caccttcact   60
gtggccagcc ccagtgaatc tagctgccca agggaggacc aggccatgtc agccatccag   120
gaccttcaga gagatagcag catccagcat gcagacctag agtccaccaa ggcccgggtc   180
agatccctgg agagtctcct ccaccagatg acctcaggcg gagttactgg gacccaggag   240
gtccaggagg ggctacaagg ccagctgggt gccctgagga gagagcggga ccagctggag   300
acgcaaacca gggatctgga ggtagcctat aacaatctcc tgagagacaa atcagctttg   360
gaggaagaga agaggcagct ggaacaagag aataaagatt tggccaggag gctagaaggc   420
agcagccagg aggtagcaag gctgaggaga ggccagtgtc cctcaaccca ccacccctct   480
caggacatgt tgccaggctc cagggaagtc tctcagtgga atttggacac gttggctttc   540
caggaactga agtcagaact aacagaggtt cctgcttccc aaatcttgaa gaatcaatct   600
ggtcatccca ggagcaaaga gggagacaaa ggatgtggag tgctaatgtg ggtaggagag   660
ccagtcaccc tgaggacagc tgagacaatc actggaaagt atggagtatg gatgagagac   720
cccaagccca ctcacccta cacccaggag accacttgga ggattgacac ggttggcaca   780
ggcatccgcc aggtgtttga gtacagtcag ataagccagt tcgagcaggg catccttca   840
aaggtccatg tgctccccca ggcactggaa agcacaggtg ctgtggtgta ctcggggagc   900
ctctatttcc agggtgctga gtccagaact gtgctcaggt atgaactgaa cacagaaaca   960
gtgaaggcag agaaggaaat tcctggagct ggctaccatg gacagttccc atacgcatgg   1020
ggtggctaca cagacatcga cttagctgtg gatgagagcg gcctctgggt catctatagc   1080
acagaggaaa ccagaggagc catagtcctc tccaaattga acccagagaa cctggaactt   1140
gagagtacct gggagaccaa catccgtaag cagtctgtgg ctaatgcctt tgttatctgt   1200
ggcatcttgt acacggtgag cagctactct tcagtccatg caaccatcaa ctttgcctat   1260
gacactaaca ctgggatcag caagaccctg accatcccat tcaagaatcg ctacaaatac   1320
agcagcatgg tcgactacaa cccccctggag aggaaactct ttgcctggga caacttcaac   1380
atggtcacct atgatatcaa gctctcagag atg   1413

SEQ ID NO: 41             moltype = DNA   length = 582
FEATURE                   Location/Qualifiers
source                    1..582
                          mol_type = other DNA
                          organism = Rattus norvegicus
SEQUENCE: 41
aggacagcac agttccgaaa ggccaacgat cggagtggtc gatgccagta caccttcact   60
gtggccagcc ccagtgaatc tagctgccca agggaggacc aggccatgtc agccatccag   120
gaccttcaga gagatagcag catccagcat gcagacctag agtccaccaa ggcccgggtc   180
agatccctgg agagtctcct ccaccagatg acctcaggcg gagttactgg gacccaggag   240
gtccaggagg ggctacaagg ccagctgggt gccctgagga gagagcggga ccagctggag   300
acgcaaacca gggatctgga ggtagcctat aacaatctcc tgagagacaa atcagctttg   360
gaggaagaga agaggcagct ggaacaagag aataaagatt tggccaggag gctagaaggc   420
agcagccagg aggtagcaag gctgaggaga ggccagtgtc cctcaaccca ccacccctct   480
caggacatgt tgccaggctc cagggaagtc tctcagtgga atttggacac gttggctttc   540
caggaactga agtcagaact aacagaggtt cctgcttccc aa   582

SEQ ID NO: 42             moltype = DNA   length = 831
FEATURE                   Location/Qualifiers
source                    1..831
                          mol_type = other DNA
                          organism = Rattus norvegicus
SEQUENCE: 42
atcttgaaga atcaatctgg tcatcccagg agcaaagagg gagacaaagg atgtggagtg   60
ctaatgtggg taggagagcc agtcaccctg aggacagctg agacaatcac tggaaagtat   120
ggagtatgg tgagagaccc caagcccact caccctaca cccaggagac cacttggagg   180
attgacacgg ttggcacagg catccgccag gtgtttgagt acagtcagat aagccagttc   240
gagcagggct atccttcaaa ggtccatgtg ctcccccagg cactggaaag cacaggtgct   300
gtggtgtact cggggagcct ctatttccag ggtgctgagt ccagaactgt gctcaggtat   360
gaactgaaca cagaaacagt gaaggcagag aaggaaattc ctggagctgg ctaccatgga   420
cagttcccat acgcatgggg tggctacaca gacatcgact tagctgtgga tgagagcgga   480
ctctgggtca tctatagcac agaggaaacc agaggagcca gtcctctc caaattgaac   540
ccagagaacc tggaacttga gagtacctgg gagaccaaca tccgtaagca gtctgtggct   600
aatgcctttg ttatctgtgg catcttgtac acggtgagca gctactcttc agtccatgca   660
accatcaact ttgcctatga cactaacact gggatcagca agaccctgac catcccattc   720
aagaatcgct acaaatacag cagcatggtc gactacaacc cctggagag gaaactcttt   780
gcctgggaca acttcaacat ggtcacctat gatatcaagc tctcagagat g   831

SEQ ID NO: 43             moltype = AA   length = 1471
FEATURE                   Location/Qualifiers
REGION                    1..1471
                          note = Synthetic
source                    1..1471
                          mol_type = protein
                          organism = synthetic construct
SEQUENCE: 43
MKRPAATKKA GQAKKKKDKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES   120
FLVEEDKKHE RHPIFGNIVD EVAYHEKYPT IYHLRKKLVD STDKADLRLI YLALAHMIKF   180
RGHFLIEGDL NPDNSDVDKL FIQLVQTYNQ LFEENPINAS GVDAKAILSA RLSKSRRLEN   240
```

-continued

```
LIAQLPGEKK NGLFGNLIAL SLGLTPNFKS NFDLAEDAKL QLSKDTYDDD LDNLLAQIGD    300
QYADLFLAAK NLSDAILLSD ILRVNTEITK APLSASMIKR YDEHHQDLTL LKALVRQQLP    360
EKYKEIFFDQ SKNGYAGYID GGASQEEFYK FIKPILEKMD GTEELLVKLN REDLLRKQRT    420
FDNGSIPHQI HLGELHAILR RQEDFYPFLK DNREKIEKIL TFRIPYYVGP LARGNSRFAW    480
MTRKSEETIT PWNFEEVVDK GASAQSFIER MTNFDKNLPN EKVLPKHSLL YEYFTVYNEL    540
TKVKYVTEGM RKPAFLSGEQ KKAIVDLLFK TNRKVTVKQL KEDYFKKIEC FDSVEISGVE    600
DRFNASLGTY HDLLKIIKDK DFLDNEENED ILEDIVLTLT LFEDREMIEE RLKTYAHLFD    660
DKVMKQLKRR RYTGWGRLSR KLINGIRDKQ SGKTILDFLK SDGFANRNFM QLIHDDSLTF    720
KEDIQKAQVS GQGDSLHEHI ANLAGSPAIK KGILQTVKVV DELVKVMGRH KPENIVIEMA    780
RENQTTQKGQ KNSRERMKRI EEGIKELGSQ ILKEHPVENT QLQNEKLYLY YLQNGRDMYV    840
DQELDINRLS DYDVDHIVPQ SFLKDDSIDN KVLTRSDKAR GKSDNVPSEE VVKKMKNYWR    900
QLLNAKLITQ RKFDNLTKAE RGGLSELDKA GFIKRQLVET RQITKHVAQI LDSRMNTKYD    960
ENDKLIREVK VITLKSKLVS DFRKDFQFYK VREINNYHHA HDAYLNAVVG TALIKKYPKL   1020
ESEFVYGDYK VYDVRKMIAK SEQEIGKATA KYFFYSNIMN FFKTEITLAN GEIRKRPLIE   1080
TNGETGEIVW DKGRDFATVR KVLSMPQVNI VKKTEVQTGG FSKESILPKR NSDKLIARKK   1140
DWDPKKYGGF DSPTVAYSVL VVAKVEKGKS KKLKSVKELL GITIMERSSF EKNPIDFLEA   1200
KGYKEVKKDL IIKLPKYSLF ELENGRKRML ASAGELQKGN ELALPSKYVN FLYLASHYEK   1260
LKGSPEDNEQ KQLFVEQHKH YLDEIIEQIS EFSKRVILAD ANLDKVLSAY NKHRDKPIRE   1320
QAENIIHLFT LTNLGAPAAF KYFDTTIDRK RYTSTKEVLD ATLIHQSITG LYETRIDLSQ   1380
LGGDSAGGGG SGGGGSGGGG SGPKKKRKVA AAGSGRADAL DDFDLDMLGS DALDDFDLDM   1440
LGSDALDDFD LDMLGSDALD DFDLDMLINC T                                  1471

SEQ ID NO: 44         moltype = AA  length = 1384
FEATURE               Location/Qualifiers
REGION                1..1384
                      note = Synthetic
source                1..1384
                      mol_type = protein
                      organism = synthetic construct
SEQUENCE: 44
MKRPAATKKA GQAKKKKDKK YSIGLAIGTN SVGWAVITDE YKVPSKKFKV LGNTDRHSIK     60
KNLIGALLFD SGETAEATRL KRTARRYTR RKNRICYLQE IFSNEMAKVD DSFFHRLEES    120
FLVEEDKKHE RHPIFGNIVD EVAYHEKYPT IYHLRKKLVD STDKADLRLI YLALAHMIKF   180
RGHFLIEGDL NPDNSDVDKL FIQLVQTYNQ LFEENPINAS GVDAKAILSA RLSKSRRLEN   240
LIAQLPGEKK NGLFGNLIAL SLGLTPNFKS NFDLAEDAKL QLSKDTYDDD LDNLLAQIGD   300
QYADLFLAAK NLSDAILLSD ILRVNTEITK APLSASMIKR YDEHHQDLTL LKALVRQQLP   360
EKYKEIFFDQ SKNGYAGYID GGASQEEFYK FIKPILEKMD GTEELLVKLN REDLLRKQRT   420
FDNGSIPHQI HLGELHAILR RQEDFYPFLK DNREKIEKIL TFRIPYYVGP LARGNSRFAW   480
MTRKSEETIT PWNFEEVVDK GASAQSFIER MTNFDKNLPN EKVLPKHSLL YEYFTVYNEL   540
TKVKYVTEGM RKPAFLSGEQ KKAIVDLLFK TNRKVTVKQL KEDYFKKIEC FDSVEISGVE   600
DRFNASLGTY HDLLKIIKDK DFLDNEENED ILEDIVLTLT LFEDREMIEE RLKTYAHLFD   660
DKVMKQLKRR RYTGWGRLSR KLINGIRDKQ SGKTILDFLK SDGFANRNFM QLIHDDSLTF   720
KEDIQKAQVS GQGDSLHEHI ANLAGSPAIK KGILQTVKVV DELVKVMGRH KPENIVIEMA   780
RENQTTQKGQ KNSRERMKRI EEGIKELGSQ ILKEHPVENT QLQNEKLYLY YLQNGRDMYV   840
DQELDINRLS DYDVDHIVPQ SFLKDDSIDN KVLTRSDKAR GKSDNVPSEE VVKKMKNYWR   900
QLLNAKLITQ RKFDNLTKAE RGGLSELDKA GFIKRQLVET RQITKHVAQI LDSRMNTKYD   960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSPEDNEQ KQLFVEQHKH YLDEIIEQIS EFSKRVILAD ANLDKVLSAY NKHRDKPIRE  1320
QAENIIHLFT LTNLGAPAAF KYFDTTIDRK RYTSTKEVLD ATLIHQSITG LYETRIDLSQ  1380
LGGD                                                              1384

SEQ ID NO: 45         moltype = AA  length = 62
FEATURE               Location/Qualifiers
REGION                1..62
                      note = Synthetic
source                1..62
                      mol_type = protein
                      organism = synthetic construct
SEQUENCE: 45
AAAGSGRADA LDDFDLDMLG SDALDDFDLD MLGSDALDDF DLDMLGSDAL DDFDLDMLIN    60
CT                                                                 62

SEQ ID NO: 46         moltype = AA  length = 4
FEATURE               Location/Qualifiers
REGION                1..4
                      note = Synthetic
source                1..4
                      mol_type = protein
                      organism = synthetic construct
SEQUENCE: 46
GGGS                                                                4

SEQ ID NO: 47         moltype = AA  length = 5
FEATURE               Location/Qualifiers
REGION                1..5
```

-continued

```
                         note = Synthetic
source                   1..5
                         mol_type = protein
                         organism = synthetic construct
SEQUENCE: 47
GGGGS                                                                         5

SEQ ID NO: 48            moltype = AA  length = 473
FEATURE                  Location/Qualifiers
REGION                   1..473
                         note = Synthetic
source                   1..473
                         mol_type = protein
                         organism = synthetic construct
SEQUENCE: 48
MASNFTQFVL VDNGGTGDVT VAPSNFANGV AEWISSNSRS QAYKVTCSVR QSSAQKRKYT   60
IKVEVPKVAT QTVGGVELPV AAWRSYLNME LTIPIFATNS DCELIVKAMQ GLLKDGNPIP  120
SAIAANSGIY SAGGGGSGGG GSGGGGSGPK KKRKVAAAGS PSGQISNQAL ALAPSSAPVL  180
AQTMVPSSAM VPLAQPPAPA PVLTPGPPQS LSAPVPKSTQ AGEGTLSEAL LHLQFDADED  240
LGALLGNSTD PGVFTDLASV DNSEFQQLLN QGVSMSHSTA EPMLMEYPEA ITRLVTGSQR  300
PPDPAPTPLG TSGLPNGLSG DEDFSSIADM DFSALLSQIS SSGQGGGGSG FSVDTSALLD  360
LFSPSVTVPD MSLPDLDSSL ASIQELLSPQ EPPRPPEAEN SSPDSGKQLV HYTAQPLFLL  420
DPGSVDTGSN DLPVLFELGE GSYFSEGDGF AEDPTISLLT GSEPPKAKDP TVS         473

SEQ ID NO: 49            moltype = AA  length = 130
FEATURE                  Location/Qualifiers
REGION                   1..130
                         note = Synthetic
source                   1..130
                         mol_type = protein
                         organism = synthetic construct
SEQUENCE: 49
MASNFTQFVL VDNGGTGDVT VAPSNFANGV AEWISSNSRS QAYKVTCSVR QSSAQKRKYT   60
IKVEVPKVAT QTVGGVELPV AAWRSYLNME LTIPIFATNS DCELIVKAMQ GLLKDGNPIP  120
SAIAANSGIY                                                        130

SEQ ID NO: 50            moltype = AA  length = 181
FEATURE                  Location/Qualifiers
REGION                   1..181
                         note = Synthetic
source                   1..181
                         mol_type = protein
                         organism = synthetic construct
SEQUENCE: 50
PSGQISNQAL ALAPSSAPVL AQTMVPSSAM VPLAQPPAPA PVLTPGPPQS LSAPVPKSTQ   60
AGEGTLSEAL LHLQFDADED LGALLGNSTD PGVFTDLASV DNSEFQQLLN QGVSMSHSTA  120
EPMLMEYPEA ITRLVTGSQR PPDPAPTPLG TSGLPNGLSG DEDFSSIADM DFSALLSQIS  180
S                                                                 181

SEQ ID NO: 51            moltype = AA  length = 124
FEATURE                  Location/Qualifiers
REGION                   1..124
                         note = Synthetic
source                   1..124
                         mol_type = protein
                         organism = synthetic construct
SEQUENCE: 51
GFSVDTSALL DLFSPSVTVP DMSLPDLDSS LASIQELLSP QEPPRPPEAE NSSPDSGKQL   60
VHYTAQPLFL LDPGSVDTGS NDLPVLFELG EGSYFSEGDG FAEDPTISLL TGSEPPKAKD  120
PTVS                                                              124

SEQ ID NO: 52            moltype = RNA  length = 34
FEATURE                  Location/Qualifiers
misc_feature             1..34
                         note = Synthetic
source                   1..34
                         mol_type = other RNA
                         organism = synthetic construct
SEQUENCE: 52
ggccaacatg aggatcaccc atgtctgcag ggcc                              34

SEQ ID NO: 53            moltype = AA  length = 18
FEATURE                  Location/Qualifiers
REGION                   1..18
                         note = Synthetic
source                   1..18
                         mol_type = protein
                         organism = synthetic construct
SEQUENCE: 53
```

```
EGRGSLLTCG DVEENPGP                                                  18

SEQ ID NO: 54            moltype = AA  length = 19
FEATURE                  Location/Qualifiers
REGION                   1..19
                         note = Synthetic
source                   1..19
                         mol_type = protein
                         organism = synthetic construct
SEQUENCE: 54
ATNFSLLKQA GDVEENPGP                                                 19

SEQ ID NO: 55            moltype = AA  length = 20
FEATURE                  Location/Qualifiers
REGION                   1..20
                         note = Synthetic
source                   1..20
                         mol_type = protein
                         organism = synthetic construct
SEQUENCE: 55
QCTNYALLKL AGDVESNPGP                                                20

SEQ ID NO: 56            moltype = AA  length = 22
FEATURE                  Location/Qualifiers
REGION                   1..22
                         note = Synthetic
source                   1..22
                         mol_type = protein
                         organism = synthetic construct
SEQUENCE: 56
VKQTLNFDLL KLAGDVESNP GP                                             22

SEQ ID NO: 57            moltype = DNA  length = 4152
FEATURE                  Location/Qualifiers
misc_feature             1..4152
                         note = Synthetic
source                   1..4152
                         mol_type = other DNA
                         organism = synthetic construct
SEQUENCE: 57
atgaaaaggc cggcggccac gaaaaaggcc ggccaggcaa aaaagaaaaa ggacaagaag   60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca cagcgacgt ggacaagctg  600
ttcatccagc tggtgcagac ctacaaccag ctgttcgagg aaaacccat caacgccagc  660
ggcgtggacg ccaaggccat cctgtctgcc agactgagca gagcagacg gctggaaaat  720
ctgatcgccc agctgcccgg cgagaagaag aatggcctgt tcggcaacct gattgccctg  780
agcctgggcc tgacccccaa cttcaagagc aacttcgacc tggccgagga tgccaaactg  840
cagctgagca aggacacta cgacgacgac ctggacaact gctggccca gatcggcgac  900
cagtacgccg acctgtttct ggccgccaag aacctgtccg acgccatcct gctgagcgac  960
atcctgagag tgaacaccga gatcaccaag gcccccctga gcgcctctat gatcaagaga 1020
tacgacgagc accaccagga cctgaccctg ctgaaagctc tcgtgcggca gcagctgcct 1080
gagaagtaca aagagatttt cttcgaccag agcaagaacg gctacgccgg ctacattgac 1140
ggcggagcca gccaggaaga gttctacaag ttcatcaagc ccatcctgga aaagatggac 1200
ggcaccgagg aactgctcgt gaagctgaac agagaggacc tgctgcggaa gcagcggacc 1260
ttcgacaacg gcagcatccc ccaccagatc cacctgggag agctgcacgc cattctgcgg 1320
cggcaggaag atttttaccc attcctgaag gacaaccggg aaaagatcga gaagatcctg 1380
accttccgca tccccctacta cgtgggccct ctggccaagg gaaacagcag attcgcctgg 1440
atgaccagaa agagcgagga aaccatcacc ccctggaact cgaggaagt ggtgacaag 1500
ggcgcttccg cccagagctt catcgagcgg atgaccaact cgataagaa cctgcccaac 1560
gagaaggtgc tgcccaagca cagcctgctg tacgagtact tcaccgtgta taacgagctg 1620
accaaagtga aatacgtgac cgagggaatg agaaagcccg ccttcctgag cggcgagcag 1680
aaaaaggcca tcgtggacct gctgttcaag accaaccgga agtgaccgt gaagcagctg 1740
aaagaggact acttcaagaa aatcgagtgc ttcgactccg tggaaatctc cggcgtggaa 1800
gatcggttca acgcctccct gggcacatac cacgatctgc tgaaaattat caaggacaag 1860
gacttcctgg acaatgagga aacgaggac attctggaag atatcgtgct gaccctgaca 1920
ctgtttgagg acagagagat gatcgaggaa cggctgaaaa cctatgccca cctgttcgac 1980
gacaaagtga tgaagcagct gaagcggcg agatacaccg gctgggcag gctgagccgg 2040
aagctgatca cggcatccg ggacaagcag tccggcaaga caatcctgga tttcctgaag 2100
tccgacggct cgccaacag aaacttcatg cagctgatcc acgacgacag cctgaccttt 2160
aaagaggaca tccagaaagc ccaggtgtcc ggcaggggcg atagcctgca cgagcacatt 2220
gccaatctgc ccggcagccc cgccattaag aagggcatct gcagacagt gaaggtggtg 2280
gacgagctcg tgaaagtgat gggccggcac aagcccgaga acatcgtgat cgaaatggcc 2340
```

```
agagagaacc agaccaccca gaagggacag aagaacagcc gcgagagaat gaagcggatc  2400
gaagagggca tcaaagagct gggcagccag atcctgaaag aacacccccgt ggaaaacacc  2460
cagctgcaga acgagaagct gtacctgtac tacctgcaga atgggcggga tatgtacgtg  2520
gaccaggaac tggacatcaa ccggctgtcc gactacgatg tggaccacat cgtgcctcag  2580
agctttctga aggacgactc catcgacaac aaggtgctga ccagaagcga caaggcccgg  2640
ggcaagagcg acaacgtgcc ctccgaaagg gtcgtgaaga agatgaagaa ctactggcgg  2700
cagctgctga acgccaagct gattacccag agaaagttcg acaatctgac caaggccgag  2760
agaggcggcc tgagcgaact ggataaggcc ggcttcatca agagacagct ggtggaaacc  2820
cggcagatca caaagcacgt ggcacagatc ctggactccc ggatgaacac taagtacgac  2880
gagaatgaca agctgatccg ggaagtgaaa gtgatcaccc tgaagtccaa gctggtgtcc  2940
gatttccgga aggatttcca gtttttacaaa gtgcgcgaga tcaacaacta ccaccacgcc  3000
cacgacgcct acctgaacgc cgtcgtggga accgccctga tcaaaaagta ccctaagctg  3060
gaaagcgagt tcgtgtacgg cgactacaag gtgtacgacg tgcggaagat gatcgccaag  3120
agcgagcagg aaatcggcaa ggctaccgcc aagtacttct tctacagcaa catcatgaac  3180
tttttcaaga ccgagattac cctggccaac ggcgagatcc ggaagcggcc tctgatcgag  3240
acaaacggcg aaaccggggga gatcgtgtgg gataagggcc gggattttgc caccgtgcgg  3300
aaagtgctga gcatgcccca agtgaatatc gtgaaaaaga ccgaggtgca gacaggcggc  3360
ttcagcaaag agtctatcct gcccaagagg aacagcgata agctgatcgc cagaaagaag  3420
gactgggacc ctaagaagta cggcggcttc gacagcccca ccgtggccta ttctgtgctg  3480
gtggtggcca aagtggaaaa gggcaagtcc aagaaactga agagtgtgaa agagctgctg  3540
gggatcacca tcatggaaag aagcagcttc gagaagaatc ccatcgactt tctggaagcc  3600
aagggctaca aagaagtgaa aaaggacctg atcatcaagc tgcctaagta ctccctgttc  3660
gagctggaaa acggccggaa gagaatgctg gcctctgccg gcgaactgca gaagggaaac  3720
gaactggccc tgccctccaa atatgtgaac ttcctgtacc tggccagcca ctatgagaag  3780
ctgaagggct cccccgagga taatgagcag aaacagctgt ttgtggaaca gcacaagcac  3840
tacctggacg agatcatcga gcagatcagc gagttctcca agagagtgat cctggccgac  3900
gctaatctgg acaaagtgct gtccgcctac aacaagcacc gggataagcc catcagagag  3960
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctgggaggcg ac                                                     4152
```

```
SEQ ID NO: 58          moltype = DNA  length = 4414
FEATURE                Location/Qualifiers
misc_feature          1..4414
                       note = Synthetic
source                 1..4414
                       mol_type = other DNA
                       organism = synthetic construct
SEQUENCE: 58
atgaaaaggc cggcggccac gaaaaaggcc ggccaggcaa aaaagaaaaa ggacaagaag  60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca cagcgacgt ggacaagctg  600
ttcatccagc tggtgcagac ctacaaccag ctgttcgagg aaaacccccat caacgccaag  660
ggcgtggacg ccaaggccat cctgtctgcc agactgagca gagcagacg ctggaaaat  720
ctgatcgccc agctgcccgg cgagaagaag aatggcctgt tcggcaacct gattgccctg  780
agcctgggcc tgacccccaa cttcaagagc aacttcgacc tggccgagga tgccaaactg  840
cagctgagca aggacacca cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gccccccctga gcgcctctat gatcaagaga  1020
tacgacgagc accaccagga cctgaccctg ctgaaagctc tcgtgcggca gcagctgcct  1080
gagaagtaca aagagatttt cttcgaccag agcaagaacg gctacgccgg ctacattgac  1140
ggcggagcca gccaggaaga gttctacaag ttcatcaagc ccatcctgga aaagatggac  1200
ggcaccgagg aactgctcgt gaagctgaac agagaggacc tgctgcggaa gcagcggacc  1260
ttcgacaacg gcagcatccc ccaccagatc cacctgggag agctgcacgc cattctgcgg  1320
cggcaggaag atttttaccc attcctgaag gacaaccggg aaaagatcga gaagatcctg  1380
accttccgca tcccctacta cgtgggccct ctggccaggg gaaacagcag attcgcctgg  1440
atgaccagaa agagcgagga aaccatcacc cctggaact tcgaggaagt ggtggacaag  1500
ggcgcttccg cccagagctt catcgagcgg atgaccaact tcgataagaa cctgcccaac  1560
gagaaggtgc tgcccaagca gcctgctg tacgagtact tcaccgtgta taacgagctg  1620
accaaagtga aatacgtgac cgagggaatg agaaagcccg ccttcctgag cggcgagcag  1680
aaaaaggcca tcgtggacct gctgttcaag accaaccgga aagtgaccgt gaagcagctg  1740
aaagaggact acttcaagaa aatcgagtgc ttcgactccg tggaaatctc cggcgtggaa  1800
gatcggttca acgcctccct gggcacatac cacgatctgc tgaaaattat caaggacaag  1860
gacttcctgg acaatgagga aaacgaggac attctggaag atatcgtgct gaccctgaca  1920
ctgtttgagg acagagagat gatcgaggaa cggctgaaaa cctatgccca cctgttcgac  1980
gacaaagtgg tgaagcagct gaagcggcgg agatacaccg gctgggcag gctgagccgg  2040
aagctgatca cggcatccg ggacaagcag tccggcaaga caatcctgga tttcctgaag  2100
tccgacggct cgccaacag aaacttcatg cagctgatcc acgacgacag cctgaccttt  2160
aaagaggaca tccagaaagc ccaggtgtcc ggcagggcg atagcctgca cgagcacatt  2220
gccaatctgg ccggcagccc cgccattaag aagggcatct gcagacagt gaaggtggtg  2280
gacgagctcg tgaaagtgat gggccggcac aagcccgaga acatcgtgat cgaaatggcc  2340
```

```
agagagaacc agaccaccca gaagggacag aagaacagcc gcgagagaat gaagcggatc  2400
gaagagggca tcaaagagct gggcagccag atcctgaaag aacaccccgt ggaaaacacc  2460
cagctgcaga acgagaagct gtacctgtac tacctgcaga atgggcggga tatgtacgtg  2520
gaccaggaac tggacatcaa ccggctgtcc gactacgatg tggaccacat cgtgcctcag  2580
agctttctga aggacgactc catcgacaac aaggtgctga ccagaagcga caaggcccgg  2640
ggcaagagcg acaacgtgcc ctccgaaagg gtcgtgaaga agatgaagaa ctactggcgg  2700
cagctgctga acgccaagct gattacccag agaaagttcg acaatctgac caaggccgag  2760
agaggcggcc tgagcgaact ggataaggcc ggcttcatca agagacagct ggtggaaacc  2820
cggcagatca caaagcacgt ggcacagatc ctggactccc ggatgaacac taagtacgac  2880
gagaatgaca agctgatccg ggaagtgaaa gtgatcaccc tgaagtccaa gctggtgtcc  2940
gatttccgga aggatttcca gttttacaaa gtgcgcgaga tcaacaacta ccaccacgcc  3000
cacgacgcct acctgaacgc cgtcgtggga accgccctga tcaaaaagta ccctaagctg  3060
gaaagcgagt tcgtgtacgg cgactacaag gtgtacgacg tgcggaagat gatcgccaag  3120
agcgagcagg aaatcggcaa ggctaccgcc aagtacttct tctacagcaa catcatgaac  3180
tttttcaaga ccgagattac cctggccaac ggcgagatcc ggaagcggcc tctgatcgag  3240
acaaacggcg aaaccgggga gatcgtgtgg gataagggcc gggattttgc caccgtgcgg  3300
aaagtgctga gcatgcccca agtgaatatc gtgaaaaaga ccgaggtgca gacaggcggc  3360
ttcagcaaag agtctatcct gcccaagagg aacagcgata agctgatcgc cagaaagaag  3420
gactgggacc ctaagaagta cggcggcttc gacagcccca ccgtggccta ttctgtgctg  3480
gtggtggcca aagtggaaaa gggcaagtcc aagaaactga agagtgtgaa agagctgctg  3540
gggatcacca tcatggaaag aagcagcttc gagaagaatc ccatcgactt tctggaagcc  3600
aagggctaca aagaagtgaa aaaggacctg atcatcaagc tgcctaagta ctccctgttc  3660
gagctggaaa acggccggaa gagaatgctg gcctctgccg gcgaactgca gaagggaaac  3720
gaactggccc tgcctccaa atatgtgaac ttcctgtacc tggccagcca ctatgagaag  3780
ctgaagggct cccccgagga taatgagcag aaacagctgt ttgtggaaca gcacaagcac  3840
tacctggacg agatcatcga gcagatcagc gagttctcca agagagtgat cctggccgac  3900
gctaatctgg acaaagtgct gtccgcctac aacaagcacc gggataagcc catcagagag  3960
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctgggaggcg acagcgctgg aggaggtgga agcggaggag gaggaagcgg aggaggaggt  4200
agcggaccta agaaaaagag gaaggtggcg gccgctggat ccggacgggc tgacgcattg  4260
gacgattttg atctggatat gctgggaagt gacgccctcg atgattttga ccttgacatg  4320
cttggttcgg atgcccttga tgactttgac ctcgacatgc tcggcagtga cgcccttgat  4380
gatttcgacc tggacatgct gattaactgt acag                              4414

SEQ ID NO: 59            moltype = DNA   length = 390
FEATURE                 Location/Qualifiers
misc_feature            1..390
                        note = Synthetic
source                  1..390
                        mol_type = other DNA
                        organism = synthetic construct
SEQUENCE: 59
atggcttcaa actttactca gttcgtgctc gtggacaatg gtgggacagg ggatgtgaca  60
gtggctcctt ctaatttcgc taatggggtg gcagagtgga tcagctccaa ctcacggagc  120
caggcctaca aggtgacatg cagcgtcagg cagtctagtg cccagaagag aaagtatacc  180
atcaaggtgg aggtccccaa agtggctacc cagacagtgg gcggagtcga actgcctgtc  240
gccgcttgga ggtcctacct gaacatggag ctcactatcc caattttcgc taccaattct  300
gactgtgaac tcatcgtgaa ggcaatgcag gggctcctca aagacggtaa tcctatccct  360
tccgccatcg ccgctaactc aggtatctac                                   390

SEQ ID NO: 60            moltype = DNA   length = 1419
FEATURE                 Location/Qualifiers
misc_feature            1..1419
                        note = Synthetic
source                  1..1419
                        mol_type = other DNA
                        organism = synthetic construct
SEQUENCE: 60
atggcttcaa actttactca gttcgtgctc gtggacaatg gtgggacagg ggatgtgaca  60
gtggctcctt ctaatttcgc taatggggtg gcagagtgga tcagctccaa ctcacggagc  120
caggcctaca aggtgacatg cagcgtcagg cagtctagtg cccagaagag aaagtatacc  180
atcaaggtgg aggtccccaa agtggctacc cagacagtgg gcggagtcga actgcctgtc  240
gccgcttgga ggtcctacct gaacatggag ctcactatcc caattttcgc taccaattct  300
gactgtgaac tcatcgtgaa ggcaatgcag gggctcctca aagacggtaa tcctatccct  360
tccgccatcg ccgctaactc aggtatctac agcgctggag gaggtggaag cggaggagga  420
ggaagcggag gaggaggtag cggacctaag aaaaagagga aggtggcggc cgctggatcc  480
ccttcagggc agatcagcaa ccaggccctg gctcctggcc ctagctccgc tccagtgctg  540
gcccagacta tggtgccctc tagtgctatg gtgcctctgg cccagccacc tgctccagcc  600
cctgtgctga ccccaggacc accccagtca ctgagcgctc cagtctacac ag          660
gccggcgagg ggactctgag tgaagctctg ctgcacctgc agttcgacgc tgatgaggac  720
ctgggagctc tgctggggaa cagcaccgat cccgagtgt tcacagatct ggcctccgtg  780
gacaactctg agtttcagca gctgctgaat caggggtgt ccatgtctca tagtacagcc  840
gaaccaatgc tgatggagta ccccgaagcc attaccggc tggtgaccgg cagccagcgg  900
cccccgacc ccgctccaac tcccctggga accagcggcc tgcctaatgg ctgtccgga   960
gatgaagact tctcaagcat cgctgatatg gactttagtg ccctgctgtc acagatttcc 1020
tctagtgggc agggaggagg tggaagcggc ttcagcgtgg acaccagtgc cctgctggac 1080
ctgttcagcc cctcggtgac cgtgcccgac atgagcctgc ctgaccttga cagcagcctg 1140
```

-continued

```
gccagtatcc aagagctcct gtctccccag gagcccccca ggcctcccga ggcagagaac   1200
agcagcccgg attcagggaa gcagctggtg cactacacag cgcagccgct gttcctgctg   1260
gaccccggct ccgtggacac cgggagcaac gacctgccgg tgctgtttga gctgggagag   1320
ggctcctact tctccgaagg ggacggcttc gccgaggacc ccaccatctc cctgctgaca   1380
ggctcggagc ctcccaaagc caaggacccc actgtctcc                          1419

SEQ ID NO: 61            moltype = DNA   length = 187
FEATURE                  Location/Qualifiers
misc_feature             1..187
                         note = Synthetic
source                   1..187
                         mol_type = other DNA
                         organism = synthetic construct
SEQUENCE: 61
gcggccgctg gatccggacg ggctgacgca ttggacgatt ttgatctgga tatgctggga   60
agtgacgccc tcgatgattt tgaccttgac atgcttggtt cggatgccct tgatgacttt   120
gacctcgaca tgctcggcag tgacgccctt gatgatttcg acctggacat gctgattaac   180
tgtacag                                                             187

SEQ ID NO: 62            moltype = DNA   length = 543
FEATURE                  Location/Qualifiers
misc_feature             1..543
                         note = Synthetic
source                   1..543
                         mol_type = other DNA
                         organism = synthetic construct
SEQUENCE: 62
ccttcagggc agatcagcaa ccaggccctg gctctggccc ctagctccgc tccagtgctg   60
gcccagacta tggtgccctc tagtgctatg gtgcctctgg cccagccacc tgctccagcc   120
cctgtgctga ccccaggacc accccagtca ctgagcgtca cagtgcccaa gtctacacag   180
gccggcgagg ggactctgag tgaagctctg ctgcacctgc agttcgacgc tgatgaggac   240
ctgggagctc tgctgtgggaa cagcaccgat cccggagtgt tcacagatct ggcctccgtg   300
gacaactctg agtttcagca gctgctgaat cagggcgtgt ccatgtctca tagtacagcc   360
gaaccaatgc tgatggagta ccccgaagcc attacccggc tggtgaccgg cagccagcgg   420
cccccgacc ccgctccaac tcccctggga accagcggcc tgcctaatgg gctgtccgga   480
gatgaagact tctcaagcat cgctgatatg gactttagtg ccctgctgtc acagatttcc   540
tct                                                                 543

SEQ ID NO: 63            moltype = DNA   length = 372
FEATURE                  Location/Qualifiers
misc_feature             1..372
                         note = Synthetic
source                   1..372
                         mol_type = other DNA
                         organism = synthetic construct
SEQUENCE: 63
ggcttcagcg tggacaccag tgccctgctg gacctgttca gcccctcggt gaccgtgccc   60
gacatgagcc tgcctgacct tgacagcagc ctggccagta tccaagagct cctgtctccc   120
caggagcccc ccaggcctcc cgaggcagag aacagcagcc cggattcagg gaagcagctg   180
gtgcactaca cagcgcagcc gctgttcctg ctggaccccg gctccgtgga caccgggagc   240
aacgacctgc cggtgctgtt tgagctggga gagggctcct acttctccga aggggacggc   300
ttcgccgagg accccaccat ctccctgctg acaggctcgg agcctcccaa agccaaggac   360
cccactgtct cc                                                       372

SEQ ID NO: 64            moltype = DNA   length = 9043
FEATURE                  Location/Qualifiers
misc_feature             1..9043
                         note = Synthetic
misc_feature             1..34
                         note = First loxP site
misc_feature             125..928
                         note = Sequence encoding neomycin phosphotransferase for
                          resistance to neomycin family antibiotics
misc_feature             937..2190
                         note = Polyadenylation signal
misc_feature             2218..2251
                         note = Second loxP site
misc_feature             2306..6457
                         note = Codon-optimized dCas9 coding sequence
misc_feature             2309..2356
                         note = NLS
misc_feature             6512..6532
                         note = NLS
misc_feature             6533..6719
                         note = VP64
misc_feature             6728..6781
                         note = T2A
misc_feature             6782..7171
                         note = MCP
```

-continued

```
misc_feature        7226..7246
                    note = NLS
misc_feature        7262..7804
                    note = p65
misc_feature        7829..8200
                    note = HSF1
misc_feature        8224..8820
                    note = Woodchuck hepatitis virus posttranscriptional
                     regulatory element
source              1..9043
                    mol_type = other DNA
                    organism = synthetic construct SEQUENCE: 64
ataacttcgt ataatgtatg ctatacgaag ttattaggtc cctcgacctg caggaattgt    60
tgacaattaa tcatcggcat agtatatcgg catagtataa tacgacaagg tgaggaacta   120
aaccatggga tcggccattg aacaagatgg attgcacgca ggttctccgg ccgcttgggt   180
ggagaggcta ttcggctatg actgggcaca acagacaatc ggctgctctg atgccgccgt   240
gttccggctg tcagcgcagg ggcgcccggt tctttttgtc aagaccgacc tgtccggtgc   300
cctgaatgaa ctgcaggacg aggcagcgcg gctatcgtgg ctggccacga cgggcgttcc   360
ttgcgcagct gtgctcgacg ttgtcactga agcgggaagg gactggctgc tattgggcga   420
agtgccgggg caggatctcc tgtcatctca ccttgctcct gccgagaaag tatccatcat   480
ggctgatgca atgcggcggc tgcatacgct tgatccggct acctgcccat tcgaccacca   540
agcgaaacat cgcatcgagc gagcacgtac tcggatggaa gccggtcttg tcgatcagga   600
tgatctggac gaagagcatc aggggctcgc gccagccgaa ctgttcgcca ggctcaaggc   660
gcgcatgccc gacggcgatg atctcgtcgt gacccatggc gatgcctgct tgccgaatat   720
catggtggaa aatggccgct tttctggatt catcgactgt ggccggctgg gtgtggcgga   780
ccgctatcag gacatagcgt tggctacccg tgatattgct gaagagcttg gcggcgaatg   840
ggctgaccgc ttcctcgtgc tttacggtat cgccgctccc gattcgcagc gcatcgcctt   900
ctatcgcctt cttgacgagt tcttctgagg ggatccgctg taagtctgca gaaattgatg   960
atctattaaa caataaagat gtccactaaa atggaagttt ttcctgtcat actttgttaa  1020
gaagggtgag aacagagtac ctacattttg aatggaagga ttggagctac ggggggtggg  1080
gtggggtggg attagataaa tgcctgctct ttactgaagg ctctttacta ttgctttatg  1140
ataatgtttc atagttggat atcataattt aaacaagcaa aaccaaatta agggccagct  1200
cattcctccc actcatgatc tatagatcta tagatctctc gtgggatcat tgtttttctc  1260
ttgattccca ctttgtggtt ctaagtactg tggtttccaa atgtgtcagt ttcatagcct  1320
gaagaacgag atcagcagcc tctgttccac atacacttca ttctcagtat tgtttttgcca  1380
agttctaatt ccatcagaag cttgcagatc tgcgactcta gaggatctgc gactctagag  1440
gatcataatc agccatacca catttgtaga ggttttactt gctttaaaaa acctcccaca  1500
cctcccccctg aacctgaaac ataaaatgaa tgcaattgtt gttgttaact tgtttattgc  1560
agcttataat ggttacaaat aaagcaatag catcacaaat ttcacaaata aagcattttt  1620
ttcactgcat tctagttgtg gtttgtccaa actcatcaat gtatcttatc atgtctggat  1680
ctgcgactct agaggatcat aatcagccat accacatttg tagaggtttt acttgcttta  1740
aaaaacctcc cacacctccc cctgaacctg aaacataaaa tgaatgcaat tgttgttgtt  1800
aacttgttta ttgcagctta taatggttac aaataaagca atagcatcac aaatttcaca  1860
aataaagcat tttttttcact gcattctagt tgtggtttgt ccaaactcat caatgtatct  1920
tatcatgtct ggatctgcga ctctagagga tcataatcag ccataccaca tttgtagagg  1980
ttttactttgc tttaaaaaac ctcccacacc tcccccctgaa cctgaaacat aaaatgaatg  2040
caattgttgt tgttaacttg tttattgcag cttataatgg ttacaaataa agcaatagca  2100
tcacaaattt cacaaataaa gcattttttt cactgcattc tagttgtggt ttgtccaaac  2160
tcatcaatgt atcttatcat gtctggatcc ccatcaagct gatccggaac ccttaatata  2220
acttcgtata atgtatgcta tacgaagtta ttaggtccct cgacctgcag cccaagctag  2280
tgcccgggaa ttcgctaggg ccaccatgaa aaggccggcg gccacgaaaa aggccggcca  2340
ggcaaaaaag aaaaaggaca agaagtacag catcggcctg gccatcggca ccaactctgt  2400
gggctgggcc gtgatcaccg acgagtacaa ggtgcccagc aagaaattca aggtgctggg  2460
caacaccgac cggcacagca tcaagaagaa cctgatcgga gccctgctgt tcgacagcgg  2520
cgaaacagcc gaggccaccc ggctgaagag aaccgccaga agaagataca ccagacggaa  2580
gaaccggatc tgctatctgc aagagatctt cagcaacgag atggccaagg tggacgacag  2640
cttcttccac agactggaag agtccttcct ggtggaagag gataagaagc acgagcggca  2700
ccccatcttc ggcaacatcg tggacgaggt ggcctaccac gagaagtacc cgacccatcta  2760
ccacctgaga aagaaactgg tggacagcac cgacaaggcc gacctgcggc tgatctatct  2820
ggccctggcc cacatgatca agttccgggg ccacttcctg atcgagggcg acctgaaccc  2880
cgacaacagc gacgtggaca agctgttcat ccagctggtg cagacctaca accagctgtt  2940
cgaggaaaac cccatcaacg ccagcggcgt ggacgccaag gccatcctgt ctgccagact  3000
gagcaagagc agacggctgg aaaatctgat cgcccagctg cccggcgaga agaagaatgg  3060
cctgttcggc aacctgattg ccctgagcct gggcctgacc cccaacttca agagcaactt  3120
cgacctggcc gaggatgcca aactgcagct gagcaaggac acctacgacg acgacctgga  3180
caacctgctg gcccagatcg gcgaccagta cgccgacctg tttctggccg ccaagaacct  3240
gtccgacgcc atcctgctga gcgacatcct gagagtgaac accgagatca ccaaggcccc  3300
cctgagcgcc tctatgatca gagatacga cgagcaccac caggacctga cctgctgaa   3360
agctctcgtg cggcagcagc tgcctgagaa gtacaaagag attttcttcg accagagcaa  3420
gaacggctac gccggctaca ttgacggcgg agccagccag gaagagttct acaagttcat  3480
caagcccatc ctgaaaagaa tggacggcac cgaggaactg ctcgtgaagc tgaacagaga  3540
ggacctgctg cggaagcagc ggaccttcga caacggcagc atccccacc agatccacct  3600
gggagagctg cacgccattc tgcggcggca gaagatttt acccattcc tgaaggacaa  3660
ccgggaaaag atcgagaaga tcctgacctt ccgcatcccc tactacgtgg gccctctggc  3720
cagggggaaac agcagattcg cctgatgac cagaaagagc gaggaaacca tcaccccctg  3780
gaacttcgag gaagtggtgg acaagggcgc ttccgcccag agcttcatcg agcggatgac  3840
caacttcgat aagaacctgc caacgagaa ggtgctgccc aagcacagcc tgctgtacga  3900
gtacttcacc gtgtataacg agctgaccaa agtgaaatac gtgaccgagg gaatgagaaa  3960
```

-continued

```
gcccgccttc ctgagcggcg agcagaaaaa ggccatcgtg gacctgctgt tcaagaccaa 4020
ccggaaagtg accgtgaagc agctgaaaga ggactacttc aagaaaatcg agtgcttcga 4080
ctccgtggaa atctccggcg tggaagatcg gttcaacgcc tccctgggca cataccacga 4140
tctgctgaaa attatcaagg acaaggactt cctggacaat gaggaaaacg aggacattct 4200
ggaagatatc gtgctgaccc tgacactgtt tgaggacgga ggatgatcg aggaacggct 4260
gaaaacctat gcccacctgt tcgacgacaa agtgatgaag cagctgaagc ggcggagata 4320
caccggctgg ggcaggctga gccggaagct gatcaacggc atccgggaca agcagtccgg 4380
caagacaatc ctggatttcc tgaagtccga cggcttcgcc aacagaaact tcatgcagct 4440
gatccacgac gacagcctga cctttaaaga ggacatccag aaagcccagg tgtccggcca 4500
gggcgatagc ctgcacgagc acattgccaa tctggccggc agccccgcca ttaagaaggg 4560
catcctgcag acagtgaagg tggtggacga gctcgtgaaa gtgatgggcc ggcacaagcc 4620
cgagaacatc gtgatcgaaa tggccagaga gaaccagacc acccagaagg acagaagaa 4680
cagccgcgag agaatgaagc ggatcgaaga gggcatcaaa gagctgggca gccagatcct 4740
gaaagaacac cccgtggaaa acacccagct gcagaacgag aagctgtacc tgtactacct 4800
gcagaatggg cgggatatgt acgtggacca ggaactggac atcaaccggc tgtccgacta 4860
cgatgtggac cacatcgtgc ctcagagctt tctgaaggac gactccatcg acaacaaggt 4920
gctgaccaga agcgacaagg cccgggggcaa gagcgacaac gtgccctccg aagaggtcgt 4980
gaagaagatg aagaactact ggcggcagct gctgaacgcc gatatgatcg cccagagaaa 5040
gttcgacaat ctgaccaagg ccgagagagg cggcctgagc gaactggata aggccggctt 5100
catcaagaga cagctggtgg aaacccggca gatcacaaag cacgtggcac agatcctgga 5160
ctcccggatg aacactaagt acgacgagaa tgacaagctg atccgggaag tgaaagtgat 5220
caccctgaag tccaagctgg tgtccgattt ccggaaggat ttccagtttt acaaagtgcg 5280
cgagatcaac aactaccacc acgcccacga cgcctacctg aacgccgtcg tgggaaccgc 5340
cctgatcaaa aagtacccta agctggaaag cgagttcgtg tacggcgact acaaggtgta 5400
cgacgtgcgc aagatgatcg ccaagagcga gcaggaaatc ggcaaggcta ccgccaagta 5460
cttcttctac agcaacatca tgaacttttt caagaccgag attaccctgg caaacgggga 5520
gatccggaag cggcctctga tcgagacaaa cggcgaaacc ggggagatcg tgtgggataa 5580
gggccgggat tttgccaccg tgcggaaagt gctgagcatg ccccaagtga atatcgtgaa 5640
aaagaccgag gtgcagacag gcggcttcag caaagagtct atcctgccca agaggaacag 5700
cgataagctg atcgccagaa agaaggactg ggacctaag aagtacggcg gcttcgacag 5760
ccccaccgtg gcctattctg tgctggtggt ggccaaagtg gaaaagggca agtccaagaa 5820
actgaagagt gtgaaagagc tgctggggat caccatcatg gaaagaagca gcttcgagaa 5880
gaatcccatc gactttctgg aagccaaggg ctacaaagaa gtgaaaaagg acctgatcat 5940
caagctgcct aagtactccc tgttcgagct ggaaaacggc cggaagagaa tgctggcctc 6000
tgccggcgaa ctgcagaagg gaaacgaact ggccctgccc tccaaatatg tgaacttcct 6060
gtacctggcc agccactatg agaagctgaa gggctccccc gaggataatg agcagaaaca 6120
gctgtttgtg gaacagcaca gcactacct ggacgagatc atcgagcaga tcagcgagtt 6180
ctccaagaga gtgatcctgg ccgacgctaa tctggacaaa gtgctgtccg cctacaacaa 6240
gcaccggagt aagcccatca gagagcaggc cgagaatatc atccacctgt ttaccctgac 6300
caatctggga gccctgccg ccttcaagta ctttgacacc accatcgacc ggaaaggta 6360
caccagcacc aaagaggtgc tggacgccac cctgatccac cagagcatca ccggcctgta 6420
cgagacacgg atcgacctgt ctcagctggg aggcgacagc gctggaggag gtggaagcgg 6480
aggaggagga gaggtagcgg acctaagaaa aagaggaagg tggcggccgc 6540
tggatccgga cgggctgacg cattggacga tttttgatctg gatatgctgg gaagtgacgc 6600
cctcgatgat tttgaccttg acatgcttgg ttcggatgcc cttgatgact ttgacctcga 6660
catgctcggc agtgacgccc ttgatgattt cgacctggac atgctgatta actgtacagg 6720
cagtggagag ggcagaggaa gtctgctaac atgcggtgac gtcgaggaa atcctggcc 6780
aatggcttca aactttactc agttcgtgct cgtggacaat ggtgggacag gggatgtgac 6840
agtggctcct tctatttcg ctaatggggt ggcagagtgg atcagctcca actcacggag 6900
ccaggcctac aaggtgacat gcagcgtcag gcagtctagt gcccagaaga gaaagtatac 6960
catcaaggtg gaggtcccca aagtggctac ccagacagtg ggcggagtcg aactgcctgt 7020
cgccgcttgg aggtcctacc tgaacatgga gctcactatc ccaattttcg ctaccaattc 7080
tgactgtgaa ctcatcgtga aggcaatgca ggggctcctc aaagacggta atcctatccc 7140
ttccgccatc gccgctaact caggtatcta cagcgctgga ggaggtggaa gcggaggagg 7200
aggaaggcggaggaggta gcggacctaa gaaaaagagg aaggtggcgg ccgctggatc 7260
cccttcaggg cagatcagca accaggccct ggctctggcc cctagctccg ctccagtgct 7320
ggcccagact atggtgccct ctagtgctat ggtgcctctg gcccagccac ctgctccagc 7380
ccctgtgctg accccaggac caccccagtc actgagcgct ccagtgccca gtctacaca 7440
ggccggcgag gggactctga gtgaagctct gctgcacctg cagttcgacg ctgatgagga 7500
cctgggagct ctgctgggga acagcaccga tcccgggagtg ttcacagatc tggcctccgt 7560
ggacaactct gagtttcagc agctgctgaa tcagggcgtg tccatgtctc atagtacagc 7620
cgaaccaatg ctgatggagt accccgaagc cattacccgg ctggtgaccg gcagccagcg 7680
gccccccgac cccgctccaa ctccctgggg aaccagcggc ctgcctaatg ggctgtccgt 7740
agatgaagac ttctcaagca tcgctgatat ggactttagt gccctgctgt cacagatttc 7800
ctctagtggg caggggaggag gtggaagcgg cttcagcgtg gacaccagtg ccctgctgga 7860
cctgttcagc ccctcggtga ccgtgcccga catgagcctg cctgaccttg acagcagcct 7920
ggccagtatc caagagctcc tgtctcccca ggagcccccc aggcctcccg aggcagaa 7980
cagcagcccg gattcaggga agcagctggt gcactacaca gcgcagccgc tgttcctgct 8040
ggaccccggc tccgtggaca ccgggagcaa cgacctgccg gtgctgtttg agctgggaga 8100
gggctcctac ttctccgaag gggacggctt cgccgaggac cccaccatct ccctgctgac 8160
aggctcggag cctcccaaag ccaaggacc cactgtctcc tgagaattcg atatcaagct 8220
tatcgataat caacctctgg attacaaaat ttgtgaaaga ttgactggta ttcttaacta 8280
tgttgctcct tttacgctat gtggatacgc tgctttaatg cctttgtatc atgctattgc 8340
ttcccgtatg gctttcattt tctcctcctt gtataaatcc tggttgctgt ctctttatga 8400
ggagttgtgg cccgttgtca ggcaacgtgg cgtggtgtgc actgtgtttg ctgacgcaac 8460
ccccactggt tggggcattg ccaccacctg tcagctcctt tccgggactt cgctttccc 8520
cctccctatt gccacggcgg aactcatcgc cgcctgcctt gcccgctgct ggacagggc 8580
tcggctgttg ggcactgaca attccgtggt gttgtcgggg aaatcatcgt cctttccttg 8640
gctgctcgcc tgtgttgcca cctggattct gcgcgggacg tccttctgct acgtcccttc 8700
```

-continued

```
ggccctcaat ccagcggacc ttccttcccg cggcctgctg ccggctctgc ggcctcttcc   8760
gcgtcttcgc cttcgccctc agacgagtcg gatctccctt tgggccgcct ccccgcatcg   8820
ataccgtcga cctcgacctc gactgtgcct tctagttgcc agccatctgt tgtttgcccc   8880
tcccccgtgc cttccttgac cctggaaggt gccactccca ctgtcctttc ctaataaaat   8940
gaggaaattg catcgcattg tctgagtagg tgtcattcta ttctgggggg tggggtgggg   9000
caggacagca aggggaggga ttgggaagac aatggcaggc atg                     9043
```

```
SEQ ID NO: 65             moltype = DNA   length = 3812
FEATURE                   Location/Qualifiers
misc_feature              1..3812
                          note = Synthetic
misc_feature              1..32
                          note = First rox site
misc_feature              111..710
                          note = Sequence encoding puromycin-N-acetyltransferase for
                           resistance to puromycin family antibiotics
misc_feature              797..2338
                          note = Polyadenylation signal
misc_feature              2363..2394
                          note = Second rox site
misc_feature              2401..2640
                          note = First U6 promoter
misc_feature              2641..2797
                          note = First guide RNA coding sequence
misc_feature              2883..3122
                          note = Second U6 promoter
misc_feature              3123..3279
                          note = Second guide RNA coding sequence
misc_feature              3364..3603
                          note = Third U6 promoter
misc_feature              3604..3760
                          note = Third guide RNA coding sequence
source                    1..3812
                          mol_type = other DNA
                          organism = synthetic construct
misc_difference           2641..2660
                          note = n = a, t, c, or g
misc_difference           3123..3142
                          note = n = a, t, c, or g
misc_difference           3604..3623
                          note = n = a, t, c, or g
SEQUENCE: 65
taactttaaa taatgccaat tatttaaagt tacctgcagg acgtgttgac aattaatcat   60
cggcatagta tatcggcata gtataatacg acaaggtgag gaactaaacc atgaccgagt   120
acaagcccac ggtgcgcctc gccacccgcg acgacgtccc cagggccgta cgcaccctcg   180
ccgccgcgtt cgccgactac cccgccacgc gccacaccgt cgatccggac cgccacatcg   240
agcgggtcac cgagctgcaa gaactcttcc tcacgcgcgt cgggctcgac atcggcaagg   300
tgtgggtcgc ggacgacggc gccgcggtgg cggtctggac cacgccggag agcgtcgaag   360
cggggggcggt gttcgccgag atcggcccgc gcatggccga gttgagcggt tcccggctgg   420
ccgcgcagca acagatggaa ggcctcctgg cgccgcaccg gcccaaggag cccgcgtggt   480
tcctggccac cgtcggcgtc tcgcccgacc accagggcaa gggtctgggc agcgccgtcg   540
tgctccccgg agtggaggcg gccgagcgcg ccggggtgcc cgccttcctg gagacctccg   600
cgccccgcaa cctccccttc tacgagcggc tcggcttcac cgtcaccgcc gacgtcgagg   660
tgcccgaagg accgcgcacc tggtgcatga cccgcaagcc cggtgcctga cgcccgcccc   720
acgacccgca gcgcccgacc gaaaggagcg cacgaccccca tgcatcgatg atctagagct   780
cgctgatcag cctcgactgt gccttctagt tgccagccat ctgttgtttg ccctcccccc   840
gtgccttcct tgaccctgga aggtgccact cccactgtcc tttcctaata aaatgaggaa   900
attgcatcgc attgtctgag taggtgtcat tctattctgg ggggtggggt ggggcaggac   960
agcaaggggg aggattggga agacaatagc aggcatgctg gggatgcggt gggctctatg   1020
gcataacttc gtataatgta tgctatacgg gggatccgct gtaagtcgtc agaaattgat   1080
gatctattaa acaataaaga tgtccactaa aatggaagtt tttcctgtca tactttgtta   1140
agaagggtga gaacagagta cctacatttt gaatggaagg attggagcta cggggggtggg   1200
ggtggggtgg gattagataa atgcctgctc tttactgaag gctctttact attgctttat   1260
gataatgttt catagttgga tatcataatt taaacaagca aaaccaaatt aaggggccagc   1320
tcattcctcc cactcatgat ctatagatct atagatctct cgtgggatca ttgttttttct   1380
cttgattccc actttgtggt tctaagtact gtggtttcca aatgtgtcag tttcatagcc   1440
tgaagaacga gatcagcagc ctctgttcca catacacttc attctcagta ttgtttttgcc   1500
aagttctaat tccatcagac ctcgacctgc agccgacgct aggtcgtcag tcaaagtacg   1560
tacctcaggt gcaggctgcc tatcagaagg tggtggctga tgtggccaat gccctgcctc   1620
acaaatacca ctgagatctt tttccctctg ccaaaaatta tggggacatc atgaagcccc   1680
ttgagcatct gacttctggc taataaagga aatttatttt cattgcaata gtgtgttgga   1740
atttttttgt tctctcactc ggaaggacat atgggagggc aaatcattta aaacatcaga   1800
atgagtattt ggtttagagt ttggcaacat atgcccatat gctggctgcc atgaacaaag   1860
gttggctata aagaggtcat cagtatatga aacagccccc tgctgtccat tccttattcc   1920
atagaaaagc cttgacttga ggttagattt ttttatatt ttgttttgtg ttatttttt    1980
ctttaacatc cctaaaattt tccttagatg ttttactagc cagatttttc ctcctctcct   2040
gactactccc agtcatagct gtccctcttc tcttatggag atccctcgag gacatgaggt   2100
cgtcgctgta atcagccata ccacatttgt agaggtttta cttgctttaa aaaacctccc   2160
acacctcccc ctgaacctga aacataaaat gaatgcaatt gttgttgtta acttgtttat   2220
```

```
tgcagcttat aatggttaca aataaagcaa tagcatcaca aatttcacaa ataaagcatt   2280
tttttcactg cattctagtt gtggtttgtc caaactcatc aatgtatctt atcatgtcga   2340
cactgggtcg tgatcgggta cctaactttta aataatgcca attatttaaa gttagctagc   2400
tttcccatga ttccttcata tttgcatata cgatacaagg ctgttagaga gataattgga   2460
attaatttga ctgtaaacac aaagatatta gtacaaaata cgtgacgtag aaagtaataa   2520
tttcttgggt agtttgcagt tttaaaatta tgtttttaaaa tggactatca tatgcttacc   2580
gtaacttgaa agtatttcga tttcttggct ttatatatct tgtggaaagg acgaaacacc   2640
nnnnnnnnnn nnnnnnnnnn gttttagagc taggccaaca tgaggatcac ccatgtctgc   2700
agggcctagc aagttaaaat aaggctagtc cgttatcaac ttggccaaca tgaggatcac   2760
ccatgtctgc agggccaagt ggcaccgagt cggtgctttt tttgttttag agctagaaat   2820
agcaagttaa aataaggcta gtccgttttg agctccataa gactcggcct tagaacaagc   2880
tttttcccat gattccttca tatttgcata tacgatacaa ggctgttaga gagataattg   2940
gaattaattt gactgtaaac acaaagatat tagtacaaaa tacgtgacgt agaaagtaat   3000
aatttcttgg gtagtttgca gttttaaaat tatgttttaa aatggactact catatgctta   3060
ccgtaacttg aaagtatttc gatttcttgg ctttatatat cttgtggaaa ggacgaaaca   3120
ccnnnnnnnn nnnnnnnnnnn nngtttttaga gctaggccaa catgaggatc acccatgtct   3180
gcagggccta gcaagttaaa ataaggctag tccgttatca acttggccaa catgaggatc   3240
acccatgtct gcagggccaa gtggcaccga gtcggtgctt ttttgttttt agagctagaa   3300
atagcaagtt aaaataaggc tagtccgttt tatgcatgtg gctcccattt atacctggcc   3360
ggctttccca tgattccttc atatttgcat atacgataca aggctgttag agagataatt   3420
ggaattaatt tgactgtaaa cacaaagata ttagtacaaa atacgtgacg tagaaagtaa   3480
taatttcttg ggtagtttgc agttttaaaa ttatgtttta aaatggacta tcatatgctt   3540
accgtaactt gaaagtattt cgatttcttg ctttatata tcttgtggaa aggacgaaac   3600
accnnnnnnn nnnnnnnnnnn nnngtttttag agctaggcca acatgaggat cacccatgtc   3660
tgcagggcct agcaagttaa aataaggcta gtccgttatc aacttggcca acatgaggat   3720
cacccatgtc tgcagggcca gtggcaccg agtcggtgct tttttgtttt tagagctaga   3780
aatagcaagt taaaataagg ctagtccgtt tt                                 3812
```

```
SEQ ID NO: 66              moltype = RNA  length = 137
FEATURE                    Location/Qualifiers
misc_feature              1..137
                           note = Synthetic
source                     1..137
                           mol_type = other RNA
                           organism = synthetic construct
SEQUENCE: 66
gttttagagc taggccaaca tgaggatcac ccatgtctgc agggcctagc aagttaaaat   60
aaggctagtc cgttatcaac ttggccaaca tgaggatcac ccatgtctgc agggccaagt   120
ggcaccgagt cggtgct                                                  137
```

```
SEQ ID NO: 67              moltype = AA  length = 1965
FEATURE                    Location/Qualifiers
REGION                     1..1965
                           note = Synthetic
source                     1..1965
                           mol_type = protein
                           organism = synthetic construct
SEQUENCE: 67
MKRPAATKKA GQAKKKKDKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES   120
FLVEEDKKHE RHPIFGNIVD EVAYHEKYPT IYHLRKKLVD STDKADLRLI YLALAHMIKF   180
RGHFLIEGDL NPDNSDVDKL FIQLVQTYNQ LFEENPINAS GVDAKAILSA RLSKSRRLEN   240
LIAQLPGEKK NGLFGNLIAL SLGLTPNFKS NFDLAEDAKL QLSKDTYDDD LDNLLAQIGD   300
QYADLFLAAK NLSDAILLSD ILRVNTEITK APLSASMIKR YDEHHQDLTL LKALVRQQLP   360
EKYKEIFFDQ SKNGYAGYID GGASQEEFYK FIKPILEKMD GTEELLVKLN REDLLRKQRT   420
FDNGSIPHQI HLGELHAILR RQEDFYPFLK DNREKIEKIL TFRIPYYVGP LARGNSRFAW   480
MTRKSEETIT PWNFEEVVDK GASAQSFIER MTNFDKNLPN EKVLPKHSLL YEYFTVYNEL   540
TKVKYVTEGM RKPAFLSGEQ KKAIVDLLFK TNRKVTVKQL KEDYFKKIEC FDSVEISGVE   600
DRFNASLGTY HDLLKIIKDK DFLDNEENED ILEDIVLTLT LFEDREMIEE RLKTYAHLFD   660
DKVMKQLKRR RYTGWGRLSR KLINGIRDKQ SGKTILDFLK SDGFANRNFM QLIHDDSLTF   720
KEDIQKAQVS GQGDSLHEHI ANLAGSPAIK KGILQTVKVV DELVKVMGRH KPENIVIEMA   780
RENQTTQKGQ KNSRERMKRI EEGIKELGSQ ILKEHPVENT QLQNEKLYLY YLQNGRDMYV   840
DQELDINRLS DYDVDHIVPQ SFLKDDSIDN KVLTRSDKAR GKSDNVPSEE VVKKMKNYWR   900
QLLNAKLITQ RKFDNLTKAE RGGLSELDKA GFIKRQLVET RQITKHVAQI LDSRMNTKYD   960
ENDKLIREVK VITLKSKLVS DFRKDFQFYK VREINNYHHA HDAYLNAVVG TALIKKYPKL   1020
ESEFVYGDYK VYDVRKMIAK SEQEIGKATA KYFFYSNIMN FFKTEITLAN GEIRKRPLIE   1080
TNGETGEIVW DKGRDFATVR KVLSMPQVNI VKKTEVQTGG FSKESILPKR NSDKLIARKK   1140
DWDPKKYGGF DSPTVAYSVL VVAKVEKGKS KKLKSVKELL GITIMERSSF EKNPIDFLEA   1200
KGYKEVKKDL IIKLPKYSLF ELENGRKRML ASAGELQKGN ELALPSKYVN FLYLASHYEK   1260
LKGSPEDNEQ KQLFVEQHKH YLDEIIEQIS EFSKRVILAD ANLDKVLSAY NKHRDKPIRE   1320
QAENIIHLFT LTNLGAPAAF KYFDTTIDRK RYTSTKEVLD ATLIHQSITG LYETRIDLSQ   1380
LGGDSAGGGG SGGGGSGGGG SGPKKKRKVA AAGSGRADAL DDFDLDMLGS DALDDFDLDM   1440
LGSDALDDFD LDMLGSDALD DFDLDMLINC TGSSGEGRGSL LTCGDVEENP GPMASNFTQF   1500
VLVDNGGTGD VTVAPSNFAN GVAEWISSNS RSQAYKVTCS VRQSSAQRKK YTIKVEVPKV   1560
ATQTVGGVEL PVAAWRSYLN MELTIPIFAT NSDCELIVKA MQGLLKDGNP IPSAIAANSG   1620
IYSAGGGGSG GGGSGGGGSG PKKKRKVAAA GSPSGQISNQ ALALAPSSAP VLAQTMVPSS   1680
AMVPLAQPPA PAPVLTPGPP QSLSAPVPKS TQAGEGTLSE ALLHLQFDAD EDLGALLGNS   1740
TDPGVFTDLA SVDNSEFQQL LNQGVSMSHS TAEPMLMEYP EAITRLVTGS QRPPDPAPTP   1800
LGTSGLPNGL SGDEDFSSIA DMDFSALLSQ ISSSGQGGGG SGFSVDTSAL LDLFSPSVTV   1860
```

```
PDMSLPDLDS SLASIQELLS PQEPPRPPEA ENSSPDSGKQ LVHYTAQPLF LLDPGSVDTG  1920
SNDLPVLFEL GEGSYFSEGD GFAEDPTISL LTGSEPPKAK DPTVS                  1965

SEQ ID NO: 68            moltype = RNA  length = 157
FEATURE                  Location/Qualifiers
misc_feature             1..157
                         note = Synthetic
misc_difference          1..20
                         note = n is a, c, g, or u
source                   1..157
                         mol_type = other RNA
                         organism = synthetic construct
SEQUENCE: 68
nnnnnnnnnn nnnnnnnnnn gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                          157

SEQ ID NO: 69            moltype = DNA  length = 5898
FEATURE                  Location/Qualifiers
misc_feature             1..5898
                         note = Synthetic
misc_feature             1..4152
                         note = dCas9
misc_feature             4228..4414
                         note = VP64
misc_feature             4423..4476
                         note = T2A
misc_feature             4477..4866
                         note = MCP
misc_feature             4957..5499
                         note = P65
misc_feature             5524..5895
                         note = HSF1
source                   1..5898
                         mol_type = other DNA
                         organism = synthetic construct
SEQUENCE: 69
atgaaaaggc cggcggccac gaaaaaggcc ggccaggcaa aaaagaaaaa ggacaagaag  60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca acagcgacgt ggacaagctg  600
ttcatccagc tggtgcagac ctacaaccag ctgttcgagg aaaaccccat caacgccagc  660
ggcgtggacg ccaaggccat cctgtctgcc agactgagca gagcagacg gctggaaaat  720
ctgatcgccc agctgcccgg cgagaagaag aatggcctgt tcggcaacct gattgccctg  780
agcctgagcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gcccccctga gcgcctctat gatcaagaga  1020
tacgacgagc accaccagga cctgaccctg ctgaaagctc tcgtgcggca gcagctgcct  1080
gagaagtaca aagagatttt cttcgaccag agcaagaacg gctacgccgg ctacattgac  1140
ggcggagcca gccaggaaga gttctacaag ttcatcaagc ccatcctgga aaagatggac  1200
ggcaccgagg aactgctcgt gaagctgaac agagaggacc tgctgcggaa gcagcggacc  1260
ttcgacaacg gcagcatccc caccagatc cacctgggag agctgcacgc cattctgcgg  1320
cggcaggaag attttttaccc attcctgaag gacaaccggg aaaagatcga gaagatcctg  1380
accttccgca tccccctacta cgtgggccct ctggccaggg aaacagcag attcgcctgg  1440
atgaccagaa agagcgagga aaccatcacc ccctggaact cgaggaagt ggtggacaag  1500
ggcgcttccg cccagagctt catcgagcgg atgaccaact cgataagaa cctgcccaac  1560
gagaaggtgc tgcccaagca cagcctgctg tacgagtact tcaccgtgta taacgagctg  1620
accaaagtga aatacgtgac cgagggaatg agaaagcccg ccttcctgag cggcgagcag  1680
aaaaaggcca tcgtggacct gctgttcaag accaaccgga aagtgaccgt gaagcagctg  1740
aaagaggact acttcaagaa aatcgagtgc ttcgactccg tggaaatctc cggcgtggaa  1800
gatcggttca acgcctccct gggcacatac cacgatctgc tgaaaattat caaggacaag  1860
gacttcctgg acaatgagga aaacgaggac attctggaag atatcgtgct gaccctgaca  1920
ctgtttgagg acagagagat gatcgaggaa cggctgaaaa cctatgccca cctgttcgac  1980
gacaaagtga tgaagcagct gaagcggcgg agatacaccg gctggggcag gctgagccgg  2040
aagctgatca cggcatccg ggacaagcag tccggcaaga caatcctgga tttcctgaag  2100
tccgacggct tcgccaacag aaacttcatg cagctgatcc acgacgacag cctgaccttt  2160
aaagagaaca gccagaaagc ccaggtgtcc ggccagggcga atagcctgca gcagcacatt  2220
gccaatctgg ccggcagccc cgccattaag aagggcatcc tgcagacagt gaaggtggtg  2280
gacgagctcg tgaaagtgat gggccggcac aagcccgaga acatcgtgat cgaaatggcc  2340
agagagaacc agaccaccca gaagggcag aagaacagcc gcgagagaat gaagcggatc  2400
gaagagggca tcaaagagct gggcagccag atcctgaaaa acacccccgt ggaaaacacc  2460
cagctgcaga acgagaagct gtacctgtac tacctgcaga tgggcgggga tatgtacgtg  2520
```

```
gaccaggaac tggacatcaa ccggctgtcc gactacgatg tggaccacat cgtgcctcag   2580
agctttctga aggacgactc catcgacaac aaggtgctga ccagaagcga caaggcccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct ctacagcaa catcatgaac   3180
tttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata agctgatcgc cagaaagaag   3420
gactgggacc ctaagaagta cggcggcttc gacagcccca ccgtggccta ttctgtgctg   3480
gtggtggcca aagtggaaaa gggcaagtcc aagaaactga gagtgtgaa agagctgctg   3540
gggatcacca tcatggaaag aagcagcttc gagaagaatc ccatcgactt tctggaagcc   3600
aagggctaca agaagtgaa aaaggacctg atcatcaagc tgcctaagta ctccctgttc   3660
gagctggaaa acggccggaa gagaatgctg gcctctgccg gcgaactgca gaagggaaac   3720
gaactggccc tgcctccaa atatgtgaac ttcctgtacc tggccagcca ctatgagaag   3780
ctgaagggct cccccgagga taatgagcag aaacagctgt ttgtggaaca gcacaagcac   3840
tacctggacg agatcatcga gcagatcagc gagttctcca agagagtgat cctggccgac   3900
gctaatctgg acaaagtgct gtccgcctac aacaagcacc gggataagcc catcagagag   3960
caggccgaga atatcatcca cctgtttacc ctgaccaatc tgggagcccc tgccgccttc   4020
aagtactttg acaccaccat cgaccggaag aggtacacca gccaaaaaga ggtgctggac   4080
gccaccctga tccaccagag catcaccggc ctgtacgaga cacggatcga cctgtctcag   4140
ctgggaggcg acagcgctgg aggaggtgga agcggaggag gaggaagcgg aggaggaggt   4200
agcggaccta agaaaaagag gaaggtggcg ccgctggat ccggacgggc tgacgcattg   4260
gacgattttg atctggatat gctgggaagt gacgccctcg atgattttga ccttgacatg   4320
cttggttcgg atgcccttga tgactttgac ctcgacatgc tcggcagtga cgcccttgat   4380
gatttcgacc tggacatgct gattaactgt acaggcagtg gagagggcag aggaagtctg   4440
ctaacatgcg gtgacgtcga ggagaatcct ggcccaatgg cttcaaactt tactcagttc   4500
gtgctcgtgg acaatggtgg gacaggggat gtgacagtgc ctccttctaa tttcgctaat   4560
ggggtggcag agtggatcag ctccaactca cggagccagg cctacaaggt gacatgcagc   4620
gtcaggcagt ctagtgccca gaagagaaag tataccatca aggtggaggt ccccaaagtg   4680
gctacccaga cagtgggcgg agtcgaactg cctgtcgccg cttggaggtc ctacctgaac   4740
atggagctca ctatcccaat tttcgctacc aattctgact gtgaactcat cgtgaaggca   4800
atgcagggc tcctcaaaga cggtaatcct atcccttccg ccatcgccgc taactcaggt   4860
atctacagcg ctggaggagg tggaagcgga ggaggaggaa gcggaggagg aggtagcgga   4920
cctaagaaaa agaggaaggt ggcggccgct ggatccccctt cagggcagat cagcaaccag   4980
gccctggctc tggcccctag ctccgctcca gtgctggccc agactatggt gcctctagt   5040
gctatgtgc ctctggccca gccacctgct ccagcccctg tgctgacccc aggaccaccc   5100
cagtcactga gcgctccagt gcccaagtct acacaggccg gcgaggggac tctgagtgaa   5160
gctctgctgc acctgcagtt cgacgctgat gaggacctgg gagctctgct ggggaacagc   5220
accgatcccg gagtgttcac agatctggcc tccgtggaca actctgagtt tcagcagctg   5280
ctgaatcagg gcgtgtccat gtctcatagt acagccgaac caatgctgat ggagtaccc   5340
gaagccatta cccggctggt gaccggcagc cagcggcccc ccgaccccgc tccaactccc   5400
ctgggaacca gcgggcctgcc taatgggctg tccggagatg aagacttctc aagcatcgct   5460
gatatggact ttagtgccct gctgtcacag atttcctcta gtgggcaggg aggaggtgga   5520
agcggcttca gcgtggacac cagtgccctg ctggacctgt tcagccccctc ggtgaccgtg   5580
cccgacatga gcctgcctga ccttgacagc agcctggcca gtatccaaga gctcctgtct   5640
ccccaggagc cccccaggcc tcccgaggca gagaacagca gcccggattc agggaagcag   5700
ctggtgcact acacagcgca gccgctgttc ctgctggacc ccggctccgt ggacaccggg   5760
agcaacgacc tgccggtgct gtttgagctg ggagagggct cctacttctc cgaaggggac   5820
ggcttcgccg aggaccccac catctccctg ctgacaggct cggagcctcc caaagccaag   5880
gacccccactg tctcctga   5898
```

```
SEQ ID NO: 70          moltype = DNA   length = 1412
FEATURE                Location/Qualifiers
misc_feature           1..1412
                       note = Synthetic
misc_feature           1..240
                       note = hU6 promoter
misc_feature           241..260
                       note = Guide
misc_difference        241..260
                       note = n = a, t, c, or g
misc_feature           261..397
                       note = SAM scaffold
misc_feature           398..449
                       note = Extended PolIII term
misc_feature           483..722
                       note = hU6 promoter
misc_feature           723..742
                       note = Guide
misc_difference        723..742
                       note = n = a, t, c, or g
misc_feature           743..879
```

-continued

```
                        note = SAM scaffold
misc_feature           880..931
                        note = Extended PolIII term
misc_feature           964..1203
                        note = hU6 promoter
misc_feature           1204..1223
                        note = Guide
misc_difference        1204..1223
                        note = n = a, t, c, or g
misc_feature           1224..1360
                        note = SAM scaffold
misc_feature           1361..1412
                        note = Extended PolIII term
source                 1..1412
                        mol_type = other DNA
                        organism = synthetic construct
SEQUENCE: 70
tttcccatga ttccttcata tttgcatata cgatacaagg ctgttagaga gataattgga   60
attaatttga ctgtaaacac aaagatatta gtacaaaata cgtgacgtag aaagtaataa  120
tttcttgggt agtttgcagt tttaaaatta tgtttaaaa tggactatca tatgcttacc  180
gtaacttgaa agtatttcga tttcttggct ttatatatct tgtggaaagg acgaaacacc  240
nnnnnnnnnn nnnnnnnnnn gttttagagc taggccaaca tgaggatcac ccatgtctgc  300
agggcctagc aagttaaaat aaggctagtc cgttatcaac ttggccaaca tgaggatcac  360
ccatgtctgc agggccaagt ggcaccgagt cggtgctttt tttgttttag agctagaaat  420
agcaagttaa aataaggcta gtccgttttg agctccataa gactcggcct tagaacaagc  480
tttttcccat gattccttca tatttgcata tacgatacaa ggctgttaga gagataattg  540
gaattaattt gactgtaaac acaaagatat tagtacaaaa tacgtgacgt agaaagtaat  600
aatttcttgg gtagtttgca gttttaaaat tatgttttaa aatggactat catatgctta  660
ccgtaacttg aaagtatttc gatttcttgg ctttatatat cttgtggaaa ggacgaaaca  720
ccnnnnnnnn nnnnnnnnnn nngttttaga gctaggccaa catgaggatc acccatgtct  780
gcagggccta gcaagttaaa ataaggctag tccgttatca acttggccaa catgaggatc  840
acccatgtct gcagggccaa gtggcaccga gtcggtgctt tttttgtttt agagctagaa  900
atagcaagtt aaaataaggc tagtccgttt tatgcatgtg gctcccattt atacctggcc  960
ggctttccca tgattccttc atatttgcat atacgataca aggctgttag agagataatt 1020
ggaattaatt tgactgtaaa cacaaagata ttagtacaaa atacgtgacg tagaaagtaa 1080
taatttcttg ggtagtttgc agttttaaaa ttatgtttta aaatggacta tcatatgctt 1140
accgtaactt gaaagtattt cgatttcttg ctttatata tcttgtggaa aggacgaaac 1200
accnnnnnnnn nnnnnnnnnn nnngtttag agctaggcca acatgaggat cacccatgtc 1260
tgcagggcct agcaagttaa aataaggcta gtccgttatc aacttggcca acatgaggat 1320
cacccatgtc tgcagggcca agtggcaccg agtcggtgct tttttgttt tagagctaga 1380
aatagcaagt taaaataagg ctagtccgtt tt                               1412

SEQ ID NO: 71         moltype = RNA  length = 139
FEATURE               Location/Qualifiers
misc_feature          1..139
                      note = Synthetic
source                1..139
                      mol_type = other RNA
                      organism = synthetic construct
SEQUENCE: 71
gttttagagc taggccaaca tgaggatcac ccatgtctgc agggcctagc aagttaaaat   60
aaggctagtc cgttatcaac ttggccaaca tgaggatcac ccatgtctgc agggccaagt  120
ggcaccgagt cggtgcttt                                                139

SEQ ID NO: 72         moltype = RNA  length = 159
FEATURE               Location/Qualifiers
misc_feature          1..159
                      note = Synthetic
misc_difference       1..20
                      note = n is a, c, g, or u
source                1..159
                      mol_type = other RNA
                      organism = synthetic construct
SEQUENCE: 72
nnnnnnnnnn nnnnnnnnnn gttttagagc taggccaaca tgaggatcac ccatgtctgc   60
agggcctagc aagttaaaat aaggctagtc cgttatcaac ttggccaaca tgaggatcac  120
ccatgtctgc agggccaagt ggcaccgagt cggtgcttt                         159

SEQ ID NO: 73         moltype = RNA  length = 16
FEATURE               Location/Qualifiers
misc_feature          1..16
                      note = Synthetic
source                1..16
                      mol_type = other RNA
                      organism = synthetic construct
SEQUENCE: 73
gttttagagc tatgct                                                   16

SEQ ID NO: 74         moltype = RNA  length = 67
```

-continued

```
FEATURE                  Location/Qualifiers
misc_feature             1..67
                         note = Synthetic
source                   1..67
                         mol_type = other RNA
                         organism = synthetic construct
SEQUENCE: 74
agcatagcaa gttaaaataa ggctagtccg ttatcaactt gaaaaagtgg caccgagtcg    60
gtgcttt                                                               67

SEQ ID NO: 75            moltype = RNA   length = 72
FEATURE                  Location/Qualifiers
misc_feature             1..72
                         note = Synthetic
source                   1..72
                         mol_type = other RNA
                         organism = synthetic construct
SEQUENCE: 75
aaacagcata gcaagttaaa ataaggctag tccgttatca acttgaaaaa gtggcaccga    60
gtcggtgctt tt                                                        72

SEQ ID NO: 76            moltype = RNA   length = 82
FEATURE                  Location/Qualifiers
misc_feature             1..82
                         note = Synthetic
source                   1..82
                         mol_type = other RNA
                         organism = synthetic construct
SEQUENCE: 76
gttggaacca ttcaaaacag catagcaagt taaaataagg ctagtccgtt atcaacttga    60
aaaagtggca ccgagtcggt gc                                             82

SEQ ID NO: 77            moltype = RNA   length = 77
FEATURE                  Location/Qualifiers
misc_feature             1..77
                         note = Synthetic
source                   1..77
                         mol_type = other RNA
                         organism = synthetic construct
SEQUENCE: 77
gttttagagc tagaaatagc aagttaaaat aaggctagtc cgttatcaac ttgaaaaagt    60
ggcaccgagt cggtgct                                                   77

SEQ ID NO: 78            moltype = RNA   length = 82
FEATURE                  Location/Qualifiers
misc_feature             1..82
                         note = Synthetic
source                   1..82
                         mol_type = other RNA
                         organism = synthetic construct
SEQUENCE: 78
gttggaacca ttcaaaacag catagcaagt taaaataagg ctagtccgtt atcaacttga    60
aaaagtggca ccgagtcggt gc                                             82

SEQ ID NO: 79            moltype = RNA   length = 76
FEATURE                  Location/Qualifiers
misc_feature             1..76
                         note = Synthetic
source                   1..76
                         mol_type = other RNA
                         organism = synthetic construct
SEQUENCE: 79
gttttagagc tagaaatagc aagttaaaat aaggctagtc cgttatcaac ttgaaaaagt    60
ggcaccgagt cggtgc                                                    76

SEQ ID NO: 80            moltype = RNA   length = 86
FEATURE                  Location/Qualifiers
misc_feature             1..86
                         note = Synthetic
source                   1..86
                         mol_type = other RNA
                         organism = synthetic construct
SEQUENCE: 80
gtttaagagc tatgctggaa acagcatagc aagtttaaat aaggctagtc cgttatcaac    60
ttgaaaaagt ggcaccgagt cggtgc                                         86

SEQ ID NO: 81            moltype = RNA   length = 83
FEATURE                  Location/Qualifiers
misc_feature             1..83
```

-continued

```
                            note = Synthetic
source                      1..83
                            mol_type = other RNA
                            organism = synthetic construct
SEQUENCE: 81
gttttagagc tagaaatagc aagttaaaat aaggctagtc cgttatcaac ttgaaaaagt   60
ggcaccgagt cggtgctttt ttt                                          83

SEQ ID NO: 82              moltype = RNA   length = 80
FEATURE                    Location/Qualifiers
misc_feature               1..80
                            note = Synthetic
source                      1..80
                            mol_type = other RNA
                            organism = synthetic construct
SEQUENCE: 82
gttttagagc tagaaatagc aagttaaaat aaggctagtc cgttatcaac ttgaaaaagt   60
ggcaccgagt cggtgctttt                                              80

SEQ ID NO: 83              moltype = RNA   length = 92
FEATURE                    Location/Qualifiers
misc_feature               1..92
                            note = Synthetic
source                      1..92
                            mol_type = other RNA
                            organism = synthetic construct
SEQUENCE: 83
gtttaagagc tatgctggaa acagcatagc aagtttaaat aaggctagtc cgttatcaac   60
ttgaaaaagt ggcaccgagt cggtgctttt tt                                92

SEQ ID NO: 84              moltype =    length =
SEQUENCE: 84
000

SEQ ID NO: 85              moltype =    length =
SEQUENCE: 85
000

SEQ ID NO: 86              moltype =    length =
SEQUENCE: 86
000

SEQ ID NO: 87              moltype = DNA   length = 17195
FEATURE                    Location/Qualifiers
source                      1..17195
                            mol_type = other DNA
                            organism = Homo sapiens
SEQUENCE: 87
atgaggttct tctgtgcacg ttgctgcagc tttgggcctg agatgccagc tgtccagctg   60
ctgcttctgg cctgcctggt gtgggatgtg ggggccagga cagctcagct caggaaggcc  120
aatgaccaga gtggccgatg ccagtatacc ttcagtgtgg ccagtcccaa tgaatccagc  180
tgcccagagc agagccaggc catgtcagtc atccataact acagagaga cagcagcacc   240
caacgcttag acctggaggc caccaaagct cgactcagct ccctggagag cctcctccac  300
caattgacct tggaccaggc tgccaggccc caggagaccc aggaggggct gcagaggag   360
ctgggcaccc tgaggcggga gcgggaccag ctggaaaccc aaaccagaga gttggagact  420
gcctacagca acctcctccg agacaagtca gttctggagg aagaagaagaa gcgactaagg  480
caagaaaatg agaatctggc caggaggttg gaaagcagca gccaggaggt agcaaggctg  540
agaagggggcc agtgtcccca gacccgagac actgctcggg ctgtgccacc aggctccaga  600
gaaggtaaga atgcagagtg gggggactct gagttcagca ggtgatatgg ctcgtagtga  660
cctgctacag gcgctccagg cctccctgcc tgccctttct cctagagact gcacagctag  720
cacaagacag atgaattaag gaaagcacag cgatcaccit caagtattac tagtaattta  780
gctcctgaga gcttcattta gattagtggt tcagagttct tgtgcccctc catgtcagtt  840
ttcacagtcc atagcaaaag gagaaataaa aggaccggg gagatgtgtc tgcatatgag  900
cagtagaaag ttgtcaattg tccctttga aaaactatcc ttttttgaac ctttgctcag  960
attgttattt gtacctttg atgttaaaat gacctttatt tatgaaatta caatagattt  1020
gggaaatgat aataagtggt aagttttgt ttattttaa atgttcttcc ctggcaaaat  1080
aaagagatgg cacctctctg tcagtttct taatatgttg ttctgaaagt tttcttactc  1140
agtccaatct gagaacctct gcttttaagt catcagacaa attcttgaga tggcttttc  1200
tgagaggctc ttctgttcat cctggtccct tcttgcctaa aggtgagtct gtgtgtgtgt  1260
gggggggtg cggggtgag gtgttggggg aggtcttctt attagctggg aagatggtat  1320
ttgtgtcact ttttgtgaaa gtgggctccc aaatattccc tgttgaggaa gtgttctaat  1380
catgaggaaa taagcaagca aatccagttg ttggacaatt agtttggact ggtcaaagat  1440
gtcagtgcca aggaagaaag aaaaaagggg tggggaaggg cttgttctat attaaagaga  1500
ctaaagaaat gtgttaacca aatgtagtgc atgagtcttg attggtgtct tcatccaagg  1560
gggaaaaagg ctatgaggaa caggtttggg ataactgagg caatttgact gctcattatt  1620
atgttactgt attaatgttc agtttcttgg tgagataatg atactgtggt tgcgaaggat  1680
aaaatctttg ttctatggag atacatgctt aagtacccag ggtgaggcgt caggatgtct  1740
gcaatttgct ctcaaatggt tgaagaaaga ctgcaaatat atagataatg agagaaagaa  1800
aggtaaaaca actgtggcaa aatattaata actggtgaat tacaaactgg tgaatctaag  1860
```

```
tatatgggga gcttattgta ctattctttc agtttttcta taggcttgaa aagcctttaaa   1920
attatgagaa aatatttcct aaaaagagcc ttctacgtga aaggcaagct cttcatagct   1980
atgggggttag aaaacctaag agccagagcc tgggcgatgac cttgggcaag ttattgaacc   2040
ctctgcatct tcatttcttg tccataacat aacaaagaaa attcctgctg tgaataattt   2100
ttgtgggtt cacatgaaat acctataaga tgtaaaggat ttttaaaaaa tgtttagatt   2160
gttagaatta gaagagatcc aattctgaat tttacaacca aggaaagtga agtcctaaga   2220
tgctaagggg ccaaggttgc ccagctggtc agtggtagag cttgagactt gaatctgtgg   2280
agacaattga aagaatcatc attaccagaa gtgtgatgag gcattactta tttcagactg   2340
ttgaatgaag ttacattctc aataaaaact cctgcatgtg tgtatgtggg tgtgggtggt   2400
gtgtgtgtgt gtgtacaaaa atagtggcaa tgtttgcct tttttttttct tttgtggtca   2460
tttaacaagt ctttggggat ttattagatg tgtttcctaa ttttatattt tttcttgatc   2520
tttccagcta ctccactttt gaaataaggg caacatccca ttatattgaa caccaaacat   2580
ggaagttctt ttctagtagt agatgttttt catgagcagg aaattacatt agtacaagaa   2640
tgtggaactg gaaagggacc taatgagcat ccggtaccgc tggctgattt ttgcagatat   2700
ggaaactgag gcccagagag gttattcagc cttgtccatgg ccatctacca gttagtggca   2760
aagctcgaat tctggcctct tcctctgaag ttcagtgact ttctttcttt tttttttgaga   2820
cagagtttca ctcttgttgc ccaggctaga gtgtaatggc acgatcttgg ctcactgaaa   2880
cctctgcctc ccgggttcaa gcaattctcc tacctcagcc tcctgagtag ctgggattat   2940
aggcatgtgc caccatgccc ggctaatttt gtatttttag tagagacagg gtttcaccat   3000
gttggtcagg ctagtctcga actcctgacc tcaggtgatc tgccgacctc ggccttccaa   3060
agcactggga ttacaggtgt gagccctccc tgtacatggc catgaggttc attgactttc   3120
aagaccttca gctgacctct ggtttataga ccctaaaggt aaaagacaga aaggtacagg   3180
aatgcttgga acaaaagatc tgtttcaagg ccagatctag ggaaaagggg gcattctgga   3240
ggctggaata taagtctagg tatgctttttt tgcaggagtg gcaagaacta ggtgtcgaagg   3300
tttgggtaga gaagcttagt gaggctgagt ggacaaaggt aaggcctgag aaggcagcct   3360
ttctgtattc cacctgcaac tcaaattgtt accaccactt tcttgatcat gtattaatag   3420
ttgttatgta gaaaaaaaatt ccttataatc atagaaatca cttgtttata catcacata   3480
atatgacata ttttactaca taactattac tacaaagtta tatataactt tttcttctct   3540
gggcttatat aaattttcat atatatacat atataaattt tatgtatata taatagtttt   3600
tgaaaagtag aaaaaaaaata caattagcca agtgtggtgg ctcacacctg taaccttagc   3660
actttgggag gccgaggtgg acagatcact tgaggtcagg agtttaagac cagcctggcc   3720
actgtggtga aaacttgtct ctactaaaaa tacaaaaatt agccgggtgt ggtggcgggc   3780
acctgtaatc cagttactcc agaggctgag gcaggagaat cgcttgaacc tgggaggcag   3840
acgttgcagt gagccaagat cacgctactg cactccagcc tgggtgacag agcgagactc   3900
catctcaaaa aaatatatat attacatata atacatataa atatatataa ttatatatat   3960
aaatttatta tatatataat aaaatacata tataatttac tagaagataa attagagttg   4020
gttattactg tcacaagaga aggactgctt tgtttgttat ttagccctg ctttggactg   4080
gtctcctgtt gaacagagcc tggaagaggg cttgtgtgca gttggtttat atggaccatg   4140
atcctagaga agagaagttg agacagggga aagtgagaca ggaaggcag gaaagccaca   4200
aaatgggggc cttctccagc tagtcaccac agtgggcaat ggaggctcaa tcccatcaag   4260
cccttcagag gggctgtgta gactgcaaca gaagaggggga ggtttacgca tggatctgat   4320
accctcttgg ccaagggcta tcccatggag tatattgcgc ttccctgata ctcagatgtg   4380
gggacgaggt ttgttcttgc agactgattt tttttttttt tttaagatgg agtcttttcc   4440
tgtcccccag gctggagtgc ggtggcacga tcttggctca ctgcaacctc cgcctcctgg   4500
gttcaagcaa ttctcctgcc tcagcctccc gagtagctgg gattacaggt gcacactacc   4560
acgcccagct aacttttgta tttttttttt tttccagtac agacagggtt tcaccatgtt   4620
ggccaggctg gtcttgaact cctgacctca agtatccacc catcttgacc tcccaaagtg   4680
ctgggattac aggcatgagc cacgcgcct ggcctgttct tgtagacttt ctatgcagaa   4740
agtcagagaa gctgggccac ggtggctgag gcgaggtccc cgcaggtgat aactgcaaga   4800
ggcaggttgc ctcagcaatg actgcaaaaa agtgggcagg atgtgagggg agggtgaggg   4860
gagaaacctg aggtgttcaa cacaagtgct gcagattccc tttcctcacc tagaatagga   4920
tggggatgag aatccctcat gggagtcatc atgcaaatta gcagtcacac agggaagcac   4980
ccagtcagc gctgagcagt ggccacccag tgaataaaat ataactagaa aggcttattt   5040
tacttgagtt ccactattgt ttttgttttt tgttttgttt tgttttttga agatggagtc   5100
tcgctctatc accaggctgg agtgcagtgg cgtggtcttg gctcactgca acctccacct   5160
cctggattca agcaattctc ctgcctcagc ctcccaagta gctgggatta caggcacacg   5220
ccaccatgcc cggctaattt ttgtattttt agtggagatg gggtttcacc atgttggcca   5280
ggctggtctt gaactcccga cctcgtgatc caccgcctc agcctccaa agtgctggga   5340
ttacaggcat gagccactgc acctggccag ggttccacta ttgttttaaa gcatcattca   5400
ataatcaata tgtcaacatg tgcataacat tttaataaca tgcgttgatt ctagagacag   5460
tacaagttag agcagtactc aggacaatag tctattagct agtcttcact ttcctaagat   5520
gtttctgaca acctgtagat aattaggcat agcttgtttt acttcattcc tttcatttat   5580
gtaatatgga ctgaactttc cagtgataga aaatatctat gaaaattatt acaatgccta   5640
tgtctacagg caaacgagtt aataaattca gtttccgggt tgaggtctct aaaatgccaa   5700
gtctataaag aagcgacggc agagaacaca gaacatttcc agaattttgt aatagacatg   5760
aacctttaaa ccacagaagg actgaattta acatttttaa aaaacctagaa aaaaaacagc   5820
tgggcgtggt ggctcacgcc tgtaatccca gcactttggg aggctgaggc aggcggatca   5880
cgaggtcagg agttcgtgac cagcctggcc aatatggtaa aaccctgtct ctactaaaaa   5940
tacaaaaatt agccaggcgt ggtggcaggc acctgtagtc ccagctactc aggaggctga   6000
ggcagaagaa tcacttgaac ccaggaggca gaggttgcaa tgagctgaga tcatgccact   6060
gtactccagc ctgggtgaca gagcgagacc ctgtctcaaa aaaaaaaaaa caaaaaaaaa   6120
aaccttaaaa aataaaagcc ccaaaaatgc taactatctg acacagtaca gcccttaata   6180
tttttcacagt ctcttttttgg ttttcctcca cattcacaat gaaatgttag tgattttaaa   6240
acattccaga gaaattttag tgttgacaca tctttattga gggccatttc atttatagtt   6300
acttatgtaa tcatccaaac aattcagctc agcatactgg ggctcagaga ggtggagtca   6360
tttacccaaa gtcacacagc tgggacatgg cagagctgaa ctaggagcta tgacttccgg   6420
cttaggtcca ggcccctttta cgagattgtt tccctgcctt tgggtttgc atcctctatt   6480
ctgggcttcc accgcatgc cagatggctc tattcctgga gtctgaccat tgccagatgc   6540
tcctggctga catgacctag aagaagccag caggctcata acttaaccat cgcccctgcc   6600
```

-continued

```
aaatgggaac tggccttgcc gtcatcctgg aagccattcc ctgacatttt gttttattgc   6660
agttcatgtt tattccagct aatgcacata aggagtggtt cctgcaaggc acaatctgaa   6720
gggctccttg ctcagagccg taagggccat ggtgggattc agcagggaac ttggcaccag   6780
ccaggcactt ttgctgcctc ttctttgcca gtgagggtag aagaactgat aagaggattg   6840
agtgcacagc ccaggagctg agagtttaca aggcaaccca ctgggacctg agctcagccc   6900
caggagtggg tcaccccaca aagtgctgag cagcatcttt gagactcttc tgaagcctcc   6960
agtagccatc tgggtccagt cgggagatag aaatcacaca gtgggttaag ctggggaagt   7020
ttactttaaa gaattactaa ccgtgatgaa agagcaacta tagatagacg tgaactccat   7080
aggcacctag ggctgaggga gggtgccgga caagcttgga aggggaaggt gaggttcagc   7140
acatcagctt gcagagaagg tggctaaggt gtgcaggcct cagctggtct gcagctgcaa   7200
taggccgcct cccagtgcag gtgaggaggg caacctgcaa cgtgtggcaa gggcatggtg   7260
ggagtcaggg caggcacagg caggaggcct ccagagcact gaggtccgtg tgcagggact   7320
ctgggttcct tgttgggagg gctgtggaaa ggttatggcc aggctgtggc tgtgaggtca   7380
cagaagaact tcgctctggg tccgtggctg gggtaggact ccaacaaatg tcctcacagt   7440
cataccacct atggacgcag gacaggaaaa ctgcagacct ttttcctccc acgatgtccc   7500
tccagcgccc tctactgaga tagttcaaca tcgcgctcac ttcaaagctc ttgttcttca   7560
gacagcatac atgggagggt gcattcagct ctgagaggca atgcgtttat aactgacaca   7620
cctcctcagc acaggatgga agagttcgca gctgccatgg cctcggaaga catgggttca   7680
agtcccagcg ataccactta gctgtgtgac cttgggcatg ttacttaacc tctctgaacc   7740
tcggtttcct catttgcaaa aggggatatt aatgttcact ttcaggacca ttatttgaaa   7800
gtagtgagta gcaagcaccc agcacagtac tggctcataa gagacactta ataagtagta   7860
gcgatagttc aactttatca ggcgctatct gcagtcctaa agccttttctc tatttctctg   7920
aaactttgaa ggcaccagat cacatttaaa aattacataa aaattacttg aaatgggcaa   7980
agagctataa atgccgacaa accatcttgt ttcacaaaaa aaaaaaaaaa aaaagctgtt   8040
ttttagagtt gcaaagccag tacatacttt agctatccac aaggaagtca tctgtgaaaa   8100
tgcctgactt ttttgggttt cactttcttc cttccctcta tagcaaaagg gcatttctt   8160
tcttaattttt ctccccactg actggtaggt aggtacccct acttttctta gtatacatct   8220
tttctcggta agttgttaaa ttaaataacc agcataaaat acatcatttt gtatgtgtaa   8280
aggggccaga tgcagggggag ggatggctcg cctgaattta atattttttt aaaaacctaa   8340
aaaaaaagc cctaaaaatg ttaacgatct gtcacaatat agcccttaat attttcataa   8400
tctcttttttg gttttcttcc acattcagaa tgaaatgtta gtgattttga aacattccag   8460
agaaattttta gtattgacac atttattaag ggaccctccc atggcaactg tggatggcat   8520
agctgaagtg tagggacaag gttggggcag tcctccagac tttgtgtaca gatggcatgc   8580
agtatttctc tctcctcaca ttgcctgaaa ccaactcctt tttttttttt ttttttttt   8640
tttgagacag agtctctctg tcacccaggc tggagtccaa tggcacaatc tcagctcact   8700
gcaacctttg cctcccaggt tcaaacgatt ctcctgactt agcctccta gttgctgaga   8760
ttacaggcat gtgccactat gcccggctaa tttttgtatt tttagtagag acagggtttc   8820
agcatgttgg tcaggctggt ctcgaactcc tgacctcatg atccacccac ctcagcctcc   8880
caaagtgctg gaattacagg cgtgagccac catgcccagc aactcttata ttctgagagt   8940
tgagacaatg aaagaaaaga aatttgagtt gtcctgaggc agagtctgca gtgatccaag   9000
aagaggtaca gatgaaagga aaccagctca attcaaggaa cttgcttaat gccctgattt   9060
tgaaaaattg tcctggcaag actttgccac atcgaatgag cctctgcaca ttgcaggagg   9120
ctggcagggc cagggagcgg tgggctgctc ctaacagcct gggtgtgtgt tctggggccta   9180
agagagaagg catggcaatc ggcgaggcag catcagagag gaaggttaca gatggttctg   9240
ccacctgtgt acaggaaggc ggtcactctc tcttacctct ccctggcagc acagaagaac   9300
agggaacctc gggcaccctg tccctctccc ccataggcag caccaagtcc ctgccggagg   9360
tgtgtgttgc ctgcacaggg ggagaaggga agcagctggt actggtctca ggtcgatcta   9420
aggaaactcc atttgaccta gtgaatcagt ccctgccctg gatacccctc taggccaatg   9480
caacctttag aatgaagaac aaaggggttt cctcacccct gcacaacctc agatagggag   9540
aaggagacgc agggaatgaa ataaaagttt ccaggactct ccaggagcca ttcagattgt   9600
ccaagaaact ggtttccgca gcagcctgga ataaaccat tttccttctc gggtatgagg   9660
actttgccag attatgattt ccttaagggc atggactagt tgtgtctttt ttttttttt   9720
tttaaacata gactagccta ttagacaaac ttgtgtctta gacacctttt tttcttgagc   9780
acctagcaca gccttgcact caataggtgc tccaatgatg tgactaaaag gatggataaa   9840
tagctctgtg gatttgaggc taggaataat gaaggcctgc catgtcccgg ggggtactcc   9900
caattgcccc tggagtttgg aatgcacatt gaggatgtcc tcagttacat atacattttg   9960
gcttatgagt ctttcttttt ttaatttttt tttttttaa gacagggtct cactctgtca  10020
cccagactgg agtgcagtgg catgatcatg gctcactgca gccttgccct cttggactca  10080
agagtcatct tcctgcctca gcctcccgag tagctgagac cacagactgc accaccacac  10140
ccagctaact cttttaattttt ttgtaaagat ggggtctcgc tatgttgccc agcctggtcc  10200
caaactcttg gcctcatgca atcctgccac ctcggcctcc caaagtgctg ggtttacagg  10260
catgagccac tgcgcctggc cagcttatgg gttttaacta cttacatggt gcactctaga  10320
ctgagggata tcccagggat ggaggaccca cccacctcca gggcattaac acttttaggg  10380
aggctaacaa ctgcagccac acagaggcag gggtgggaag ggagggaagg tagctgggat  10440
caggggcagg cagctgcagc agctactgag ctggctcact gtgggcagca tggctgtctg  10500
gcccagcctg cacctgagag ctagctgaat gtttttcttca cctccttcca gggagaaatt  10560
ttttccagta ctataatttg ttgaagctga accccagcaa ctcaaacaag gtaccctgac  10620
tctggagatg tgaaatgta aaataatgtg tggctttgat gaaatgtggt agaaccagag  10680
gattaagact tctgtggtga tcctctctgc ctgaaatcta aatttaggag agctgagcaa  10740
acaaatgatc aaaggcagaa catgtcttcc cgaccctctc ggctgtgtag gcgctccggc  10800
ctcagggat gcactgactt tcctcccact gtcctgaaca cctgagaatc ctgagcgggg  10860
aacaagttgc tcaaagggca gagaagtgac tcagaggttc agcaagagaa aagcccagtg  10920
tattaagcat gtcttttttat tctgatgctt tgctgtctgg gccttgcaaa cgtgagaggg  10980
actgcccctc ccaggggtag ccagttccta cggttagcaa aggactcacc tgggaggaca  11040
gctttcatat gcaaaccaac caatccagag cccacaccct gtgaccacct ccatctggct  11100
caaactcaag gccactgtcc ccctgaccta atcacccagg gcctggtacc agacaattag  11160
agataactcc tgtgaccca gatcctgctg aaattattca aactccccaa tcctaaacct  11220
gcttaccctg cctcccctt ctttccttcc catggaaaga ataaaggcgc tttcccacat  11280
tttcccctgg tgcctcttc tggagcaacc ctggtgcttc cccaggtggc ctcctgggct  11340
```

-continued

```
tagtgtgccc ccttcctctt gggctctgtg agtacaacaa cttgtaaaga taattttttt   11400
ttagagcagt tttatgttca cagccaaatt gagagaaaag tacaaacagt tcccagatac   11460
tactggcccc cacacatgca cagcctcccc gattatcatc atctcccgcc acagcagttg   11520
ttacaactga tgaacctgca tcagcacgca caacacccaa ggtccacggt ttaaattagg   11580
gttcattttt ggtgttgcgc cttctatggg tttagacaaa tgcatagtga catgtgtcca   11640
ccattatagt atcatacaca gtattcattg ccctaaaaat cgtctgtgcc tcacctagtc   11700
atccctCCT cacccaacaa ctgctgatct ttttactgtc tccataattt tgctttaact   11760
tgcttttcag tgacaattgc ctcctgggat gttggccttg ccacacctga ataatcatca   11820
aacctgcatt ttatttgttt ttatgtgtat gtgatgggt ttttgggagg ttggagggga   11880
ggacagggtc tcactctacg ccagggctgg agtgcagagg tacgatcact gctcaccaca   11940
gccttgacct cccggtctca agtgatcctc ccacctcagc ctcccaagta gctgggactg   12000
caggtacaca tcaccaccca ggctaacttt ttgtagtttt tgtagagatg ggatttcacc   12060
atgttgccca ggtttgtctt gaactcctgg gctccagtga tctgtctacc ttggcttccc   12120
aaagtgctgg gattacaggt atgagccact gggcctggcc aaactgcatt ttaaaatagc   12180
caagcctgtt ccttgtgact attgcctcat ccttgtattc aagactgctg taagatcata   12240
atcctaagca agagtagaga catgtagcac accatgatca cttactgtct aaccaatgct   12300
gcccacccgc ttcccttctg tatggctcac caccccccacc ccaaactcct ataggaactc   12360
tgcacacact ccctctccat tatgcaaaac tggtctcaga aaggaatcag acagaatatt   12420
tctactgaaa gtataaagct taatatgtta cttcttacaa gaatatttgc atataacaag   12480
ggaaaaaacc ttaagtcatg cagtaaactt ttatctttt tttttttta acaggagtct   12540
ccctatgttg cccaagctgg tcttgaacac ctgggctcaa gtactcctcc tgtcttggcc   12600
tcccaaagtg ctgggattac agacatgagc cacacttctt tttttttttt tttttttttt   12660
tttttcttga gacagagtct tgctctgttg cccagactgg agtacagttg cacaatcccg   12720
gctccctgca acctttgcct cctgggttca agtgatcctc aacctcctga gtatctggaa   12780
ctacaggcat gtgccaccac accctgctaa ttcttgtatt tctagtaaag atggaatttc   12840
accacgtgg ccaggctagt cttgaactcc tggccttaag tgatccgcct gcctcggcct   12900
cccaaagtgc tgggatttca gtgtgagcca ctgtgcccgg tctctttttt tttttttttg   12960
agaccttgag accgggcctt gctctgttac ccaagctgga gtgcagtggc aggatcatag   13020
ctcactgcag ccttgaactt ctgggctcaa gcaatcctcc cacatcagcc tcccaagtac   13080
ctaggactgc agatgcttac caccatgccc agctaatttt tcatgaattt ttaattattg   13140
aaattcagac atctaagaag atgctgagga ctgtctccat attcctgaaa ttacgactca   13200
cctattcaca aaccagccct tctagtggaa ttaaaatatt atttgatttt gaataccCTA   13260
ctctaaggta ggcacattgc cctgcaattt attatttatg aggttttTAA ttatggaatt   13320
gttcaaatat tcacaaaagt agagagacta caatgaactc caatgtagcc atcactcagg   13380
cccaactgtt atcagcacag tccaatcatg ttttatcttc ccttctctga cccccaaccc   13440
atccccagtc cttatctaaa atcaaatctc aaacaccata tctttgggag cctatttatt   13500
tagttagtta gtttttcagac agagtttctt tcttgttgcc caagctggag tacaatagtg   13560
tagtctcggc tcacagcaat ctcccctcc ttggttcaag caattctcct gcctcagtct   13620
cccaagaagc tgggattata ggcacctgcc accacatcca gctaattctt ttgtgttttt   13680
agcaaagaca gggtttcacc atgttggcca ggctggtctc gaactcctga cctcaggtga   13740
tccgcctgcc tcggcctccc aaagtgctgg gattacaggc atgagccacc acgcctggcc   13800
ggcagcctat ttaaatgtca tcctcaacat agtcaatcct tgggccattt tttcttacag   13860
taaaattttg tctctttctt ttaatgcagt ttctacgtgg aatttggaca ctttggcctt   13920
ccaggaactg aagtccgagc taactgaagt tcctgcttcc cgaattttga aggagagccc   13980
atctggctat ctcaggagtg gagagggaga caccggtatg aagttaagtt tcttcccttt   14040
tgtgcccacg tggtctttat tcatgtctag tgctgtgttc agagaatcag tatagggtaa   14100
atgcccaccc aaggggaaca ttaacttccc tgggagcaga gggaggggag gagaagagga   14160
acagaactct ctctctctct ctgttccctt gtcagagcag gtctgcagga gtcagccttt   14220
ccctaacaaa gccctctatc ctatcaccca cacttgggag gctgggctgg gctgcacagg   14280
gcaagatgag agatgtgttg atttcatcca cttgattgtc atgtagaatt agatatactt   14340
gagaagttac atttttcagt agcgccttca tatctttatt ttagggacag gtatacacca   14400
agcaccatct cagccacaat ctgttactaa cagtatgttt tctgaacttt ggccacttag   14460
gaaaagtaca gtttggctct ctccaaagtg ttccctgaaa gtccaacttt atgactaata   14520
ctgtgatttc cagaaacttt gactatccat gttattgaca atgattacta gcactgaagg   14580
gcatgcatgc aagtaggggt tatgaaatat ttaaaacacg gttctctaag atatgagcag   14640
caaagtgttt ctaccttcta tgagggaacc gaaggtgcca ttaaaagtag agaaatctgg   14700
accaggcatg gtggctcatg cctgtaatcc cagcactttg ggaggctgag gcgggcggat   14760
cacttgaggt caggagttca agaccagcct ggccaacatg gtgaaacact gtctctacta   14820
aaaatacaaa aattagccag gcatggtggc agtcatctgt aatcccagct acttgggagg   14880
ctgaggcagg aaaattgctt gaacccagga ggcagaggtt gcagtgagcc gagatcacac   14940
cactgccctc cagcctgggc gacagagtga gactctgtct caaaaaaaaa aaaaatacag   15000
acatctgttg tgattctggt aactctaaat tttcaaccgt ctcttcacta catttaaaaa   15060
attattttct aaaccaaatt agccaggtgt ggtagcaggc acctgtagtc ccagcaactc   15120
aggaggctga gatgggaggg gtgcttgagc ctggaagctc gaggctgcag tgcactgtga   15180
ttgcaccact gcactccagc ctaggtaaca gtgcaagacc ctgtctcaaa aataattat   15240
tttcatgttt attatattaa aatgatgtat gaaatatgtg actcatcagg gcttgaaaaa   15300
ctttgttgta tggagattat tcttatgagt tgatttttct ctctcctacc ttatagtaat   15360
gaaataaacc aggcatgaaa gtcacaataa gtaatacaat gaacacccat gggtccctgc   15420
ccagcttaag tagaatatta caaatgcagt tgaagccctc tgtgcaactt tcatccttac   15480
aactgatact gagtgaattg tactttaaat attttatagc tcccactccc atgcatgccc   15540
ctcagtgata gcaataattg tcaataacat gaaacacaga ttgatcatat agcatttacc   15600
atatatttac tctataccaa gcacttaaca tatataatta catttaaaat ttacaacagc   15660
cctactaccc aaaacactat tagtatcccc ttttacaaat gcgataactg aggcgtagag   15720
agctaagtaa cttactgaaa gtcacacagc cagcgggtgg tagagcctag ctttaaaccc   15780
agacgatttg tctccagggc tgtcacatct actgggctctg ccaagcttcc gcatgatcat   15840
tgtctgtgtt tggaaagatt atggattaag tggtgcttcg ttttcttttc tgaatttacc   15900
aggatgtgga gaactagttt gggtaggaga gcctctcacg ctgagaacag cagaaacaat   15960
tactggcaag tatggtgtgt ggatgcgaga ccccaagccc acctacccct acacccagga   16020
gaccacgtgg agaatcgaca cagttggcac ggatgtccgc caggttttg agtatgacct   16080
```

```
catcagccag tttatgcagg gctacccttc taaggttcac atactgccta ggccactgga   16140
aagcacgggt gctgtggtgt actcggggag cctctatttc cagggcgctg agtccagaac   16200
tgtcataaga tatgagctga ataccgagac agtgaaggct gagaaggaaa tccctggagc   16260
tggctaccac ggacagttcc cgtattcttg gggtggctac acggacattg acttggctgt   16320
ggatgaagca ggcctctggg tcatttacag caccgatgag gccaaaggtg ccattgtcct   16380
ctccaaactg aacccagaga atctggaact cgaacaaacc tgggagacaa acatccgtaa   16440
gcagtcagtc gccaatgcct tcatcatctg tggcaccttg cacaccgtca gcagctacac   16500
ctcagcagat gctaccgtca actttgctta tgacacaggc acaggtatca gcaagaccct   16560
gaccatccca ttcaagaacc gctataagta cagcagcatg attgactaca accccctgga   16620
gaagaagctc tttgcctggg acaacttgaa catggtcact tatgacatca agctctccaa   16680
gatgtgaaaa gcctccaagc tgtacaggca atggcagaag gagatgctca gggctcctgg   16740
ggggagcagg ctgaagggag agccagccag ccagggccca ggcagctttg actgctttcc   16800
aagttttcat taatccagaa ggatgaacat ggtcaccatc taactattca ggaattgtag   16860
tctgagggcg tagacaattt catataataa atatccttta tcttctgtca gcatttatgg   16920
gatgtttaat gacatagttc aagttttctt gtgatttggg gcaaaagctg taaggcataa   16980
tagtttcttc ctgaaaacca ttgctcttgc atgttacatg gttaccacaa gccacaataa   17040
aaagcataac ttctaaagga agcagaatag ctcctctggc cagcatcgaa tataagtaag   17100
atgcatttac tacagttggc ttctaatgct tcagatagaa tacagttggg tctcacataa   17160
cccttacat tgtgaaataa aattttctta cccaa                                17195
```

```
SEQ ID NO: 88              moltype = DNA  length = 22934
FEATURE                    Location/Qualifiers
misc_feature               1..22934
                           note = Synthetic
misc_feature               1..114
                           note = Mouse 5' UTR
misc_feature               115..718
                           note = Human Exon
misc_feature               719..14003
                           note = Human Intron
misc_feature               14004..14129
                           note = Human Exon
misc_feature               14130..16016
                           note = Human Intron
misc_feature               16017..16801
                           note = Human Exon
misc_feature               16595
                           note = Y437H (T to C)
misc_feature               16802..17309
                           note = Human 3' UTR
misc_feature               17417..17450
                           note = LoxP
misc_feature               17457..18137
                           note = Protamine promoter
misc_feature               18138..19378
                           note = Cre with Intron
misc_feature               19291..19520
                           note = SV40 pA
misc_feature               19575..20787
                           note = hUB promoter
misc_feature               20788..20854
                           note = EM7 promoter
misc_feature               20855..21880
                           note = Hygromycin Resistance
misc_feature               21881..22365
                           note = PGK-PolyA
misc_feature               22371..22404
                           note = LoxP
misc_feature               22411..22436
                           note = I-Ceu
misc_feature               22443..22934
                           note = Mouse 3' UTR
source                     1..22934
                           mol_type = other DNA
                           organism = synthetic construct
SEQUENCE: 88
gagccagcag ggccacccat ccagacacct tgcaggagaa ctttccagaa gaaacctcac   60
ccagcctcca cactgctgtc cttctctgca cgctgctgca gctgtggtcc caagatgagg   120
ttcttctgtg cacgttgctg cagctttggg cctgagatgc cagctgtcca gctgctgctt   180
ctggcctgcc tggtgtggga tgtgggggcc aggacagctc agctcaggaa ggccaatgac   240
cagagtggcc gatgccagta taccttcagt gtggccagtc ccaatgaatc cagctgccca   300
gagcagagcc aggccatgtc agtcatccat aacttacaga gagacagcag cacccaacgc   360
ttagacctgg aggccaccaa agctcgactc agctccctgg agagcctcct ccaccaattg   420
accttggacc aggctgccag gccccaggag acccaggagg ggctgcagag ggagctgggc   480
accctgagcc gggagcggga ccagctggaa acccaaacca gagagttgga gactgcctac   540
agcaacctcc tccgagacaa gtcagttctg gaggaagaga agaagcgact aaggcaagaa   600
aatgagaatc tggccaggag gttggaaagc agcagccagg aggtagcaag ctgagaagg   660
ggccagtgtc cccagacccg agacactgct cgggctgtgc caccaggctc agagaaggt   720
aagaatgcag agtgggggga ctctgagttc agcaggtgat atggctcgta gtgacctgct   780
```

-continued

```
acaggcgctc caggcctccc tgcctgccct ttctcctaga gactgcacag ctagcacaag   840
acagatgaat taaggaaagc acagcgatca ccttcaagta ttactagtaa tttagctcct   900
gagagcttca tttagattag tggttcagag ttcttgtgcc cctccatgtc agttttcaca   960
gtccatagca aaaggagaaa taaaaggacc gggtgagatg tgtctgcata tgagcagtag  1020
aaagttgtca attgtccctt ttgaaaaact atcctttttt gaacctttgc tcagattgtt  1080
atttgtacct tttgatgtta aaatgacctt tatttatgaa attacaatag atttgggaaa  1140
tgataataag tggtaagttt ttgtttattt ttaaatgttc ttccctggca aaataaagag  1200
atggcacctc tctgtcagtt ttcttaatat gttgttctga aagttttctt actcagtcca  1260
atctgagaac ctctgctttt aagtcatcag acaaattctt gagatggctt tttctgagag  1320
gctcttctgt tcatcctggt cccttcttgc ctaaaggtga gtctgtgtgt gtgtggggg g  1380
ggtgcggggg tgaggtgttg ggggaggtct tcttattagc tgggaagatg gtatttgtgt  1440
cacttttttgt gaaagtgggc tcccaaatat tccctgttga ggaagtgttc taatcatgag  1500
gaaataagca agcaaatcca gttgttggac aattagtttg gactggtcaa agatgtcagt  1560
gccaaggaag aaagaaaaaa gggtggggga agggcttgtt ctatattaaa gagactaaag  1620
aaatgtgtta accaaatgta gtgcatgagt cttgattggt gtcttcatcc aaggggggaaa  1680
aaggctatga ggaacaggtt tgggataact gaggcaattt gactgctcat tattatgtta  1740
ctgtattaat gttcagtttc ttggtgagat aatgatactg tggttgcgaa ggataaaatc  1800
tttgttctat ggagatacat gcttaagtac ccagggtgag gcgtcaggat gtctgcaatt  1860
tgctctcaaa tggttgaaga aagactgcaa atatatagat aatgagagaa agaaaggtaa  1920
aacaactgtg gcaaaatatt aataactggt gaattacaaa ctggtgaatc taagtatatg  1980
gggagcttat tgtactattc tttcagtttt tctataggct tgaaaagctt taaaattatg  2040
agaaaatatt tcctaaaaag agccttctac gtgaaaggca agtcttcat agctatggg g  2100
ttagaaaacc taagagccag agcctgggga tgaccttggg caagttattg aaccctctgc  2160
atcttcattt cttgtccata acataacaaa gaaaattcct gctgtgaata attttttgtg g  2220
ggttcacatg aaatacctat aagatgtaaa ggattttttaa aaaatgttta gattgttaga  2280
attagaagag atccaattct gaattttaca accaaggaaa gtgaagtcct aagatgctaa  2340
ggggccaagg ttgcccagct ggtcagtggt agagcttgag acttgaatct gtggagacaa  2400
ttgaaagaat catcattacc agaagtgtga tgaggcatta cttatttcag actgttgaat  2460
gaagttacat tctcaataaa aactcctgca tgtgtgtatg tgggtgtggg tggtgtgtgt  2520
gtgtgtgtac aaaaatagtg gcaatgtttt gcctttttt t ttcttttgtg gtcatttaac  2580
aagtctttgg ggatttatta gatgtgtttc ctaatttttat attttttctt gatctttcca  2640
gctactccac ttttgaaata agggcaacat cccattatat tgaacaccaa acatggaagt  2700
tcttttctag tagtagatgt ttttcatgag caggaaatta cattagtaca agaatgtgga  2760
actggaaagg gacctaatga gcatccggta ccgctggctg atttttgcag atatggaaac  2820
tgaggcccag agaggttatt cagcttgtcc atggccatct accagttagt ggcaaagctc  2880
gaattctggc ctcttcctct gaagttcagt gactttcttt ctttttttt t gagacagagt  2940
ttcactcttg ttgcccaggc tagagtgtaa tggcacgatc ttggctcact gaaacctctg  3000
cctcccgggt tcaagcaatt ctcctacctc agcctcctga gtagctggga ttataggcat  3060
gtgccaccat gcccggctaa ttttgtattt ttagtagaga cagggtttca ccatgttggt  3120
caggctagtc tcgaactcct gacctcaggt gatctgccga cctcggcctt ccaaagcact  3180
gggattacag gtgtgagccc tccctgtaca tggccatgag gttcattgac tttcaagacc  3240
ttcagctgac ctctggttta tagaccctaa aggtaaaaga cagaaaggta caggaatgct  3300
tggaacaaaa gatctgtttc aaggccagat ctagggaaaa gggggcattc tggaggctgg  3360
aatataagtc taggtatgct ttttttgcagg agtggcaaga actaggtgtg aaggtttggg  3420
tagagaagct tagtgaggct gagtggacaa aggtaaggcc tgagaaggca gcctttctgt  3480
attccacctg caactcaaat tgttaccacc actttcttga tcatgtatta atagttgtta  3540
tgtagaaaaa aattccttat aatcatagaa atcacttgtt tatacataca cataatatga  3600
catattttac tacataacta ttactacaaa gttatatata actttttctt ctctgggctt  3660
atataaattt tcatatatat acatatataa attttatgta tatataatag ttttttgaaaa  3720
gtagaaaaaa aatacaatta gccaagtgtg gtggctcaca cctgtaacct tagcactttg  3780
ggaggccgag gtggacagat cacttgaggt caggagttta agaccagcct ggccactgtg  3840
gtgaaaactt gtctctacta aaaatacaaa aattagccgg gtgtggtggc gggcacctgt  3900
aatccagtta ctccagaggc tgaggcagga gaatcgcttg aacctgggag gcagacgttg  3960
cagtgagcca agatcacgct actgcactcc agcctgggtg acagagcgag actccatctc  4020
aaaaaaatat atattattaca taataacat ataaatatat ataattatat ataaaatttt  4080
attatatata taataaaata catatataat ttactagaag ataaattaga gttggttatt  4140
actgtcacaa gagaaggact gctttgtttg ttatttagcc cctgctttgg actggtctcc  4200
tgttgaacag agcctggaag agggcttgtg tgcagttggt ttatatggac catgatccta  4260
gagaagagaa gttgagacag gggaagtgaa gacagggaag gcaggaaagc cacaaaatgg  4320
gggccttctc cagctagtca ccacagtggg caatggagc tcaatcccat caagcccttc  4380
agaggggctg tgtagactgc aacagaagag gggaggttta cgcatggatc tgataccctc  4440
ttggccaagg gctatcccat ggagtatatt gcgcttccct gatactcaga tgtgggggacg  4500
aggtttgttc ttgcagactg atttttttttt tttttttaag atggagtctt tctctgtccc  4560
ccaggctgga gtgcggtggc acgatcttgg ctcactgcaa cctccgcctc ctgggttcaa  4620
gcaattctcc tgcctcagcc tcccgagtag ctgggattac aggtgcacac taccacgccc  4680
agctaacttt tgtattttttt tttttttcca gtacagacag ggtttcacca tgttggccag  4740
gctggtcttg aactcctgac ctcaagtatc cacccatctt gacctcccaa agtgctggga  4800
ttacaggcat gagccacggc gcctggcctg ttcttgtaga ctttctatgc agaaagtcag  4860
agaagctggg ccacggtggc tgaggcgagg tccccgcagg tgataactgc aagaggcagg  4920
ttgcctcagc aatgactgca aaaaagtggg caggatgtga ggggagggtg aggggagaaa  4980
cctgaggtgt tcaacacaag tgctgcagat tcccttcct cacctagaat aggatgggga  5040
tgagaatccc tcatgggagt catcatgcaa attagcagtc acacaggaa gcacccagtg  5100
cagcgctgag cagtggccac ccagtgaata aaatataact agaaaggctt attttacttg  5160
agttccacta ttgtttttgt ttttttgttt gtttttgttt ttgaagatgg agtctcgctc  5220
tatcaccagg ctggagtgca gtggcgtggt cttggctcac tgcaacctcc acctcctgga  5280
ttcaagcaat tctcctgcct cagcctccca agtagctggg attacaggca cacgccacca  5340
tgcccggcta attttttgtat ttttagtgga gatgggggttt caccatgttg gccaggctgg  5400
tcttgaactc ccgacctcgt gatccacccg cctcagcctc ccaaagtgct gggattacag  5460
gcatgagcca ctgcacctgg ccagggttcc actattgttt taaagcatca ttcaataatc  5520
```

-continued

```
aatatgtcaa catgtgcata acattttaat aacatgcgtt gattctagag acagtacaag   5580
ttagagcagt actcaggaca atagtctatt agctagtctt cactttccta agatgtttct   5640
gacaacctgt agataattag gcatagcttg ttttacttca ttcctttcat ttatgtaata   5700
tggactgaac tttccagtga tagaaaatat ctatgaaaat tattacaatg cctatgtcta   5760
caggcaaacg agttaataaa ttcagtttcc gggttgaggt ctctaaaatg ccaagtctat   5820
aaagaagcga cggcagagaa cacagaacat ttccagaatt ttgtaataga catgaacctt   5880
taaaccacag aaggactgaa tttaacattt taaaaaacct agaaaaaaaa cagctgggcg   5940
tggtggctca cgcctgtaat cccagcactt tgggaggctg aggcaggcgg atcacgaggt   6000
caggagttcg tgaccagcct ggccaatatg gtaaaaccct gtctctacta aaaatacaaa   6060
aattagccag gcgtggtggc aggcacctgt agtcccagct actcaggagg ctgaggcaga   6120
agaatcactt gaacccagga ggcagaggtt gcaatgagct gagatcatgc cactgtactc   6180
cagcctgggt gacagagcga gaccctgtct caaaaaaaaa aaaacaaaaa aaaaaacctt   6240
aaaaaataaa agccccaaaa atgctaacta tctgacacag tacagccctt aatattttca   6300
cagtctcttt ttggttttcc tccacattca caatgaaatg ttagtgattt taaaacattc   6360
cagagaaatt ttagtgttga cacatctttta ttgagggcca tttcatttat agttacttat   6420
gtaatcatcc aaacaattca gctcagcata ctggggctca gagaggtgga gtcatttacc   6480
caaagtcaca cagctgggac atggcagagc tgaactagga gctatgactt ccggcttagg   6540
tccaggcccc tttacgagat tgtttccctg cctttgggtt ttgcatcctc tattctgggc   6600
ttccacccgc atgccagatg gctctattcc tggagtctga ccattgccag atgctcctgg   6660
ctgacatgac ctagaagaag ccagcaggct cataacttaa ccatcgcccc tgccaaatgg   6720
gaactggcct tgccgtcatc ctggaagcca ttccctgaca ttttgttttta ttgcagttca   6780
tgtttattcc agctaatgca cataaggagt ggttcctgca aggcacaatc tgaagggctc   6840
cttgctcaga gccgtaaggg ccatggtggg attcagcagg gaacttggca ccagccaggc   6900
acttttgctg cctcttcttt gccagtgagg gtagaagaac tgataagagg attgagtgca   6960
cagcccagga gctgagagtt tacaaggcaa cccactggga cctgagctca gccccaggag   7020
tgggtcaccc cacaaagtgc tgagcagcat ctttgagact cttctgaagc ctccagtagc   7080
catctgggtc cagtcgggag atagaaatca cacagtgggt taagctgggg aagtttactt   7140
taaagaatta ctaaccgtga tgaaagagca actatagata gacgtgaact ccataggcac   7200
ctagggctga gggagggtgc cggacaagct tggaagggga aggtgaggtt cagcacatca   7260
gcttgcagag aaggtggcta aggtgtgcag gcctcagctg gtctgcagct gcaatagcc   7320
gcctcccagt gcaggtgagg agggcaacct gcaacgctgtg gcaagggcat ggtgggagtc   7380
agggcaggca caggcaggag gcctccagag cactgaggtc cgtgtgcagg gactctgggt   7440
tccttgttgg gagggctgtg gaaaggttat ggccaggctg tggctgtgag gtcacagaag   7500
aacttcgctc tgggtccgtg gctgggggtag gactccaaca aatgtcctca cagtcatacc   7560
acctatggac gcaggacagg aaaactgcag acctttttcc tcccacgatg tccctccagc   7620
gccctctact gagatagttc aacatcgcgc tcacttcaaa gctcttgttc ttcagacagc   7680
atacatggga gggtgcattc agctctgaga ggcaatgcgt ttataactga cacacctcct   7740
cagcacagga tggaagagtt cgcagctgcc atggcctcgg aagacatggg ttcaagtccc   7800
agcgatacca cttagctgtg tgaccttggg catgttactt aacctctctg aacctcggtt   7860
tcctcatttg caaaagggga tattaatgtt cactttcagg accattattt gaaagtagtg   7920
agtagcaagc acccagcaca gtactggctc ataagagaca cttaataagt agtagcgata   7980
gttcaacttt atcaggcgct atctgcagtc ctaaagcctt tctctatttc tctgaaactt   8040
tgaaggcacc agatcacatt taaaaattac ataaaaatta cttgaaatgg gcaaagagct   8100
ataaatgccg acaaaccatc ttgtttcaca aaaaaaaaaa aaaaaaaagc tgtttttttag   8160
agttgcaaag ccagtacata ctttagctat ccacaaggaa gtcatctgtg aaaatgcctg   8220
actttttttgg gtttcacttt cttccttccc tctatagcaa aagggcatt tctttcttaa   8280
ttttctcccc actgactggt aggtaggtac ccctactttt cttagtatac atcttttctc   8340
ggtaagttgt taaattaaat aaccagcata aaatacatca ttttgtatgt gtaaaggggc   8400
cagatgcagg ggagggatgg ctcgcctgaa tttaatattt ttttaaaaac ctaaaaaaaa   8460
aagccctaaa aatgttaacg atctgtcaca atatagccct taatattttc ataatctctt   8520
tttggttttc ttccacattc agaatgaaat gttagtgatt ttgaaacatt ccagagaaat   8580
tttagtattg acacatttat taagggaccc tcccatggca actgtggatg gcatagctga   8640
agtgtaggga caaggttggg gcagtcctcc agactttgtg tacagatggc atgcagtatt   8700
tctctctcct cacattgcct gaaaccaact ccttttttttt tttttttttt tttttttgag   8760
acagagtctc tctgtcaccc aggctggagt ccaatggcac aatctcagct cactgcaacc   8820
tttgcctccc aggttcaaac gattctcctg acttagcctc cctagttgct gagattacag   8880
gcatgtgcca ctatgcccgg ctaattttgt tattttttagt agagacaggg tttcagcatg   8940
ttggtcaggc tggtctcgaa ctcctgacct catgatccac ccacctcagc ctcccaaagt   9000
gctggaatta caggcgtgag ccaccatgcc cagcaactct tatattctga gagttgagac   9060
aatgaaagaa aagaaatttg agttgtcctg aggcagagtc tgcagtgatc caagaagagg   9120
tacagatgaa aggaaaccag ctcaattcaa ggaacttgct taatgccctg attttgaaaa   9180
attgtcctgg caagactttg ccacatcgaa tgagcctctg cacattgcag gaggctggca   9240
gggccaggga gcggtgggct gctcctaaca gcctgggtgt gtgttctggg cctaagagag   9300
aaggcatggc aatcggcgag gcagcatcag agaggaaggt tacagatggt tctgccacct   9360
gtgtacagga aggcggtcac tctctcttac ctctccctgg cagcacagaa gaacagggaa   9420
cctcgggcac cctgtccctc tcccccatag gcagcaccaa gtccctgccg gaggtgtgtg   9480
ttgcctgcac aggggggagaa gggaagcagc tggtactggt ctcaggtcga tctaaggaaa   9540
ctccatttga cctagtgaat cagtccctgc cctggatacc ttcctaggcc aatgcaacct   9600
ttagaatgaa gaacaaaggg gtttcctcac ccctgcacaa cctcagatag ggagaaggag   9660
acgcagggaa tgaaataaaa gtttccagga ctctccagga gccattcaga ttgtccaaga   9720
aactggtttc cgcagcagcc tggaataaac ccattttcct tctcgggtat gaggactttg   9780
ccagattatg atttccttaa gggcatggac tgattgtgtc tttttttttt tttttttaaa   9840
catagactag cctattagac aaacttgtgt cttagacacc tttttttctt gagcacctag   9900
cacagcctg cactcaatag gtgctccaat gatgtgacta aaaggatgga taaatagctc   9960
tgtggatttg aggctaggaa taatgaaggc ctgccatgtc ccgggggggta ctcccaattg  10020
cccctgggagt ttggaatgca cattgaggat gtcctcagtt acatatacat tttggcttat  10080
gagtctttct ttttttaatt ttttttttttt ttaagacagg gtctcactct gtcacccaga  10140
ctggagtgca gtggcatgat catggctcac tgcagccttg ccctcttgga ctcaagagtc  10200
atcttcctgc ctcagcctcc cgagtagctg agaccacaga ctgcaccacc acaccagct  10260
```

-continued

```
aactctttaa tttttgtaa agatgggtc tcgctatgtt gcccagcctg gtcccaaact    10320
cttggcctca tgcaatcctg ccacctcggc ctcccaaagt gctgggttta caggcatgag    10380
ccactgcgcc tggccagctt atgggttta actacttaca tggtgcactc tagactgagg    10440
gatatcccag ggatggagga cccacccacc tccagggcat taacactttt agggaggcta    10500
acaactgcag ccacacagag gcagggggtgg agaggagaga agggtagctg ggatcagggg    10560
caggcagctg cagcagctac tgagctggct cactgtgggc agcatggctg tctggcccag    10620
cctgcacctg agagctagct gaatgttttc ttcacctcct tccagggaga aatttttttcc   10680
agtactataa tttgttgaag ctgaacccca gcaactcaaa caaggtaccc tgactctgga    10740
gatgtgaaaa tgtaaaataa tgtgtggctt tgatgaaatg tggtagaacc agaggattaa    10800
gacttctgtg gtgatcctct ctgcctgaaa tctaaattta ggagagctga gcaaacaaat    10860
gatcaaaggc agaacatgtc ttcccgaccc tctcggctgt gtaggcgctc cggcctcagg    10920
ggatgcactg actttcctcc cactgtcctg aacacctgag aatcctgagc ggggaacaag    10980
ttgctcaaag ggcagagaag tgactcagag gttcagcaag agaaaagccc agtgtattaa    11040
gcatgtcttt ttattctgat gctttgctgt ctgggccttg caaacgtgag agggactgcc    11100
cctcccaggg gtagccagtt cctacggtta gcaaaggact cacctgggag gacagctttc    11160
atatgcaaac caaccaatcc agagcccaca ccctgtgacc acctccatct ggctcaaact    11220
caaggccact gtcccctga cctaatcacc cagggcctgg taccagacaa ttagagataa    11280
ctcctgtgac cccagatcct gctgaaatta ttcaaactcc ccaatcctaa acctgcttac    11340
cctgcctccc ctttctttcc ttcccatgga aagaataaag gcgctttccc acattttccc    11400
ctggtgccct cttctggagc aaccctggtg cttccccagg tggcctcctg ggcttagtgt    11460
gcccccttcc tcttgggctc tgtgagtaca acaacttgta aagataattt tttttttagag   11520
cagtttatg ttcacagcca aattgagaga aaagtacaaa cagttcccag atactactgg    11580
cccccacaca tgcacagcct ccccgattat catcatctcc cgccacagca gttgttacaa    11640
ctgatgaacc tgcatcagca cgcacaacac ccaaggtcca cggtttaaat taggggttcat   11700
ttttggtgtt gcgccttcta tgggtttaga caaatgcata gtgacatgtg tccaccatta    11760
tagtatcata cacagtattc attgccctaa aaatcgtcct tgcctcacct agtcatccct    11820
tcctcaccca acaactgctg atctttttac tgtctccata attttgcttt aacttgcttt    11880
tcagtgacaa ttgcctcctg ggatgttggc cttgccacac ctgaataatc atcaaacctg    11940
cattttattt gtttttatgt gtatgtgatg ggttttttgg gaggttggag gggaggacag    12000
ggtctcactc tacgccaggg ctggagtgca gaggtacgat cactgctcac cacagccttg    12060
acctcccggt ctcaagtgat cctcccacct cagcctccca agtagctggg actgcaggta    12120
cacatcacca cccaggctaa cttttgtag tttttgtaga gatgggattt caccatgttg    12180
cccaggtttg tcttgaactc ctgggctcca gtgatctgtc taccttggct tcccaaagtg    12240
ctgggattac aggtatgagc cactgggcct ggccaaactg cattttaaaa tagccaagcc    12300
tgttccttgt gactattgcc tcatccttgt attcaagact gctgtaagat cataatccta    12360
agcaagagta gagacatgta gcacaccatg atcacttact gtctaaccaa tgctgcccac    12420
ccgcttccct tctgtatggc tcaccacccc caccccaaac tcctatagga actctgcaca    12480
cactccctct ccattatgca aaactggtct cagaaaggaa tcagacagaa tatttctact    12540
gaaagtataa agcttaatat gttacttctt acaagaaatat ttgcatataa caagggaaaa    12600
aaccttaagt catgcagtaa acttttatct ttttttttttt tttaacagga gtctccctat    12660
gttgcccaag ctggtcttga acacctgggc tcaagtactc ctcctgtctt ggcctcccaa    12720
agtgctggga ttacagacat gagccacact tcttttttttt ttttttttttt ttttttttttc   12780
ttgagacaga gtcttgctct gttgcccaga ctggagtaca gttgcacaat cccggctccc    12840
tgcaacctttt gcctcctggg ttcaagtgat cctcaacctc ctgagtatct ggaactacag    12900
gcatgtgcca ccacacccctg ctaattcttg tatttctagt aaagatggaa tttcaccacg    12960
ctggccaggc tagtcttgaa ctcctggcct taagtgatcc gcctgcctcg gcctcccaaa    13020
gtgctgggat ttcagtgtga gccactgtgc ccggtctctt ttttttttttt tttgagacct   13080
tgagaccggg ccttgctctg ttacccaagc tggagtgcag tggcaggatc atagctcact    13140
gcagccttga acttctgggc tcaagcaatc ctcccacatc agcctcccaa gtacctagga    13200
ctgcagatgc ttaccaccat gcccagctaa ttttttcatga atttttaatt attgaaattc     13260
agacatctaa gaagatgctg aggactgtct ccatattcct gaaattacga ctcacctatt    13320
cacaaaccag cccttctagt ggaattaaaa tattatttga ttttgaatac cctactctaa    13380
ggtaggcaca ttgccctgca atttattatt tatgaggttt ttaattatgg aattgttcaa    13440
atattcacaa aagtagagag actacaatga actccaatgt agccatcact caggcccaac    13500
tgttatcagc acagtccaat catgtttat cttccctct ctgacccca acccatcccc    13560
agtccttatc taaaatcaaa tctcaaacac catatctttg ggagcctatt tatttagtta    13620
gttagttttc agacagagtt tctttcttgt tgcccaagct ggagtacaat agtgtagtct    13680
cggctcacag caatctcccc ctccttggtt caagcaattc tcctgcctca gtctcccaag    13740
aagctgggat tataggcacc tgccaccaca tccagctaat tctttttgtgt ttttagcaaa    13800
gacagggttt caccatgttg gccaggctgc tctcgaactc ctgacctcag gtgatccgcc    13860
tgcctcggcc tcccaaagtg ctgggattac aggcatgagc caccacgcct ggccggcagc    13920
ctatttaaat gtcatcctca acatagtcaa tccttgggcc atttttttctt acagtaaaat    13980
tttgtctctt tcttttaatg cagtttctac gtggaatttg gacactttgg ccttccagga    14040
actgaagtcc gagctaactg aagttcctgc ttcccgaatt ttgaaggaga gcccatctgg    14100
ctatctcagg agtggagagg gagacaccgg tatgaagtta agtttcttcc cttttgtgcc    14160
cacgtggtct ttattcatgt ctagtgctgt gttcagagaa tcagtatagg gtaaatgccc    14220
acccaagggg gaaattaact tccctgggag cagagggagg ggaggagaag aggaacagaa    14280
ctctctctct ctctctgttc ccttgtcaga gcaggtctgc aggagtcagc ctttccctaa    14340
caaagccctc tatcctatca cccacacttg ggaggctggg ctgggctgca caggggcaaga   14400
tgagagatgt gttgatttca tccacttgat tgtcatgtag aattagatat acttgagaag    14460
ttacatttttt cagtagcgcc ttcatatctt tatttttaggg acaggtatac accaagcacc    14520
atctcagcca caatctgtta ctaacagtat gttttctgaa ctttggcac ttaggaaaag    14580
tacagtttgg ctctctccaa agtgttccct gaaagtccaa ctttatgact aatactgtga    14640
tttccagaaa ctttgactat ccatgttatt gacaatgatt actagcactg aagggcatgc    14700
atgcaagtag gggttatgaa atatttaaaa cacggttctc taagatatga gcagcaaagt    14760
gtttctacct tctatgaggg aaccgaaggt gccattaaaa gtagagaaat ctggaccagg    14820
catggtggct catgcctgta atcccagcac tttgggaggc tgaggcgggc ggatcacttg    14880
aggtcaggag ttcaagacca gcctggccaa catggtgaaa cactgtctct actaaaaata    14940
caaaaattag ccaggcatgg tggcagtcat ctgtaatccc agctacttgg gaggctgagg    15000
```

-continued

```
caggaaaatt gcttgaaccc aggaggcaga ggttgcagtg agccgagatc acaccactgc   15060
cctccagcct gggcgacaga gtgagactct gtctcaaaaa aaaaaaaaat acagacatct   15120
gttgtgattc tggtaactct aaattttcaa ccgtctcttc actacattta aaaaattatt   15180
ttctaaacca aattagccag gtgtggtagc aggcacctgt agtcccagca actcaggagg   15240
ctgagatggg aggggtgctt gagcctggaa ggtcgaggct gcagtgcact gtgattgcac   15300
cactgcactc cagcctaggt aacagtgcaa gaccctgtct caaaaaataa ttattttcat   15360
gtttattata ttaaaatgat gtatgaaata tgtgactcat cagggcttga aaaactttgt   15420
tgtatggaga ttattcttat gagttgattt ttctctctcc taccttatag taatgaaata   15480
aaccaggcat gaaagtcaca ataagtaata caatgaacac ccatgggtcc ctgcccagct   15540
taagtagaat attacaaatg cagttgaagc cctctgtgca actttcatcc ttacaactga   15600
tactgagtga attgtacttt aaatatttta tagctcccac tcccatgcat gcccctcagt   15660
gatagcaata attgtcaata acatgaaaca cagattgatc atatagcatt taccatatat   15720
ttactctata ccaagcactt aacatatata attacattta aaatttacaa cagccctact   15780
acccaaaaca ctattagtat cccctttac aaatgcgata actgaggcgt agagagctaa   15840
gtaacttact gaaagtcaca cagccagcgg gtggtagagc ctagctttaa acccagacga   15900
tttgtctcca gggctgtcac atctactggc tctgccaagc ttccgcatga tcattgtctg   15960
tgtttggaaa gattatggat taagtggtgc ttcgttttct tttctgaatt taccaggatg   16020
tggagaacta gtttgggtag gagagcctct cacgctgaga acagcagaaa caattactgg   16080
caagtatggt gtgtggatgc gagaccccaa gcccacctac ccctacaccc aggagaccac   16140
gtggagaatc gacacagttg gcacggatgt ccgccaggtt tttgagtatg acctcatcag   16200
ccagtttatg cagggctacc cttctaaggt tcacatactg cctaggccac tggaaagcac   16260
gggtgctgtg gtgtactcgg ggagcctcta tttccagggc gctgagtcca gaactgtcat   16320
aagatatgag ctgaataccg agacagtgaa ggctgagaag gaaatccctg gagctggcta   16380
ccacggacag ttcccgtatt cttggggtgg ctacacggac attgacttgg ctgtggatga   16440
agcaggcctc tgggtcattt acagcaccga tgaggccaaa ggtgccattg tcctctccaa   16500
actgaaccca gagaatctgg aactcgaaca aacctgggag acaaacatcc gtaagcagtc   16560
agtcgccaat gccttcatca tctgtgtgcac cttgcacacc gtcagcagct acacctcagc   16620
agatgctacc gtcaactttg cttatgacac aggcacaggt atcagcaaga ccctgaccat   16680
cccattcaag aaccgctata agtacagcag catgattgac tacaaccccc tggagaagaa   16740
gctcttttgcc tgggacaact tgaacatggt cacttatgac atcaagctct ccaagatgtg   16800
aaaagcctcc aagctgtaca ggcaatggca gaaggagatg ctcagggctc ctggggggag   16860
caggctgaag ggagagccag ccagccaggg cccaggcagc tttgactgct ttccaagttt   16920
tcattaatcc agaaggatga acatggtcac catctaacta ttcaggaatt gtagtctgag   16980
ggcgtagaca atttcatata ataaatatcc tttatcttct gtcagcattt atgggatgtt   17040
taatgacata gttcaagttt tcttgtgatt tggggcaaaa gctgtaaggc ataatagttt   17100
cttcctgaaa accattgctc ttgcatgtta catggttacc acaagccaca ataaaaagca   17160
taacttctaa aggaagcaga atagctcctc tggccagcat cgaatataag taagatgcat   17220
ttactacagt tggcttctaa tgcttcgat agaatacagt tgggtctcac ataacccttt   17280
acattgtgaa ataaaatttt cttacccaac gttctcttcc ttgaactttg tgggaatctt   17340
tgcttaagag aaggatatag attccaacca tcaggtaatt ccttcaggtt gggagatgtg   17400
attgcaggat ctcgagataa cttcgtataa tgtatgctat acgaagttat atgcatgcca   17460
gtagcagcac ccacgtccac cttctgtcta gtaatgtcca acacctccct cagtccaaac   17520
actgctctgc atccatgtgg ctcccattta tacctgaagc acttgatggg gcctcaatgt   17580
tttactagag cccaccccccc tgcaactctg agaccctctg gatttgtctg tcagtgcctc   17640
actgggcgt tggataattt cttaaaaggt caagttccct cagcagcatt ctctgagcag   17700
tctgaagatg tgtgctttttc acagttcaaa tccatgtggc tgtttcaccc acctgcctgg   17760
ccttggtta tctatcagga cctagcctag aagcaggtgt gtggcactta acacctaagc   17820
tgagtgacta actgaacact caagtggatg ccatctttgt cacttcttga ctgtgacaca   17880
agcaactcct gatgccaaag ccctgcccac ccctctcatg cccatatttg gacatggtac   17940
aggtcctcac tggccatggt ctgtgaggtc ctggtcctct ttgacttcat aattcctagg   18000
ggccactagt atctataaga ggaagagggt gctggctccc aggccacagc ccacaaaatt   18060
ccacctgctc acaggttggc tggctcgacc caggtggtgt ccctgctct gagccagctc   18120
ccggccaagc cagcaccatg ggaacccca agaagaagag gaaggtgcgt accgatttaa   18180
attccaattt actgaccgta caccaaaatt tgcctgcatt accggtcgat gcaacgagtg   18240
atgaggttcg caagaacctg atggacatgt tcagggatcg ccaggcgttt tctgagcata   18300
cctggaaaat gcttctgtcc gtttgccggt cgtgggcggc atggtgcaag ttgaataacc   18360
ggaaatggtt tcccgcagaa cctgaagatg ttcgcgatta tcttctatat cttcaggcgc   18420
gcggtctggc agtaaaaact atccagcaac atttgggcca gctaaacatg cttcatcgtc   18480
ggtccgggct gccacgacca agtgacagca atgctgtttc actggttatg gcgcggatcc   18540
gaaaagaaaa cgttgatgcc ggtgaacgtg caaaacaggt aaatataaaa tttttaagtg   18600
tataatgatg ttaaactact gattctaatt gtttgtgtat tttaggctct agcgttcgaa   18660
cgcactgatt tcgaccaggt tcgttcactc atggaaaata gcgatcgctg ccaggatata   18720
cgtaatctgg catttctggg gattgcttat aacaccctgt tacgtatagc cgaaattgcc   18780
aggatcaggg ttaaagatat ctcacgtact gacggtggga gaatgttaat ccatattgct   18840
agaacgaaaa cgctggttag caccgcaggt gtagagaagg cacttagcct gggggtaact   18900
aaactggtcg agcgatggat ttccgtctct ggtgtagctg atgatccgaa taactacctg   18960
ttttgccggg tcagaaaaaa tggtgttgcc gcgccatctg ccaccagcca gctatcaact   19020
cgcgcccctgg aagggatttt tgaagcaact catcgattga tttacggcgc taaggatgac   19080
tctggtcaga gatacctggc ctggtctgga cacagtgccc gtgtcggagc cgcgcgagat   19140
atggcccgcg ctggagtttc aataccggag atcatgcaag ctggtggctg gaccaatgta   19200
aatattgtca tgaactatat ccgtaacctg gatagtgaaa caggggcaat ggtgcgcctg   19260
ctggaagatg gcgattaggc ggccggccgc taatcagcca taccacattt gtagaggttt   19320
tacttgcttt aaaaaacctc ccacacctcc ccctgaacct gaaacataaa atgaatgcaa   19380
ttgttgttgt taacttgttt attgcagctt caataaagc aatagcatca   19440
caaatttcac aaataaagca ttttttttcac tgcattctag ttgtggtttg tccaaactca   19500
tcaatgtatc ttatcatgtc tggatccccc ggctagagtt taaacactag aactagtgga   19560
tccccgggga tcatgcctc cgcgcgggt tttggcgct cccgcgggcg cccccctcct   19620
cacggcgagc gctgccacgt cagacgaagg gcgcagcgag cgtcctgatc cttccgcccg   19680
gacgctcagg acagcggccc gctgctcata agactcggcc ttagaacccc agtatcagca   19740
```

```
gaaggacatt ttaggacggg acttgggtga ctctagggca ctggtttct ttccagagag    19800
cggaacaggc gaggaaaagt agtcccttct cggcgattct gcggagggat ctccgtgggg    19860
cggtgaacgc cgatgattat ataaggacgc gccgggtgtg gcacagctag ttccgtcgca    19920
gccgggattt gggtcgcggt tcttgtttgt ggatcgctgt gatcgtcact tggtgagtag    19980
cgggctgctg ggctggccgg ggctttcgtg gccgccgggc cgctcggtgg gacggaagcg    20040
tgtggagaga ccgccaaggg ctgtagtctg ggtccgcgag caaggttgcc ctgaactggg    20100
ggttgggggg agcgcagcaa aatgcggct gttcccgagt cttgaatgga agacgcttgt    20160
gaggcgggct gtgaggtcgt tgaaacaagg tggggggcat ggtgggcggc aagaacccaa    20220
ggtcttgagg ccttcgctaa tgcgggaaag ctcttattcg ggtagatgg gctggggcac    20280
catctgggga ccctgacgtg aagtttgtca ctgactgagg aactcggttt gtcgtctgtt    20340
gcgggggcgg cagttatggc ggtgccgttg ggcagtgcac ccgtacccttt gggagcgcgc    20400
gccctcgtcg tgtcgtgacg tcacccgttc tgttggctta taatgcaggg tggggccacc    20460
tgccggtagg tgtgcggtag gcttttctcc gtcgcaggac gcagggttcg ggcctagggt    20520
aggctctcct gaatcgacag gcgccggacc tctggtgagg ggaggggataa gtgaggcgtc    20580
agtttctttg gtcggtttta tgtacctatc ttcttaagta gctgaagctc cggttttgaa    20640
ctatgcgctc ggggttggcg agtgtgtttt gtgaagtttt ttaggcacct tttgaaatgt    20700
aatcatttgg gtcaatatgt aattttcagt gttagactag taaattgtcc gctaaattct    20760
ggccgttttt ggctttttg ttagacgtgt tgacaattaa tcatcggcat agtatatcgg    20820
catagtataa tacgacaagg tgaggaacta aaccatgaaa aagcctgaac tcaccgcgac    20880
gtctgtcgag aagtttctga tcgaaaagtt cgacagcgtg tccgacctga tgcagctctc    20940
ggagggcgaa gaatctcgtg ctttcagctt cgatgtagga gggcgtggat atgtcctgcg    21000
ggtaaatagc tgcgccgatg gtttctacaa agatcgttat gtttatccgc actttgcatc    21060
ggccgcgctc ccgattccgg aagtgcttga cattggggaa ttcagcgaga gcctgaccta    21120
ttgcatctcc cgccgtgcac agggtgtcac gttgcaagac ctgcctgaaa ccgaactgcc    21180
cgctgttctg cagccggtcg cggaggccat ggatgcgatt gctgcggccg atcttagcca    21240
gacgagcggg ttcggcccat tcggaccgca aggaatcggt caatacacta catggcgtga    21300
tttcatatgc gcgattgctg atccccatgt gtatcactgg caaactgtga tggacgacac    21360
cgtcagtgcg tccgtcgcgc aggctctcga tgagctgatg ctttgggccg aggactgccc    21420
cgaagtccgg cacctcgtgc acgcggattt cggctccaac aatgtcctga cggacaatgg    21480
ccgcataaca gcggtcattg actggagcga ggcgatgttc ggggattccc aatacgaggt    21540
cgccaacatc ttcttctgga ggccgtggtt ggcttgtatg gagcagcaga cgcgctactt    21600
cgagcggagg catccggagc ttgcaggatc gccgcggctc cgggcgtata tgctccgcat    21660
tggtcttgac caactctatc agagcttggt tgacggcaat ttcgatgatg cagcttgggc    21720
gcagggtcga tgcgacgcaa tcgtccgatc cggagccggg actgtcgggc gtacacaaat    21780
cgcccgcaga agcgcggccg tctggaccga tggctgtgta gaagtactcg ccgatagtgg    21840
aaaccgacgc cccagcactc gtccgagggc aaaggaatag ggggatccgc tgtaagtctg    21900
cagaaattga tgatctatta aacaataaag atgtccacta aaatgaagt ttttcctgtc    21960
atactttgtt aagaagggtg agaacagagt acctacattt tgaatggaag gattggagct    22020
acgggggtgg gggtggggtg ggattagata aatgcctgct ctttactgaa ggctctttac    22080
tattgcttta tgataatgtt tcatagttgg atatcataat ttaaacaagc aaaaccaaat    22140
taagggccag ctcattcctc ccactcatga tctatagatc tatagatctc tcgtgggatc    22200
attgtttttc tcttgattcc cactttgtgg ttctaagtac tgtggtttcc aaatgtgtca    22260
gtttcatagc ctgaagaacg agatcagcag cctctgttcc acatacactt cattctcagt    22320
attgttttgc caagttctaa ttccatcaga cctcgacctg cagcccctag ataacttcgt    22380
ataatgtatg ctatacgaag ttatgctagg taactataac ggtcctaagg tagcgagcta    22440
gcggagcctc tatgcctacc agcaaaggcc agaaaaggtg aagttccggg ctcccgggtg    22500
aagcagctgt cagcagaggc agccagatgc atggagtttc tcctcctgct aaagattttg    22560
tttatccggg tcaatgtaca gctagctccc ctctgactga cacgtcctcc aggcttgtat    22620
agtcgcatag actctgttct cttctgtcag cttttcaaagg gctgttcctc tttttaaaaat    22680
cacatagtgt agcagtccag aggaaaaact agaagtaagg ttgtttcttc atgaaaccat    22740
tgcttttgca cgctattatg gttaccataa gctttgcgag gcagcggcgg ttctgcggag    22800
cgaccgctcc tgtggttaga actgctcctg ccgaaggtgt attatactcc aggggggcttc    22860
tagtgctaca gatacagcat gtggttgggt ggtacgtaaa ccctttgccc tgtgaaataa    22920
agttatctta catg                                                       22934
```

```
SEQ ID NO: 89            moltype = DNA   length = 17980
FEATURE                  Location/Qualifiers
misc_feature            1..17980
                         note = Synthetic
misc_feature            1..114
                         note = Mouse 5' UTR
misc_feature            115..718
                         note = Human Exon
misc_feature            719..14003
                         note = Human Intron
misc_feature            14004..14129
                         note = Human Exon
misc_feature            14130..16016
                         note = Human Intron
misc_feature            16017..16801
                         note = Human Exon
misc_feature            16595
                         note = Y437H (T to C)
misc_feature            16802..17309
                         note = Human 3' UTR
misc_feature            17417..17450
                         note = LoxP
misc_feature            17457..17482
                         note = I-Ceu
```

-continued

```
misc_feature          17489..17980
                      note = Mouse 3' UTR
source                1..17980
                      mol_type = other DNA
                      organism = synthetic construct
SEQUENCE: 89
gagccagcag ggccacccat ccagacacct tgcaggagaa ctttccagaa gaaacctcac      60
ccagcctcca cactgctgtc cttctctgca cgctgctgca gctgtggtcc caagatgagg     120
ttcttctgtg cacgttgctg cagctttggg cctgagatgc cagctgtcca gctgctgctt     180
ctggcctgcc tggtgtggga tgtggggggcc aggacagctc agctcaggaa ggccaatgac     240
cagagtggcc gatgccagta taccttcagt gtggccagtc ccaatgaatc cagctgccca     300
gagcagagcc aggccatgtc agtcatccat aacttacaga gagacagcag cacccaacgc     360
ttagacctgg aggccaccaa agctcgactc agctccctgg agagcctcct ccaccaattg     420
accttggacc aggctgccag gccccaggag acccaggagg ggctgcagag ggagctgggc     480
accctgaggc gggagcggga ccagctggaa acccaaacca gagagttgga gactgcctac     540
agcaacctcc tccgagacaa gtcagttctg gaggaagaga agaagcgact aaggcaagaa     600
aatgagaatc tggccaggag gttggaaagc agcagccagg aggtagcaag gctgagaagg     660
ggccagtgtc cccagacccg agacagtgct cgggctgtgc caccaggctc cagagaaggt     720
aagaatgcag agtgggggga ctctgagttc agcaggtgat atggctcgta gtgacctgct     780
acaggcgctc caggcctccc tgcctgccct ttctcctaga gactgcacag ctagcacaag     840
acagatgaat taaggaaagc acagcgatca ccttcaagta ttactagtaa tttagctcct     900
gagagcttca tttagattag tggttcagag ttcttgtgcc cctccatgtc agttttcaca     960
gtccatagca aaaggagaaa taaaaggacc gggtgagatg tgtctgcata tgagcagtag    1020
aaagttgtca attgtccctt ttgaaaaact atcctttttt gaacctttgc tcagattgtt    1080
atttgtacct tttgatgtta aaatgacctt tatttatgaa attacaatag atttgggaaa    1140
tgataataag tggtaagttt ttgtttattt ttaaatgttc ttccctggca aaataaagag    1200
atggcacctc tctgtcagtt ttcttaatat gttgttctga aagttttctt actcagtcca    1260
atctgagaac ctctgctttt aagtcatcag acaaattctt gagatggctt tttctgagag    1320
gctcttctgt tcatcctggt cccttcttgc ctaaaggtga gtctgtgtgt gtgtggggggg    1380
ggtgcggggg tgaggtgttg ggggaggtct tcttattagc tgggaagatg gtatttgtgt    1440
cactttttgt gaaagtgggc tcccaaatat tccctgttga ggaagtgttc taatcatgag    1500
gaaataagca agcaaatcca gttgttggac aattagtttg gactggtcaa agatgtcagt    1560
gccaaggaag aaagaaaaaa ggggtgggga agggcttgtt ctatattaaa gagactaaag    1620
aaatgtgtta accaaatgta gtgcatgagt cttgattggt gtcttcatcc aaggggggaaa    1680
aaggctatga ggaacaggtt tgggataact gaggcaattt gactgctcat tattatgtta    1740
ctgtattaat gttcagtttc ttggtgagat aatgatactg tggttgcgaa ggataaaatc    1800
tttgttctat ggagatacat gcttaagtac ccagggtgag gcgtcaggat gtctgcaatt    1860
tgctctcaaa tggttgaaga aagactgcaa atatatagat aatgagagaa agaaaggtaa    1920
aacaactgtg gcaaaatatt aataactggt gaattacaaa ctgtgaatc taagtatatg    1980
gggagcttat tgtactattc tttcagtttt tctataggct tgaaaagctt taaaattatg    2040
agaaaatatt tcctaaaaag agccttctac gtgaaaggca agctcttcat agctatgggg    2100
ttagaaaacc taagagccag agcctgggga tgaccttggg caagttattg aaccctctgc    2160
atcttcattt cttgtccata acataacaaa gaaaattcct gctgtgaata atttttgtgg    2220
ggttcacatg aaatacctat aagatgtaaa ggatttttaa aaaatgttta gattgttaga    2280
attagagag atccaattct gaattttaca accaaggaaa gtgaagtcct aagatgctaa    2340
ggggccaagg ttgcccagct ggtcagtggt agagcttgag acttgaatct gtggagacaa    2400
ttgaaagaat catcattacc agaagtgtga tgaggcatta cttatttcag actgttgaat    2460
gaagttacat tctcaataaa aactcctgca tgtgtgtatg tgggtgtggg tggtgtgtgt    2520
gtgtgtgtac aaaaatagtg gcaatgtttt gcctttttt ttcttttgtg gtcatttaac    2580
aagtctttgg ggatttatta gatgtgtttc ctaattttat attttttctt gatctttcca    2640
gctactccac ttttgaaata agggcaacat cccattatat tgaacaccaa acatggaagt    2700
tcttttctag tagtagatgt ttttcatgag caggaaatta cattagtaca agaatgtgaa    2760
actgaaaagg gacctaatga gcatccggta ccgctggctg attttttgcag atatggaaac    2820
tgaggccag agaggttatt cagcttgtcc atggccatct accagttagt ggcaaagctc    2880
gaattctggc ctcttcctct gaagttcagt gactttcttt cttttttttt gagacagagt    2940
ttcactcttg ttgcccaggc tagagtgtaa tggcacgatc ttggctcact gaaacctctg    3000
cctcccgggt tcaagcaatt ctcctacctc agcctcctga gtagctggga ttataggcat    3060
gtgccaccat gcccggctaa ttttgtattt ttagtagaga cagggtttca ccatgttggt    3120
caggctgatc tcgaactcct gacctcaggt gatctgccga cctcggcctt ccaaagcact    3180
gggattacag gtgtgagccc tccctgtaca tggccatgag gttcattgac tttcaagacc    3240
ttcagctgac ctctggttta tagaccctaa aggtaaaaga cagaaaggta caggaatgct    3300
tggaacaaaa gatctgtttc aaggccagat ctagggaaaa gggggcattc tggaggctgg    3360
aatataagtc taggtatgct tttttgcagg agtggcaaga actaggtgtg aaggtttggg    3420
tagagaagct tagtgaggct gagtggacaa aggtaaggcc tgagaaggca gccttttctgg    3480
attccacctg caactcaaat tgttaccacc actttcttga tcatgtatta atagttgtta    3540
tgtagaaaaa aattccttat aatcatagaa atcacttgtt tatacataca cataatatga    3600
catattttac tacataacta ttactacaaa gttatatata acttttttctt ctctgggctt    3660
ataaaatttt tcatatatat acatatataa attttatgta tatataatag tttttgaaaa    3720
gtagaaaaaa aatacaatta gccaagtgtg gtggctcaca cctgtaacct tagcactttg    3780
ggaggccgag gtggacagat cacttgaggt caggagttta agaccagcct ggccactgtg    3840
gtgaaaactt gtctctacta aaaatacaaa aattagccgg gtgtggtggc gggcacctgt    3900
aatccagtta ctccagaggc tgaggcagga gaatcgcttg aacctgggag gcagacgttg    3960
cagtgagcca agatcacgct actgcactcc agcctgggtg acagagcgag actccatctc    4020
aaaaaaaat atattacca tataatacat ataaatatat ataattatat atataaattt    4080
attatatata taataaaata catatataat ttactagaag ataaattaga gttggttatt    4140
actgtcacaa gagaaggact gctttgtttg ttatttagcc cctgctttgg actggtctcc    4200
tgttgaacag agcctggaag agggcttgtg tgcagttggt ttatatggac catgatccta    4260
gagaagagaa gttgagacag gggaaagtga gacaggaag gcaggaaagc cacaaaatgg    4320
gggccttctc cagctagtca ccacagtggg caatggaggc tcaatcccat caagcccttc    4380
```

-continued

```
agaggggctg tgtagactgc aacagaagag gggaggttta cgcatggatc tgataccctc   4440
ttggccaagg gctatcccat ggagtatatt gcgcttccct gatactcaga tgtgggggacg   4500
aggtttgttc ttgcagactg attttttttt tttttttaag atggagtctt tctctgtccc   4560
ccaggctgga gtgcggtggc acgatcttgg ctcactgcaa cctccgcctc ctgggttcaa   4620
gcaattctcc tgcctcagcc tcccgagtag ctgggattac aggtgcacac taccacgccc   4680
agctaacttt tgtattttt ttttttttcca gtacagacag ggtttcacca tgttggccag   4740
gctggtcttg aactcctgac ctcaagtatc cacccatctt gacctcccaa agtgctggga   4800
ttacaggcat gagccacggc gcctggcctg ttcttgtaga ctttctatgc agaaagtcag   4860
agaagctggg ccacggtggc tgaggcgagg tccccgcagg tgataactgc aagaggcagg   4920
ttgcctcagc aatgactgca aaaaagtggg caggatgtga ggggagggtg aggggagaaa   4980
cctgaggtgt tcaacacaag tgctgcagat tccctccct cacctagaat aggatgggga   5040
tgagaatccc tcatgggagt catcatgcaa attagcagtc acacagggaa gcacccagtg   5100
cagcgctgag cagtggccac ccagtgaata aaatataact agaaaggctt attttacttg   5160
agttccacta ttgtttttgt tttttgtttt gttttgtttt ttgaagatgg agtctcgctc   5220
tatcaccagg ctggagtgca gtggcgtggt cttggctcac tgcaacctcc acctcctgga   5280
ttcaagcaat tctcctgcct cagcctccca agtagctggg attacaggca cacgccacca   5340
tgcccggcta atttttgtat ttttagtgga gatggggttt caccatgttg gccaggctgg   5400
tcttgaactc ccgacctcgt gatccacccg cctcagcctc ccaaagtgct gggattacag   5460
gcatgagcca ctgcacctgg ccaggggtcc actattgttt taaagcatca ttcaataatc   5520
aatatgtcaa catgtgcata acattttaat aacatgcgtt gattctagag acagtacaag   5580
ttagagcagt actcaggaca atagtctatt agctagtctt cactttccta agatgtttct   5640
gacaacctgt agataattag gcatagcttg ttttacttca ttcctttcat ttatgtaata   5700
tggactgaac tttccagtga tagaaaatat ctatgaaaat tattacaatg cctatgtcta   5760
caggcaaacg agttaataaa ttcagtttcc gggttgaggt ctctaaaatg ccaagtctat   5820
aaagaagcga cggcagagaa cacagaacat ttccagaatt ttgtaataga catgaacctt   5880
taaaccacag aaggactgaa tttaacattt taaaaaacct agaaaaaaaa cagctgggcg   5940
tggtggctca cgcctgtaat cccagcactt tgggaggctg aggcaggcgg atcacgaggt   6000
caggagttcg tgaccagcct ggccaatatg gtaaaaccct gtctctacta aaaatacaaa   6060
aattagccag gcgtggtggc aggcacctgt agtcccagct actcaggagg ctgaggcaga   6120
agaatcactt gaacccagga ggcagaggtt gcaatgagct gagatcatgc cactgtactc   6180
cagcctgggt gacagagcga gaccctgtct caaaaaaaaa aaaacaaaaa aaaaaacctt   6240
aaaaaataaa agcccaaaa atgctaacta tctgacacag tacagccctt aatattttca   6300
cagtctcttt ttggttttcc tccacattca caatgaaatg ttagtgattt taaaacattc   6360
cagagaaatt ttagtgttga cacatcttta ttgagggcca tttcatttat agttacttat   6420
gtaatcatcc aaacaattca gctcagcata ctggggctca gagaggtgga gtcatttacc   6480
caaagtcaca cagctgggac atggcagagc tgaactagga gctatgactt ccggcttagg   6540
tccaggcccc tttacgagat tgtttccctg cctttgggtt ttgcatcctc tattctgggc   6600
ttccaccgc atgccagatg gctctattcc tggagtctga ccattgccag atgctcctgg   6660
ctgacatgac ctagaagaag ccagcaggct cataacttaa ccatcgcccc tgccaaatgg   6720
gaactggcct tgccgtcatc ctggaagcca ttccctgaca ttttgttta ttgcagttca   6780
tgtttattcc agctaatgca cataaggagt ggttcctgca aggcacaatc tgaagggctc   6840
cttgctcaga gccgtaaggg ccatggtggg attcagcagg gaacttggca ccagccaggc   6900
acttttgctg cctcttcttt gccagtgagg gtagaagaac tgataagagg attgagtgca   6960
cagcccagga gctgagagtt tacaaggcaa cccactggga cctgagctca gccccaggag   7020
tgggtcaccc cacaaagtgc tgagcagcat cttttgagact cttctgaagc ctccagtagc   7080
catctgggtc cagtcgggag atagaaatca cacagtgggt taagctgggg aagtttactt   7140
taaagaatta ctaaccgtga tgaaagagca actatagata gacgtgaact ccataggcac   7200
ctagggctga gggagggtgc cggacaagct tggaagggga aggtgaggtt cagcacatca   7260
gcttgcagag aaggtggcta aggtgtgcag gcctcagctg gtctgcagct gcaataggcc   7320
gcctcccagt gcaggtgagg agggcaacct gcaacgtgtg gcaagggcat ggtgggagtc   7380
agggcaggca caggcaggag gcctccagag cactgaggtc cgtgtgcagg gactctggtt   7440
tccttgttgg gagggctgtg gaaaggttat ggccaggctg tggctgtgag gtcacagaag   7500
aacttcgctc tgggtccgtg gctgggggtag gactccaaca aatgtcctca cagtcatacc   7560
acctatggac gcaggacagg aaaactgcag accttttttcc tcccacgatg tccctccagc   7620
gccctctact gagatagttc aacatcgcgc tcacttcaaa gctctttgttc ttcagacagc   7680
atacatggga gggtgcattc agctctgaga ggcaatgcgt ttataactga cacacctcct   7740
cagcacagga tggaagagtt cgcagctgcc atggcctcgg aagacatggg ttcaagtccc   7800
agcgatacca cttagctgtg tgaccttggg catgttactt aacctctctg aacctcggtt   7860
tcctcatttg caaaaggga tattaatgtt cactttcagg accattattt gaaagtagtg   7920
agtagcaagc acccagcaca gtactggctc ataagagaca cttaataagt agtagcgata   7980
gttcaacttt atcaggcgct atctgcagtc ctaaagcctt tctctatttc tctgaaactt   8040
tgaaggcacc agatcacatt taaaaattac ataaaaatta cttgaaatgg gcaaagagct   8100
ataaatgccg acaaaccatc ttgtttcaca aaaaaaaaa aaaaaaaagc tgttttttag   8160
agttgcaaag ccagtacata ctttagctat ccacaaggaa gtcatctgtg aaaatgcctg   8220
acttttttgg gtttcacttt cttccttccc tctatagcaa aaggggcatt tcttctttaa   8280
ttttctcccc actgactggt aggtaggtac ccctactttt cttagtatac atcttttctc   8340
ggtaagttgt taaattaaat aaccagcata aaatacatca ttttgtatgt gtaaagggc   8400
cagatgcagg ggagggatgg ctcgcctgaa tttaatattt ttttaaaaac ctaaaaaaaa   8460
aagccctaaa aatgttaacg atctgtcaca atatagccct taatattttc ataatctctt   8520
tttggttttc ttccacattc agaatgaaat gttagtgatt ttgaaacatt ccagagaaat   8580
tttagtattg acacatttat taagggaccc tcccatggca actgtggatg gcatagctga   8640
agtgtaggga caaggttggg gcagtcctcc agacttgtg tacagatggc atgcagtatt   8700
tctctctcct cacattgcct gaaaccaact cctttttttt tttttttttt tttttttgag   8760
acagagtctc tctgtcaccc aagctggagt ccaatggcac aatctcagct cactgcaacc   8820
tttgcctccc aggttcaaac gattctcctg acttagcctc cctagttgct gagattacag   8880
gcatgtgcca ctatgcccgg ctaatttttg tatttttagt agagacaggg tttcagcatg   8940
ttggtcaggc tggtctcgaa ctcctgacct catgatccac ccacctcagc ctcccaaagt   9000
gctggaatta caggcgtgag ccaccatgcc cagcaactct tatattctga gagttgagac   9060
aatgaaagaa aagaaatttg agttgtcctg aggcagagtc tgcagtgatc caagaagagg   9120
```

-continued

```
tacagatgaa aggaaaccag ctcaattcaa ggaacttgct taatgccctg attttgaaaa   9180
attgtcctgg caagactttg ccacatcgaa tgagcctctg cacattgcag gaggctggca   9240
gggccaggga gcggtgggct gctcctaaca gcctgggtgt gtgttctggg cctaagagag   9300
aaggcatggc aatcggcgag gcagcatcag agaggaaggt tacagatggt tctgccacct   9360
gtgtacagga aggcggtcac tctctcttac ctctccctgg cagcacagaa gaacagggaa   9420
cctcgggcac cctgtccctc tcccccatag gcagcaccaa gtccctgccg gaggtgtgtg   9480
ttgcctgcac aggggggagaa gggaagcagc tggtactggt ctcaggtcga tctaaggaaa   9540
ctccatttga cctagtgaat cagtccctgc cctggatacc ctcctaggcc aatgcaacct   9600
ttagaatgaa gaacaaaggg gtttcctcac ccctgcacaa cctcagatag ggagaaggag   9660
acgcagggaa tgaaataaaa gtttccagga ctctccagga gccattcaga ttgtccaaga   9720
aactggtttc cgcagcagcc tggaataaac ccattttcct tctcgggtat gaggactttg   9780
ccagattatg atttccttaa gggcatggac tgattgtgtc ttttttttttt tttttttaaa   9840
catagactag cctattagac aaacttgtgt cttagacacc tttttttctt gagcacctag   9900
cacagccttg cactcaatag gtgctccaat gatgtgacta aaaggatgga taaatagctc   9960
tgtggatttg aggctaggaa taatgaaggc ctgccatgtc ccgggggggta ctcccaattg  10020
cccctggagt ttggaatgca cattgaggat gtcctcagtt acatatacat tttggcttat  10080
gagtctttct ttttttaatt tttttttttt ttaagacagg gtctcactct gtcacccaga  10140
ctggagtgca gtggcatgat catggtcac tgcagccttg ccctcttgga ctcaagagtc   10200
atcttcctgc ctcagcctcc cgagtagctg agaccacaga ctgcaccacc acacccagct  10260
aactctttaa tttttgtaa agatgggtc tcgctatgtt gcccagcctg gtcccaaact   10320
cttggcctca tgcaatcctg ccacctcggc ctcccaaagt gctgggttta caggcatgag  10380
ccactgcgcc tggccagctt atgggttta actacttaca tggtgcactc tagactgagg  10440
gatatcccag ggatggagga cccacccacc tccagggcat taacacttttt agggaggcta  10500
acaactgcag ccacacagag gcaggggtgg agaggagaga agggtagctg ggatcagggg  10560
caggcagctg cagcagctac tgagctggct cactgtgggc agcatggctg tctggcccag  10620
cctgcacctg agagctagct gaatgtttc ttcacctcct tccagggaga aattttttcc  10680
agtactataa tttgttgaag ctgaacccca gcaactcaaa caaggtaccc tgactctgga  10740
gatgtgaaaa tgtaaaataa tgtgtggctt tgatgaaatg tggtagaacc agaggattaa  10800
gacttctgtg gtgatcctct ctgcctgaaa tctaaattta ggagagctga gcaaacaaat  10860
gatcaaaggc agaacatgtc ttcccgaccc tctcggctgt gtaggcgctc cggcctcagg  10920
ggatgcactg actttcctcc cactgtcctg aacacctgag aatcctgagc ggggaacaag  10980
ttgctcaaag ggcagagaag tgactcagag gttcagcaag agaaaagccc agtgtattaa  11040
gcatgtcttt ttattctgat gctttgctgt ctgggccttg caaacgtgag agggactgcc  11100
cctcccaggg gtagccagtt cctacggtta gcaaaggact cacctgggag gacagcttc  11160
atatgcaaac caaccaatcc agagcccaca ccctgtgacc acctcccatct ggctcaaact  11220
caaggccact gtcccctga cctaatcacc cagggcctgg taccagacaa ttagagataa  11280
ctcctgtgac cccagatcct gctgaaatta ttcaaactcc ccaatcctaa acctgcttac  11340
cctgcctccc ctttctttcc ttcccatgga aagaataaag gcgctttccc acattttccc  11400
ctggtgccct cttctggagc aaccctggtg cttccccagg tggcctcctg ggcttagtgt  11460
gcccccttcc tcttgggctc tgtgagtaca acaacttgta aagataattt tttttagag  11520
cagtttttatg ttcacagcca aattgagaga aaagtacaaa cagttcccag atactactgg  11580
cccccacaca tgcacagcct ccccgattat catcatctcc cgccacagca gttgttacaa  11640
ctgatgaacc tgcatcagca cgcacaacac ccaaggtcca cggtttaaat tagggttcat  11700
ttttggtgtt gcgccttcta tgggtttaga caaatgcata gtgacatgtg tccaccatta  11760
tagtatcata cacagtattc attgccctaa aaatcgtctg tgcctcacct agtcatccct  11820
tcctcaccca acaactgctg atcttttttac tgtctccata attttgcttt aacttgcttt  11880
tcagtgacaa ttgcctcctg ggatgttggac cttgccacac ctgaataatc atcaaacctg  11940
catttttattt gttttttatgt gtatgtgatg ggttttttgg gaggtggag gggaggacag  12000
ggtctcactc tacgccaggg ctggagtgca gaggtacgat cactgctcac cacagccttg  12060
acctcccggt ctcaagtgat cctcccacct cagcctccca agtagctggg actgcaggta  12120
cacatcacca cccaggctaa cttttttgtag ttttttgtaga gatgggattt caccatgttg  12180
cccaggtttg tcttgaactc ctgggctcca gtgatctgtc taccttggct tcccaaagtg  12240
ctgggattac aggtatgagc cactgggcct ggccaaactg cattttaaaa tagccaagcc  12300
tgttccttgt gactattgcc tcatccttgt attcaagact gctgtaagat cataatccta  12360
agcaagagta gagacatgta gcacaccatg atcacttact gtctaaccaa tgctgcccac  12420
ccgcttccct tctgtatggc tcaccacccc caccccaaac tcctatagga actctgcaca  12480
cactccctct ccattatgca aaactggtct cagaaaggaa tcagcagaa tatttctact  12540
gaaagtataa agcttaatat gttacttctt acaagaatat ttgcatataa caagggaaaa  12600
aaccttaagt catgcagtaa acttttatct tttttttttt tttaacagga gtctccctat  12660
gttgcccaag ctggtcttga acacctgggc tcaagtactc ctcctgtctt ggcctcccaa  12720
agtgctggga ttacagacat gagccacact tctttttttt tttttttttt ttttttttttc  12780
ttgagacaga gtcttgctct gttgcccaga ctggagtaca gttgcacaat cccggctccc  12840
tgcaacctttt gcctcctggg ttcaagtgat cctcaacctc ctgagtatct ggaactacag  12900
gcatgtgcca ccacaccctg ctaattcttg tatttctagt aaagatggaa tttcaccacg  12960
ctggccaggc tagtcttgaa ctcctggcct taagtgatcc gcctgcctcg gcctcccaaa  13020
gtgctgggat ttcagtgtga gccactgtgc ccggtctctt tttttttttt tttgagacct  13080
tgagaccggg ccttgctctg ttacccaagc tggagtgcag tggcaggatc atagctcact  13140
gcagccttga acttctgggc tcaagcaatc ctcccacatc agcctcccaa gtacctagga  13200
ctgcagatgc ttaccaccat gcccagctaa tttttcatga attttttaatt attgaaattc  13260
agacatctaa gaagatgctg aggactgtct ccatattcct gaaattacga ctcacctatt  13320
cacaaaccag cccttctagt ggaattaaaa tattatttga ttttgaatac cctactctaa  13380
ggtaggcaca ttgccctgca atttattatt tatgaggttt ttaattatgg aattgttcaa  13440
atattcacaa aagtagagag actacaatga actccaatgt agccatcact caggcccaac  13500
tgttatcagc acagtccaat catgttttat cttccctttct ctgacccca acccatccca  13560
agtccttatc taaaatcaaa tctcaaacac catatctttg ggagcctatt tatttagtta  13620
gttagtttc agacagagtt tctttcttgt tgcccaagct ggagtacaat agtgtagtct  13680
cggctcacaa caatctcccc ctccttggtt caagcaattc tcctgcctca gtctcccaag  13740
aagctgggat tataggcacc tgccaccaca tccagctaat tctttgtgt tttagcaaa  13800
gacagggttt caccatgttg gccaggctgg tctcgaactc ctgacctcag gtgatccgcc  13860
```

```
tgcctcggcc tcccaaagtg ctgggattac aggcatgagc caccacgcct ggccggcagc  13920
ctatttaaat gtcatcctca acatagtcaa tccttgggcc attttttctt acagtaaaat  13980
tttgtctctt tcttttaatg cagtttctac gtggaatttg gacactttgg ccttccagga  14040
actgaagtcc gagctaactg aagttcctgc ttcccgaatt ttgaaggaga gcccatctgg  14100
ctatctcagg agtggagagg gagacaccgg tatgaagtta agtttcttcc cttttgtgcc  14160
cacgtggtct ttattcatgt ctagtgctgt gttcagagaa tcagtatagg gtaaatgccc  14220
acccaagggg gaaattaact tccctgggag cagagggagg ggaggagaag aggaacagaa  14280
ctctctctct ctctctgttc ccttgtcaga gcaggtctgc aggagtcagc ctttccctaa  14340
caaagccctc tatcctatca cccacacttg ggaggctggg ctgggctgca cagggcaaga  14400
tgagagatgt gttgatttca tccacttgat tgtcatgtag aattagatat acttgagaag  14460
ttacattttt cagtagcgcc ttcatatctt tattttaggg acaggtatac accaagcacc  14520
atctcagcca caatctgtta ctaacagtat gttttctgaa ctttggccac ttaggaaaag  14580
tacagtttgg ctctctccaa agtgttccct gaaagtccaa ctttatgact aatactgtga  14640
tttccagaaa ctttgactat ccatgttatt gacaatgatt actagcactg aagggcatga  14700
atgcaagtag gggttatgaa atatttaaaa cacggttctc taagatatga gcagcaaagt  14760
gtttctacct tctatgaggg aaccgaaggt gccattaaaa gtagagaaat ctggaccagg  14820
catggtggct catgcctgta atcccagcac tttgggaggc tgaggcgggc ggatcacttg  14880
aggtcaggag ttcaagacca gcctggccaa catggtgaaa cactgtctct actaaaaata  14940
caaaaattag ccaggcatgg tggcagtcat ctgtaatccc agctacttgg gaggctgagg  15000
caggaaaatt gcttgaaccc aggaggcaga ggttgcagtg agccgagatc acaccactgc  15060
cctccagcct gggcgacaga gtgagactct gtctcaaaaa aaaaaaaaat acagacatct  15120
gttgtgattc tggtaactct aaatttttcaa ccgtctcttc actacattta aaaaattatt  15180
ttctaaacca aattagccag gtgtggtagc aggcacctgt agtcccagca actcaggagg  15240
ctgagatggg aggggtgctt gagcctggaa ggtcgaggct gcagtgcact gtgattgcac  15300
cactgcactc cagcctaggt aacagtgcaa gaccctgtct caaaaaataa ttattttcat  15360
gtttattata ttaaaatgat gtatgaaata tgtgactcat cagggcttga aaaactttgt  15420
tgtatggaga ttattcttat gagttgattt ttctctctcc taccttatag taatgaaata  15480
aaccaggcat gaaagtcaca ataagtaata caatgaacac ccatgggtcc ctgcccagct  15540
taagtagaat attacaaatg cagttgaagc cctctgtgca actttcatcc ttacaactga  15600
tactgagtga attgtacttt aaatatttta tagctcccac tcccatgcat gcccctcagt  15660
gatagcaata attgtcaata acatgaaaca cagattgatc atatagcatt taccatatat  15720
ttactctata ccaagcactt aacatatata attacattta aaatttacaa cagccctact  15780
acccaaaaca ctattagtat cccctttttac aaatgcgata actgaggcgt agagagctaa  15840
gtaacttact gaaagtcaca cagccagcgg gtggtagagc ctagctttaa acccagacga  15900
tttgtctcca gggctgtcac atctactggc tctgccaagc ttccgcatga tcattgtctg  15960
tgtttggaaa gattatggat taagtggtgc ttcgttttct ttttctgaatt taccaggatg  16020
tggagaacta gtttgggtag gagagcctct cacgctgaga acagcagaaa caattactgg  16080
caagtatggt gtgtggatgc gagacccaa gcccacctac ccctacaccc aggagaccac  16140
gtggagaatc gacacagttg gcacggatgt ccgccaggtt tttgagtatg acctcatcag  16200
ccagtttatg cagggctacc cttctaaggt tcacatactg cctaggccac tggaaagcac  16260
gggtgctgtg gtgtactcgg ggagcctcta tttccagggc gctgagtcca gaactgtcat  16320
aagatatgag ctgaataccg agacagtgaa ggctgagaag gaaatccctg gagctggcta  16380
ccacggacag ttcccgtatt cttggggtgg ctacacggac attgacttgg ctgtggatga  16440
agcaggcctc tgggtcattt acagcaccga tgaggccaaa ggtgccattg tcctctccaa  16500
actgaaccca gagaatctgg aactcgaaca aacctgggag acaaacatcc gtaagcagtc  16560
agtcgccaat gccttcatca tctgtggcac cttgcacacc gtcagcagct acacctcagc  16620
agatgctacc gtcaactttg cttatgcac aggcacaggt atcagcaaga ccctgaccat  16680
cccattcaag aaccgctata agtacagcag catgattgac tacaacccccc tggagaagaa  16740
gctctttgcc tgggacaact tgaacatggt cacttatgac atcaagctct ccaagatgtg  16800
aaaagcctcc aagctgtaca ggcaatggca gaaggagatg ctcagggctc ctggggggag  16860
caggctgaag ggagagccag ccagccaggg cccaggcagc tttgactgct ttccaagttt  16920
tcattaatcc agaaggatga acatggtcac catctaacta ttcaggaatt gtagtctgag  16980
ggcgtagaca atttcatata ataaatatcc tttatcttct gtcagcattt atgggatgtt  17040
taatgacata gttcaagttt tcttgtgatt tggggcaaaa gctgtaaggc ataatagttt  17100
cttcctgaaa accattgctc ttgcatgtta catggttacc acaagccaca ataaaaagca  17160
taacttctaa aggaagcaga atagctcctc tggccagcat cgaatataag taagatgcat  17220
ttactacagt tggcttctaa tgcttcagat agaatacagt tgggtctcac ataaccctttt  17280
acattgtgaa ataaaatttt cttacccaac gttctcttcc ttgaactttg tgggaatctt  17340
tgcttaagag aaggatatag attccaacca tcaggtaatt ccttcaggtt gggagatgtg  17400
attgcaggat ctcgagataa cttcgtataa tgtatgctat acgaagttat gctaggtaac  17460
tataacggtc ctaaggtagc gagctagcgg agcctctatg cctaccagca aaggccagaa  17520
aaggtgaagt tccgggctcc cgggtgaagc agctgtcagc agaggcagcc agatgcatgg  17580
agtttctcct cctgctaaag attttgttta tccgggtcaa tgtacagcta gctcccctct  17640
gactgacacg tcctccaggc ttgtatagtc gcatagactc tgttctcttc tgtcagcttt  17700
caaagggctg ttcctctttt aaaaatcaca tagtgtagca gtccagagga aaaactagaa  17760
gtaaggttgt ttcttcatga aaccattgct tttgcacgct attatggtta ccataagctt  17820
tgcgaggcag cggcggttct gcggagcgac cgctcctgtg gttagaactg ctcctgccga  17880
aggtgtatta tactccaggg ggcttctagt gctacagata cagcatgtgg ttgggtggta  17940
cgtaaaccct ttgccctgtg aaataaagtt atcttacatg  17980
```

SEQ ID NO: 90          moltype = DNA   length = 20
FEATURE                Location/Qualifiers
misc_feature           1..20
                       note = Synthetic
source                 1..20
                       mol_type = other DNA
                       organism = synthetic construct
SEQUENCE: 90
aaagacattt atatatcctg                                                  20

-continued

```
SEQ ID NO: 91            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 91
ctttaaaaac aaagtgccgg                                                  20

SEQ ID NO: 92            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 92
ctgggttgga ccagccatgg                                                  20

SEQ ID NO: 93            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 93
agaggtgatc acatgaagct                                                  20

SEQ ID NO: 94            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 94
gtaatcctcc tatccccca                                                   20

SEQ ID NO: 95            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 95
acttcaggct tgagccagca                                                  20

SEQ ID NO: 96            moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 96
aaagacattt atatatcctg                                                  20

SEQ ID NO: 97            moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 97
ctttaaaaac aaagtgccgg                                                  20

SEQ ID NO: 98            moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 98
```

-continued

```
ctgggttgga ccagccatgg                                          20

SEQ ID NO: 99            moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 99
agaggtgatc acatgaagct                                          20

SEQ ID NO: 100           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 100
gtaatcctcc tatccccca                                           20

SEQ ID NO: 101           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 101
acttcaggct tgagccagca                                          20

SEQ ID NO: 102           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 102
gccaatgcct tcatcatctg t                                        21

SEQ ID NO: 103           moltype = DNA   length = 14
FEATURE                  Location/Qualifiers
misc_feature             1..14
                         note = Synthetic
source                   1..14
                         mol_type = other DNA
                         organism = synthetic construct
SEQUENCE: 103
ccttgtacac cgtc                                                14

SEQ ID NO: 104           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 104
ggtagcatct gctgaggtgt agct                                     24

SEQ ID NO: 105           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 105
gccaatgcct tcatcatctg t                                        21

SEQ ID NO: 106           moltype = DNA   length = 16
FEATURE                  Location/Qualifiers
misc_feature             1..16
                         note = Synthetic
source                   1..16
                         mol_type = other DNA
                         organism = synthetic construct
```

-continued

```
SEQUENCE: 106
caccttgcac accgtc                                                    16

SEQ ID NO: 107        moltype = DNA   length = 24
FEATURE               Location/Qualifiers
misc_feature          1..24
                      note = Synthetic
source                1..24
                      mol_type = other DNA
                      organism = synthetic construct
SEQUENCE: 107
ggtagcatct gctgaggtgt agct                                           24

SEQ ID NO: 108        moltype = DNA   length = 23
FEATURE               Location/Qualifiers
misc_feature          1..23
                      note = Synthetic
source                1..23
                      mol_type = other DNA
                      organism = synthetic construct
SEQUENCE: 108
catggttacc acaagccaca ata                                            23

SEQ ID NO: 109        moltype = DNA   length = 27
FEATURE               Location/Qualifiers
misc_feature          1..27
                      note = Synthetic
source                1..27
                      mol_type = other DNA
                      organism = synthetic construct
SEQUENCE: 109
taaaggaagc agaatagctc ctctggc                                        27

SEQ ID NO: 110        moltype = DNA   length = 23
FEATURE               Location/Qualifiers
misc_feature          1..23
                      note = Synthetic
source                1..23
                      mol_type = other DNA
                      organism = synthetic construct
SEQUENCE: 110
agaagccaac tgtagtaaat gca                                            23

SEQ ID NO: 111        moltype = DNA   length = 20
FEATURE               Location/Qualifiers
misc_feature          1..20
                      note = Synthetic
source                1..20
                      mol_type = other DNA
                      organism = synthetic construct
SEQUENCE: 111
gcctgccctt tctcctagag                                                20

SEQ ID NO: 112        moltype = DNA   length = 25
FEATURE               Location/Qualifiers
misc_feature          1..25
                      note = Synthetic
source                1..25
                      mol_type = other DNA
                      organism = synthetic construct
SEQUENCE: 112
tgcacagcta gcacaagaca gatga                                          25

SEQ ID NO: 113        moltype = DNA   length = 21
FEATURE               Location/Qualifiers
misc_feature          1..21
                      note = Synthetic
source                1..21
                      mol_type = other DNA
                      organism = synthetic construct
SEQUENCE: 113
ggtgatcgct gtgctttcct t                                              21

SEQ ID NO: 114        moltype = DNA   length = 20
FEATURE               Location/Qualifiers
misc_feature          1..20
                      note = Synthetic
source                1..20
                      mol_type = other DNA
```

-continued

```
                              organism = synthetic construct
SEQUENCE: 114
gggagaagga agctgaaacc                                            20

SEQ ID NO: 115           moltype = DNA   length = 29
FEATURE                  Location/Qualifiers
misc_feature             1..29
                         note = Synthetic
source                   1..29
                         mol_type = other DNA
                         organism = synthetic construct
SEQUENCE: 115
tgctgccttt tctagacata tgtactgga                                  29

SEQ ID NO: 116           moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 116
acctagccct ccaaggttg                                             19

SEQ ID NO: 117           moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 117
gggccaggac agcacagtt                                             19

SEQ ID NO: 118           moltype = DNA   length = 23
FEATURE                  Location/Qualifiers
misc_feature             1..23
                         note = Synthetic
source                   1..23
                         mol_type = other DNA
                         organism = synthetic construct
SEQUENCE: 118
ccgaaaggcc aatgatcgga gtg                                        23

SEQ ID NO: 119           moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 119
tggccacagt gaaggtgta                                             19

SEQ ID NO: 120           moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 120
gcacagcact gtaaaggca                                             19

SEQ ID NO: 121           moltype = DNA   length = 29
FEATURE                  Location/Qualifiers
misc_feature             1..29
                         note = Synthetic
source                   1..29
                         mol_type = other DNA
                         organism = synthetic construct
SEQUENCE: 121
acggaactcg aaggaattgg tattgttgt                                  29

SEQ ID NO: 122           moltype = DNA   length = 23
FEATURE                  Location/Qualifiers
misc_feature             1..23
                         note = Synthetic
source                   1..23
```

-continued

```
                          mol_type = other DNA
                          organism = synthetic construct
SEQUENCE: 122
acacagctat gggagaaaga ctg                                        23

SEQ ID NO: 123           moltype = DNA   length = 17
FEATURE                  Location/Qualifiers
misc_feature             1..17
                          note = Synthetic
source                   1..17
                          mol_type = other DNA
                          organism = synthetic construct
SEQUENCE: 123
tgcggccgat cttagcc                                               17

SEQ ID NO: 124           moltype = DNA   length = 21
FEATURE                  Location/Qualifiers
misc_feature             1..21
                          note = Synthetic
source                   1..21
                          mol_type = other DNA
                          organism = synthetic construct
SEQUENCE: 124
acgagcgggt tcggcccatt c                                          21

SEQ ID NO: 125           moltype = DNA   length = 18
FEATURE                  Location/Qualifiers
misc_feature             1..18
                          note = Synthetic
source                   1..18
                          mol_type = other DNA
                          organism = synthetic construct
SEQUENCE: 125
ttgaccgatt ccttgcgg                                              18
```